(12) United States Patent
Kitamura et al.

(10) Patent No.: US 9,525,139 B2
(45) Date of Patent: Dec. 20, 2016

(54) MATERIALS FOR AN ORGANIC ELECTROLUMINESCENCE ELEMENT, ELECTROLUMINESCENT, DISPLAY AND ILLUMINATING DEVICES USING THE ELEMENTS

(71) Applicant: UDC Ireland Limited, Dublin (IE)

(72) Inventors: Tetsu Kitamura, Kanagawa (JP); Tenka Ouyo, Kanagawa (JP); Yuki Hirai, Kanagawa (JP); Koji Takaku, Kanagawa (JP); Wataru Sotoyama, Kanagawa (JP); Masaru Kinoshita, Kanagawa (JP); Kuniyuki Kaminaga, Kanagawa (JP); Yosuke Yamamoto, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 584 days.

(21) Appl. No.: 13/758,546

(22) Filed: Feb. 4, 2013

(65) Prior Publication Data
US 2013/0264547 A1    Oct. 10, 2013

(30) Foreign Application Priority Data

Feb. 6, 2012    (JP) ................................ 2012-023175
Mar. 30, 2012   (JP) ................................ 2012-083304

(51) Int. Cl.
*H01L 51/00*    (2006.01)
*C09K 11/06*    (2006.01)
(Continued)

(52) U.S. Cl.
CPC ............. *H01L 51/006* (2013.01); *C09K 11/06* (2013.01); *H01L 51/0056* (2013.01);
(Continued)

(58) Field of Classification Search
CPC ............. C09K 11/06; C09K 2211/1007; C09K 2211/1011; C09K 2211/1014; C09K 2211/1029; C09K 2211/1044; H01L 51/0056; H01L 51/006; H01L 51/0061; H01L 51/0072; H01L 51/5012; H05B 33/14
See application file for complete search history.

(56) References Cited

U.S. PATENT DOCUMENTS 9,287,507 B2 *  3/2016  Watanabe ........... H01L 51/0058
2004/0076853 A1 *  4/2004  Jarikov ........................ 428/690
(Continued)

FOREIGN PATENT DOCUMENTS

JP    11-251063    9/1999
JP    2002-063988   2/2002
(Continued)

*Primary Examiner* — Dawn Garrett
(74) *Attorney, Agent, or Firm* — Riverside Law LLP

(57) ABSTRACT

An organic electroluminescent element including a substrate, a pair of electrodes including an anode and a cathode, disposed on the substrate, and at least one layer of organic layers including a light emitting layer, disposed between the electrodes, in which at least one of the organic layers contains a compound represented by the following general formula:

(Continued)

General Formula (1)

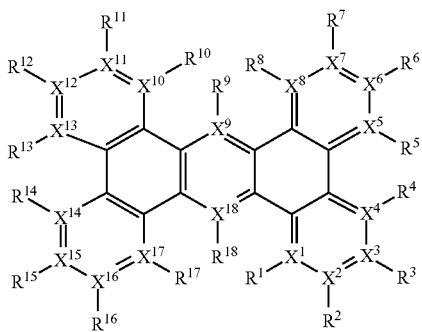

($R^1$ to $R^{18}$ each independently represent a hydrogen atom or a substituent, and at least one of $R^1$ to $R^8$ and $R^{10}$ to $R^{17}$ represents -L-$NR^{19}R^{20}$ ($R^{19}$ and $R^{20}$ each independently represent any of an alkyl group, an aryl group, a heteroaryl group. $R^{19}$ and $R^{20}$ may be combined to each other to form a ring. L represents a single bond or a divalent linking group). $X^1$ to $X^{18}$ each independently represent a carbon atom or a nitrogen atom, and when $X^1$ to $X^{18}$ represent nitrogen atoms, $R^1$ to $R^{18}$ for bonding do not present.)

12 Claims, 2 Drawing Sheets

(51) Int. Cl.
  *H05B 33/14* (2006.01)
  *H01L 51/50* (2006.01)
(52) U.S. Cl.
  CPC ...... *H01L 51/0061* (2013.01); *H01L 51/0072* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *H01L 51/5012* (2013.01)

(56) References Cited

U.S. PATENT DOCUMENTS

2013/0214259 A1* 8/2013 Watanabe et al. .......... 257/40
2014/0008621 A1* 1/2014 Kaminaga et al. .......... 257/40

FOREIGN PATENT DOCUMENTS

| JP | 2007157899 | 6/2007 |
| JP | 2007227717 | 9/2007 |
| JP | 200850308 | 3/2008 |
| JP | 4185097 | 11/2008 |
| JP | 2009292760 | 12/2009 |
| JP | 2010-171205 | 8/2010 |
| JP | 2011-187959 | 9/2011 |

* cited by examiner

US 9,525,139 B2

MATERIALS FOR AN ORGANIC ELECTROLUMINESCENCE ELEMENT, ELECTROLUMINESCENT, DISPLAY AND ILLUMINATING DEVICES USING THE ELEMENTS

CROSS-REFERENCE TO RELATED APPLICATIONS

The present application claims priority benefit from Japanese Patent Application No. 2012-083304, filed 30 Mar. 2012, and Japanese Patent Application No. 2012-023175, filed 6 Feb. 2012, all of which are hereby incorporated by reference herein in their entirety.

FIELD OF INVENTION

The present invention relates to an organic electroluminescent element, and a compound and a material for the organic electroluminescent element capable of being used therefor. In addition, the present invention also relates to a light emitting device, a display device, or an illumination device, using the organic electroluminescent element.

BACKGROUND OF INVENTION

An organic electroluminescent element (hereinafter also referred to as an "element" or an "organic EL element") has been actively studied since it provides light emission with high brightness with low voltage driving. The organic electroluminescent element has an organic layer between a pair of electrodes. Further, the electrons injected from a cathode with a hole injected from an anode are recombined in the organic layer, and the energy of excitons produced are used for light emission. The organic electroluminescent element can be provided as an element having various light emitting wavelengths, and since the element has a high response speed, and is relatively thin in thickness and is light in weight, a wide range of applications is expected. Among them, development of the organic electroluminescent element having high blue chromatic purity and high light emitting efficiency is important in application or the like to a full-color display, and various development research results have been reported so far.

For example, in Patent Document 1, it is described that an organic electroluminescent element having a blue luminous color or high light emitting efficiency and excellent heat resistance is obtained by using tetrabenzanthracene "phenanthro triphenylene" derivative. In Patent Document 1, an alkyl group or an aryl group is used as a substituent of the compound, and a compound having a bicyclic or tricyclic oligoaryl group is used as an example, however, a compound having an amino group as a substituent is not disclosed.

In Patent Document 2, it is described that an organic electroluminescent element having excellent solvent solubility or heat resistance, low driving voltage even in a case of formation by a wet film forming method, and sufficient life time is obtained by using a triphenylene-based compound which is substituted with a diarylamino group through an allylene group. In Patent Document 2, a case where substituents that substitute triphenylene scaffold form a fused ring is not described.

In Patent Documents 3 and 4, it is described that an organic electroluminescent element having high light emitting efficiency and excellent stabilization at the time of repeated use is obtained by using a compound obtained by substituting 9- and 10-positions of anthracene by a diarylamino group. In Patent Documents 3 and 4, a compound having an aminophenanthro triphenylene scaffold in which substituents of 1- and 2-positions, 3- and 4-positions, 5- and 6-positions, and 7- and 8-positions of anthracene of a compound having a diarylamino group in 9- and 10-positions of anthracene, form a fused ring, is used as an example, however, the performance thereof is not investigated. In addition, as the compound disclosed in Patent Documents 3 and 4, a compound in which a diarylamino group is introduced to positions other than 9- and 10-positions of anthracene is not described.

In Patent Document 5, it is described that an organic electroluminescent element having high brightness and long life time is obtained by using a triphenylene-based compound which is substituted with a diarylamino group. In Patent Document 5, it is described that substituents that substitute triphenylene scaffold may be formed a fused ring, however, a case in which the substituents that substitute triphenylene scaffold form a fused ring in practice, is not investigated.

RELATED ART DOCUMENT

Patent Document

[Patent Document 1] JP-A-2008-50308
[Patent Document 2] JP-A-2009-292760
[Patent Document 3] JP-A-2007-157899
[Patent Document 4] JP-A-2007-227717
[Patent Document 5] JP-A-11-251063

SUMMARY OF INVENTION

However, the present inventors have researched and they have found that the organic electroluminescent elements described in Patent Document 1 still have rooms for improvement in light emitting efficiency and blue chromatic purity. Further, it was also clear that, if the organic electroluminescent element described in Patent Document 1 is used for a long time, chromaticity is changed with driving degradation which degrades luminescence intensity (hereinafter, also referred to as chromaticity change which occurs with driving degradation). In addition, investigating the organic electroluminescent element described in Patent Document 2, it is found that light emitting efficiency and chromatic purity are degraded and chromaticity change which occurs with driving degradation is also degraded depending on an element configuration, in some cases. In the organic electroluminescent element described in Patent Document 5, it is found that chromatic purity and chromaticity change which occurs with the driving degradation are degraded.

Further, when the inventors manufactures an organic electroluminescent element using a compound having an aminophenanthro triphenylene scaffold substituted by a diarylamino group on specified positions described in Patent Documents 3 and 4, it has been found that, in the obtained organic electroluminescent element, light emitting efficiency, chromatic purity, and chromaticity change which occurs with driving degradation are degraded.

Here, the present inventors have made extensive investigation aimed at providing an organic electroluminescent element having high light emitting efficiency, excellent blue chromatic purity, and small chromaticity change which occurs with driving degradation. As a result, they found that the problems described above can be solved, if an aminophenanthro triphenylene compound having a specified structure or a derivative thereof is used, and thus the present invention described below is provided.

[1] An organic electroluminescent element including a substrate, a pair of electrodes including an anode and a cathode, disposed on the substrate, and at least one layer of organic layers including a light emitting layer, disposed between the electrodes, in which at least one of the organic layers contains a compound represented by the following general formula (1).

General Formula (1)

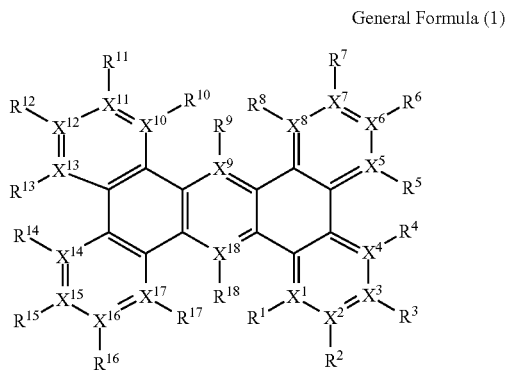

(In the general formula (1), $R^1$ to $R^{18}$ each independently represent a hydrogen atom or a substituent, and at least one of $R^1$ to $R^8$ and $R^{10}$ to $R^{17}$ represents -L-$NR^{19}R^{20}$ ($R^{19}$ and $R^{20}$ each independently represent any of an alkyl group, an aryl group, a heteroaryl group. $R^{19}$ and $R^{20}$ may be combined to each other to form a ring. L represents a single bond or a divalent linking group). $X^1$ to $X^{18}$ each independently represent a carbon atom or a nitrogen atom, and when $X^1$ to $X^{18}$ represent nitrogen atoms, $R^1$ to $R^{18}$ for bonding do not present.)

[2] The organic electroluminescent element as described in [1], in which, in the general formula (1), at least one of $R^3$, $R^6$, $R^{12}$, and $R^{15}$ is -L-$NR^{19}R^{20}$.

[3] The organic electroluminescent element as described in [1] or [2], in which, in the general formula (1), both $R^{19}$ and $R^{20}$ are aryl groups.

[4] The organic electroluminescent element as described in any one of [1] to [3], in which, in the general formula (1), all of $X^1$ to $X^{18}$ are carbon atoms.

[5] The organic electroluminescent element as described in any one of [1] to [4], in which, in the general formula (1), two of $R^1$ to $R^{18}$ represent -L-$NR^{19}R^{20}$.

[6] The organic electroluminescent element as described in any one of [1] to [5], in which, in the general formula (1), L represents a single bond.

[7] The organic electroluminescent element as described in any one of [1] to [6], in which the compound represented by the general formula (1) is a compound represented by the following general formula (2).

General Formula (2)

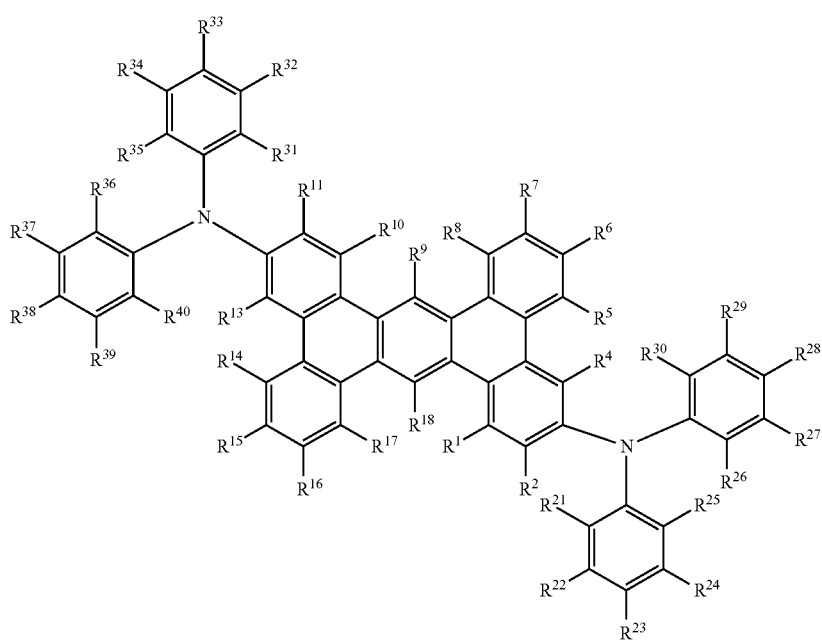

(In the general formula (2), $R^1$, $R^2$, $R^4$ to $R^{11}$, $R^{13}$ to $R^{18}$, and $R^{21}$ to $R^{40}$ each independently represent a hydrogen atom or a substituent. A plurality of $R^{21}$ to $R^{30}$ and $R^{31}$ to $R^{40}$ may be combined to each other to form a ring.)

[8] The organic electroluminescent element as described in any one of [1] to [6], in which the compound represented by the general formula (1) is a compound represented by the following general formula (3).

General Formula (3)

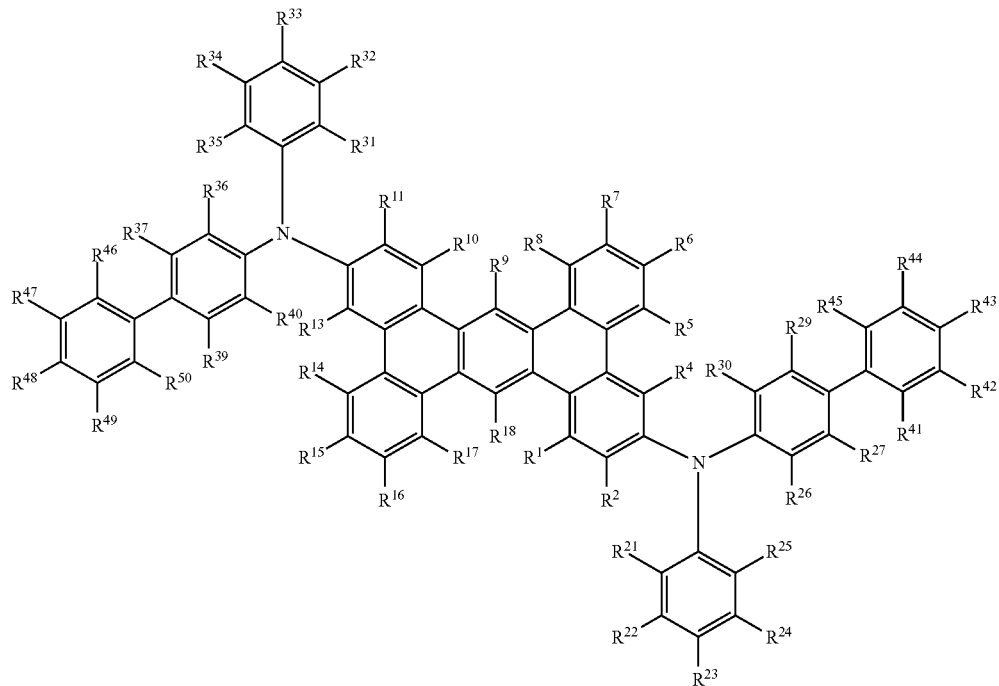

(In the general formula (3), $R^1$, $R^2$, $R^4$ to $R^{11}$, $R^{13}$ to $R^{18}$, $R^{21}$ to $R^{40}$, and $R^{41}$ to $R^{50}$ each independently represent a hydrogen atom or a substituent. A plurality of $R^{21}$ to $R^{30}$, $R^{31}$ to $R^{40}$, and $R^{41}$ to $R^{50}$ may be combined to each other to form a ring.)

[9] The organic electroluminescent element as described in any one of [1] to [6], in which the compound represented by the general formula (1) is a compound represented by the following general formula (4).

General Formula (4)

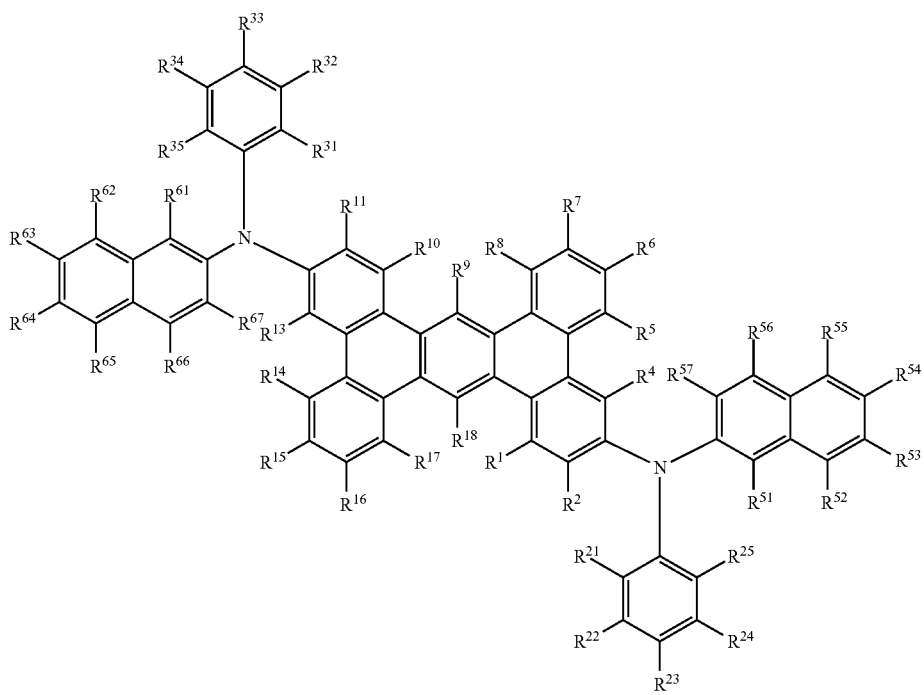

(In the general formula (4), $R^1$, $R^2$, $R^4$ to $R^{11}$, $R^{13}$ to $R^{18}$, $R^{21}$ to $R^{25}$, $R^{31}$ to $R^{35}$, $R^{51}$ to $R^{57}$, and $R^{61}$ to $R^{67}$ each independently represent a hydrogen atom or a substituent. A plurality of $R^{21}$ to $R^{30}$, $R^{31}$ to $R^{40}$, $R^{51}$ to $R^{57}$, and $R^{61}$ to $R^{67}$ may be combined to each other to form a ring.)

[10] The organic electroluminescent element as described in any one of [1] to [6], in which the compound represented by the general formula (1) is a compound represented by the following general formula (5).

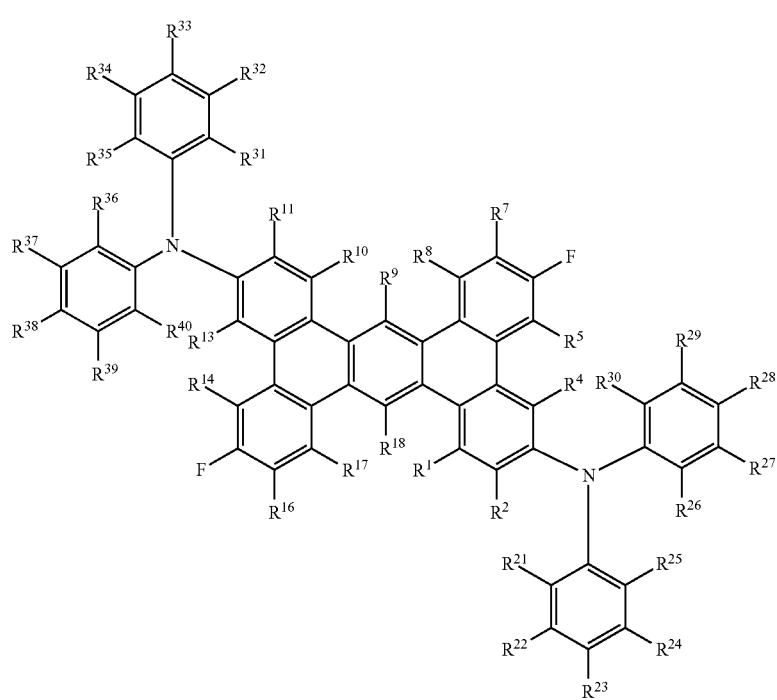

General Formula (5)

(In the general formula (5), $R^1$, $R^2$, $R^4$, $R^5$, $R^7$ to $R^{11}$, $R^{13}$, $R^{14}$, $R^{16}$ to $R^{18}$, and $R^{21}$ to $R^{40}$ each independently represent a hydrogen atom or a substituent. A plurality of $R^{21}$ to $R^{30}$ and $R^{31}$ to $R^{40}$ may be combined to each other to form a ring.)

[11] The organic electroluminescent element as described in any one of [1] to [6], in which the compound represented by the general formula (1) is a compound represented by the following general formula (6).

General Formula (6)

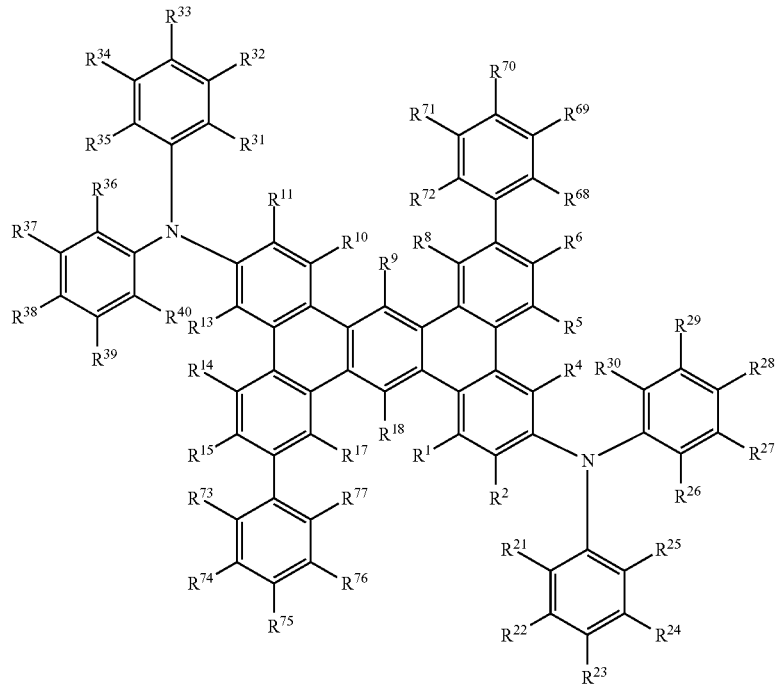

(In the general formula (6), $R^1$, $R^2$, $R^4$ to $R^6$, $R^8$ to $R^{11}$, $R^{13}$ to $R^{15}$, $R^{17}$, $R^{18}$, $R^{21}$ to $R^{40}$, and $R^{68}$ to $R^{77}$ each independently represent a hydrogen atom or a substituent. A plurality of $R^{21}$ to $R^{30}$ and $R^{31}$ to $R^{40}$ may be combined to each other to form a ring.)

[12] The organic electroluminescent element as described in any one of [1] to [11], in which a molecular weight of the compound represented by the general formula (1) is equal to or less than 1200.

[13] The organic electroluminescent element as described in any one of [1] to [12], in which at least one layer of the organic layers including the compound represented by the general formula (1) is the light emitting layer.

[14] The organic electroluminescent element as described in any one of [1] to [13], in which the compound represented by the general formula (1) is a light emitting material.

[15] The organic electroluminescent element as described in any one of [1] to [14], in which at least one of the organic layers contains a compound represented by the following general formula (An-1).

General Formula (An-1)

(In the general formula (An-1), $Ar^1$ and $Ar^2$ each independently represent an aryl group or a heteroaryl group, and $R^{301}$ to $R^{308}$ each independently represent a hydrogen atom or a substituent. $R^{301}$ and $R^{302}$, $R^{302}$ and $R^{303}$, $R^{303}$ and $R^{304}$, $R^{305}$ and $R^{306}$, $R^{306}$ and $R^{307}$, and $R^{307}$ and $R^{308}$ may be combined to each other to form a ring.)

[16] The organic electroluminescent element as described in [15], in which the compound represented by the general formula (An-1) is a compound represented by the following general formula (An-2).

General Formula (An-2)

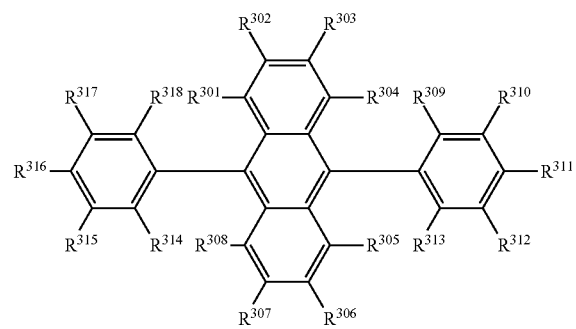

(In the general formula (An-2), $R^{301}$ and $R^{318}$ each independently represent a hydrogen atom or a substituent. $R^{301}$ and $R^{302}$, $R^{302}$ and $R^{303}$, $R^{303}$ and $R^{304}$, $R^{305}$ and $R^{306}$, $R^{306}$ and $R^{307}$, $R^{307}$ and $R^{308}$, $R^{309}$ and $R^{310}$, $R^{310}$ and $R^{311}$, $R^{311}$ and $R^{312}$, $R^{312}$ and $R^{313}$, $R^{314}$ and $R^{315}$, $R^{315}$ and $R^{316}$, $R^{316}$ and $R^{317}$, and $R^{317}$ and $R^{318}$ may be combined to each other to form a ring.)

[17] The organic electroluminescent element as described in [15] or [16], in which at least one layer of the organic layers including the compound represented by the general formula (An-1) is the light emitting layer.

[18] The organic electroluminescent element as described in any one of [1] to [17], in which at least one of the organic layers contains a compound represented by the following general formula (P-1).

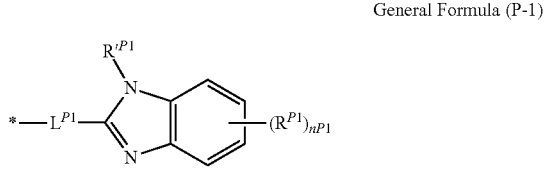

General Formula (P-1)

(In the general formula (P-1), $R^{P1}$ and $R'^{P1}$ each independently represent an alkyl group, an aryl group, or a heteroaryl group. $n^{P1}$ represents an integer of 0 to 4, and when a plurality of $R^{P1}$'s are present, they may be the same as or different from each other. $L^{P1}$ represents any one of a single bond and a divalent linking group consisting of an aryl ring or a heteroaryl ring. * represents a bonding position with the anthracene ring of the general formula (P).)

[19] The organic electroluminescent element as described in any one of [1] to [18], in which at least one layer of the organic layers contains a compound represented by the following general formula (P-2).

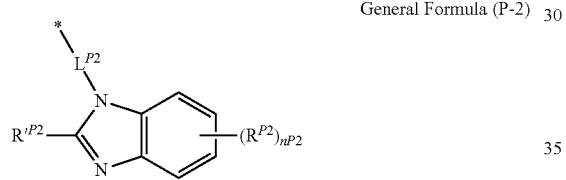

General Formula (P-2)

(In the general formula (P-2), $R^{P2}$ and $R'^{P2}$ each independently represent an alkyl group, an aryl group, or a heteroaryl group. $n^{P2}$ represents an integer of 0 to 4, and when a plurality of $R^{P2}$'s are present, they may be the same as or different from each other. $L^{P2}$ represents any one of a single bond and a divalent linking group consisting of an aryl ring or a heteroaryl ring. * represents a bonding position with the anthracene ring of the general formula (P).)

[20] The organic electroluminescent element as described in any one of [1] to [19], in which at least one of the organic layers contains a compound represented by the following general formula (P-3).

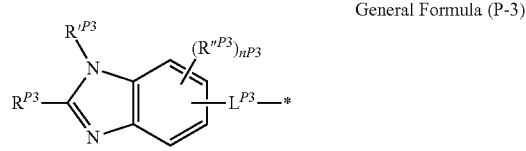

General Formula (P-3)

(In the general formula (P-3), $R^{P3}$, $R'^{P3}$, and $R''^{P3}$ each independently represent an alkyl group, an aryl group, or a heteroaryl group. $n^{P3}$ represents an integer of 0 to 4, and when a plurality of $R^{P3}$'s are present, they may be the same as or different from each other. $L^{P3}$ represents any one of a single bond and a divalent linking group consisting of an aryl ring or a heteroaryl ring. * represents a bonding position with the anthracene ring of the general formula (P).)

[21] The organic electroluminescent element as described in any one of [1] to [20], in which at least one of the organic layers contains a compound represented by the following general formula (P-4).

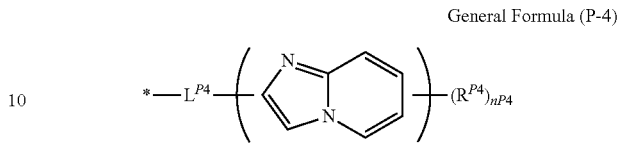

General Formula (P-4)

(In the general formula (P-4), $R^{P4}$ represents an alkyl group, an aryl group, or a heteroaryl group. $n^{P4}$ represents an integer of 0 to 4, and when a plurality of $R^{P4}$'s are present, they may be the same as or different from each other. $L^{P4}$ represents anyone of a single bond and a divalent linking group consisting of an aryl ring or a heteroaryl ring. * represents a bonding position with the anthracene ring of the general formula (P).)

[22] The organic electroluminescent element as described in any one of [1] to [21], in which at least one of the organic layers contains a compound represented by the following general formula (P-5).

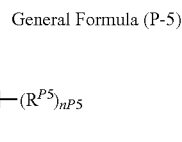

General Formula (P-5)

(In the general formula (P-5), $R^{P5}$ represents an alkyl group, an aryl group, or a heteroaryl group. $n^{P5}$ represents an integer of 0 to 4, and when a plurality of $R^{P5}$'s are present, they may be the same as or different from each other. $L^{P5}$ represents anyone of a single bond and a divalent linking group consisting of an aryl ring or a heteroaryl ring. * represents a bonding position with the anthracene ring of the general formula (P).)

[23] A light emitting device using the organic electroluminescent element as described in any one of [1] to [22].

[24] A display device using the organic electroluminescent element as described in any one of [1] to [22].

[25] An illumination device using the organic electroluminescent element as described in any one of [1] to [22].

[26] A compound represented by the following general formula (1)

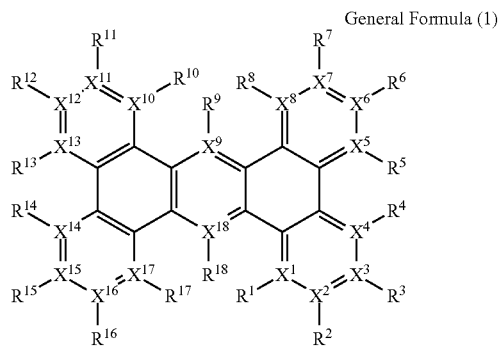

General Formula (1)

(In the general formula (1), $R^1$ to $R^{18}$ each independently represent a hydrogen atom or a substituent, and at least one of $R^1$ to $R^8$ and $R^{10}$ to $R^{17}$ represents -L-$NR^{19}R^{20}$ ($R^{19}$ and $R^{20}$ each independently represent any of an alkyl group, an aryl group, and a heteroaryl group. $R^{19}$ and $R^{20}$ may be combined to each other to form a ring. L represents a single bond or a divalent linking group.). $X^1$ to $X^{18}$ each independently represent a carbon atom or a nitrogen atom, and when $X^1$ to $X^{18}$ represent nitrogen atoms, $R^1$ to $R^{18}$ for combination do not present.)

[27] The compound as described in [26], in which, in the general formula (1), at least one of $R^3$, $R^6$, $R^{12}$, and $R^{15}$ is -L-$NR^{19}R^{20}$.

[28] The compound as described in [26] or [27], in which, in the general formula (1), both $R^{19}$ and $R^{20}$ are aryl groups.

[29] The compound as described in any one of [26] to [28], in which, in the general formula (1), all of $X^1$ to $X^{18}$ are carbon atoms.

[30] The compound as described in any one of [26] to [29], in which, in the general formula (1), two of $R^1$ to $R^{18}$ represent -L-$NR^{19}R^{20}$.

[31] The compound as described in any one of [26] to [30], in which, in the general formula (1), L represents a single bond.

[32] The compound as described in any one of [26] to [31], in which the compound represented by the general formula (1) is a compound represented by the following general formula (2).

General Formula (2)

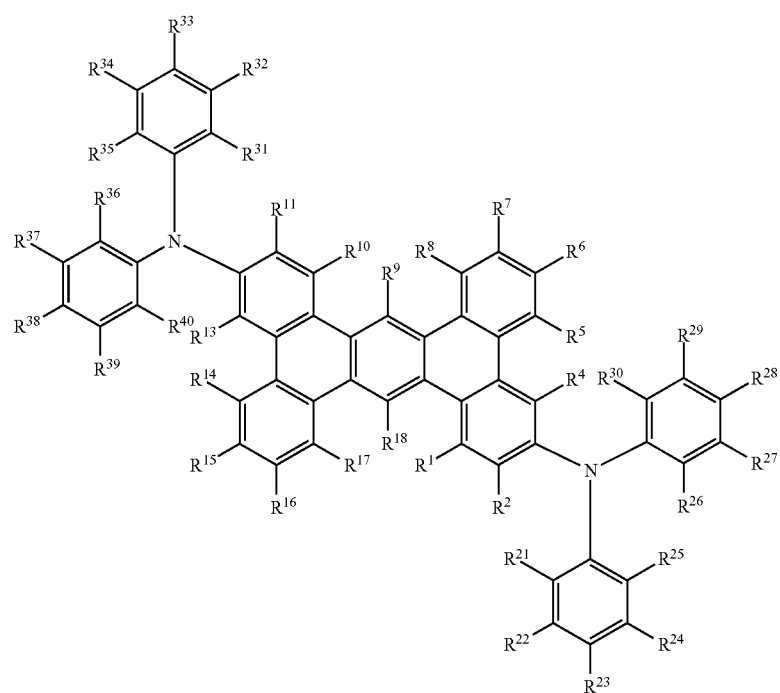

(In the general formula (2), $R^1$, $R^2$, $R^4$ to $R^{11}$, $R^{13}$ to $R^{18}$, and $R^{21}$ to $R^{40}$ each independently represent a hydrogen atom or a substituent. A plurality of $R^{21}$ to $R^{30}$ and $R^{31}$ to $R^{40}$ may be combined to each other to form a ring.)

[33] The compound as described in any one of [26] to [31], in which the compound represented by the general formula (1) is a compound represented by the following general formula (3).

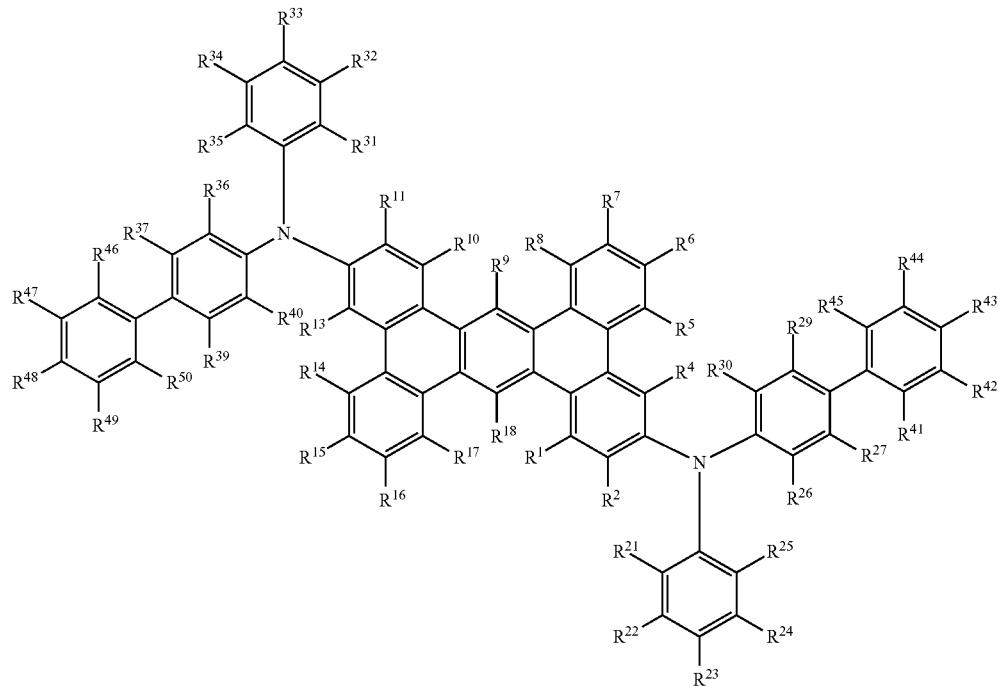

General Formula (3)

(In the general formula (3), $R^1$, $R^2$, $R^4$ to $R^{11}$, $R^{13}$ to $R^{18}$, $R^{21}$ to $R^{40}$, and $R^{41}$ to $R^{50}$ each independently represent a hydrogen atom or a substituent. A plurality of $R^{21}$ to $R^{30}$, $R^{31}$ to $R^{40}$, and $R^{41}$ to $R^{50}$ may be combined to each other to form a ring.)

[34] The compound as described in any one of [26] to [31], in which the compound represented by the general formula (1) is a compound represented by the following general formula (4).

General Formula (4)

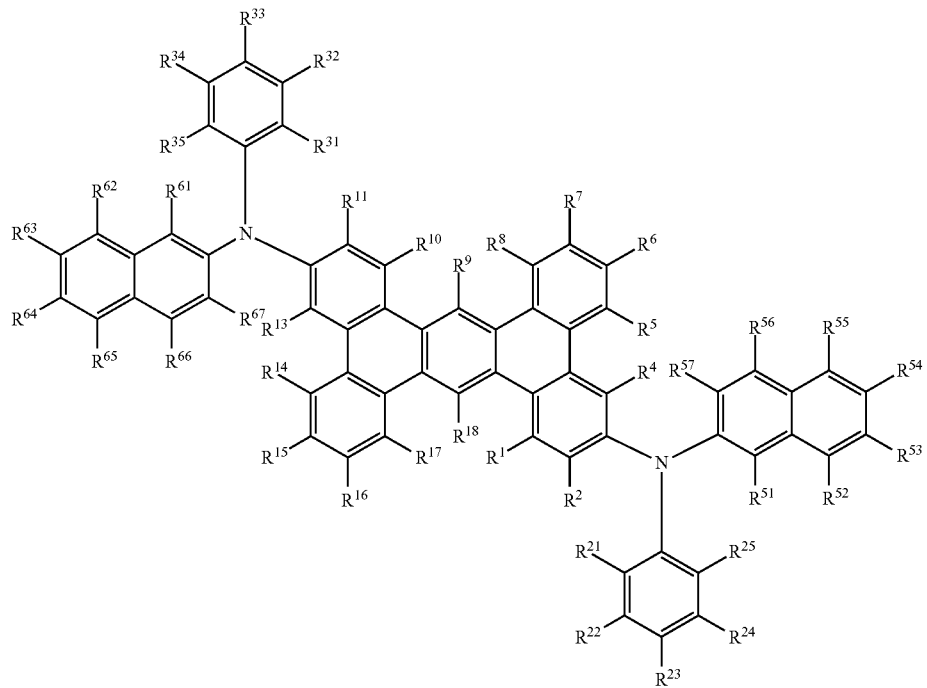

(In the general formula (4), $R^1$, $R^2$, $R^4$ to $R^{11}$, $R^{13}$ to $R^{18}$, $R^{21}$ to $R^{25}$, $R^{31}$ to $R^{35}$, $R^{51}$ to $R^{57}$, and $R^{61}$ to $R^{67}$ each independently represent a hydrogen atom or a substituent. A plurality of $R^{21}$ to $R^{25}$, $R^{31}$ to $R^{35}$, $R^{51}$ to $R^{57}$, and $R^{61}$ to $R^{67}$ may be combined to each other to form a ring.)

[35] The compound as described in any one of [26] to [31], in which the compound represented by the general formula (1) is a compound represented by the following general formula (5).

General Formula (5)

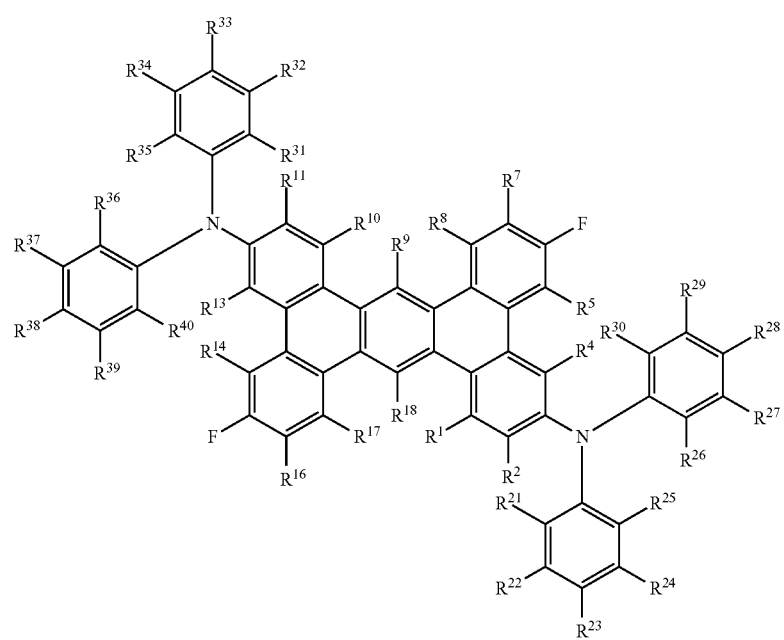

(In the general formula (5), $R^1$, $R^2$, $R^4$, $R^5$, $R^7$ to $R^{11}$, $R^{13}$, $R^{14}$, $R^{16}$ to $R^{18}$, and $R^{21}$ to $R^{40}$ each independently represent a hydrogen atom or a substituent. A plurality of $R^{21}$ to $R^{30}$ and $R^{31}$ to $R^{40}$ may be combined to each other to form a ring.)

[36] The compound as described in any one of [26] to [31], in which the compound represented by the general formula (1) is a compound represented by the following general formula (6).

General Formula (6)

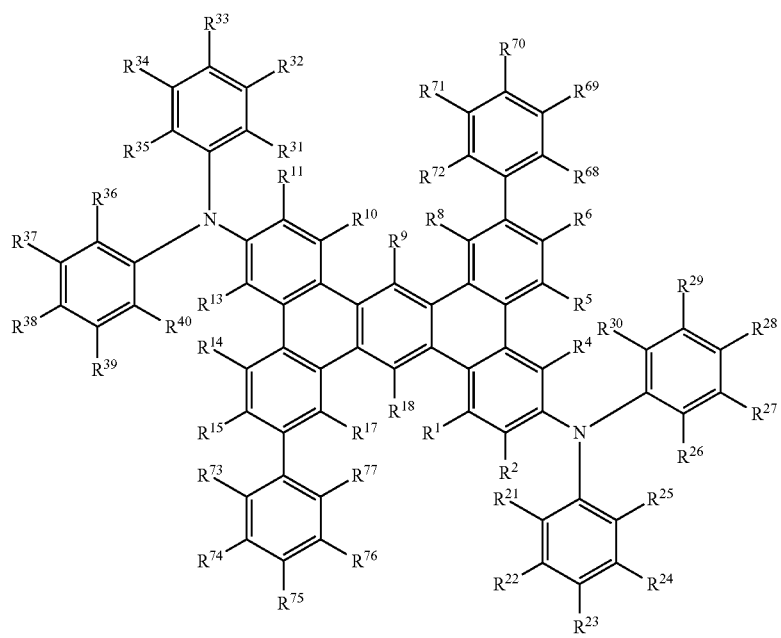

(In the general formula (6), $R^1$, $R^2$, $R^4$ to $R^6$, $R^8$ to $R^{11}$, $R^{13}$ to $R^{15}$, $R^{17}$, $R^{18}$, $R^{21}$ to $R^{40}$, and $R^{68}$ to $R^{77}$ each independently represent a hydrogen atom or a substituent. A plurality of $R^{21}$ to $R^{30}$ and $R^{31}$ to $R^{40}$ may be combined to each other to form a ring.)

[37] The compound as described in any one of [26] to [36], in which a molecular weight of the compound represented by the general formula (1) is equal to or less than 1200.

[38] A material for an organic electroluminescent element consisting of the compound as described in any one of [26] to

[39] The material for an organic electroluminescent element as described in [38] which is a light emitting material.

The organic electroluminescent element of the present invention has advantageous effects which are high light emitting efficiency, excellent blue chromatic purity, and small chromaticity change which occurs with driving degradation. In addition, if the compound of the present invention is used, it is possible to easily manufacture such excellent organic electroluminescent element. Further, the light emitting device, the display device, and the illumination device of the present invention have advantageous effects which are small power consumption, excellent blue chromatic purity, and chromaticity which hardly changes even after being used for a long time.

DETAILED DESCRIPTION OF INVENTION

Figure 1:
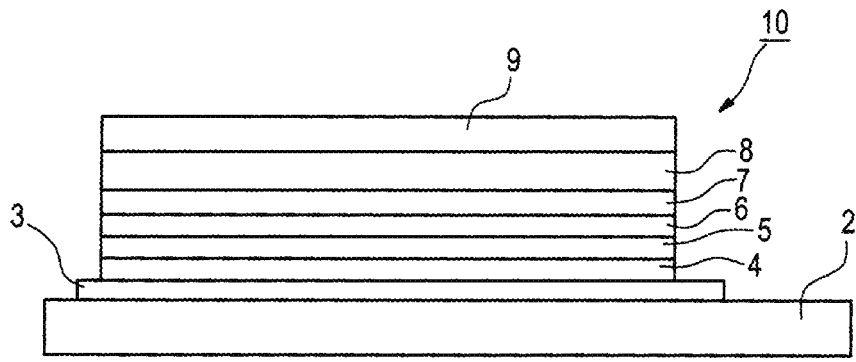
FIG. 1 is a schematic view showing one example of a configuration of the organic electroluminescent element according to the present invention.

Hereinbelow, the details of the present invention will be described. The description of the configuration requirements below is based on representative embodiments or detailed examples of the present invention, but the present invention is not limited to these embodiments or detailed examples. Incidentally, in the present specification, the numerical range expressed with "to" means a range including the numerical values before and after "to" as the lower limit and the upper limit, respectively.

[Organic Electroluminescent Element]

The organic electroluminescent element of the present invention may include a substrate, a pair of electrodes including an anode and a cathode, disposed on the substrate, and at least one layer of organic layers including a light emitting layer, disposed between the electrodes, and at least one of the organic layers contains a compound represented by the following general formula (1).

General Formula (1)

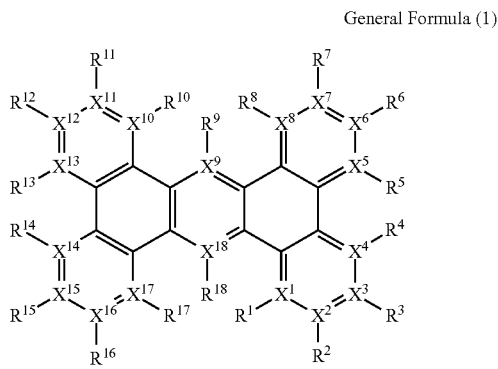

(In the general formula (1), $R^1$ to $R^{18}$ each independently represent a hydrogen atom or a substituent, and at least one of $R^1$ to $R^8$ and $R^{10}$ to $R^{17}$ represents -L-$NR^{19}R^{20}$ ($R^{19}$ and $R^{20}$ each independently represent any of an alkyl group, an aryl group, a heteroaryl group. $R^{19}$ and $R^{20}$ may be combined to each other to form a ring. L represents a single bond or a divalent linking group). $X^1$ to $X^{18}$ each independently represent a carbon atom or a nitrogen atom, and when $X^1$ to $X^{18}$ represent nitrogen atoms, $R^1$ to $R^{18}$ for bonding do not present.)

By including the compound represented by the general formula (1) at least in one layer of the organic layers, in the organic electroluminescent element of the present invention, the light emitting spectrum is sharpened and the blue chromatic purity may be improved. It is known a fact that the shortening of the light emitting wavelength is effective to improve the blue chromatic purity. However, if the light emitting wavelength of the light emitting material is short, since $S_1$ (lowest excited singlet energy unit) of the light emitting material becomes higher, the difference between $S_1$ of the light emitting material and $S_1$ of a host material may be small, or $S_1$ of the host material may become higher than $S_1$ of the light emitting material. Accordingly, there are problems in that the light emitting efficiency is decreased, and the blue chromatic purity is decreased with secondary light emitting of the host material. With respect to this, if the compound represented by the general formula (1) is used according to the present invention, it is possible to realize the high light emitting efficiency, the sharpened spectrum, and the improved blue chromatic purity.

Meanwhile, as factors of the chromaticity change which occurs with the driving degradation, light emitting position change due to change of element-charge balance (optical interference effect due to this), association formation of the light emitting material due to heat generation or the like generated with the driving, light emitting component generation due to chemical reaction degradation of the light emitting material and/or the host material due to the element driving, and the like are considered, and it is necessary to use a material in which all of the above factors hardly occur. Since the compound of the present invention is stable with respect to holes (oxidation) and the electron (reduction), the injecting/transporting properties of the charge are high, the association formation of phenanthro triphenylene rings hardly occurs, and the chemical reaction degradation due to the element driving also hardly occurs, the chromaticity change hardly occurs.

<<Compound Represented by General Formula (1)>>

First, the compound represented by the general formula (1) will be described below in detail.

In the present invention, a hydrogen atom in the description of the general formula (1) further includes isotopes (a deuterium atom and the like), and atoms further constituting the substituent also include isotopes thereof.

In the present invention, the "substituent" at each occurrence may be further substituted. For example, in the present invention, examples of the "alkyl group" at each occurrence include an alkyl group substituted with a fluorine atom (for example, a trifluoromethyl group), an alkyl group substituted with an aryl group (for example, a triphenylmethyl group), however, examples of the "alkyl group having 1 to 6 carbon atoms" at each occurrence show that 1 to 6 carbon atoms are included in all groups including the substituted groups.

The compound of the present invention is the compound represented by the following general formula (1).

General Formula (1)

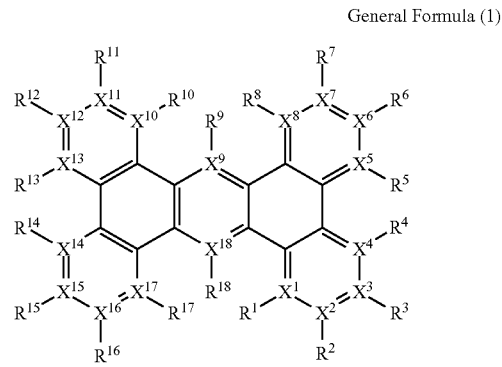

In the general formula (1), $R^1$ to $R^{18}$ each independently represent a hydrogen atom or a substituent, and at least one of $R^1$ to $R^8$ and $R^{10}$ to $R^{17}$ represents -L-$NR^{19}R^{20}$ ($R^{19}$ and $R^{20}$ each independently represent any of an alkyl group, an aryl group, a heteroaryl group. $R^{19}$ and $R^{20}$ may be combined to each other to form a ring. L represents a single bond or a divalent linking group). $X^1$ to $X^{18}$ each independently represent a carbon atom or a nitrogen atom, and when $X^1$ to $X^{18}$ represent nitrogen atoms, $R^1$ to $R^{18}$ for bonding do not present.

In the general formula (1), $R^1$ to $R^{18}$ each independently represent a hydrogen atom or a substituent, and at least one of $R^1$ to $R^8$ and $R^{10}$ to $R^{17}$ represents -L-$NR^{19}R^{20}$.

A plurality of $R^1$ to $R^{18}$ may be combined to each other to form a ring.

L represents a single bond or a divalent linking group. L is particularly preferably a single bond.

$R^{19}$ and $R^{20}$ each independently represent any of an alkyl group, an aryl group, a heteroaryl group.

$R^{19}$ and $R^{20}$ may be combined to each other to form a ring.

In addition, in a case where a plurality of $R^1$ to $R^{18}$ combine to each other to form a ring, in detail, $R^{19}$ or $R^{20}$, and any of $R^1$ to $R^{18}$ other than -L-$NR^{19}R^{20}$ including $R^{19}$ or $R^{20}$ may be combined to each other to form a ring.

As the alkyl group represented by $R^{19}$ or $R^{20}$ is preferably an alkyl group having 1 to 30 carbon atoms, more preferably an alkyl group having 1 to 20 carbon atoms, and particularly preferably a alkyl group having 1 to 10 carbon atoms, and examples thereof include a methyl group, an ethyl group, an n-propyl group, an isopropyl group, a tert-butyl, an n-octyl group, an n-decyl group, an n-hexadecyl group, a cyclopropyl group, a cyclopentyl group, a cyclohexyl group and more particularly preferably a methyl group, an ethyl group, an n-propyl group.

The alkyl group represented by $R^{19}$ or $R^{20}$ may further include substituents. Examples of the substituents include substituents included in a Substituent Group A which will be described later, and among them, the aryl group is preferable and the phenyl group is more preferable.

When $R^{19}$ and $R^{20}$ represent the alkyl group, $R^{19}$ and $R^{20}$ are preferable to be combined to each other to form a ring, and the ring formed in this case is preferably a 5- or 6-membered ring, more preferably 6-membered ring, and particularly preferably a piperidine ring.

In addition, when $R^{19}$ or $R^{20}$ represent the alkyl group, $R^{19}$ or $R^{20}$, and any of $R^1$ to $R^{18}$ other than -L-$NR^{19}R^{20}$ including $R^{19}$ or $R^{20}$ (preferably any of $R^1$ to $R^{18}$ adjacent to $R^1$ to $R^{18}$ represented by -L-$NR^{19}R^{20}$ including $R^{19}$ or $R^{20}$) are preferably combined to each other to form a ring, and the ring formed in this case is preferably a saturated 5- or 6-membered ring, and more preferably a saturated 6-membered ring.

Examples of the aryl group represented by $R^{19}$ or $R^{20}$ are preferably an aryl group having 6 to 30 carbon atoms, more preferably an aryl group having 6 to 20 carbon atoms (for example, a phenyl group, a naphthyl group, an anthranil group, a phenanthrenyl group, and a triphenylenyl group), particularly preferably an aryl group having 6 to 15 carbon atoms, more particularly preferably a phenyl group, 1-naphthyl group, and 2-naphthyl group, and even more particularly preferably a phenyl group and 2-naphthyl group.

The aryl group represented by $R^{19}$ or $R^{20}$ may further include substituents. Examples of the substituents include substituents included in the Substituent Group A which will be described later, and among them, an alkyl group (an alkyl group having 1 to 5 carbon atoms is preferable, a methyl group, an ethyl group, an n-propyl group, an isopropyl group, and a tert-butyl group are more preferable, and a methyl group is particularly preferable), an aryl group (an aryl group having 6 to 10 carbon atoms is preferable, and a phenyl group is more preferable. The aryl group may further include substituents, and in this case, the substituent is preferably included in para position), a halogen atom (preferably a fluorine atom), and a silyl group (preferably a trimethylsilyl group or a triphenylsilyl group) are preferable, and an alkyl group and an aryl group are more preferable.

When a plurality of substituents of the aryl group represented by $R^{19}$ or $R^{20}$ are present, these substituents may be combined to each other to form a ring, and the ring formed in this case is preferably a 5- or 6-membered ring, and more preferably a 5-membered ring. The formed 5- or 6-membered ring is preferably any one of a hydrocarbon ring and a heterocycle, and more preferably a 5-membered heterocycle or a 5-membered hydrocarbon ring.

When $R^{19}$ or $R^{20}$ represents an aryl group, $R^{19}$ and $R^{20}$ are also preferably combined to each other to form a ring, and the ring formed in this case is preferably 5- or 6-membered ring. The case where $R^{19}$ and $R^{20}$ are combined to each other to form a ring includes a case where $R^{19}$ and $R^{20}$ form a ring through a single bond, a case where the substituent which is further included in $R^{19}$, and $R^{20}$ form a ring, a case where the substituent which is further included in $R^{20}$, and $R^{19}$ form a ring, and a case where the substituent which is further included in $R^{19}$, and the substituent which is further included in $R^{20}$ form a ring. In the cases except for the case where $R^{19}$ and $R^{20}$ form a ring through a single bond, $R^{19}$ and $R^{20}$ are preferably combined to each other through a linking group L'. The linking group L' is preferably $CR^{112}R^{113}$, $NR^{114}$, $SiR^{115}R^{116}$ ($R^{112}$, $R^{113}$, $R^{114}$, $R^{115}$ and $R^{116}$ each independently represent a substituent, and preferably represent a fluorine atom, an alkyl group, an aryl group, or a heteroaryl group), an O atom, an S atom, more preferably $CR^{112}R^{113}$, $NR^{114}$, an O atom, or an S atom, and particularly preferably $CR^{112}R^{113}$, $NR^{114}$, or an O atom. As $R^{112}$, $R^{113}$, $R^{115}$ and $R^{116}$ (substituents on carbon atoms and substituents on silicon atoms), ones in the following Substituent Group A may be employed.

<<Substituent Group A>>

Examples thereof are an alkyl group (preferably having 1 to 30 carbon atoms, more preferably having 1 to 20 carbon atoms, and particularly preferably having 1 to 10 carbon atoms, and examples of the alkyl group include methyl, ethyl, isopropyl, tert-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms, and examples of the alkenyl group include vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms, and examples of the alkynyl group include propargyl and 3-pentynyl), an aryl group (preferably having 6 to 30 carbon atoms, more preferably having 6 to 20 carbon atoms, and particularly preferably having 6 to 12 carbon atoms, and examples of the aryl group include phenyl, p-methylphenyl, naphthyl, and anthranil), an amino group (preferably having 0 to 30 carbon atoms, more preferably having 0 to 20 carbon atoms, and particularly preferably having 0 to 10 carbon atoms, and examples of the amino group include amino, methylamino, dimethylamino, diethylamino, dibenzylamino, diphenylamino, and ditolylamino), an alkoxy group (preferably having 1 to 30 carbon atoms, more preferably having 1 to 20 carbon atoms, and particularly preferably having 1 to 10 carbon atoms, and examples of the alkoxy group include methoxy, ethoxy, butoxy, and 2-ethylhexyloxy), an aryloxy group (preferably having 6 to 30 carbon atoms, more preferably having 6 to 20 carbon atoms, and particularly preferably having 6 to 12 carbon atoms, and examples of the aryloxy group include phenyloxy, 1-naphthyloxy, and 2-naphthyloxy), a heterocyclic oxy group (preferably having 1 to 30 carbon atoms, more preferably having 1 to 20 carbon atoms, and particularly preferably having 1 to 12 carbon atoms, and examples of the heterocyclic oxy group include pyridyloxy, pyrazyloxy, pyrimidyloxy, and quinolyloxy), an acyl group (preferably having 2 to 30 carbon atoms, more preferably having 2 to 20 carbon atoms, and particularly preferably having 2 to 12 carbon atoms, and examples of the acyl group include acetyl, benzoyl, formyl, and pivaloyl), an alkoxycarbonyl group (preferably having 2 to 30 carbon atoms, more preferably having 2 to 20 carbon atoms, and particularly preferably having 2 to 12 carbon atoms, and examples of the alkoxycarbonyl group include methoxycarbonyl and ethoxycarbonyl), an aryloxycarbonyl group (preferably having 7 to 30 carbon atoms, more preferably having 7 to 20 carbon atoms, and particularly preferably having 7 to 12 carbon atoms, and examples of the aryloxycarbonyl group include phenyloxycarbonyl), an acyloxy group (preferably having 2 to 30 carbon atoms, more preferably having 2 to 20 carbon atoms, and particularly preferably having 2 to 10 carbon atoms, and examples of the acyloxy group include acetoxy and benzoyloxy), an acylamino group (preferably having 2 to 30 carbon atoms, more preferably having 2 to 20 carbon atoms, and particularly preferably having 2 to 10 carbon atoms, and examples of the acylamino group include acetylamino and benzoylamino), an alkoxycarbonylamino group (preferably having 2 to 30 carbon atoms, more preferably having 2 to 20 carbon atoms, and particularly preferably having 2 to 12 carbon atoms, and examples of the alkoxycarbonylamino group include methoxycarbonylamino), an aryloxycarbonylamino group (preferably having 7 to 30 carbon atoms, more preferably having 7 to 20 carbon atoms and particularly preferably having 7 to 12 carbon atoms, and examples of the aryloxycarbonylamino group include phenyloxycarbonylamino), a sulfonylamino group (preferably having 1 to 30 carbon atoms, more preferably having 1 to 20 carbon atoms, and particularly preferably having 1 to 12 carbon atoms, and examples of the sulfonylamino group include methanesulfonylamino and benzenesulfonylamino), a sulfamoyl group (preferably having 0 to 30 carbon atoms, more preferably having 0 to 20 carbon atoms, and particularly preferably having 0 to 12 carbon atoms, and examples of the sulfamoyl group include sulfamoyl, methylsulfamoyl, dimethylsulfamoyl, and phenylsulfamoyl), a carbamoyl group (preferably having 1 to 30 carbon atoms, more preferably having 1 to 20 carbon atoms, and particularly preferably having 1 to 12 carbon atoms, and examples of the carbamoyl group include carbamoyl, methylcarbamoyl, diethylcarbamoyl, and phenylcarbamoyl), an alkylthio group (preferably having 1 to 30 carbon atoms, more preferably having 1 to 20 carbon atoms, and particularly preferably having 1 to 12 carbon atoms, and examples of the alkylthio group include methylthio and ethylthio), an arylthio group (preferably having 6 to 30 carbon atoms, more preferably having 6 to 20 carbon atoms, and particularly preferably having 6 to 12 carbon atoms, and examples of the arylthio group include phenylthio), a heterocyclic thio group (preferably having 1 to 30 carbon atoms, more preferably having 1 to 20 carbon atoms, and particularly preferably having 1 to 12 carbon atoms, and examples of the heterocyclic thio group include pyridylthio, 2-benzimizolylthio, 2-benzoxazolylthio, and 2-benzthiazolylthio), a sulfonyl group (preferably having 1 to 30 carbon atoms, more preferably having 1 to 20 carbon atoms, and particularly preferably having 1 to 12 carbon atoms, and examples of the sulfonyl group include mesyl and tosyl), a sulfinyl group (preferably having 1 to 30 carbon atoms, more preferably having 1 to 20 carbon atoms, and particularly preferably having 1 to 12 carbon atoms, and examples of the sulfinyl group include methanesulfinyl and benzenesulfinyl), a ureido group (preferably having 1 to 30 carbon atoms, more preferably having 1 to 20 carbon atoms, and particularly preferably having 1 to 12 carbon atoms, and examples of the ureido group include ureido, methylureido, and phenylureido), a phosphoric acid amide group (preferably having 1 to 30 carbon atoms, more preferably having 1 to 20 carbon atoms, and particularly preferably having 1 to 12 carbon atoms, and examples of the phosphoric acid amide group include diethylphosphoric acid amide, and phenylphosphoric acid amide), a hydroxy group, a mercapto group, a halogen atom (for example, a fluorine atom, a chlorine atom, a bromine atom, and iodine atom), a cyano group, a sulfo group, a carboxyl group, a nitro group, a hydroxamic acid group, a sulfino group, a hydrazino group, an imino group, a heterocyclic group (including an aromatic heterocyclic group, and preferably having 1 to 30 carbon atoms, and more preferably having 1 to 12 carbon atoms, examples of the hetero atom include a nitrogen atom, an oxygen atom, a sulfur atom, a phosphorous atom, a silicon atom, a selenium atom, and a tellurium atom, and specifically pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, an azepinyl group, and a silolyl group), a silyl group (preferably having 3 to 40 carbon atoms, more preferably having 3 to 30 carbon atoms, and particularly preferably having 3 to 24 carbon atoms, and examples of the silyl group include trimethylsilyl, and triphenylsilyl), and a silyloxy group (preferably having 3 to 40 carbon atoms, more preferably 3 to 30 carbon atoms, and particularly preferably having 3 to 24 carbon atoms, and examples of the silyloxy group include trimethylsilyloxy and triphenylsilyloxy), and a phosphoryl group (for example, a diphenylphosphoryl group and a dimethylphosphoryl group). These substituents may be further substituted, and examples of further substituents include groups selected from the Substituent Group A as described above. Further, the substituent that substitutes the substituent may be further substituted, and examples of further substituents include groups selected from the Substituent Group A as described above. In addition, a substituent that substitutes the substituent that substitutes the substituent may be further substituted, and examples of further substituents include groups selected from the Substituent Group A as described above.

$R^{112}$, $R^{113}$, $R^{115}$ and $R^{116}$ each independently preferably represent an alkyl group, particularly preferably represent a linear, branched, or cyclic alkyl group having 1 to 10 carbon atoms, and more particularly preferably represent a linear, branched, or cyclic alkyl group having 1 to 6 carbon atoms. In addition, from a viewpoint of easy synthesis, $R^{112}$ and $R^{113}$ are preferably the same substituents. Further, from the same viewpoint described above, $R^{115}$ and $R^{116}$ are preferably the same substituents.

As $R^{114}$ (substituents on nitrogen atoms), the following Substituent Group B can be used.

<<Substituent Group B>>

Examples thereof include an alkyl group (preferably having 1 to 30 carbon atoms, more preferably having 1 to 20 carbon atoms, and particularly preferably having 1 to 10 carbon atoms, and examples of the alkyl group include methyl, ethyl, isopropyl, tert-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms, and examples of the alkenyl group include vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms, and examples of the alkynyl group include propargyl and 3-pentynyl), an aryl group (preferably having 6 to 30 carbon atoms, more preferably having 6 to 20 carbon atoms, and particularly preferably 6 to 12 carbon atoms, and examples of the aryl group include phenyl, p-methylphenyl, naphthyl, and anthranil), a cyano group, a heterocyclic group (including an aromatic heterocyclic group, and preferably having 1 to 30 carbon atoms, and more preferably having 1 to 12 carbon atoms, examples of the hetero atom include a nitrogen atom, an oxygen atom, a sulfur atom, a phosphorous atom, a silicon atom, a selenium atom, and a tellurium atom, and specifically pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, an azepinyl group, and a silolyl group). These substituents may be further substituted, and examples of further substituents include groups selected from the Substituent Group A as described above. Further, the substituent that substitutes the substituent may be further substituted, and examples of further substituents include groups selected from the Substituent Group A as described above. In addition, a substituent that substitutes the substituent that substitutes the substituent may be further substituted, and examples of further substituents include groups selected from the Substituent Group A as described above.

$R^{114}$ more preferably represent an aryl group, and particularly preferably represent a phenyl group.

A heteroaryl group represented by $R^{19}$ or $R^{20}$ is preferably a heteroaryl group having 5 to 30 ring members, more preferably a heteroaryl group having 5 to 10 ring members, and particularly preferably an heteroaryl group having 5 or 6 ring members. A hetero atom configuring the heteroaryl group is preferably a nitrogen atom, an oxygen atom, or a sulfur atom. The number of hetero atoms included in the heteroaryl group is preferably 1 to 3, and more preferably 1. The heteroaryl group represented by $R^{19}$ or $R^{20}$ is particularly preferably a pyridyl group, a furanyl group, and a thiophenyl group, and more particularly preferably a 2-pyridyl group, a 2-furanyl group, and a 2-thiophenyl group.

The heteroalkyl group represented by $R^{19}$ or $R^{20}$ may further include substituents. Examples of the substituents include substituents included in the Substituent Group A, and among them, an alkyl group is preferable, an alkyl group having 1 to 3 carbon atoms is more preferable, and a methyl group is particularly preferable.

In the compound of the present invention, in the general formula (1), $R^{19}$ and $R^{20}$ each independently preferably represent an aryl group or a heteroaryl group from the viewpoint of light emitting efficiency, and all of $R^{19}$ and $R^{20}$ preferably represent an aryl group, and more preferably represent any of an unsubstituted phenyl group, a 1-naphthyl group, a 2-naphthyl group, a biphenyl group (preferably p-phenylphenyl group), and a methylphenyl group (preferably p-methylphenyl group), from the viewpoint of light emitting efficiency.

When all of $R^{19}$ and $R^{20}$ are aryl groups, the combination of $R^{19}$ and $R^{20}$ is not particularly limited.

In the compound of the present invention, in the general formula (1), at least one of $R^1$ to $R^8$ and $R^{10}$ to $R^{17}$ is -L-$NR^{19}R^{20}$, at least one of $R^2$, $R^3$, $R^6$, $R^7$, $R^{11}$, $R^{12}$, $R^{15}$, and $R^{16}$ is preferably -L-$NR^{19}R^{20}$, and at least one of $R^3$, $R^6$, $R^{12}$, and $R^{15}$ is more preferably -L-$NR^{19}R^{20}$, from the viewpoint of light emitting efficiency.

In the compound of the present invention, in the general formula (1), one to four of $R^1$ to $R^{18}$ each independently preferably represent -L-$NR^{19}R^{20}$, one or two thereof each independently more preferably represent -L-$NR^{19}R^{20}$, and two thereof each independently particularly preferably represent -L-$NR^{19}R^{20}$, from the viewpoint of blue chromatic purity.

In the compound of the present invention, in the general formula (1), $R^3$ and $R^{12}$ are preferably -L-$NR^{19}R^{20}$ or $R^6$ and $R^{15}$ are preferably -L-$NR^{19}R^{20}$, from viewpoints of easy synthesis and light emitting intensity (transition vibrator intensity).

In the compound of the present invention, in the general formula (1), when groups represented by -L-$NR^{19}R^{20}$ are two or more, the combination of the groups represented by -L-$NR^{19}R^{20}$ is not particularly limited, however, two or more -L-$NR^{19}R^{20}$ are preferably the same with each other from the viewpoint of easy synthesis.

In the compound of the present invention, in the general formula (1), $R^9$ and $R^{18}$ may include or may not include substituents, however, in a case where $R^9$ and $R^{18}$ include substituents, the substituents are preferably substituents other than -L-$NR^{19}R^{20}$, from viewpoints of shortening of the light emitting wavelength and setting pure blue region.

In the compound of the present invention, in the general formula (1), $R^9$ and $R^{18}$ is particularly preferably hydrogen atoms, from viewpoints for maintaining flatness of the phenanthro triphenylene scaffold and for improving the blue chromatic purity and the light emitting intensity.

Examples of the substituents other than -L-$NR^{19}R^{20}$ represented by $R^1$ to $R^{18}$ in the general formula (1) include the substituents included in the Substituent Group A.

Among them, the substituents other than -L-$NR^{19}R^{20}$ represented by $R^1$ to $R^{18}$ are preferably an alkyl group, an aryl group, a heteroaryl group, a halogen atom, a cyano group and a silyl group, and more preferably an alkyl group, an aryl group, a halogen atom, and a silyl group.

The alkyl group represented by $R^1$ to $R^{18}$ is preferably an alkyl group having 1 to 6 carbon atoms, more preferably a methyl group, an ethyl group, an n-propyl group, an i-propyl group, a tert-butyl group, a pentyl group, and a cyclohexyl group, and particularly preferably a methyl group and a tert-butyl group. The alkyl group represented by $R^1$ to $R^{18}$ may further include substituents. Examples of the substituents include substituents included in the Substituent Group A, and among them, the halogen atom is preferable, and the fluorine atom is more preferable.

The aryl group represented by $R^1$ to $R^{18}$ is preferably an aryl group having 6 to 10 carbon atoms and more preferably a phenyl group. The phenyl group is preferably introduced to any of $R^5$ to $R^8$ and $R^{14}$ to $R^{17}$ of the general formula (1), since association of the phenanthro triphenylene rings is effectively suppressed. Among them, the phenyl group is particularly preferably introduced to the positions of $R^7$ and $R^{16}$ from the viewpoint of transition vibrator intensity. The aryl group represented by $R^1$ to $R^{18}$ may further include substituents. Examples of the substituents include substituents included in the Substituent Group A, and among them, an alkyl group, an aryl group, and an amino group are preferable, an alkyl group is more preferable, and a trifluoromethyl group is particularly preferable.

In addition, the aryl group represented by $R^1$ to $R^{18}$ may include an amino group (for example, the L-$NR^{19}R^{20}$ group), and the aryl group represented by $R^1$ to $R^{18}$ is preferably an unsubstituted or alkyl group-substituted, from the viewpoints of sharpening the light emitting spectrum to improve blue chromatic purity.

The heteroaryl group represented by $R^1$ to $R^{18}$ is preferably a heteroaryl group having 5 to 10 ring members, and more preferably a heteroaryl group having 5 or 6 ring members. The hetero atom configuring the heteroaryl group is preferably a nitrogen atom, an oxygen atom, or a sulfur atom. The number of hetero atoms included in the heteroaryl group is preferably 1 to 3, and more preferably 1. The heteroaryl group represented by $R^1$ to $R^{18}$ is particularly preferably a pyridyl group and a thiophenyl group, and more particularly preferably a 2-pyridyl group and a 2-2-thiophenyl group.

The halogen atom represented by $R^1$ to $R^{18}$ is preferably a fluorine atom. The fluorine atom is preferably introduced into a molecule since a sublimation temperature is decreased. Among them, the fluorine atom F is particularly preferably introduced into the positions of $R^6$ and $R^{15}$ of the general formula (1), since the transition vibration intensity becomes great.

The silyl group represented by $R^1$ to $R^{18}$ is preferably a trimethylsilyl group, a triphenylsilyl group, and more preferably a trimethylsilyl group.

In the compound of the present invention, in the general formula (1), the number of the substituents other than -L-NR$^{19}$R$^{20}$ represented by $R^1$ to $R^{18}$ is preferably 0 to 6, more preferably 0 to 4, particularly preferably 0 to 2, and more particularly preferably 0 or 2.

In the general formula (1), the positions of the substituents other than -L-NR$^{19}$R$^{20}$ represented by $R^1$ to $R^{18}$ are not particularly limited, however, preferably $R^2$, $R^3$, $R^6$, $R^7$, $R^{11}$, $R^{12}$, $R^{15}$, or $R^{16}$, and more preferably $R^3$, $R^6$, $R^{12}$ or $R^{15}$.

The ring formed by combining of $R^1$ to $R^{18}$ in the general formula (1) is preferably 5- or 6-membered ring. Two of $R^1$ to $R^{18}$ which are adjacent to each other are more preferably combined to form a ring, the ring formed in this case is also preferably 5- or 6-membered ring.

In the compound of the present invention, in the general formula (1), $X^1$ to $X^{18}$ each independently represent a carbon atom or a nitrogen atom. Among $X^1$ to $X^{18}$, at least two or more of $X^2$, $X^3$, $X^6$, $X^7$, $X^{11}$, $X^{12}$, $X^{15}$, and $X^{16}$ are preferably carbon atoms, and at least two or more of $X^3$, $X^6$, $X^{12}$, and $X^{15}$ are more preferably carbon atoms.

In the general formula (1), 12 or more of $X^1$ to $X^{18}$ are preferably carbon atoms, 14 or more thereof are more preferably carbon atoms, and 16 or more thereof are particularly preferably carbon atoms.

In the compound of the present invention, in the general formula (1), all of $X^1$ to $X^{18}$ are particularly preferably carbon atoms.

In the compound of the present invention, the compound represented by the general formula (1) is preferably represented by the following general formula (2).

General Formula (2)

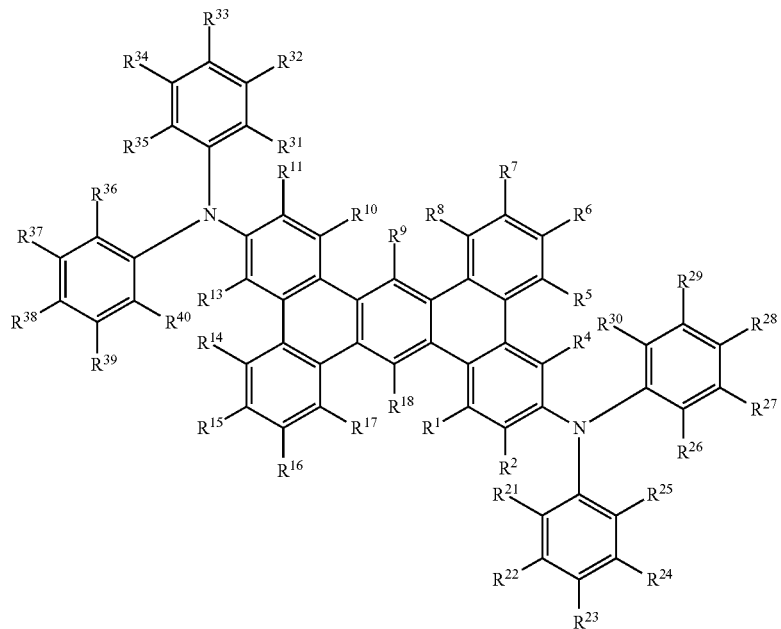

In the general formula (2), $R^1$, $R^2$, $R^4$ to $R^{11}$, $R^{13}$ to $R^{18}$, and $R^{21}$ to $R^{40}$ each independently represent a hydrogen atom or a substituent. A plurality of $R^{21}$ to $R^{30}$ and $R^{31}$ to $R^{40}$ may be combined to each other to form a ring.

The description and the preferred ranges of $R^1$, $R^2$, $R^4$ to $R^{11}$, $R^{13}$ to $R^{18}$ in the general formula (2) are the same as the description and the preferred ranges of $R^1$, $R^2$, $R^4$ to $R^{11}$, $R^{13}$ to $R^{18}$ in the general formula (1).

The preferred ranges of the substituents represented by $R^{21}$ to $R^{30}$ and $R^{31}$ to $R^{40}$ in the general formula (2) are the same as the preferred ranges of the substituents of the aryl group when $R^{19}$ or $R^{20}$ represents the aryl group in the general formula (1).

The term "a plurality of $R^{21}$ to $R^{30}$ and $R^{31}$ to $R^{40}$ may be combined to each other to form a ring" of the general formula (2) means that the compound represented by the general formula (2) includes a compound in which polycyclic condensed aromatic group is formed as a result of forming an aromatic ring by combining $R^{21}$ to $R^{25}$ to each other, a compound in which polycyclic condensed aromatic group is formed as a result of forming an aromatic ring by combining $R^{26}$ to $R^{30}$ to each other, a compound in which polycyclic condensed aromatic group is formed as a result of forming an aromatic ring by combining $R^{31}$ to $R^{35}$ to each other, and a compound in which polycyclic condensed aromatic group is formed as a result of forming an aromatic ring by combining $R^{36}$ to $R^{40}$ to each other. For example, the compound represented by the general formula (2) also includes a compound in which a phenyl group including $R^{21}$ to $R^{25}$ as a result of combining of $R^{21}$ and $R^{22}$ to each other forms a naphthyl group.

More preferred ranges of $R^{21}$ to $R^{25}$ in the general formula (2) will be described.

$R^{21}$ to $R^{25}$ in the general formula (2) represent hydrogen atoms or substituents, and in $R^{21}$ to $R^{25}$, the number of substituents is preferably 0 to 4, more preferably 0 to 3, particularly preferably 0 to 2, or more particularly preferably 0 or 1.

In $R^{21}$ to $R^{25}$ in the general formula (2), positions of the substituents in a case of three substituents are preferably $R^{21}$, $R^{23}$, and $R^{25}$, positions of the substituents in a case of two substituents are preferably any of $R^{22}$ to $R^{24}$, and a position of the substituent in a case of one substituent is preferably any of $R^{22}$ to $R^{24}$.

The substituents represented by $R^{21}$ to $R^{25}$ in the general formula (2) are preferably an alkyl group (preferably an alkyl group having 1 to 5 carbon atoms, more preferably a methyl group, an ethyl group, n-propyl group, an isopropyl group, and a tert-butyl group, and particularly preferably a methyl group), an aryl group (preferably an aryl group having 6 to 10 carbon atoms, and more preferably a phenyl group. The aryl group may further include substituents.), a halogen atom (preferably a fluorine atom), and a silyl group (preferably a trimethylsilyl group or a triphenylsilyl group), and more preferably an alkyl group and an aryl group.

$R^{21}$ to $R^{25}$ in the general formula (2) may be combined to each other to form a ring, and the ring formed in this case is preferably 5- or 6-membered ring, and more preferably 5-membered ring. The formed 5- or 6-membered ring is preferably any one of a hydrocarbon ring and a heterocycle, and more preferably a 5-membered heterocycle or a 5-membered hydrocarbon ring. Among $R^{21}$ to $R^{25}$, $R^{22}$ and $R^{23}$ are preferably combined to each other to form a ring.

Any carbon atom of benzene rings including $R^{21}$ to $R^{25}$ in the general formula (2), and any one substituent of $R^{21}$ to $R^{25}$ may be condensed to form a ring through a single bond or the linking group L'. The ring formed in this case is preferably 5- or 6-membered ring, and more preferably 5-membered ring.

The preferred ranges of $R^{26}$ to $R^{30}$ in the general formula (2) are the same as the preferred ranges of $R^{21}$ to $R^{25}$ in the general formula (2).

The number of the substituents in $R^{26}$ to $R^{30}$ in the general formula (2) is the same as the number of the substituents in $R^{21}$ to $R^{25}$.

The positions of the substituents in $R^{26}$ to $R^{30}$ in the general formula (2) are preferably $R^{26}$, $R^{28}$, and $R^{30}$, the positions of the substituents in a case of two substituents are preferably any of $R^{27}$ to $R^{29}$, and a position of the substituent in a case of one substituent is preferably any of $R^{27}$ to $R^{29}$.

In the general formula (2), any group of $R^{21}$ to $R^{25}$ and any group of $R^{26}$ to $R^{30}$ may be combined to each other to form a ring, and the ring formed in this case is preferably 5- or 6-membered ring. When any group of $R^{21}$ to $R^{25}$ and any group of $R^{26}$ to $R^{30}$ are combined to each other to form a ring, the ring may be formed through a single bond, or the groups may be combined through the linking group L'. When any group of $R^{21}$ to $R^{25}$ and any group of $R^{26}$ to $R^{30}$ are combined to each other to form a ring, $R^{25}$ and $R^{30}$ are preferably combined to each other to form a ring.

$R^{26}$ to $R^{30}$ may be combined to each other to form a ring, and the preferred ranges of the ring formed in this case are the same as that of the case where $R^{21}$ to $R^{25}$ are combined to each other to form a ring. Among $R^{26}$ to $R^{30}$, $R^{28}$ and $R^{29}$ are preferably combined to each other to form a ring.

Any carbon atom of benzene rings including $R^{26}$ to $R^{30}$ in the general formula (2), and any one substituent of $R^{26}$ to $R^{30}$ may be condensed to form a ring through a single bond or the linking group L'. The ring formed in this case is preferably 5- or 6-membered ring, and more preferably 5-membered ring.

The more preferred ranges of the substituents represented by $R^{31}$ to $R^{40}$ in the general formula (2) are the same as the preferred ranges of the substituents represented by $R^{21}$ to $R^{30}$ in the general formula (2), respectively.

In the compound of the present invention, the compound represented by the general formula (1) is preferably represented by the following general formula (3).

General Formula (3)

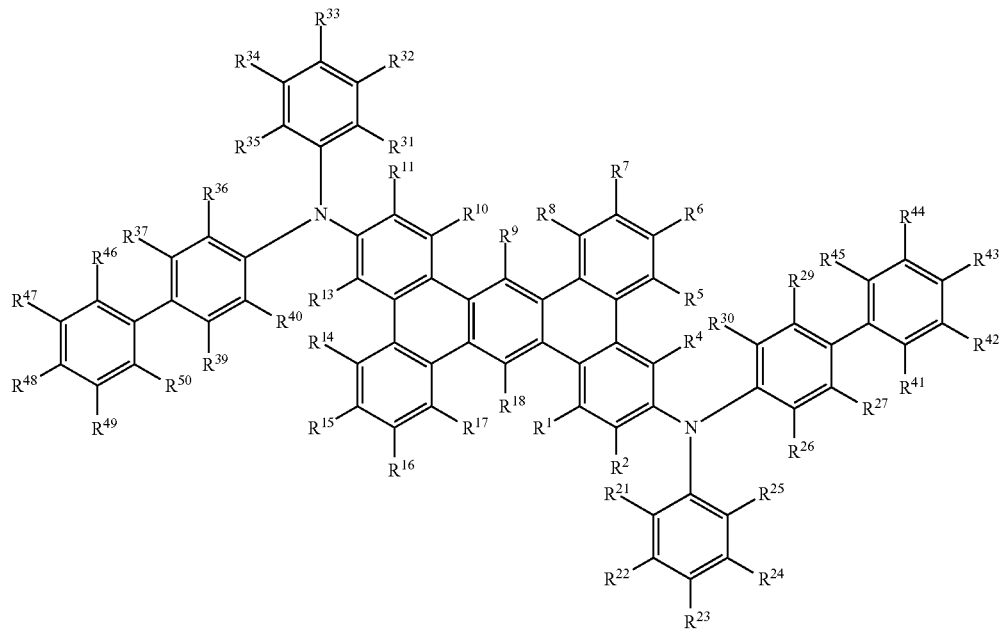

In the general formula (3), $R^1$, $R^2$, $R^4$ to $R^{11}$, $R^{13}$ to $R^{18}$, $R^{21}$ to $R^{40}$, and $R^{41}$ to $R^{50}$ each independently represent a hydrogen atom or a substituent. A plurality of $R^{21}$ to $R^{30}$, $R^{31}$ to $R^{40}$, and $R^{41}$ to $R^{50}$ may be combined to each other to form a ring.

The description and the preferred ranges of $R^1$, $R^2$, $R^4$ to $R^{11}$, $R^{13}$ to $R^{18}$ in the general formula (3) are the same as the description and the preferred ranges of $R^1$, $R^2$, $R^4$ to $R^{11}$, $R^{13}$ to $R^{18}$ in the general formula (1).

The term "a plurality of $R^{21}$ to $R^{30}$, $R^{31}$ to $R^{40}$, and $R^{41}$ to $R^{50}$ may be combined to each other to form a ring" of the general formula (3) means that the compound represented by the general formula (2) includes a compound in which polycyclic condensed aromatic group is formed as a result of forming an aromatic ring by combining $R^{21}$ to $R^{25}$ to each other, a compound in which polycyclic condensed aromatic group is formed as a result of forming an aromatic ring by combining $R^{26}$ to $R^{30}$ to each other, a compound in which polycyclic condensed aromatic group is formed as a result of forming an aromatic ring by combining $R^{31}$ to $R^{35}$ to each other, a compound in which polycyclic condensed aromatic group is formed as a result of forming an aromatic ring by combining $R^{36}$ to $R^{40}$ to each other, a compound in which polycyclic condensed aromatic group is formed as a result of forming an aromatic ring by combining $R^{41}$ to $R^{45}$ to each other, and a compound in which polycyclic condensed aromatic group is formed as a result of forming an aromatic ring by combining $R^{46}$ to $R^{50}$ to each other. For example, the compound represented by the general formula (3) also includes a compound in which a phenyl group including $R^{21}$ to $R^{25}$ as a result of combining of $R^{21}$ and $R^{22}$ to each other forms a naphthyl group.

The preferred ranges of the substituents represented by $R^{21}$ to $R^{40}$ in the general formula (3) are the same as the preferred ranges of the substituents of the aryl group when $R^{19}$ or $R^{20}$ represents the aryl group in the general formula (1), and the more preferred ranges thereof are the same as the preferred ranges of the substituents represented by $R^{21}$ to $R^{40}$ in the general formula (2).

However, in the general formula (3), any group of $R^{21}$ to $R^{25}$ and any group of $R^{26}$ to $R^{30}$ are not preferably combined to each other to form a ring, and any group of $R^{31}$ to $R^{35}$ and any group of $R^{36}$ to $R^{40}$ are not preferably combined to each other to form a ring. In addition, in the general formula (3), $R^{26}$ to $R^{30}$ are not preferably combined to each other to form a ring, and $R^{36}$ to $R^{40}$ are not preferably combined to each other to form a ring.

Examples of the substituents represented by $R^{41}$ to $R^{45}$ in the general formula (3) include the substituents included in the Substituent Group A, and among them, the aryl group is preferable, the phenyl group is more preferable, and the unsubstituted phenyl group is particularly preferable.

In $R^{41}$ to $R^{45}$, the number of the substituents is preferably 0 to 2, more preferably 0 or 1, and particularly preferably 0. The position of the substituent in a case where $R^{41}$ to $R^{45}$ have the substituent is preferably $R^{43}$.

The preferred ranges of the substituents represented by $R^{46}$ to $R^{50}$ in the general formula (3) are the same as the preferred ranges of the substituent represented by $R^{41}$ to $R^{45}$.

In $R^{46}$ to $R^{50}$, the preferred ranges of the number of the substituents are the same as the preferred ranges of the number of the substituents in $R^{41}$ to $R^{45}$. The position of the substituent in a case where $R^{46}$ to $R^{50}$ have the substituents is preferably $R^{48}$.

In the compound of the present invention, the compound represented by the general formula (1) is preferably represented by the following general formula (4).

General Formula (4)

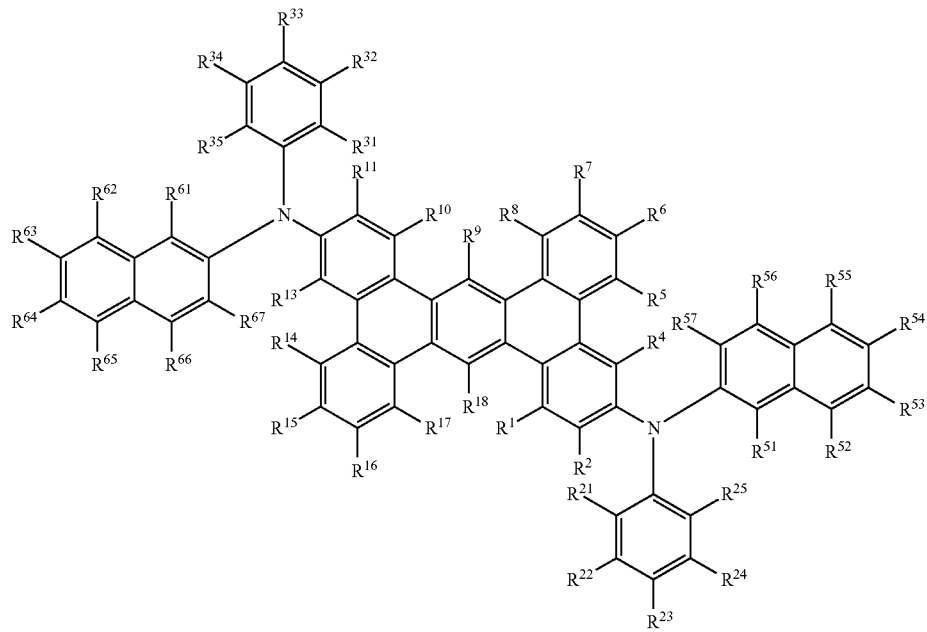

In the general formula (4), $R^1$, $R^2$, $R^4$ to $R^{11}$, $R^{13}$ to $R^{18}$, $R^{21}$ to $R^{25}$, $R^{31}$ to $R^{35}$, $R^{51}$ to $R^{57}$, and $R^{61}$ to $R^{67}$ each independently represent a hydrogen atom or a substituent. A plurality of $R^{21}$ to $R^{25}$, $R^{31}$ to $R^{35}$, $R^{51}$ to $R^{57}$, and $R^{61}$ to $R^{67}$ may be combined to each other to form a ring.

The description and the preferred ranges of $R^1$, $R^2$, $R^4$ to $R^{11}$, $R^{13}$ to $R^{18}$ in the general formula (4) are the same as the description and the preferred ranges of $R^1$, $R^2$, $R^4$ to $R^{11}$, $R^{13}$ to $R^{18}$ in the general formula (1).

The term "a plurality of $R^{21}$ to $R^{30}$, $R^{31}$ to $R^{40}$, $R^{51}$ to $R^{57}$, and $R^{61}$ to $R^{67}$ may be combined to each other to form a ring" of the general formula (4) means that the compound represented by the general formula (2) includes a compound in which polycyclic condensed aromatic group is formed as a result of forming an aromatic ring by combining $R^{21}$ to $R^{25}$ to each other, a compound in which polycyclic condensed aromatic group is formed as a result of forming an aromatic ring by combining $R^{31}$ to $R^{35}$ to each other, a compound in which polycyclic condensed aromatic group is formed as a result of forming an aromatic ring by combining $R^{51}$ to $R^{57}$ to each other, and a compound in which polycyclic condensed aromatic group is formed as a result of forming an aromatic ring by combining $R^{61}$ to $R^{67}$ to each other. For example, the compound represented by the general formula (4) also includes a compound in which a phenyl group including $R^{21}$ to $R^{25}$ as a result of combining of $R^{21}$ and $R^{22}$ to each other forms a naphthyl group.

The preferred ranges of the substituents represented by $R^{21}$ to $R^{25}$ and $R^{31}$ to $R^{35}$ in the general formula (4) are the same as the preferred ranges of the substituents of the aryl group when $R^{19}$ or $R^{20}$ represents the aryl group in the general formula (1), and the more preferred ranges thereof are the same as the preferred ranges of the substituents represented by $R^{21}$ to $R^{25}$ and $R^{31}$ to $R^{35}$ in the general formula (2).

In the general formula (4), any group of $R^{21}$ to $R^{25}$ and any group of $R^{51}$ to $R^{57}$ are not preferably combined to each other to form a ring, and any group of $R^{31}$ to $R^{35}$ and any group of $R^{61}$ to $R^{67}$ are not preferably combined to each other to form a ring.

Examples of the substituents represented by $R^{51}$ to $R^{57}$ in the general formula (4) include the substituents included in the Substituent Group A, and among them, the alkyl group and the aryl group are preferable, the alkyl group having 1 to 5 carbon atoms and the aryl group having 6 to 10 carbon atoms are more preferable, and the methyl group, the ethyl group, and the phenyl group are particularly preferable.

In $R^{51}$ to $R^{57}$, the number of the substituents is preferably 0 to 2, more preferably 0 or 1, and particularly preferably 0. The positions of the substituents in a case where $R^{51}$ to $R^{57}$ have the substituents are preferably $R^{53}$, $R^{54}$, $R^{56}$, and $R^{57}$.

The preferred ranges of the substituents represented by $R^{61}$ to $R^{67}$ in the general formula (4) are the same as the preferred ranges of the substituent represented by $R^{51}$ to $R^{57}$.

In $R^{61}$ to $R^{67}$, the preferred ranges of the number of the substituents are the same as the preferred ranges of the number of the substituents in $R^{51}$ to $R^{57}$. The positions of the substituents in a case where $R^{61}$ to $R^{67}$ have the substituents are preferably $R^{63}$, $R^{64}$, $R^{66}$, and $R^{67}$.

In compound of the present invention, the compound represented by the general formula (1) is preferably represented by the following general formula (5).

General Formula (5)

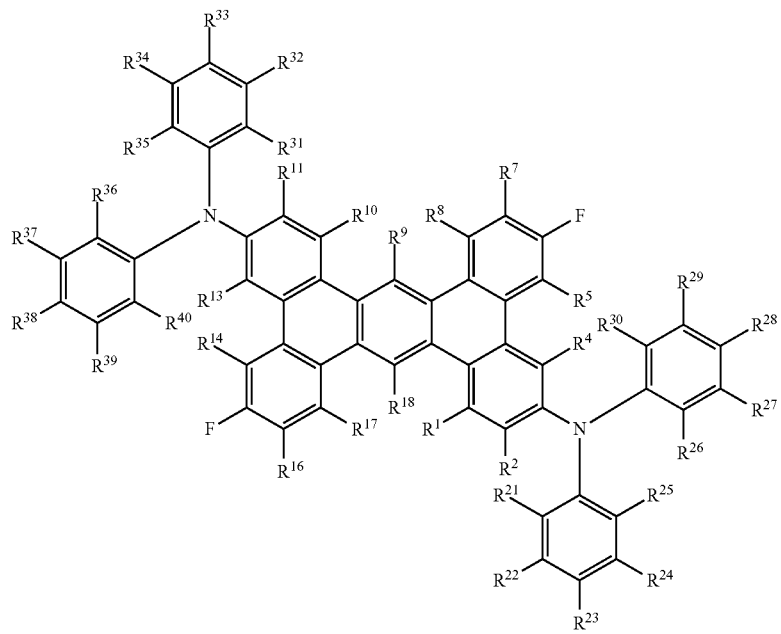

In the general formula (5), $R^1$, $R^2$, $R^4$, $R^5$, $R^7$ to $R^{11}$, $R^{13}$, $R^{14}$, $R^{16}$ to $R^{18}$, and $R^{21}$ to $R^{40}$ each independently represent a hydrogen atom or a substituent. A plurality of $R^{21}$ to $R^{30}$ and $R^{31}$ to $R^{40}$ may be combined to each other to form a ring.

The description and the preferred ranges of $R^1$, $R^2$, $R^4$, $R^5$, $R^7$ to $R^{11}$, $R^{13}$, $R^{14}$, $R^{16}$ to $R^{18}$ in the general formula (5) are the same as the description and the preferred ranges of $R^1$, $R^2$, $R^4$, $R^5$, $R^7$ to $R^{11}$, $R^{13}$, $R^{14}$, $R^{16}$ to $R^{18}$ in the general formula (1).

Examples of the substituents represented by $R^{21}$ to $R^{40}$ in the general formula (5) include the substituents included in the Substituent Group A, and among them, the aryl group is preferable, the phenyl group is more preferable, and the unsubstituted phenyl group is particularly preferable.

In each group of $R^{21}$ to $R^{25}$, $R^{26}$ to $R^{30}$, $R^{31}$ to $R^{35}$, and $R^{36}$ to $R^{40}$, the number of the substituents is preferably 0 to 2, more preferably 0 or 1, and particularly preferably 0.

In the compound of the present invention, the compound represented by the general formula (1) is preferably represented by the following general formula (6).

General Formula (6)

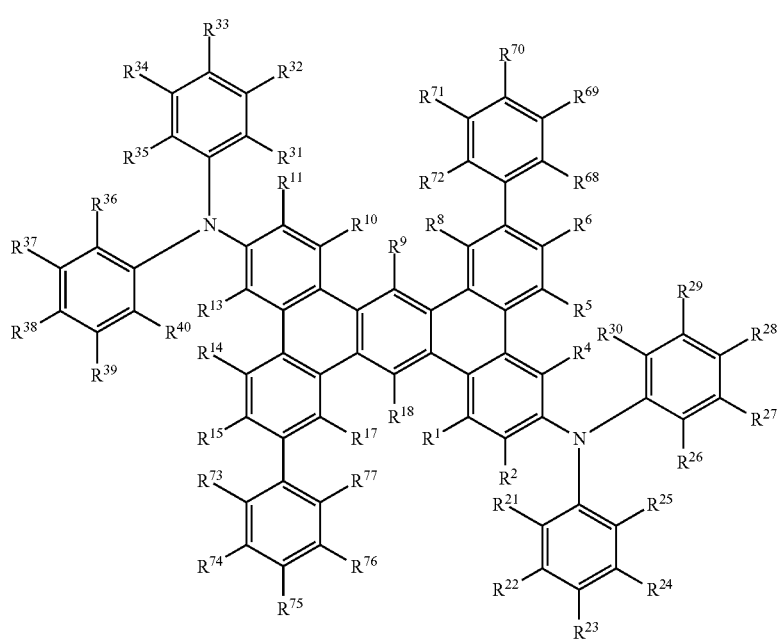

In the general formula (6), $R^1$, $R^2$, $R^4$ to $R^6$, $R^8$ to $R^{11}$, $R^{13}$ to $R^{15}$, $R^{17}$, $R^{18}$, $R^{21}$ to $R^{40}$, and $R^{68}$ to $R^{77}$ each independently represent a hydrogen atom or a substituent. A plurality of $R^{21}$ to $R^{30}$ and $R^{31}$ to $R^{40}$ may be combined to each other to form a ring.

The description and the preferred ranges of $R^1$, $R^2$, $R^4$ to $R^6$, $R^8$ to $R^{11}$, $R^{13}$ to $R^{15}$, $R^{17}$, and $R^{18}$ in the general formula (6) are the same as the description and the preferred ranges of $R^1$, $R^2$, $R^4$ to $R^6$, $R^8$ to $R^{11}$, $R^{13}$ to $R^{15}$, $R^{17}$, and $R^{18}$ in the general formula (1).

In each group of $R^{21}$ to $R^{25}$, $R^{26}$ to $R^{30}$, $R^{31}$ to $R^{35}$, $R^{36}$ to $R^{40}$, $R^{68}$ to $R^{72}$, and $R^{73}$ to $R^{77}$, the number of the substituents is preferably 0 to 2, more preferably 0 or 1, and particularly preferably 0.

In a case where the compound represented by the general formula (1) is used as a light emitting material, the maximum light emitting wavelength of the organic electroluminescent element is normally less than 460 nm. The maximum light emitting wavelength is preferably equal to or more than 400 nm and less than 460 nm, more preferably equal to or more than 420 nm and less than 455 nm, still more preferably equal to or more than 430 nm and less than 455 nm, and from the viewpoint of acquiring blue light emitting with high chromatic purity, most preferably equal to or more than 440 nm and less than 455 nm. The maximum light emitting wavelength in a thin film state of the compound represented by the general formula (1) is particularly preferably equal to or more than 440 nm and less than 455 nm, since the blue light emitting with high chromatic purity is acquired.

The molecular weight of the compound represented by the general formula (1) is preferably equal to or less than 1100, more preferably equal to or less than 1000, still more preferably equal to or less than 950, and particularly preferably equal to or less than 900. By decreasing the molecular weight, since it is possible to decrease the sublimation temperature, it is possible to prevent thermal decomposition of the compound at the time of vapor deposition. In addition, it is possible to shorten the vapor-deposition time and to suppress the energy necessary for the vapor deposition. Herein, since the thermal decomposition can occur at the time of vapor deposition for a long time with a material with a high sublimation temperature, it is preferable that the sublimation temperature is not too high, from a viewpoint of deposition suitability. The sublimation temperature (means a temperature decreased by 10% by mass, in the specification) represented by the general formula (1) is preferably 425° C., more preferably equal to or lower than 400° C., still more preferably equal to or lower than 375° C., and most preferably equal to or lower than 350° C. Since in the compound represented by the general formula (1), the phenanthro triphenylene scaffold is rigid, the thermal decomposition hardly occurs even with a high sublimation temperature, and thus, the molecular weight can be designed to be relatively higher.

Specific examples of the compound represented by the general formula (1) are shown below, but the compound represented by the general formula (1) which can be used in the present invention is not limitedly interpreted by the specific examples.

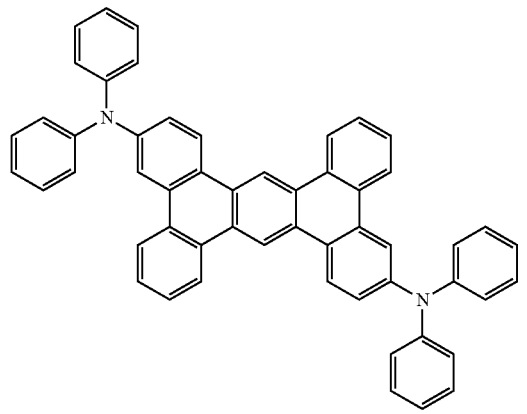

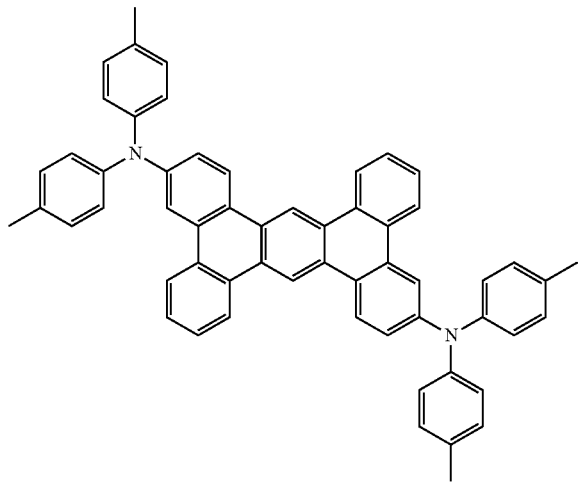

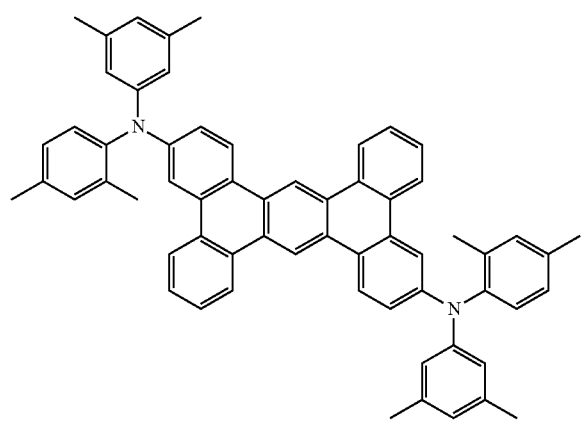

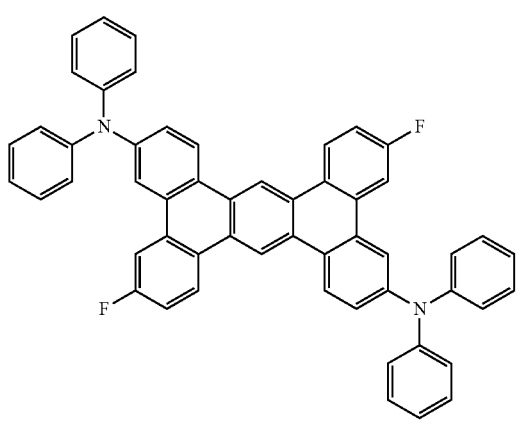

-continued
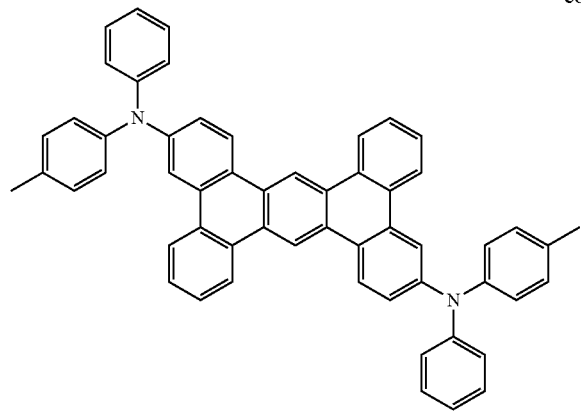
41
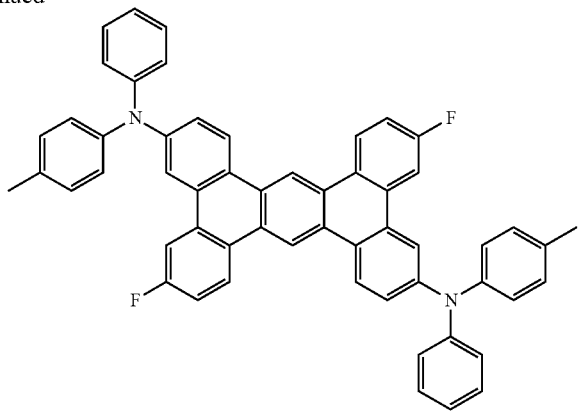
42
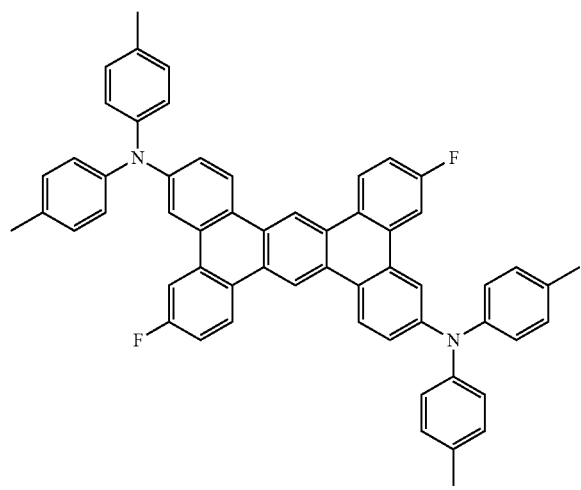
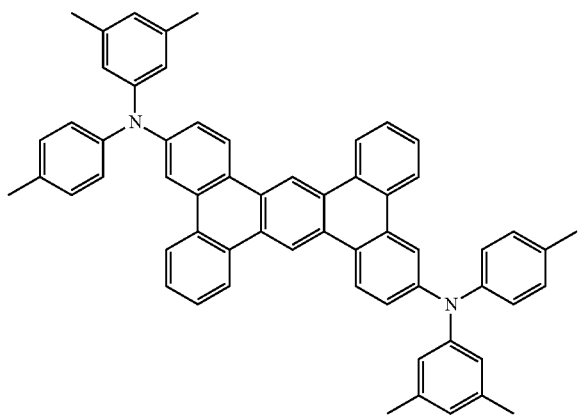
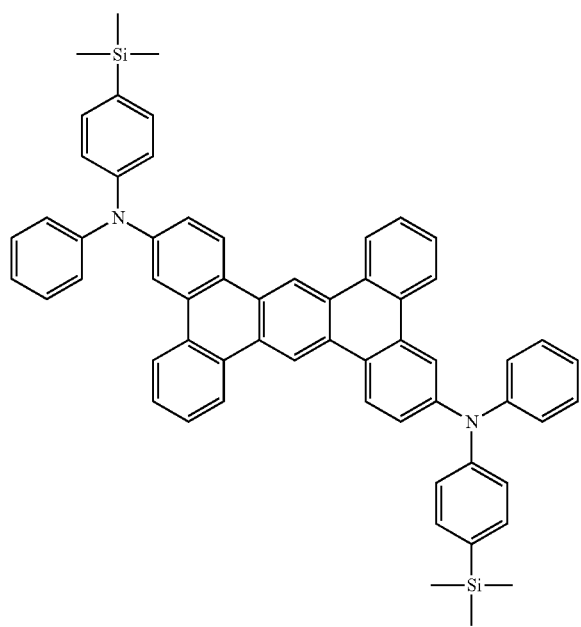
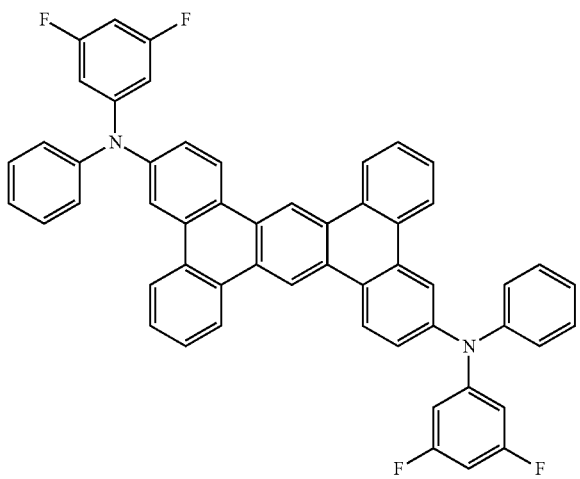

-continued
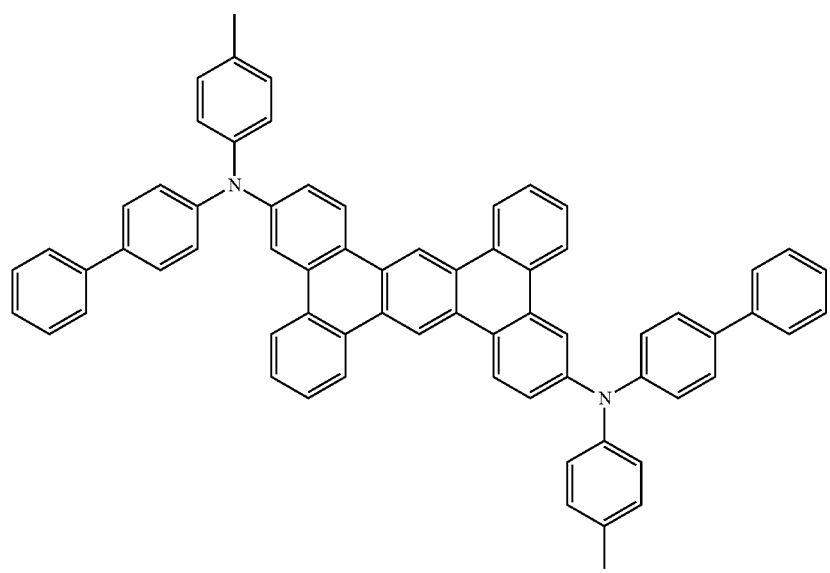
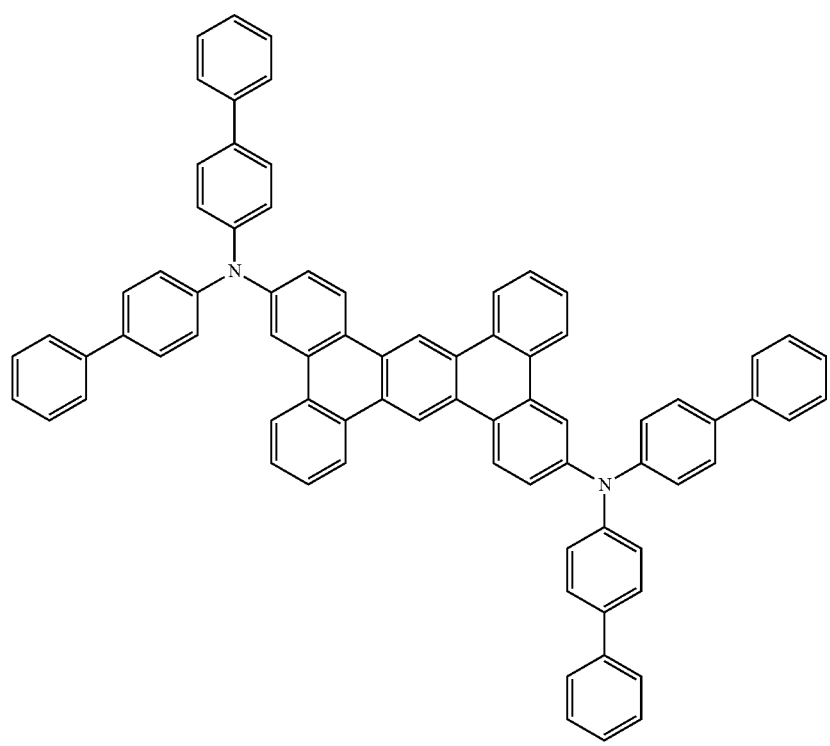

-continued
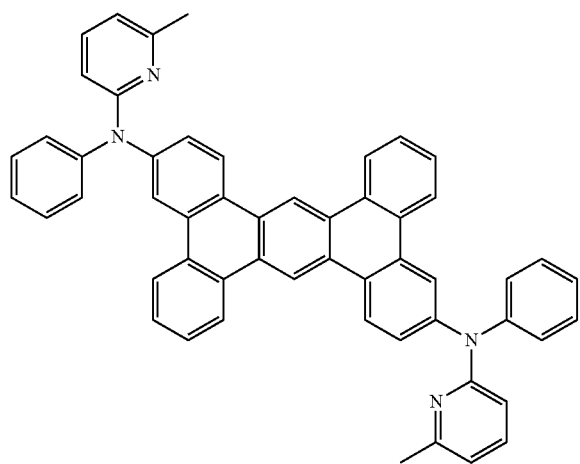
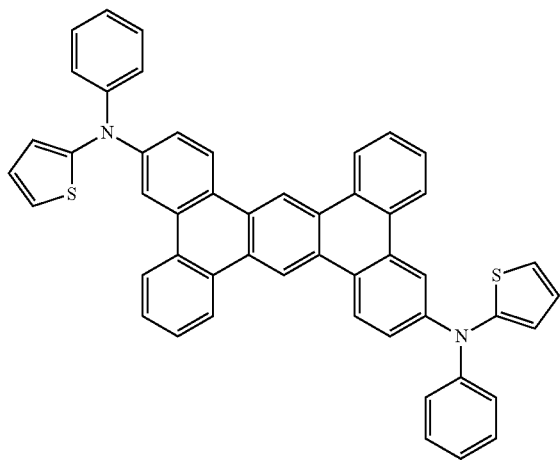
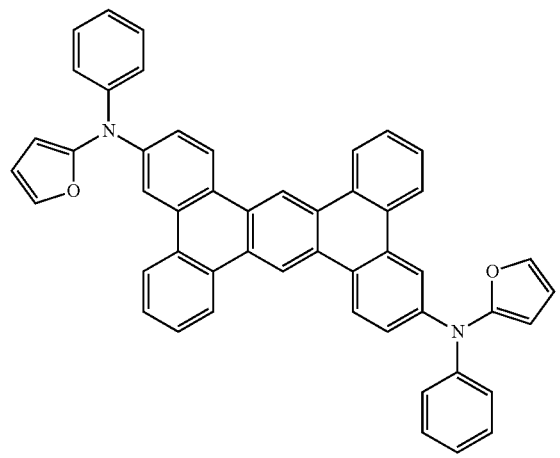
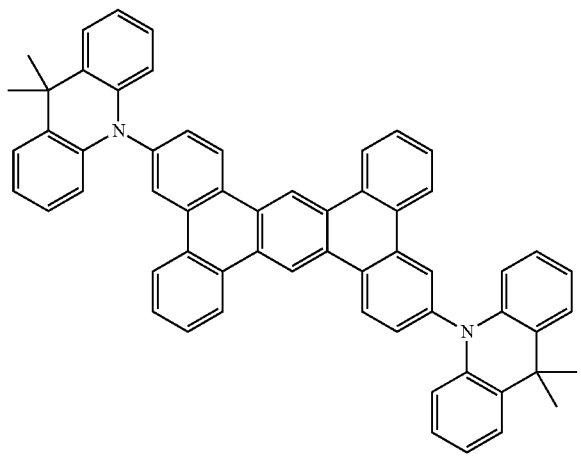
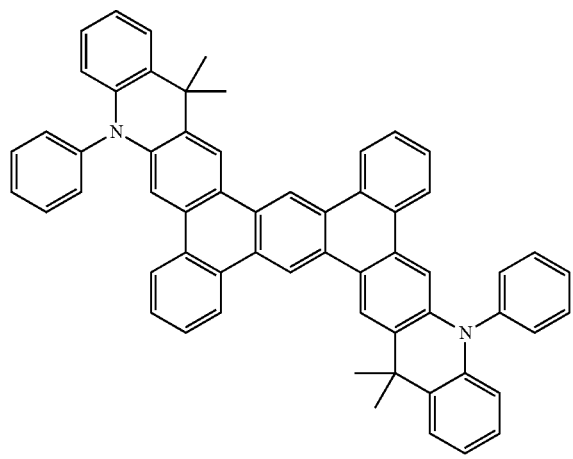
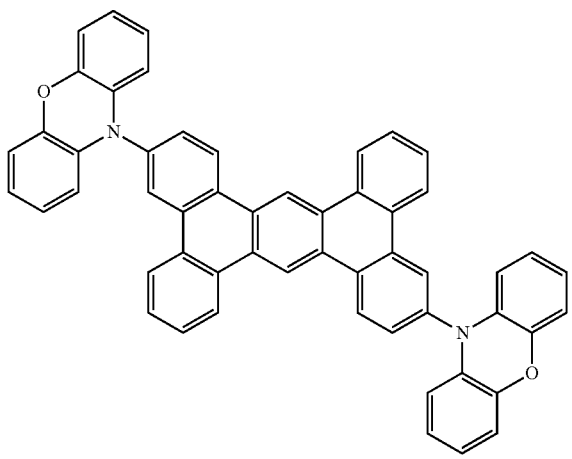

-continued
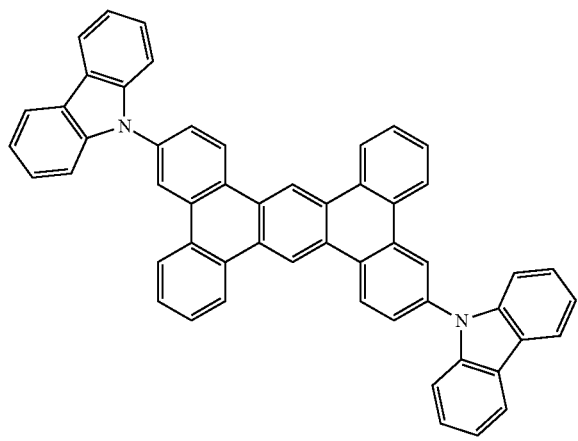
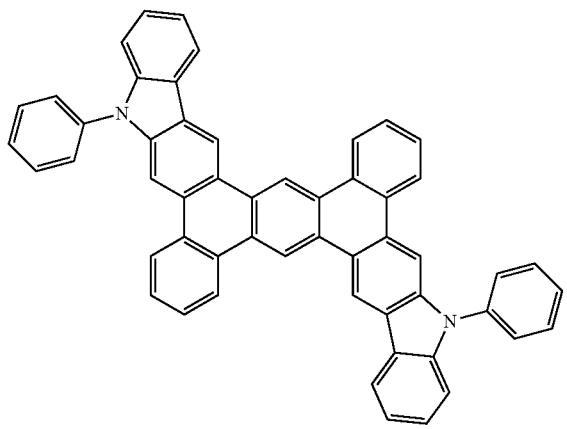
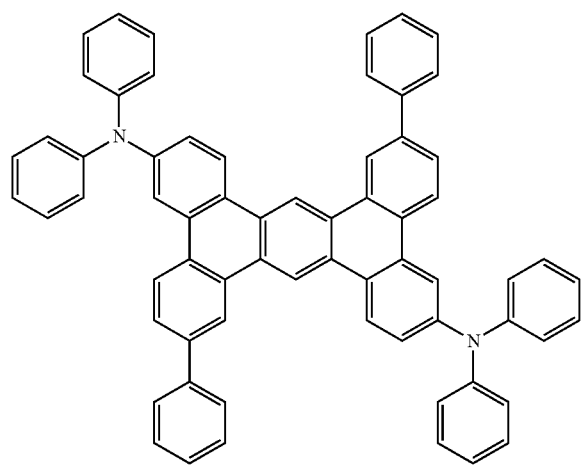
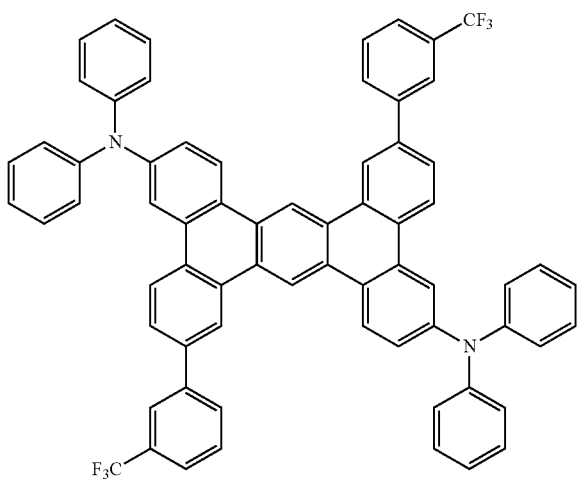
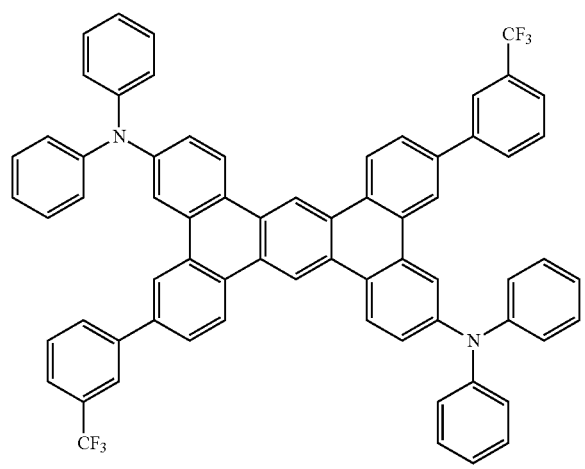
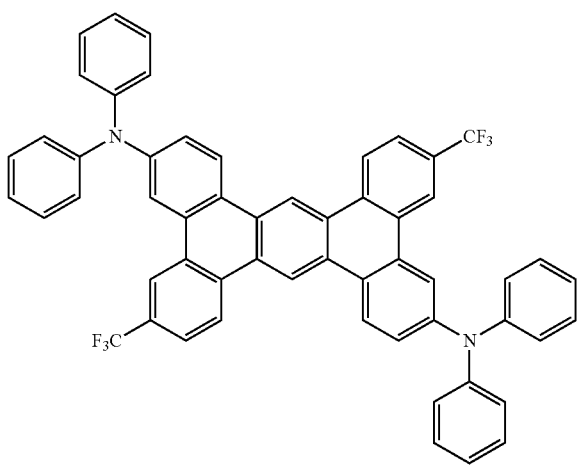

-continued
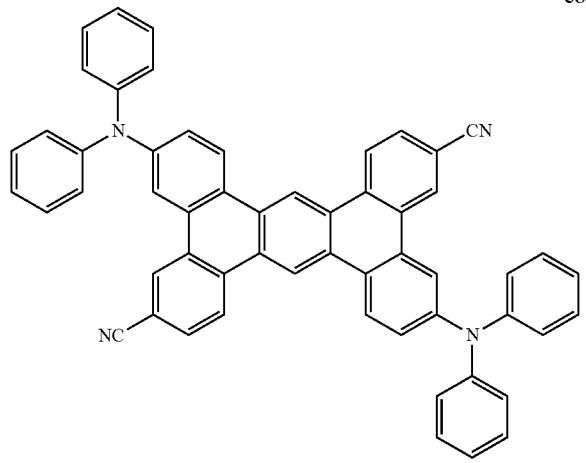
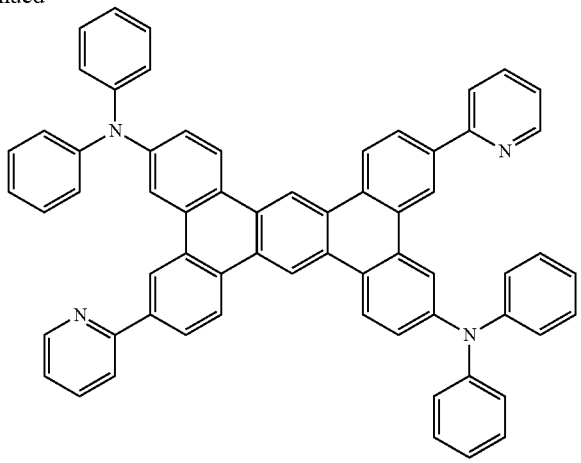
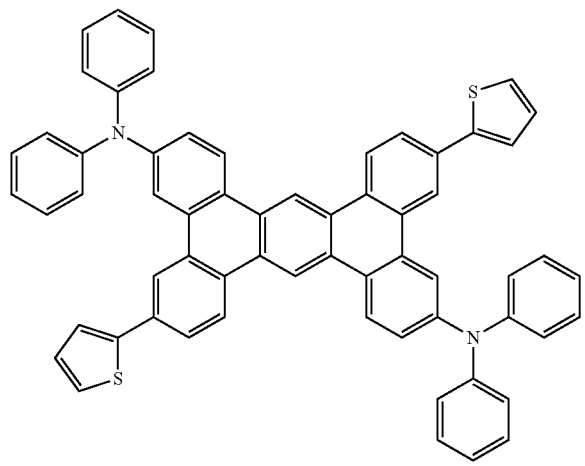
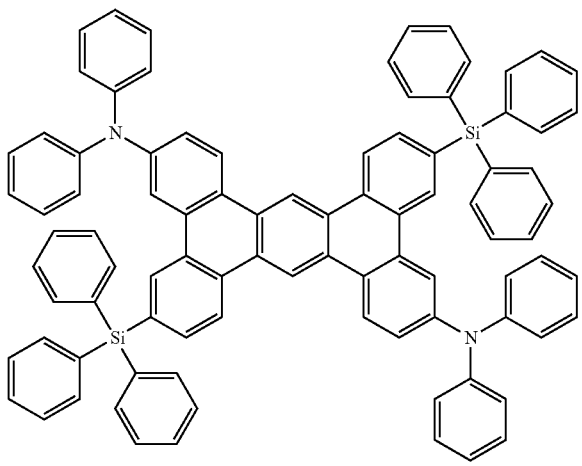
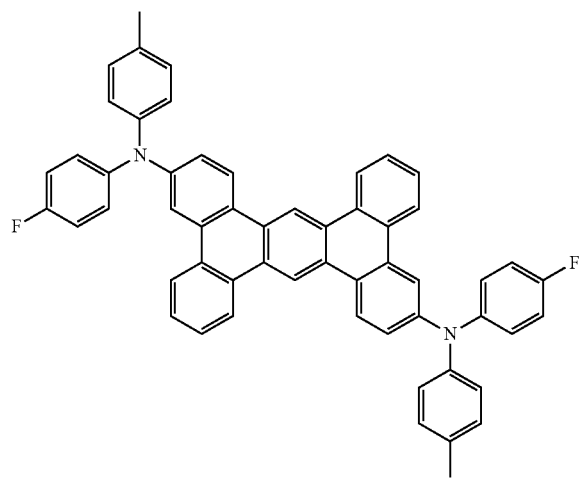
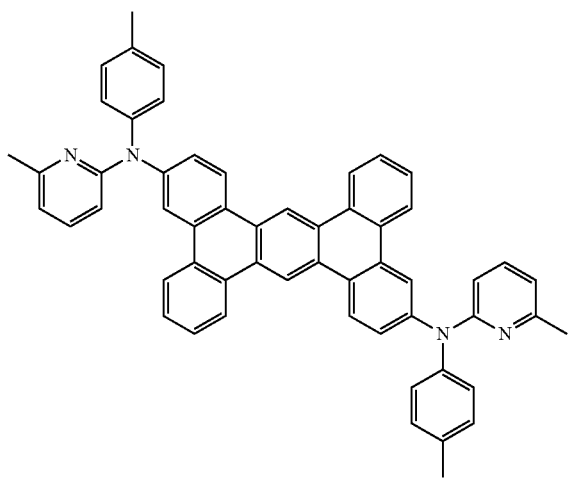

51
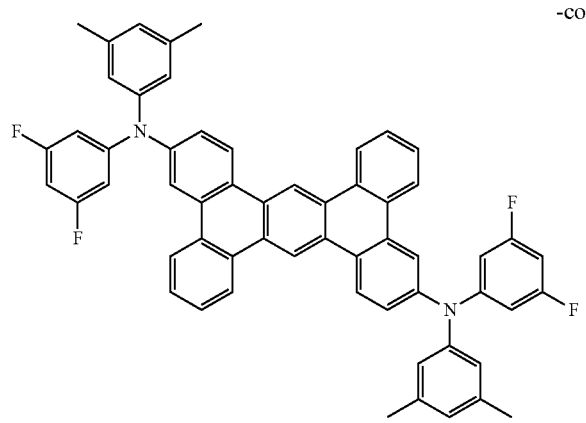
-continued
52
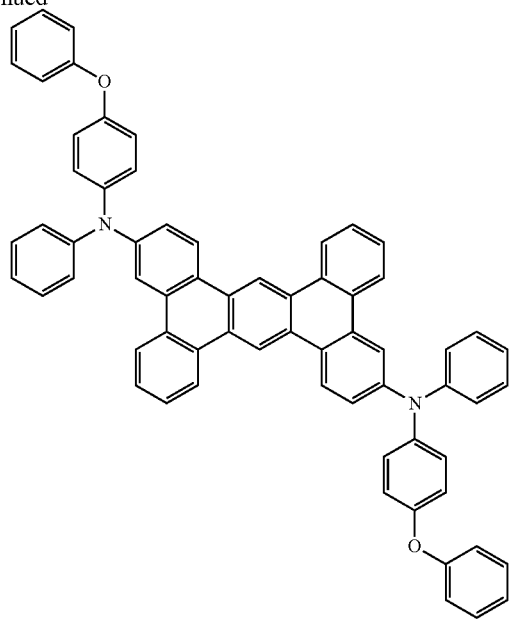
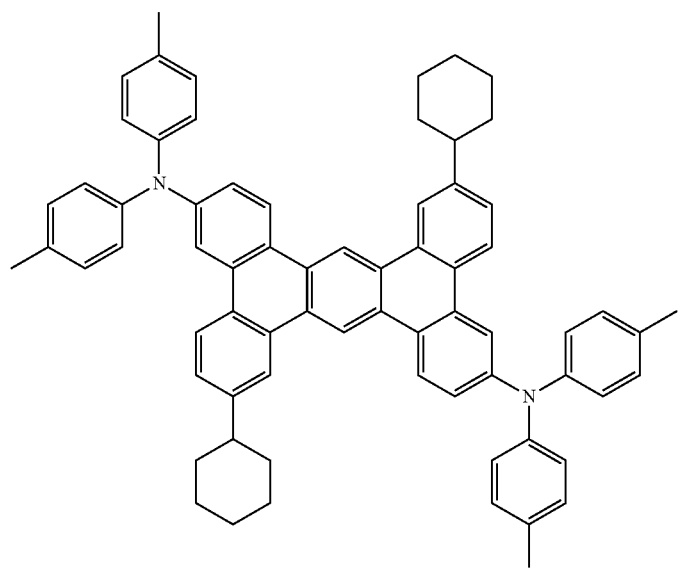
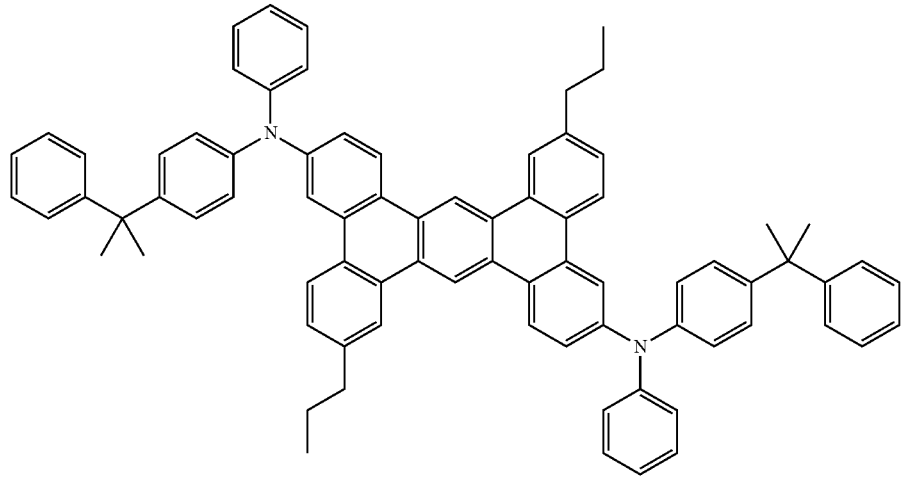

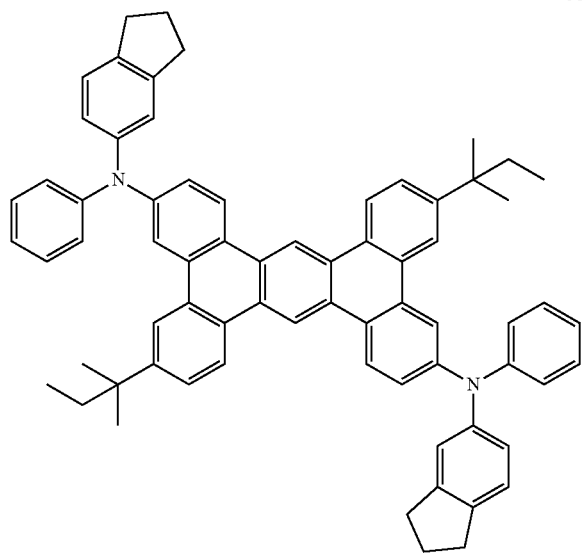

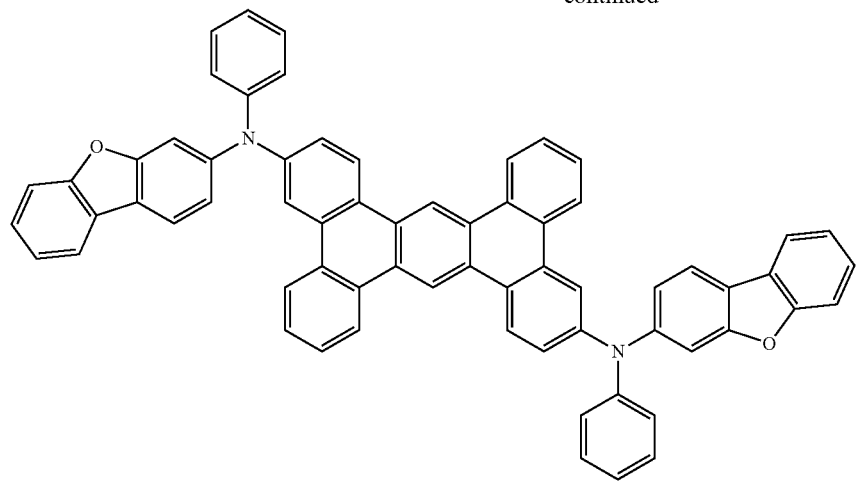
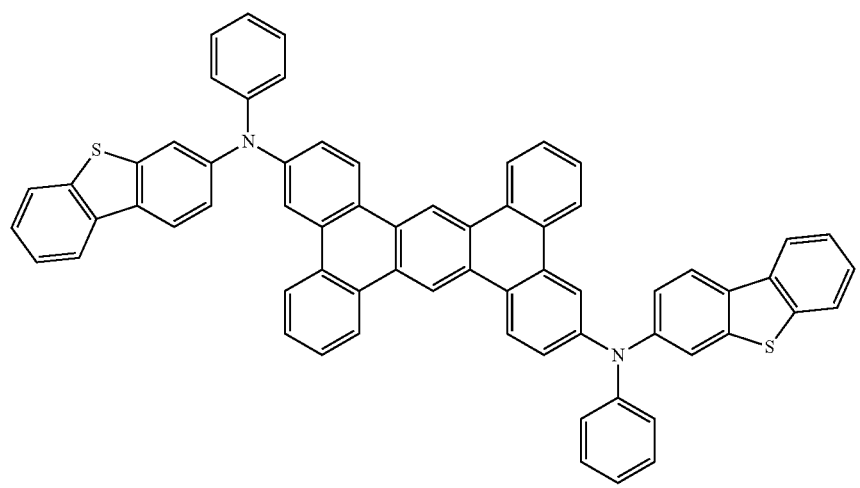
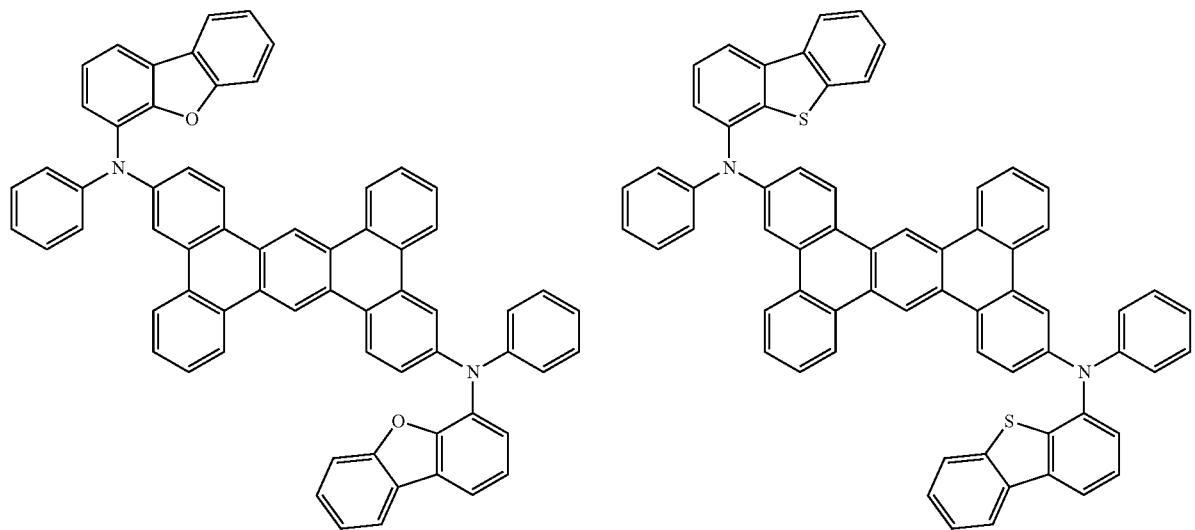

-continued
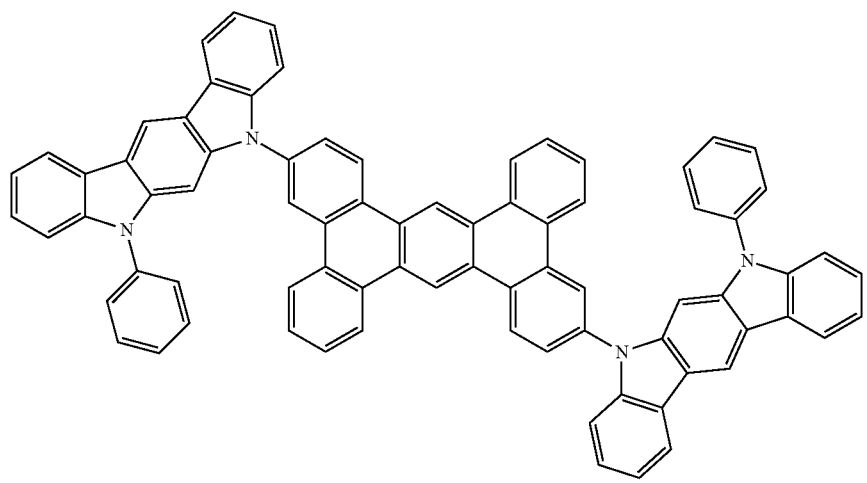
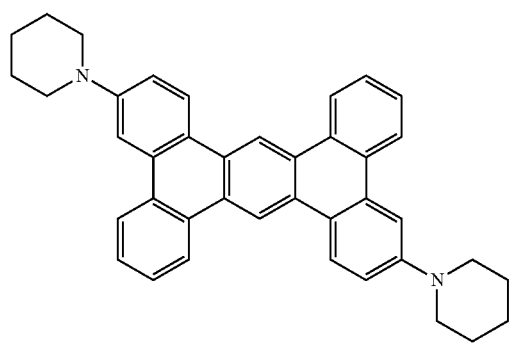
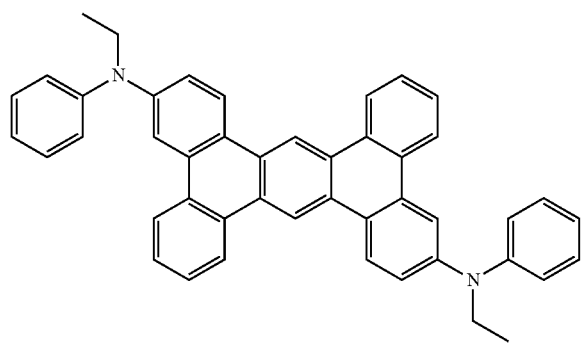
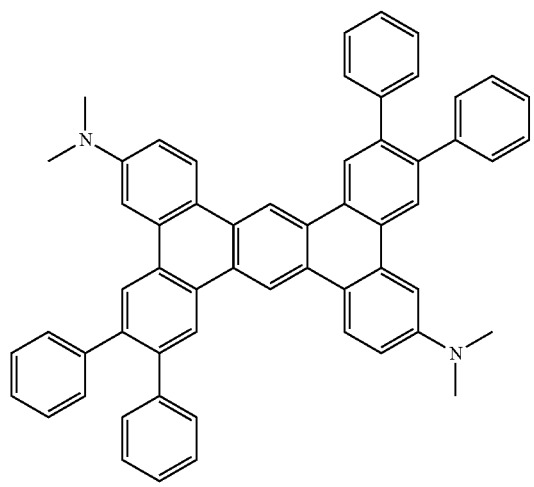
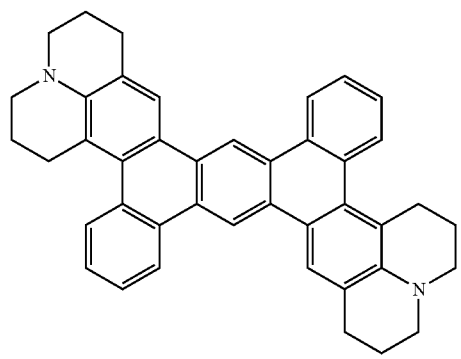

-continued
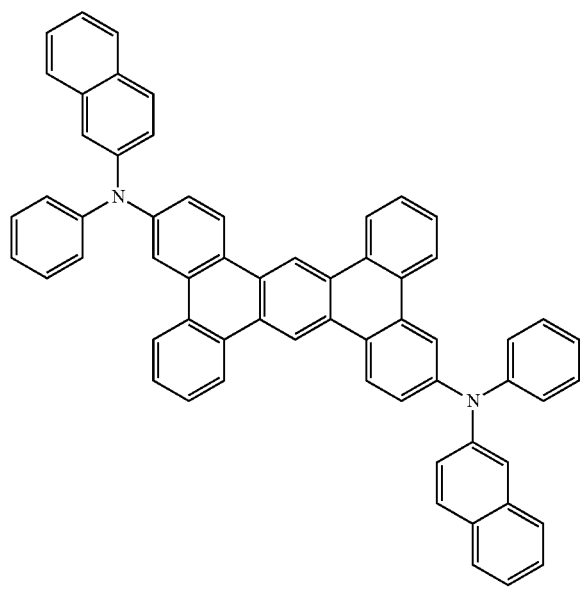
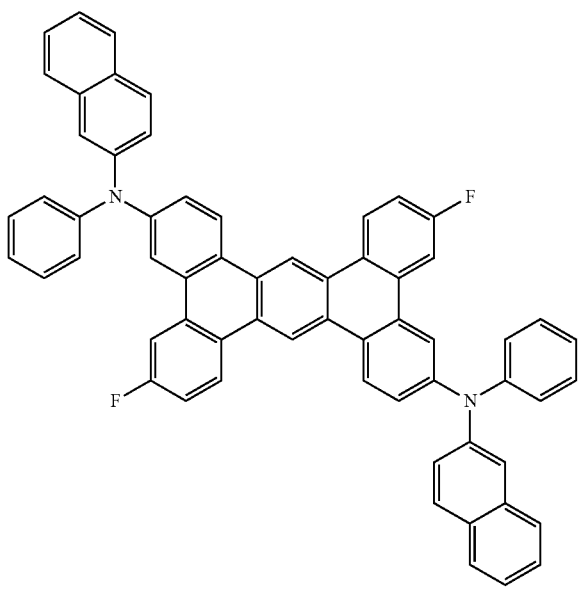
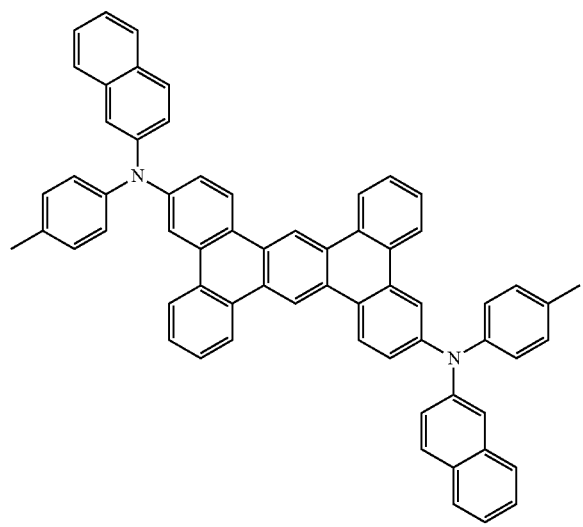
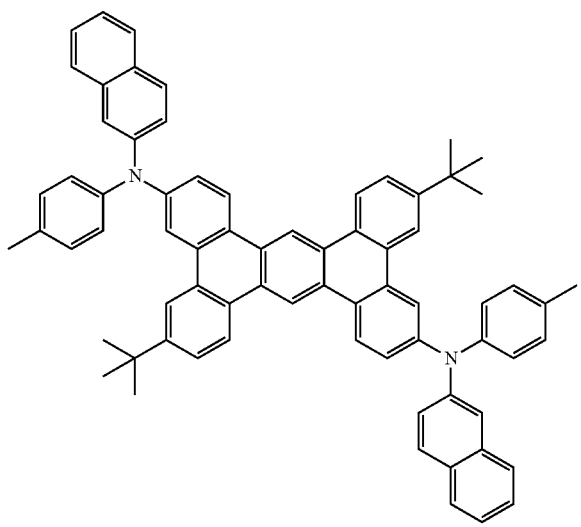
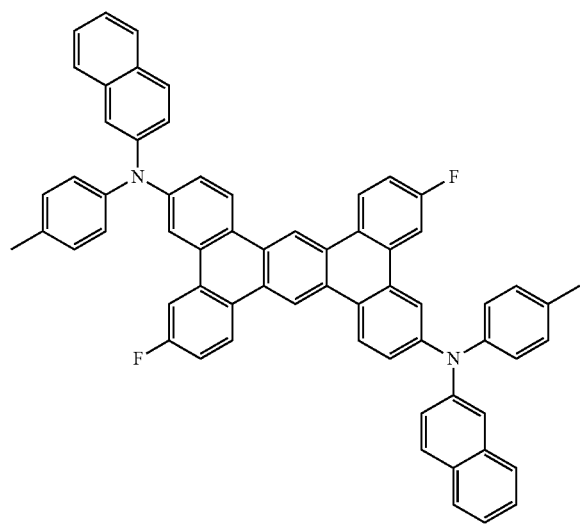
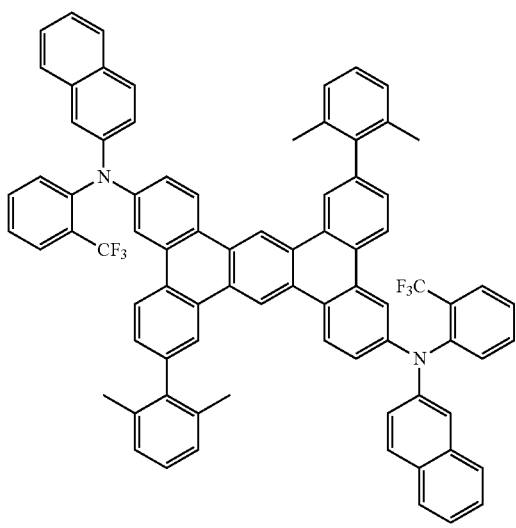

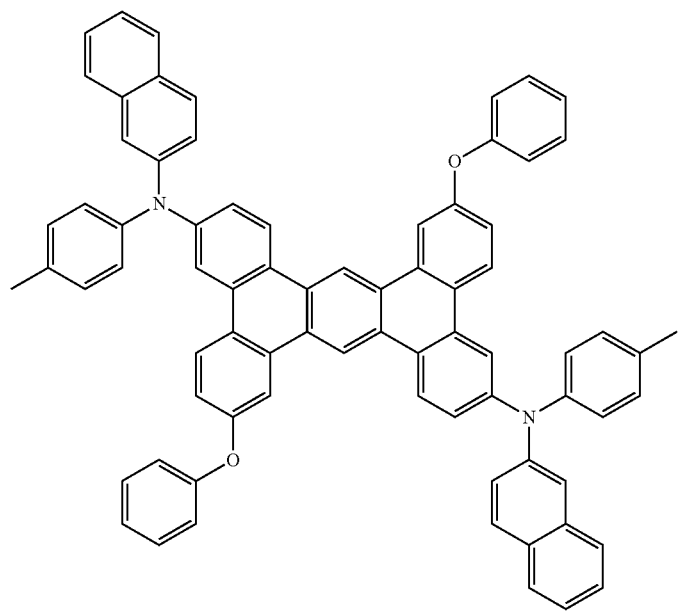
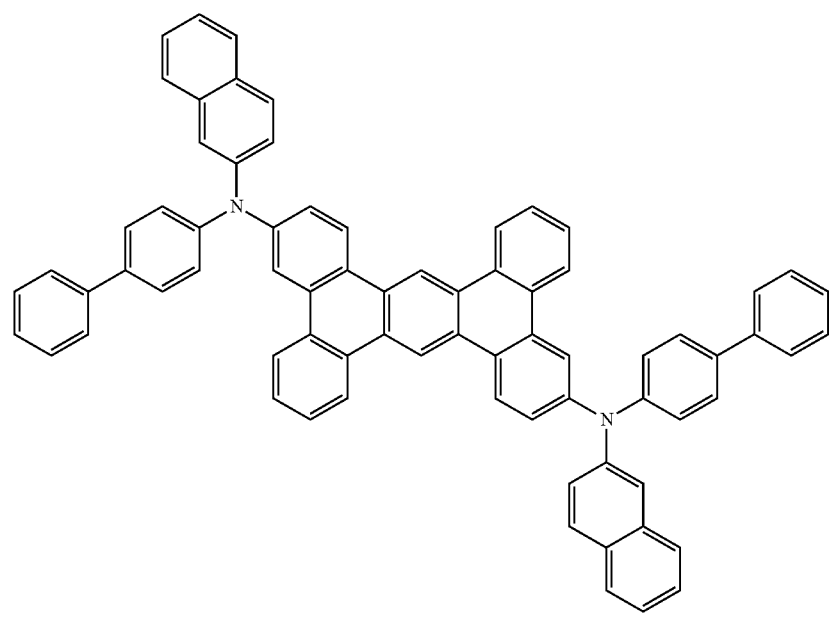

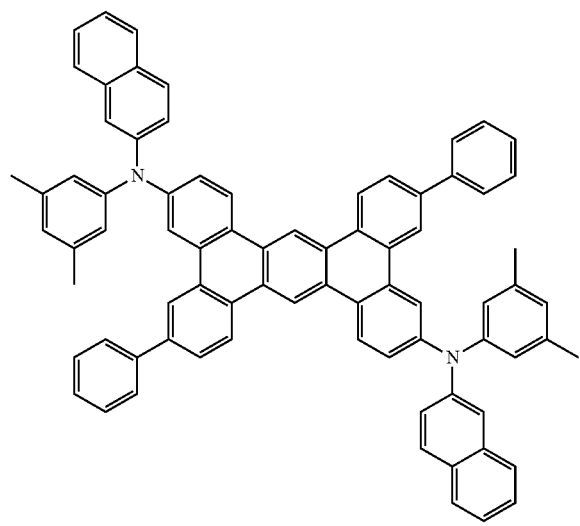
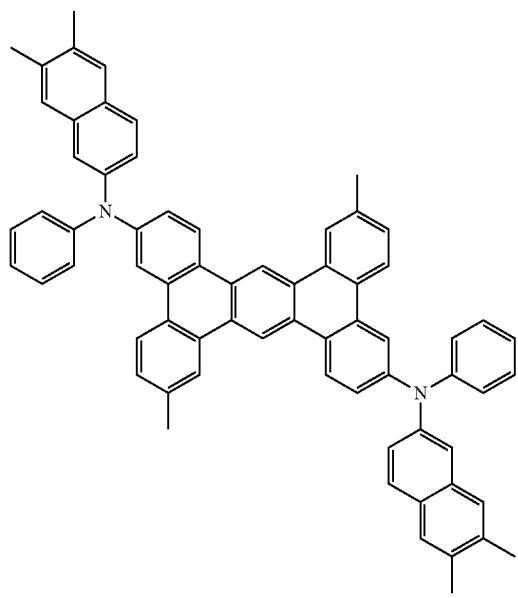
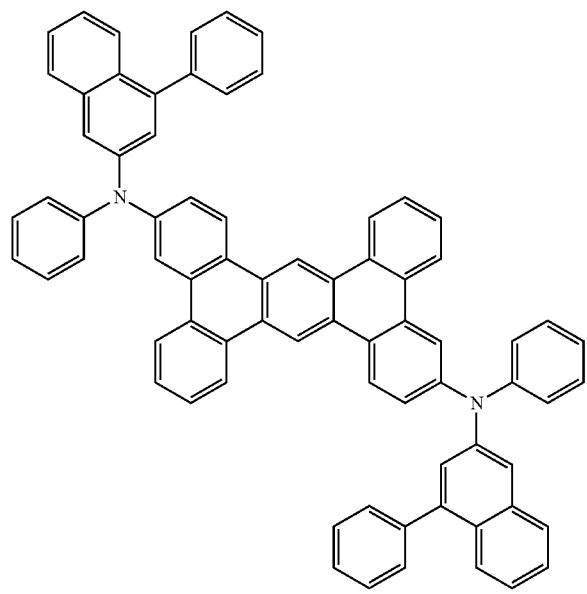

-continued
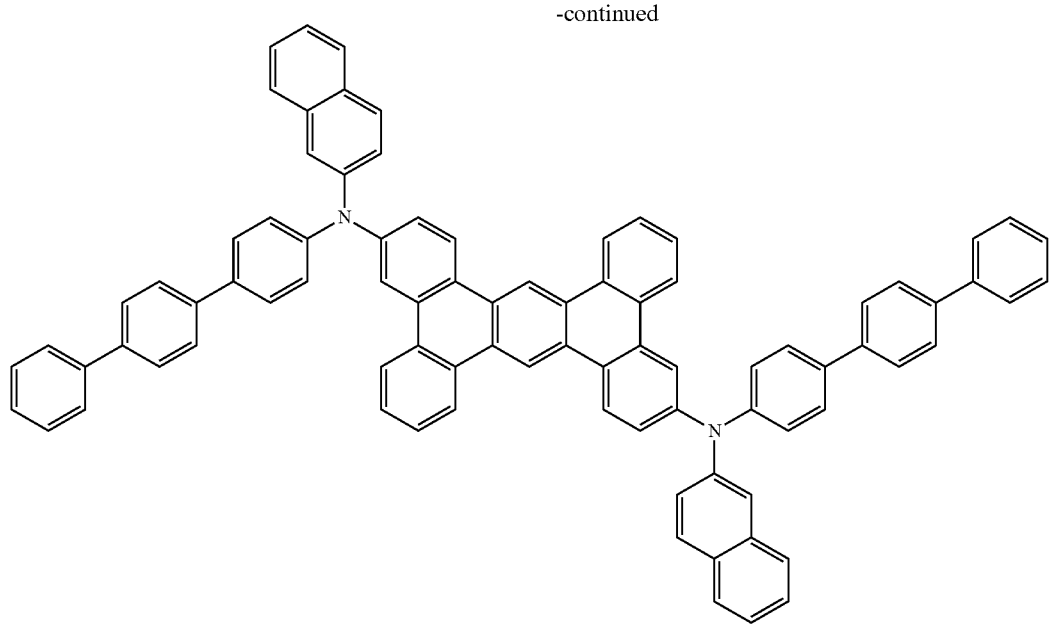
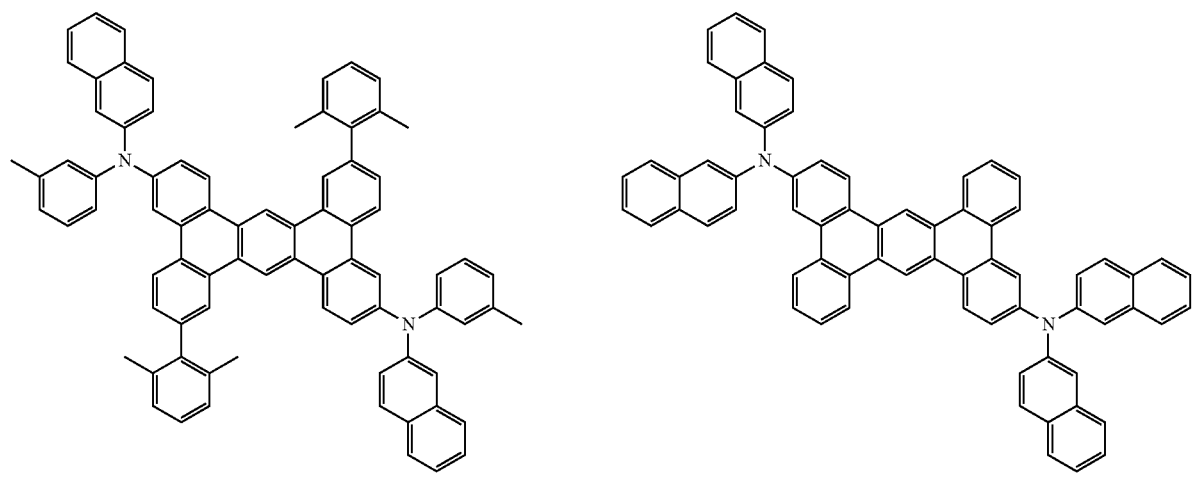
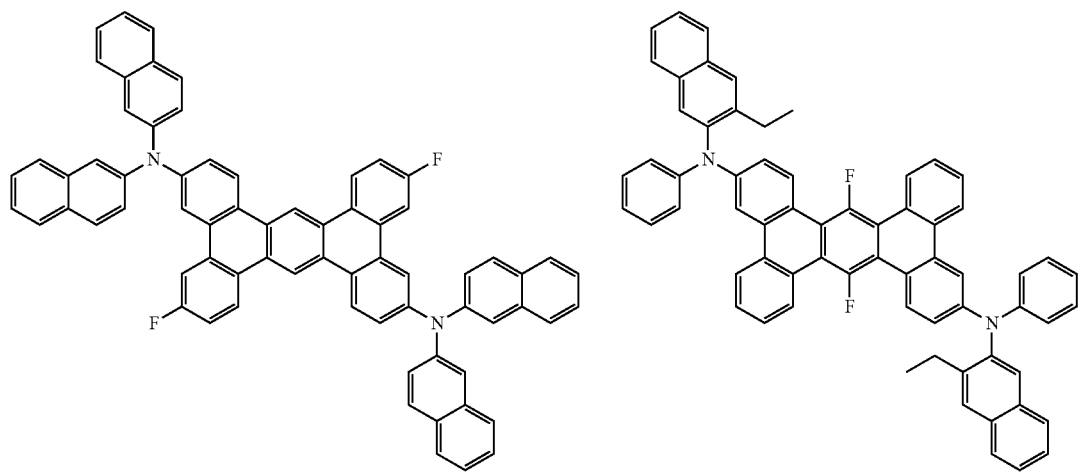

-continued
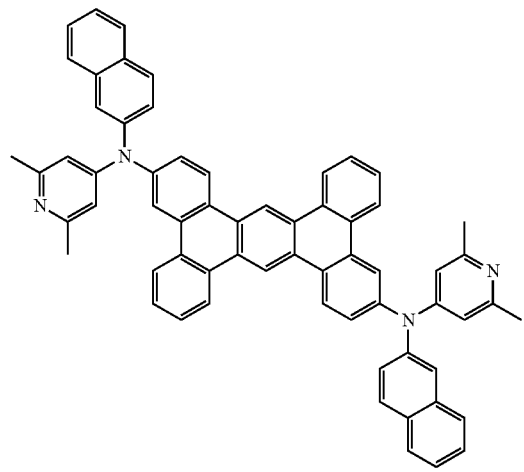
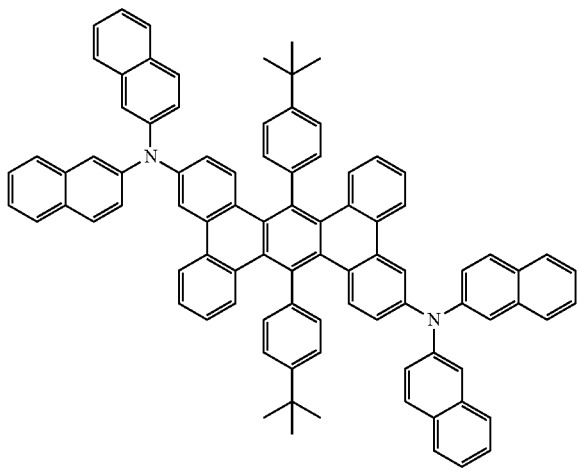
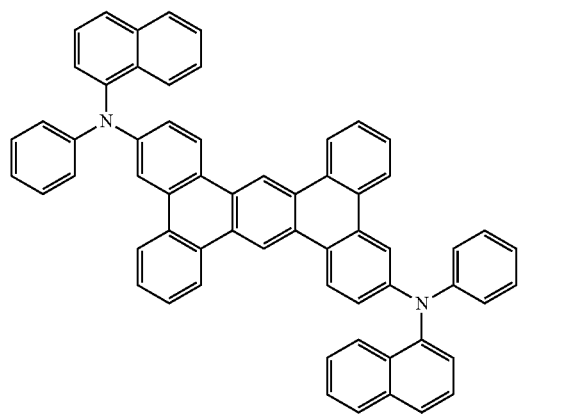
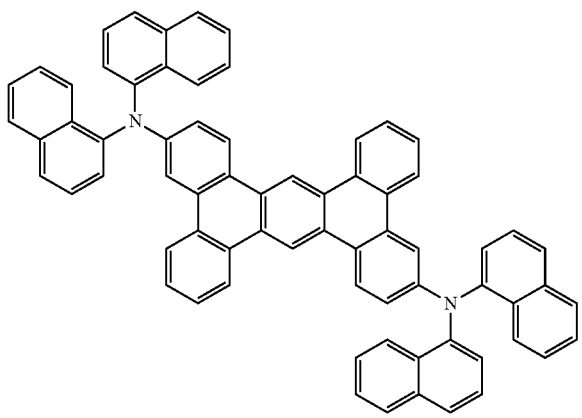
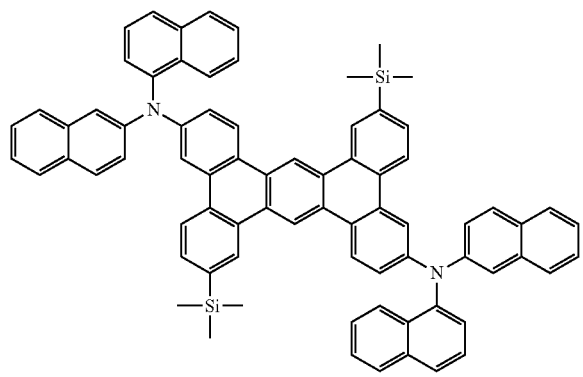
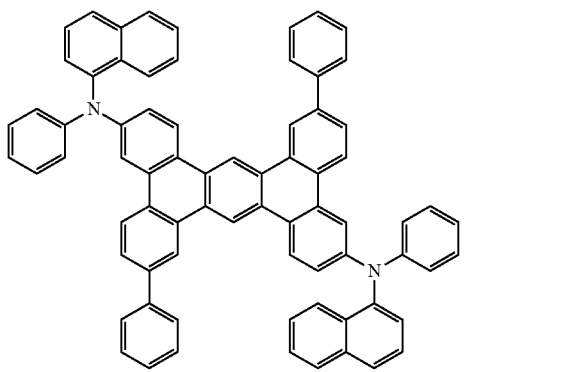
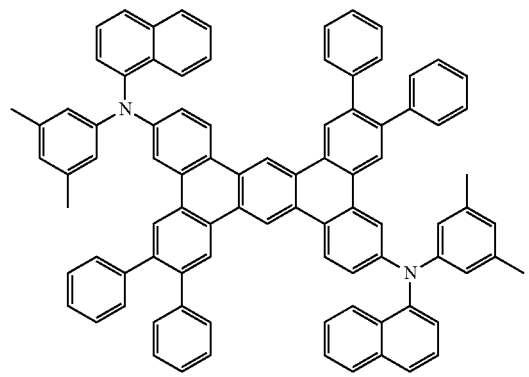
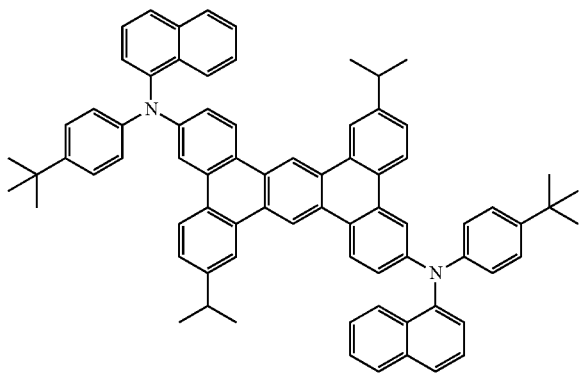

-continued
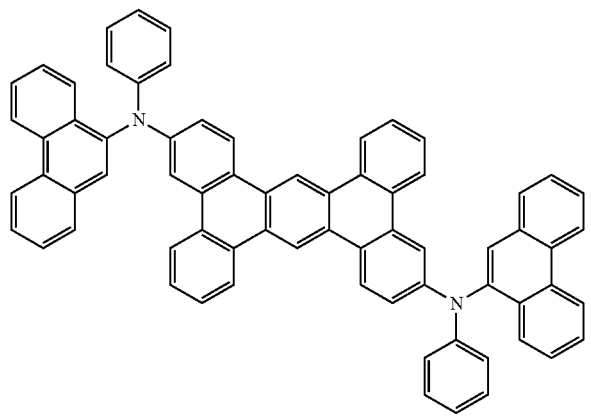 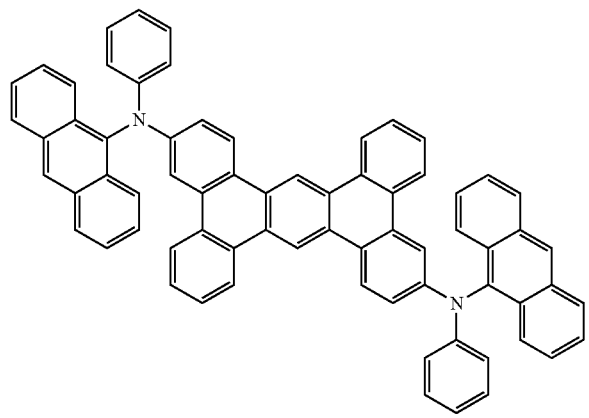
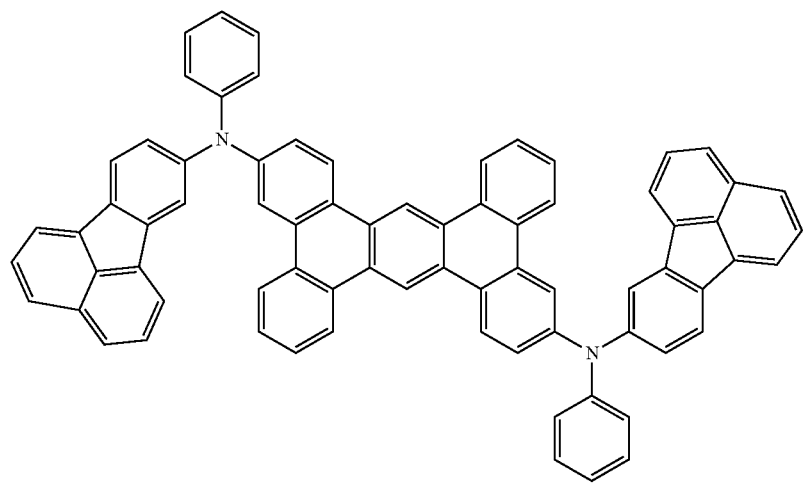
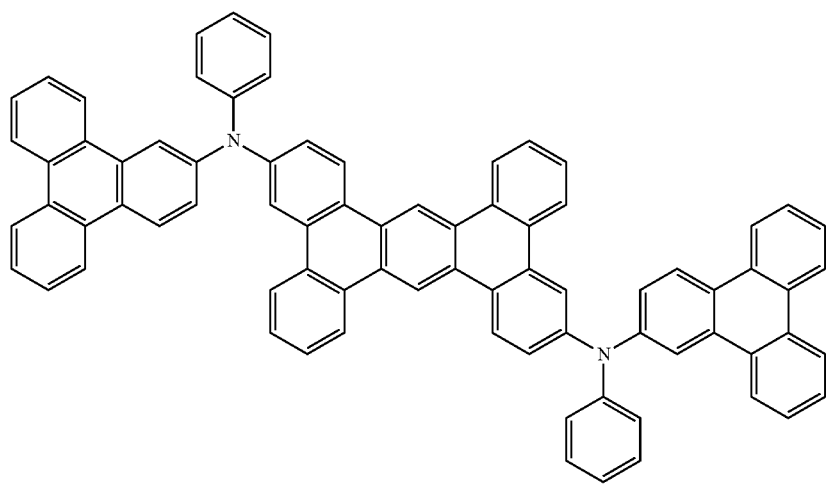

-continued
71
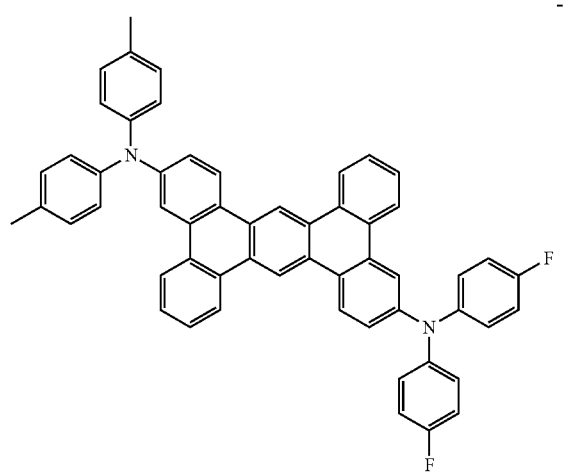
72
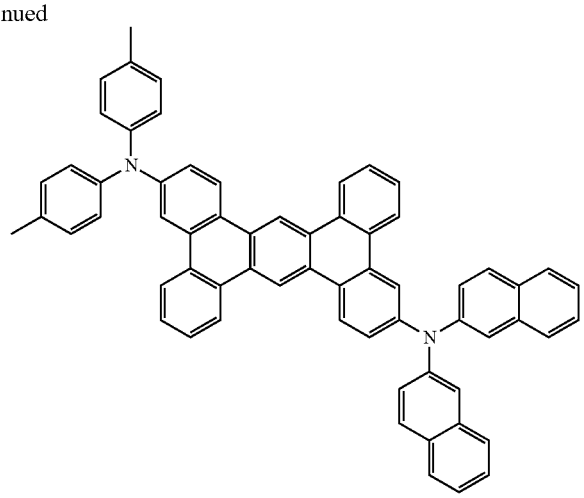
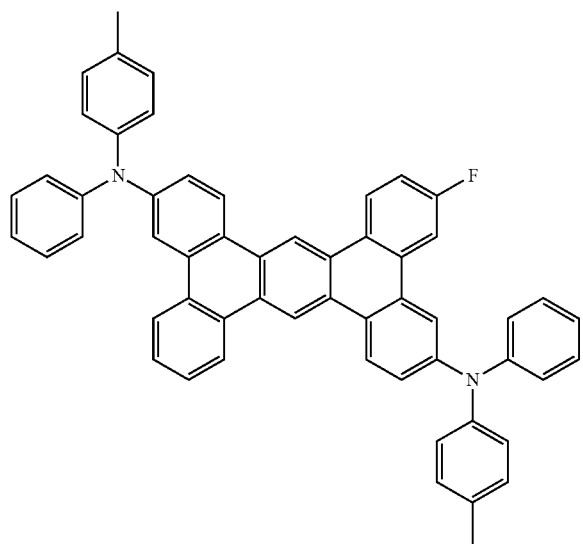
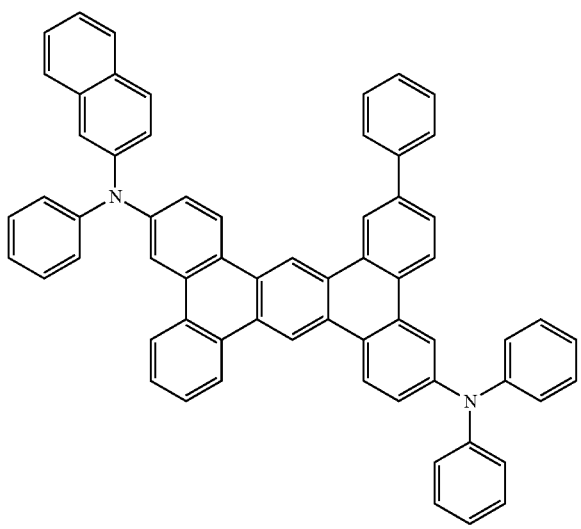
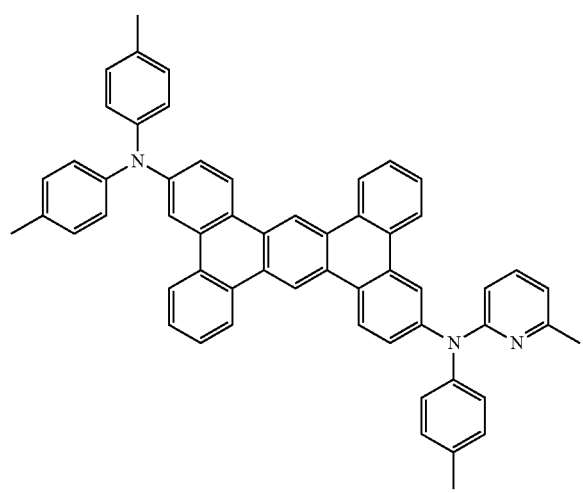
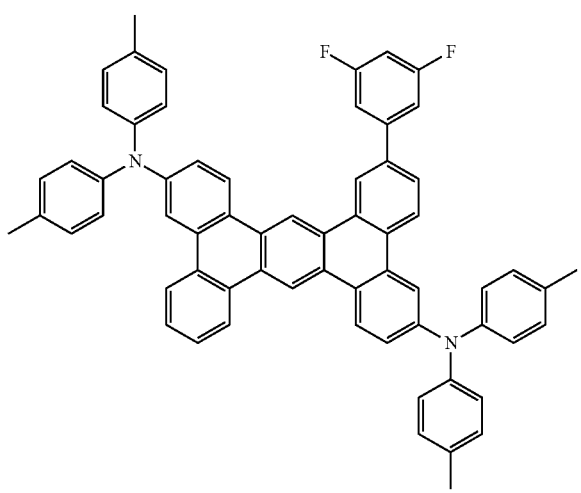

-continued
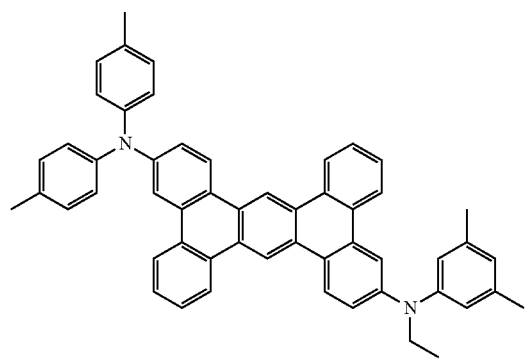
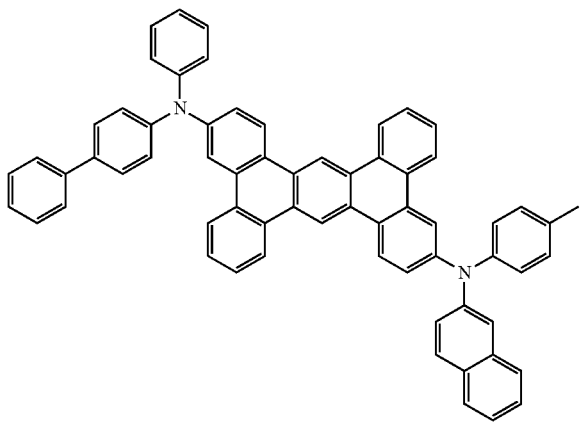
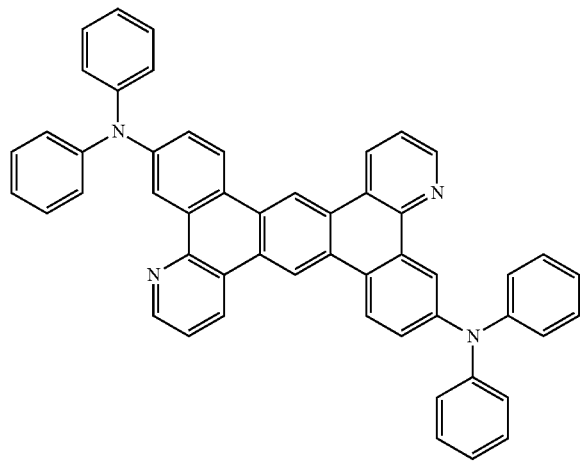
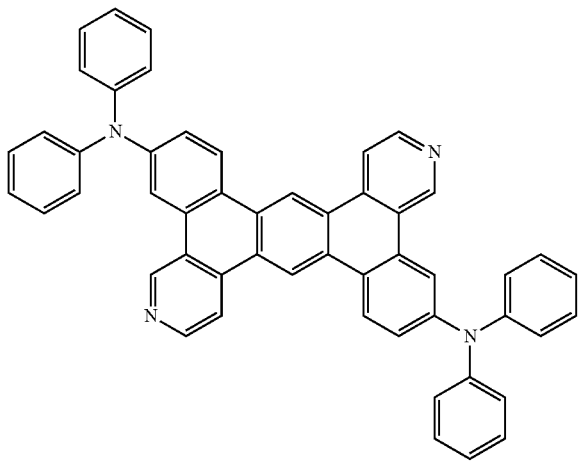
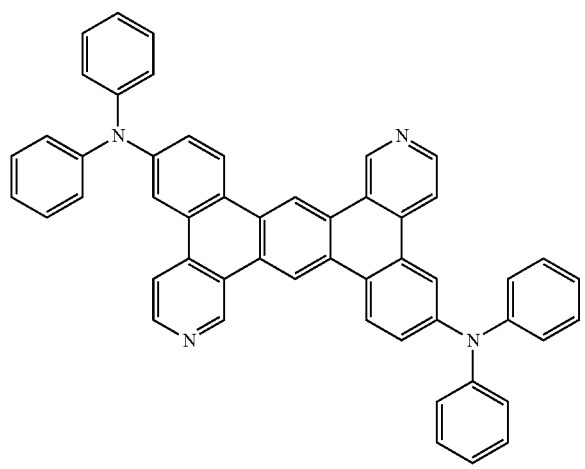
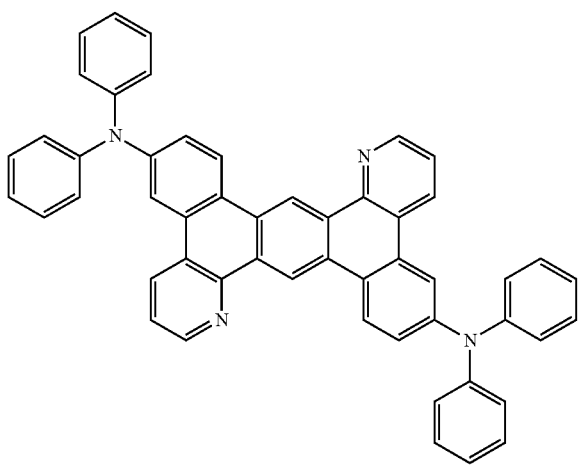

-continued
75
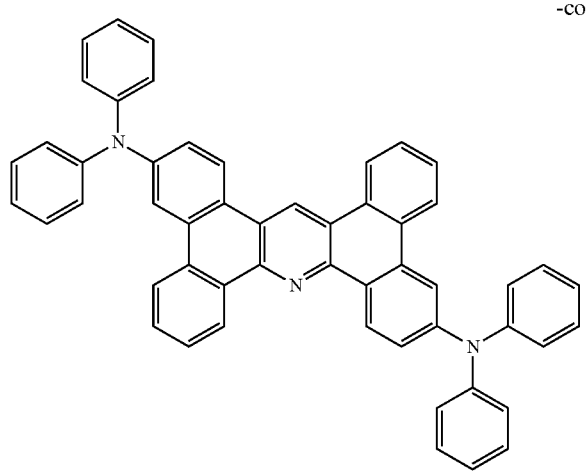
76
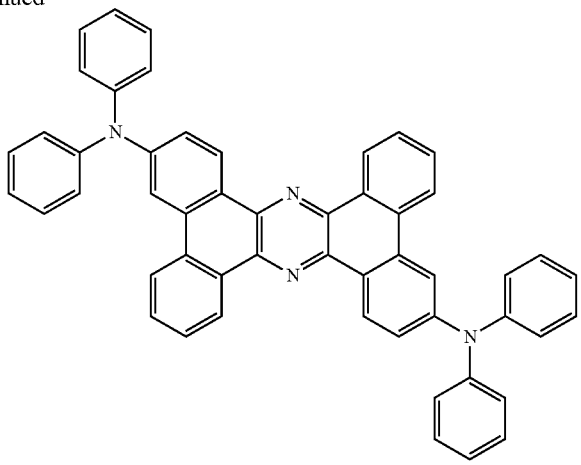
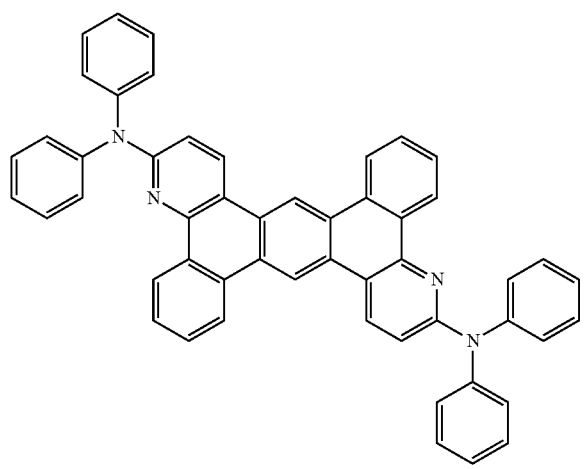
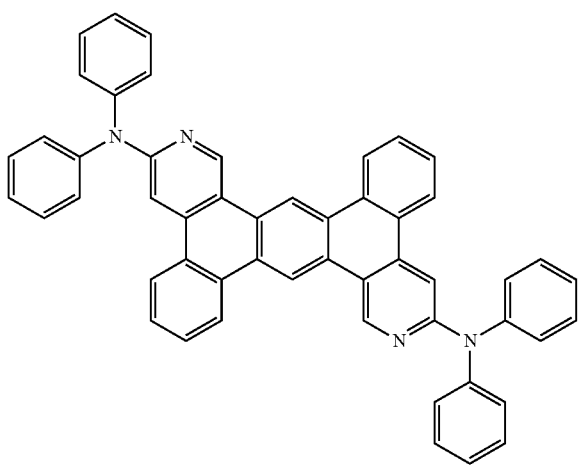
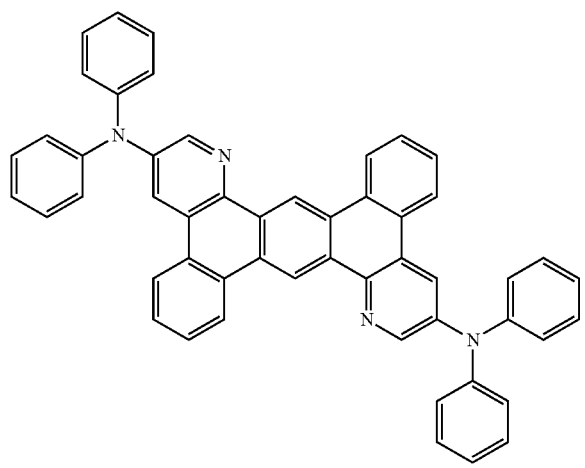
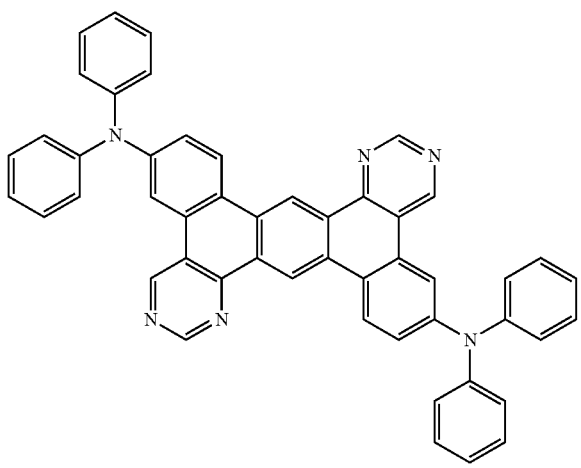

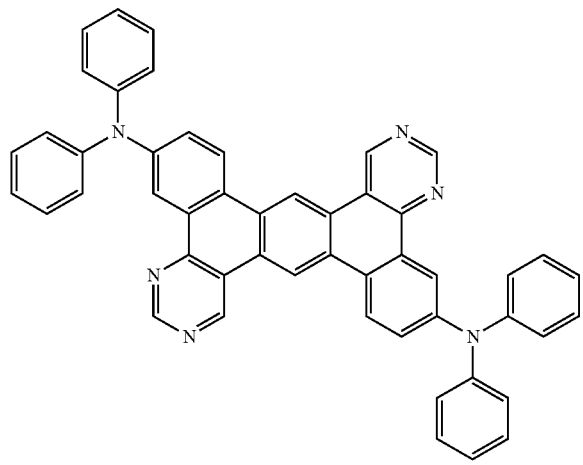
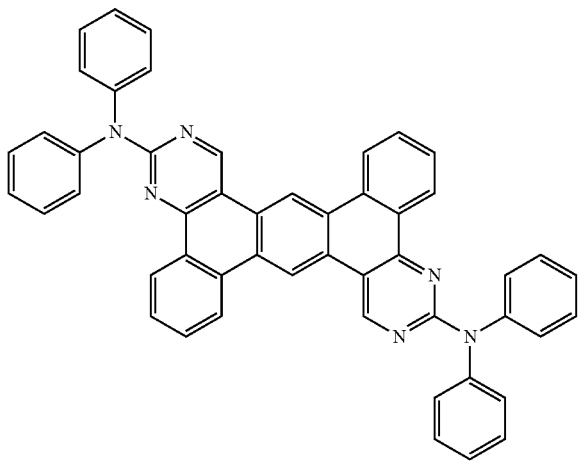
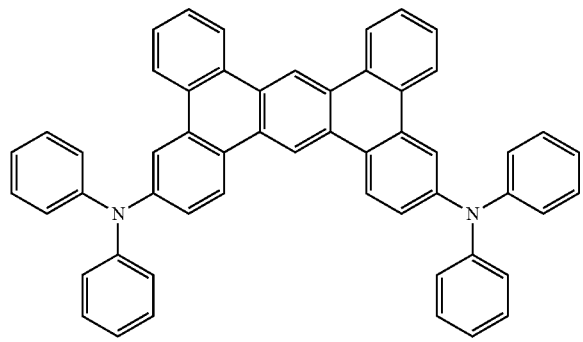
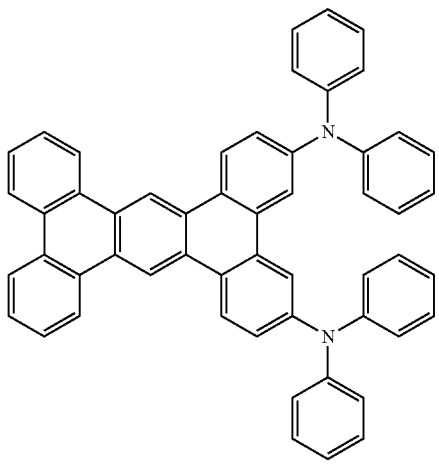
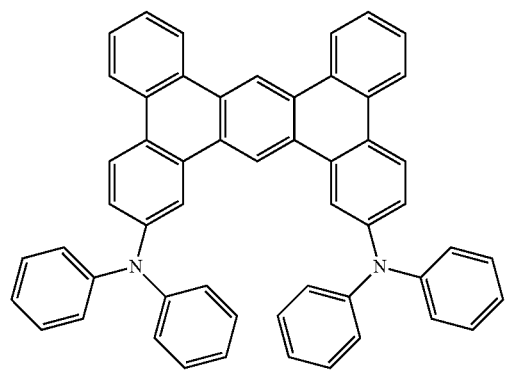
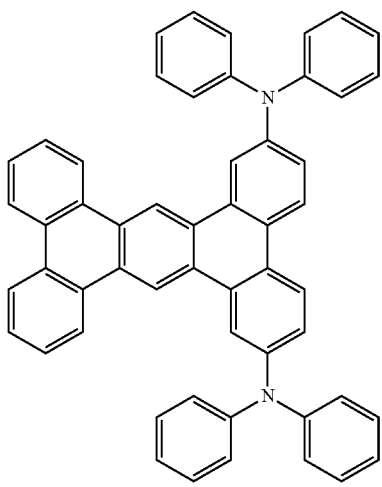

-continued
79
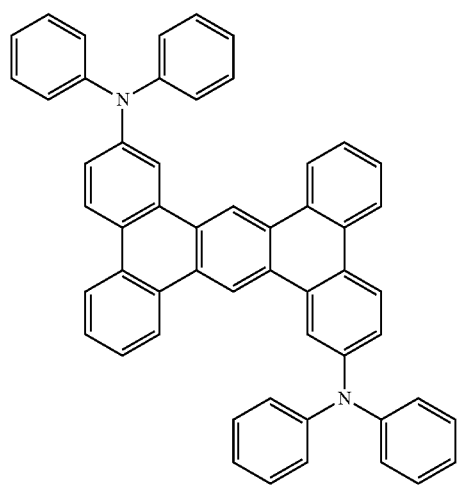
80
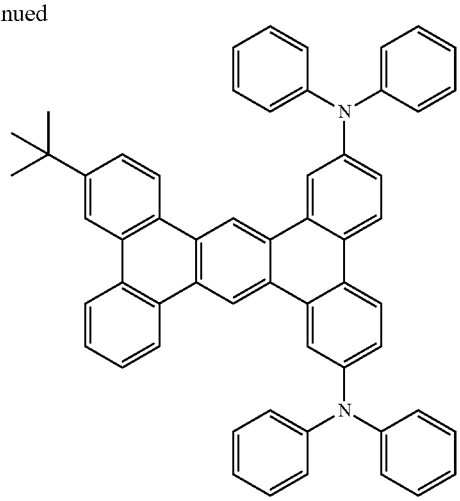
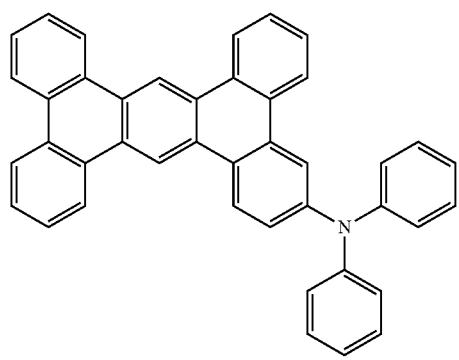
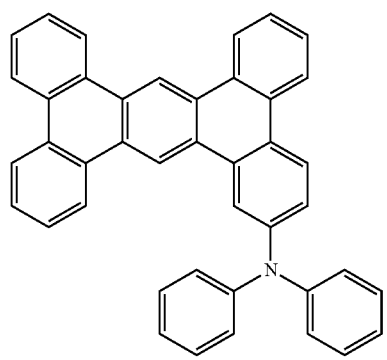
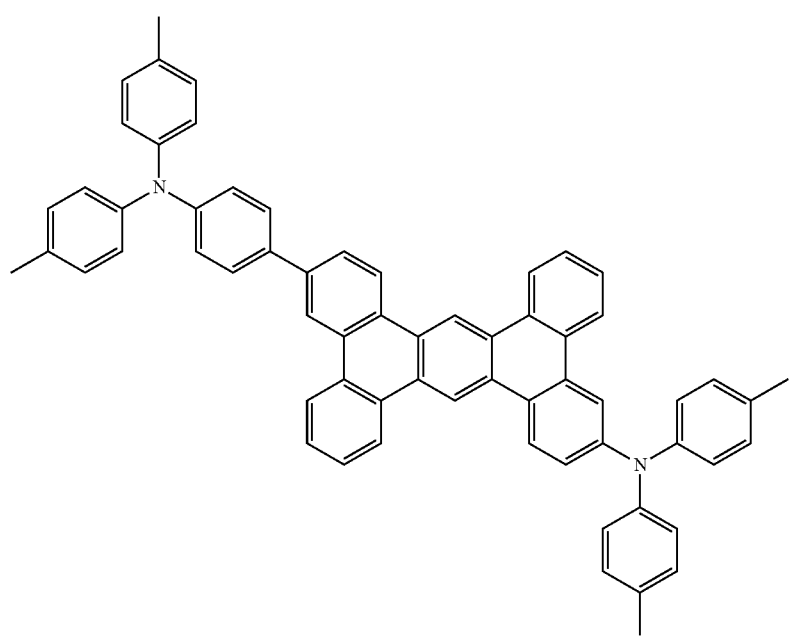

-continued
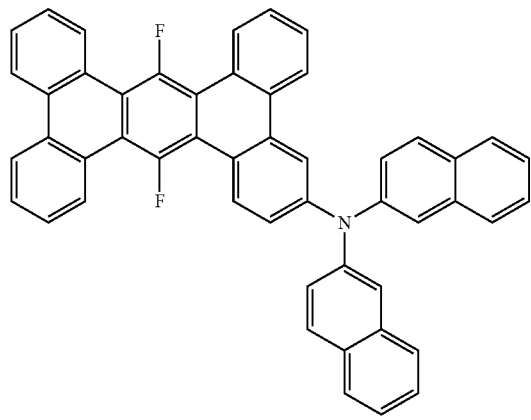
81
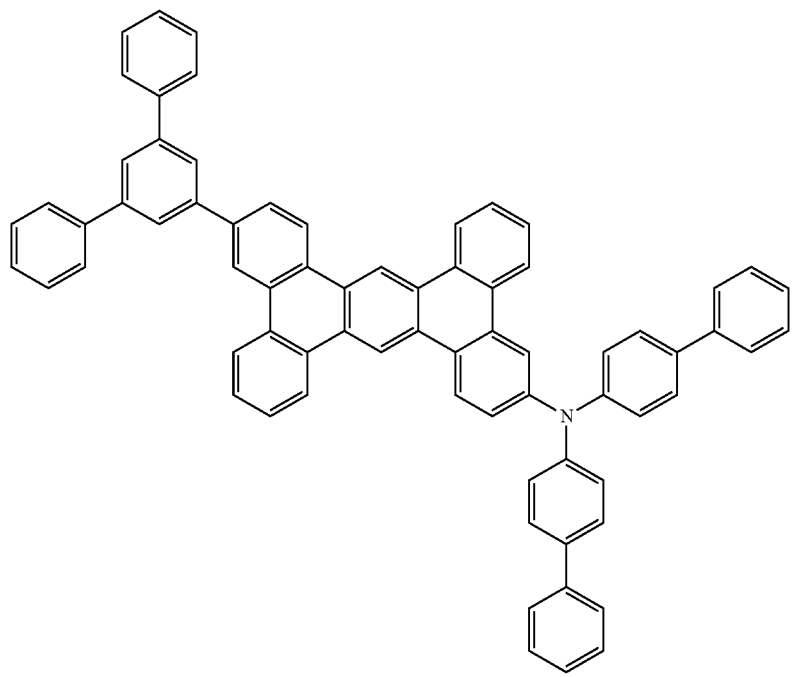
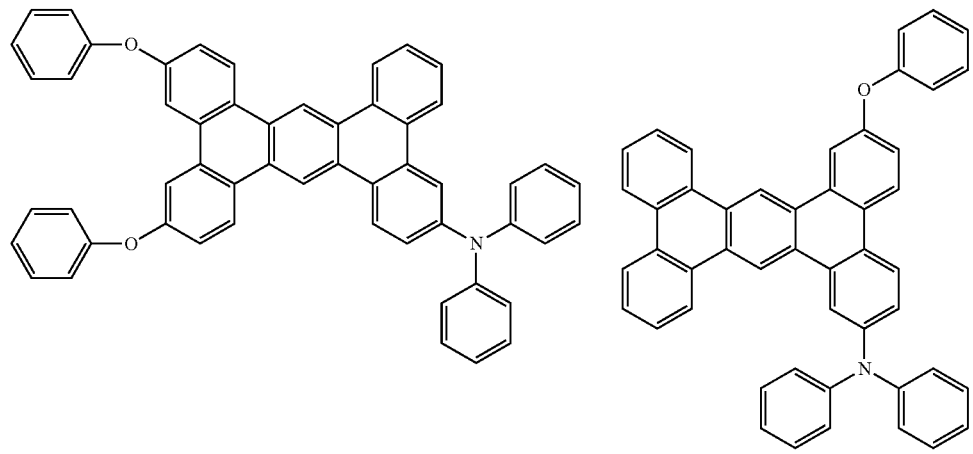
82

-continued
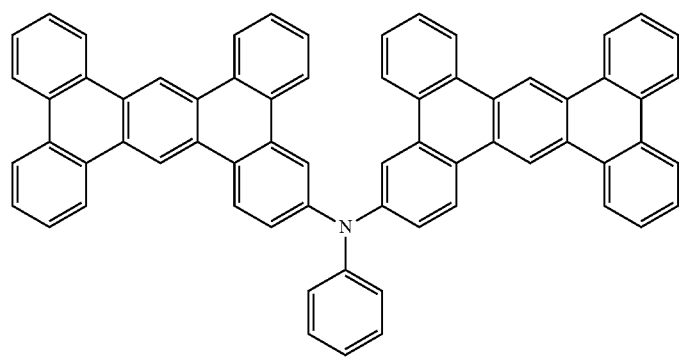
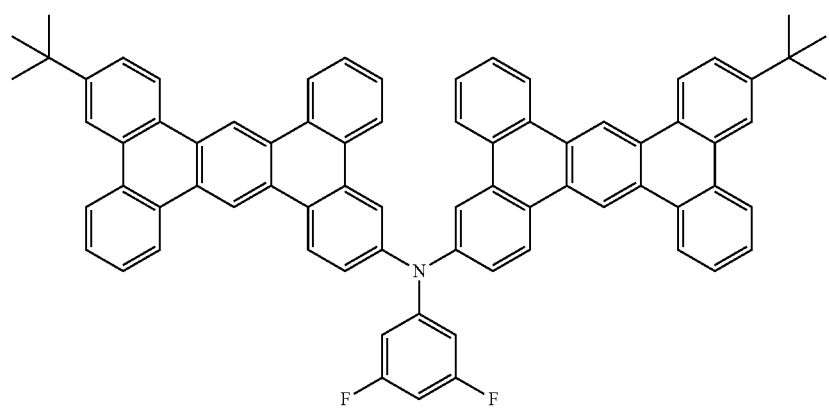
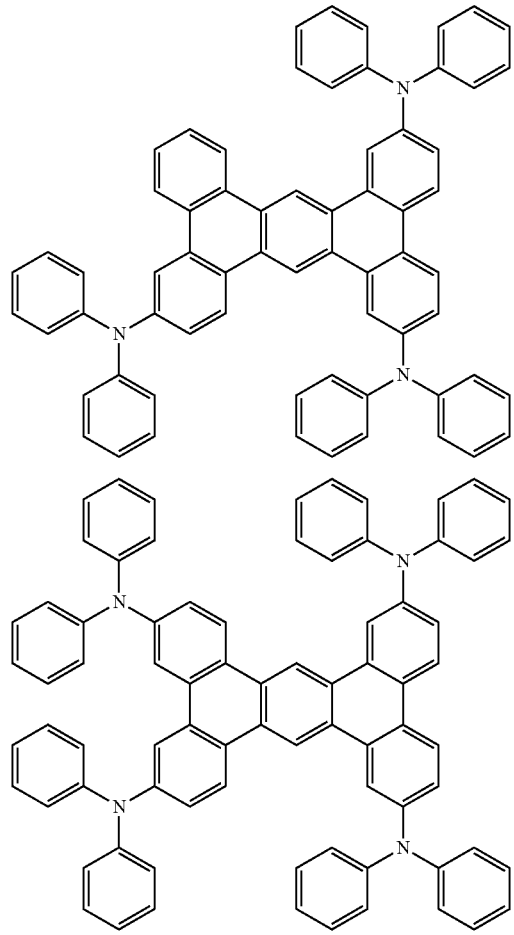
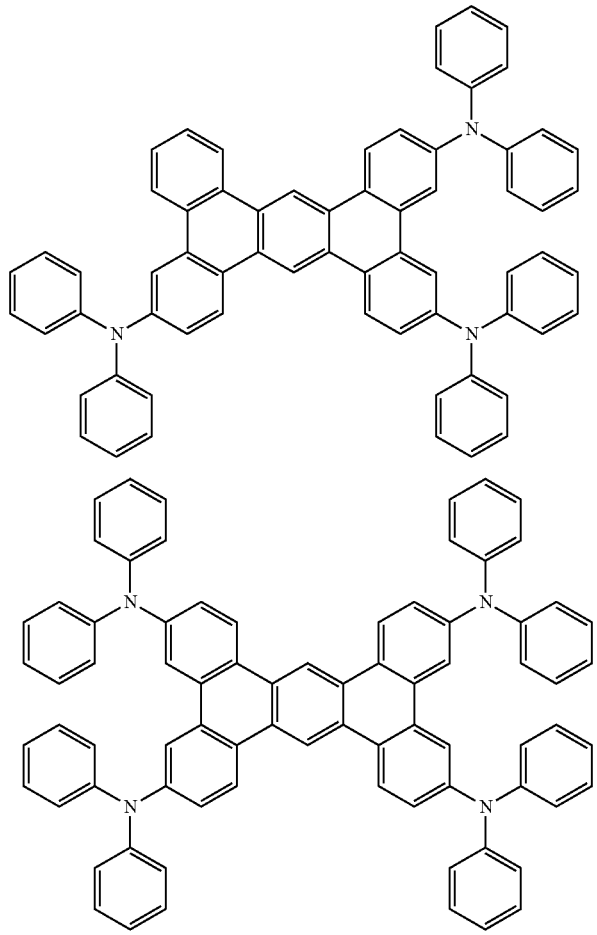

-continued
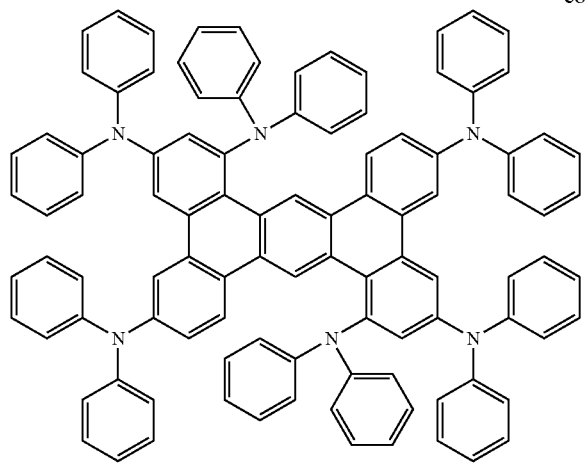
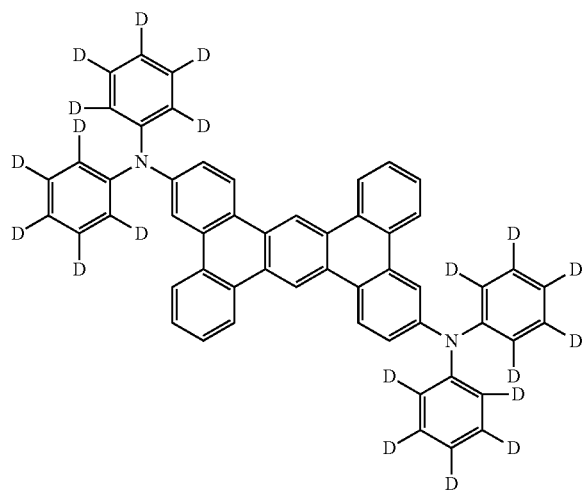
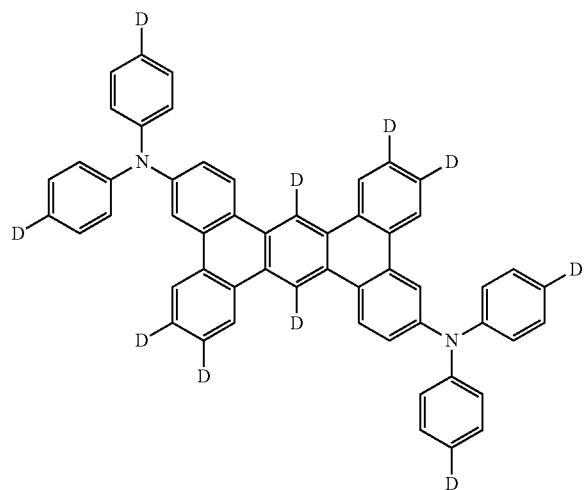
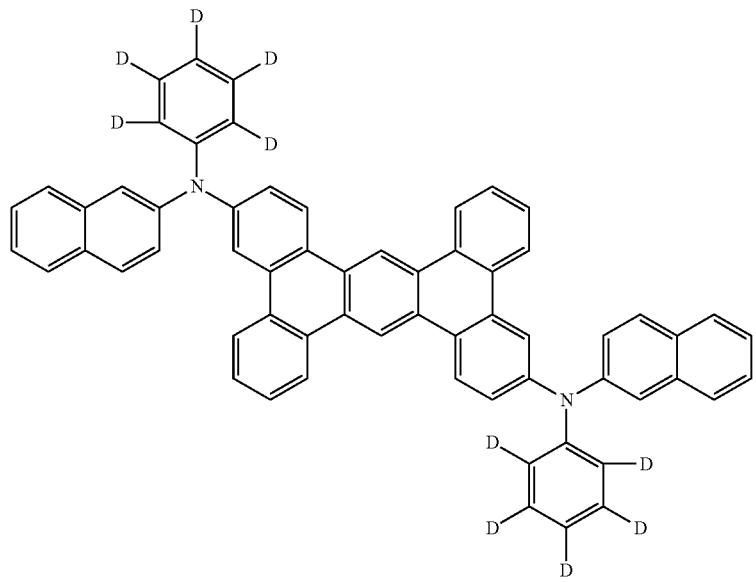

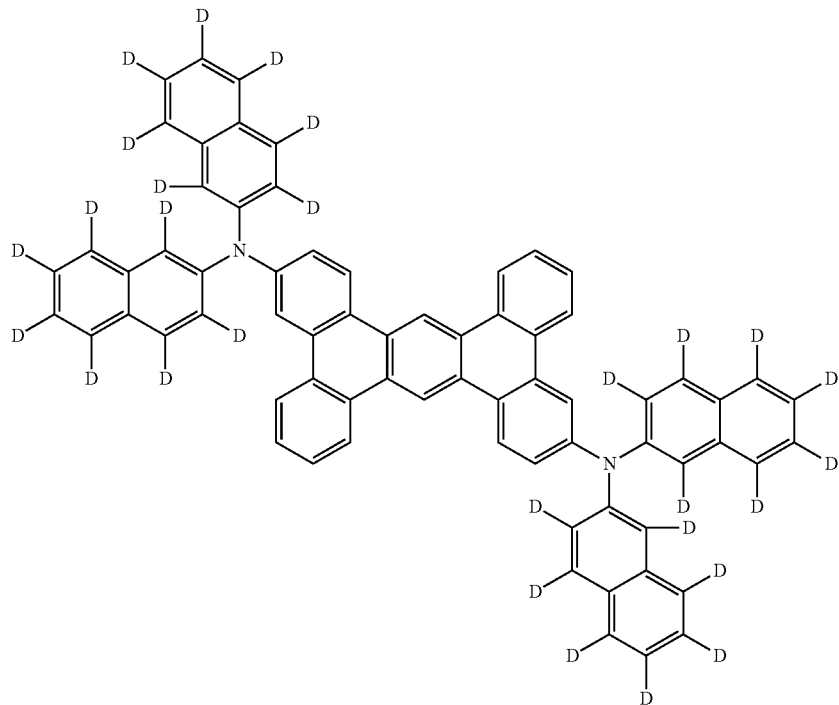
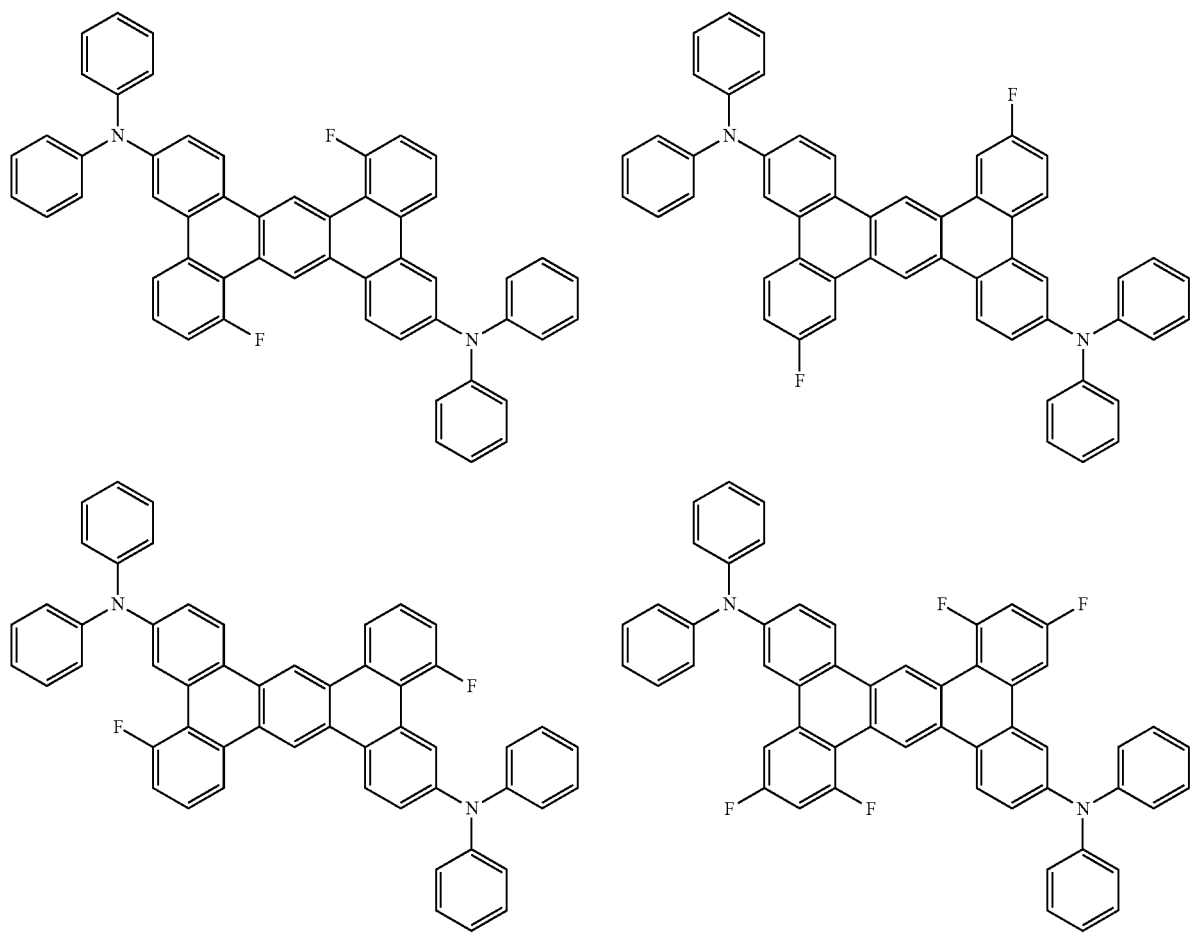

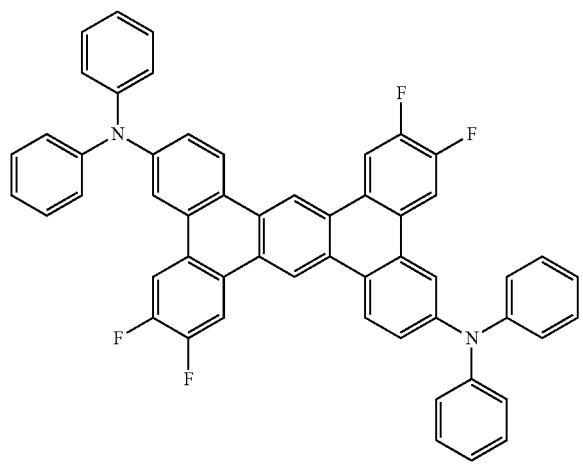
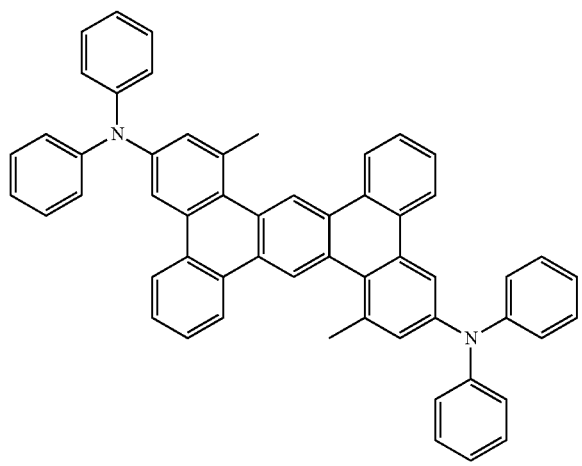
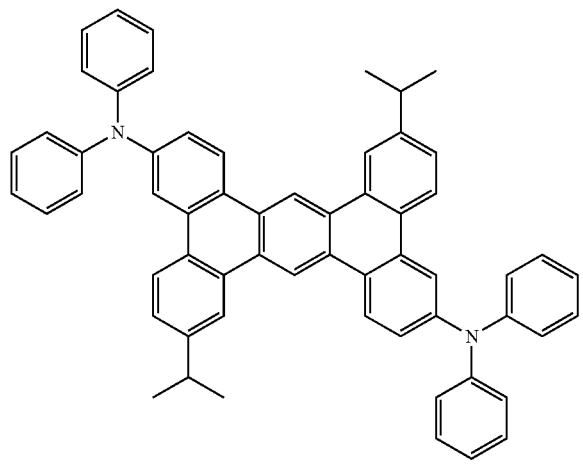
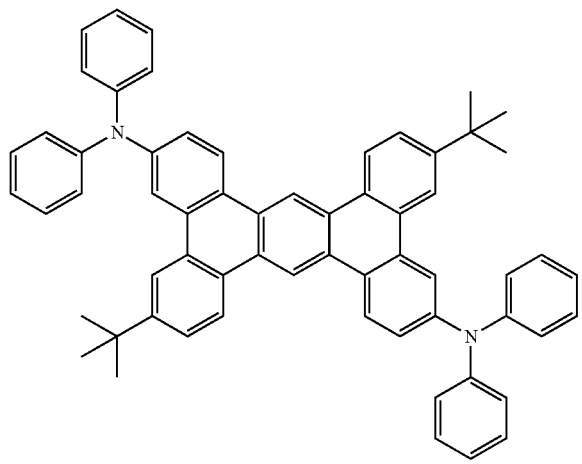
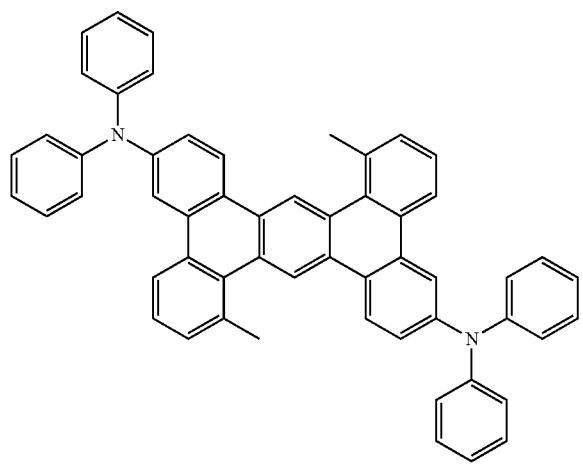
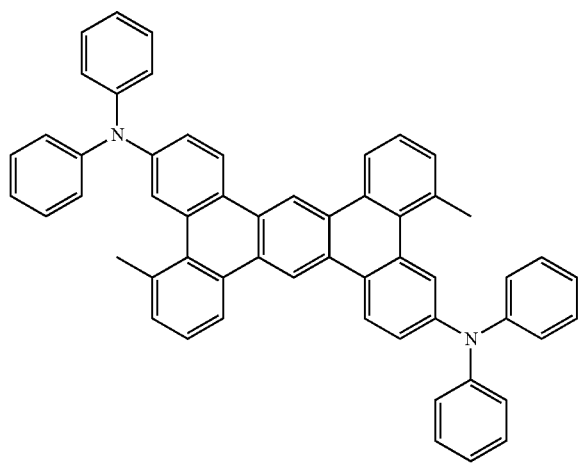

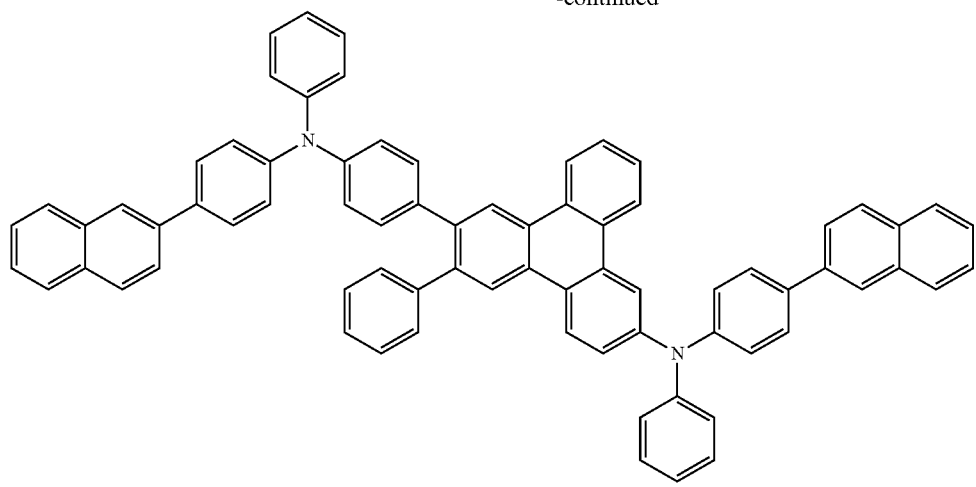
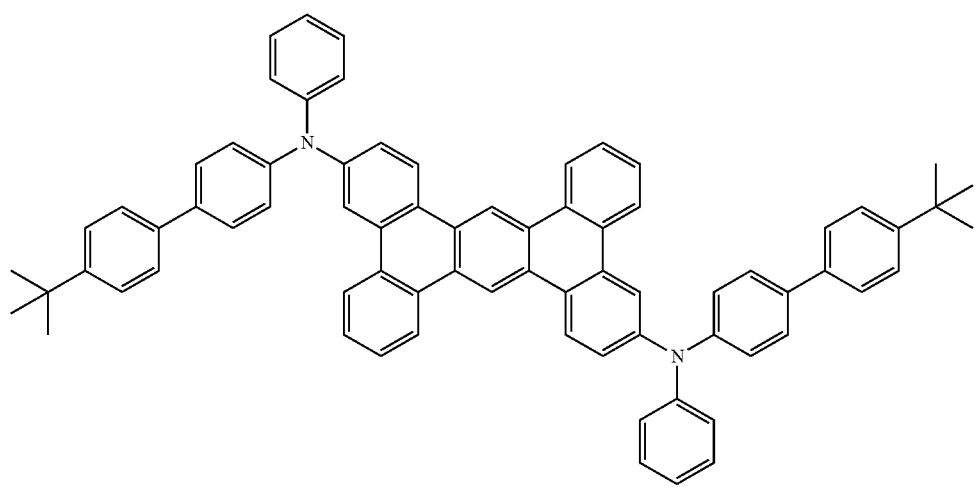
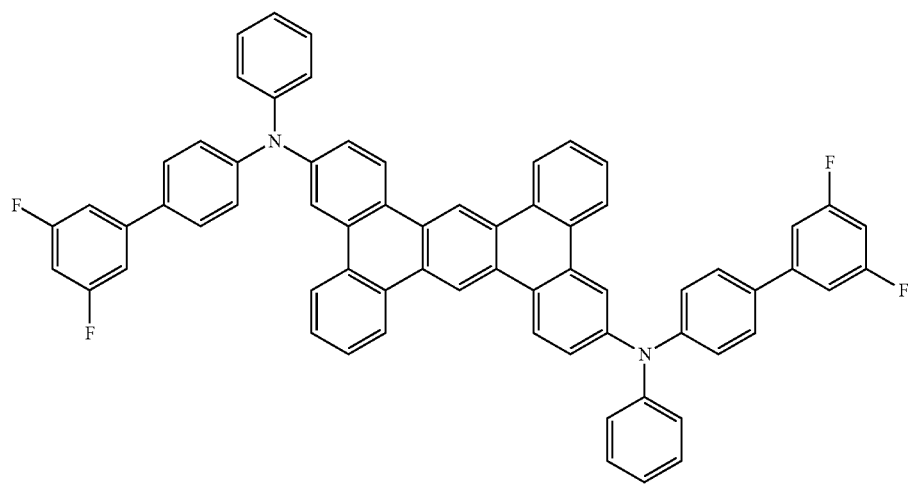

-continued
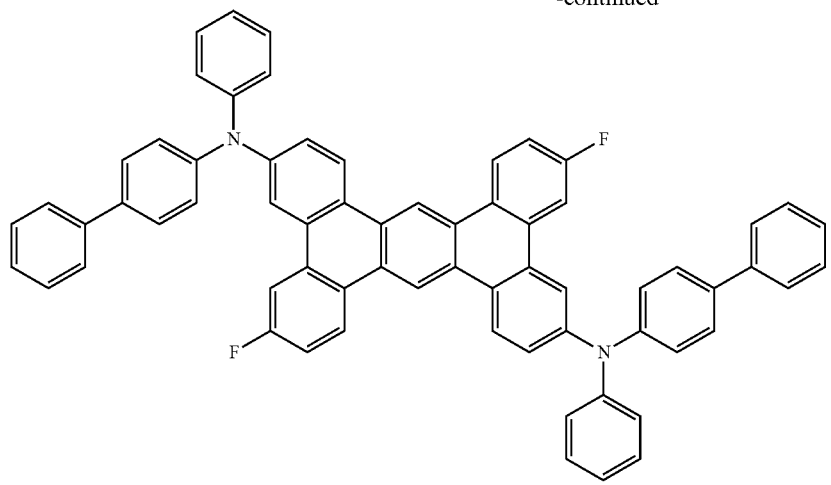
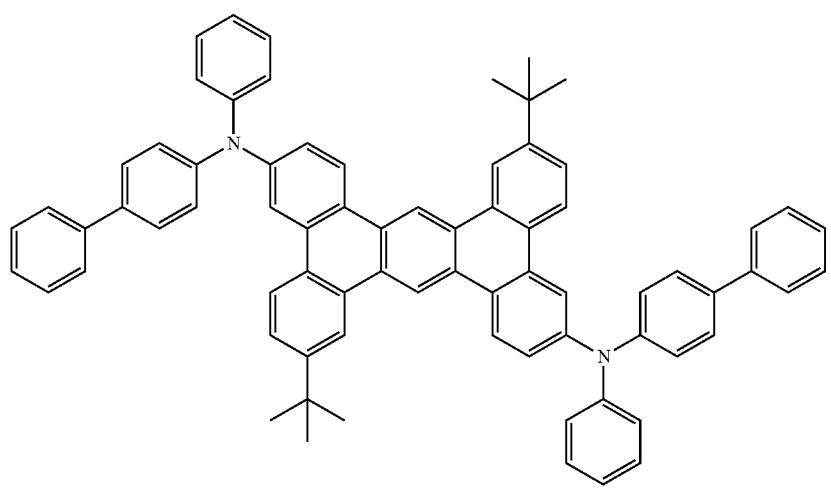
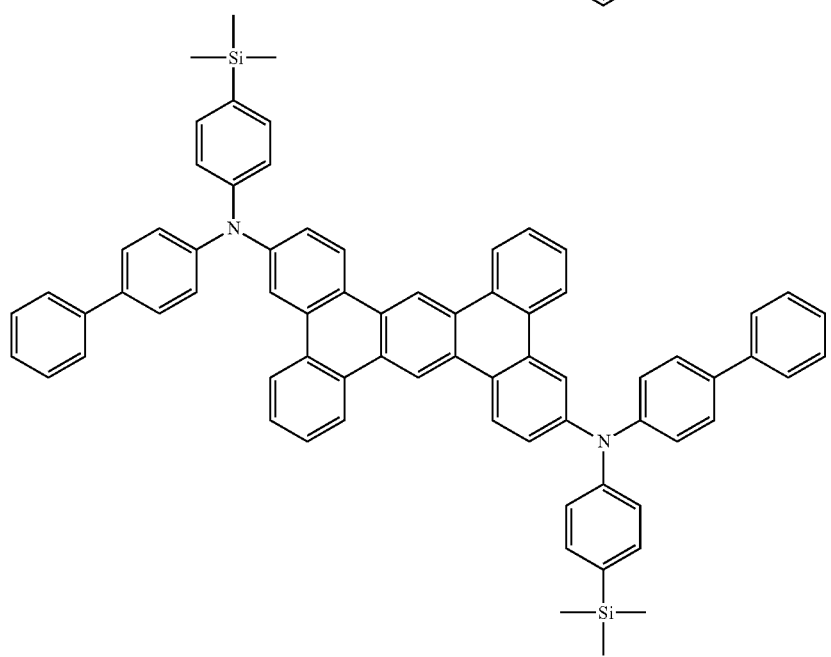

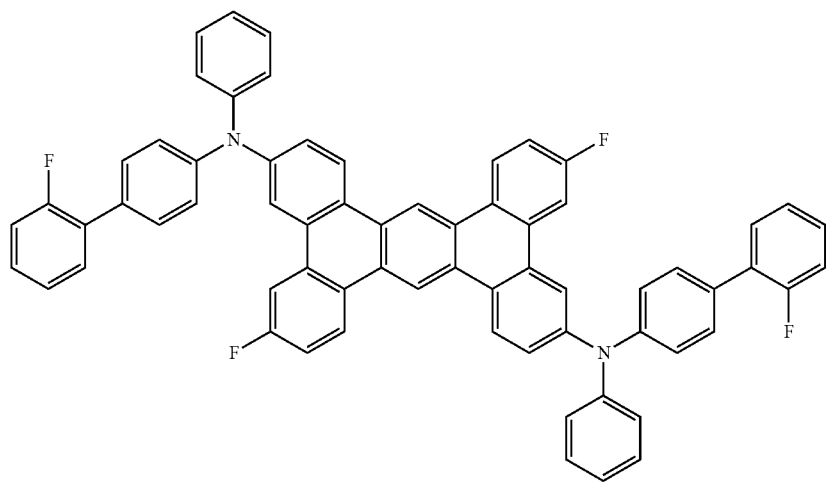
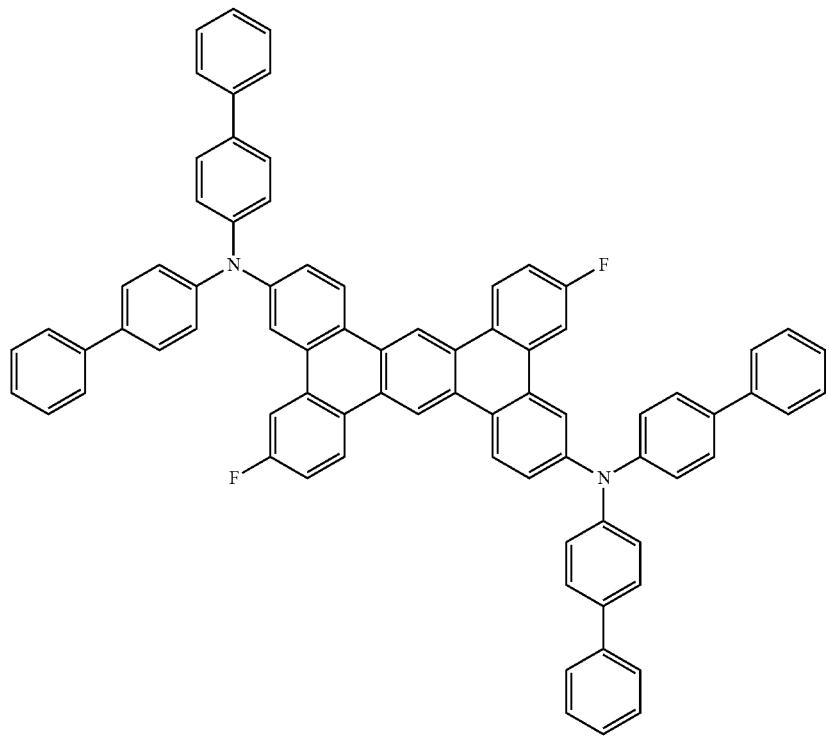

-continued
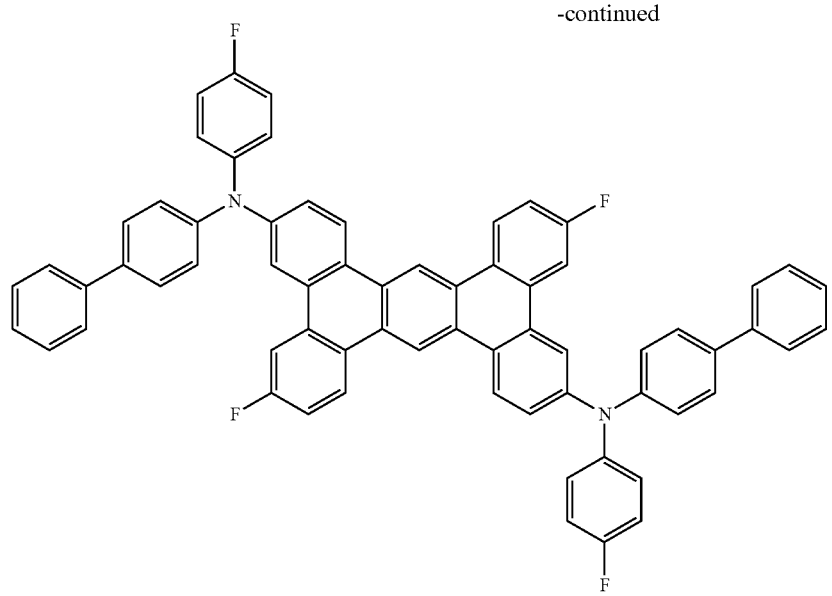
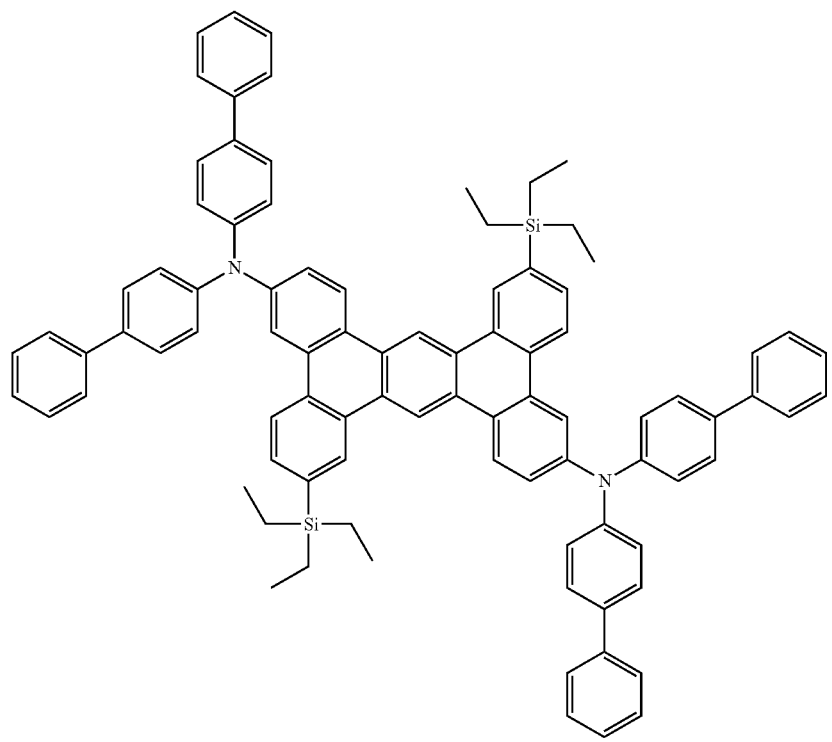

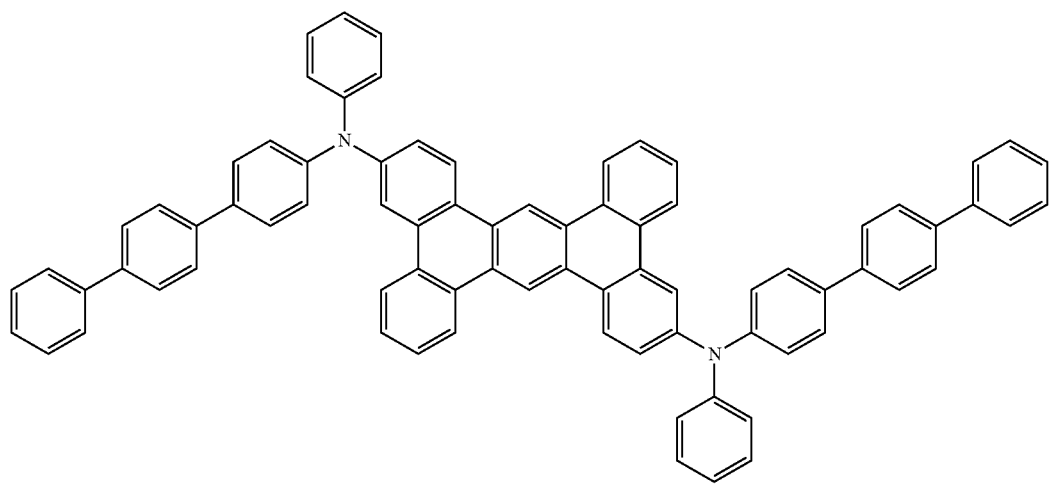
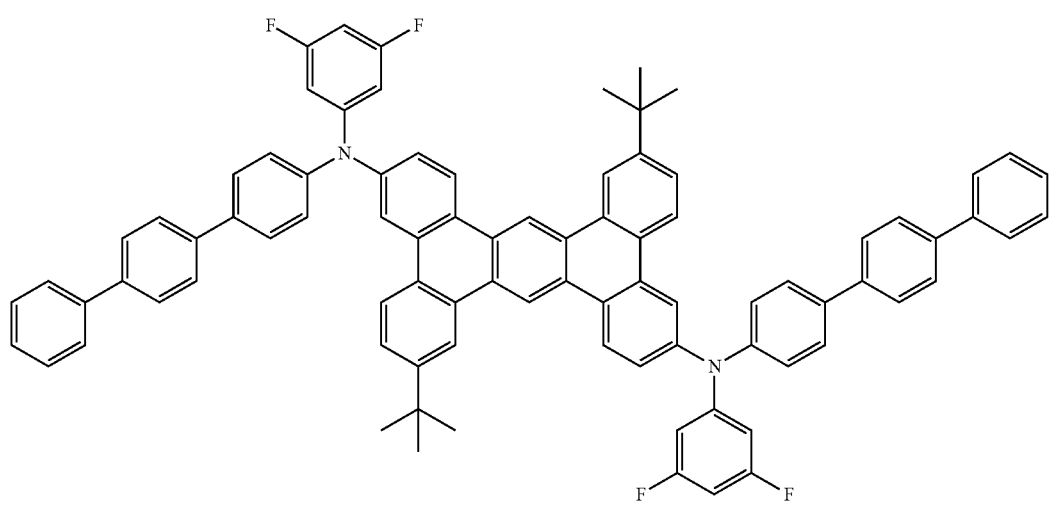
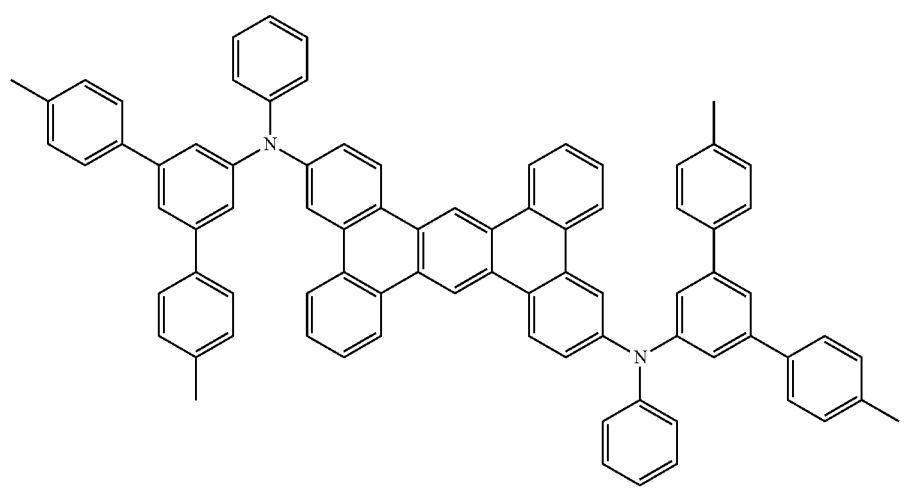

101
102
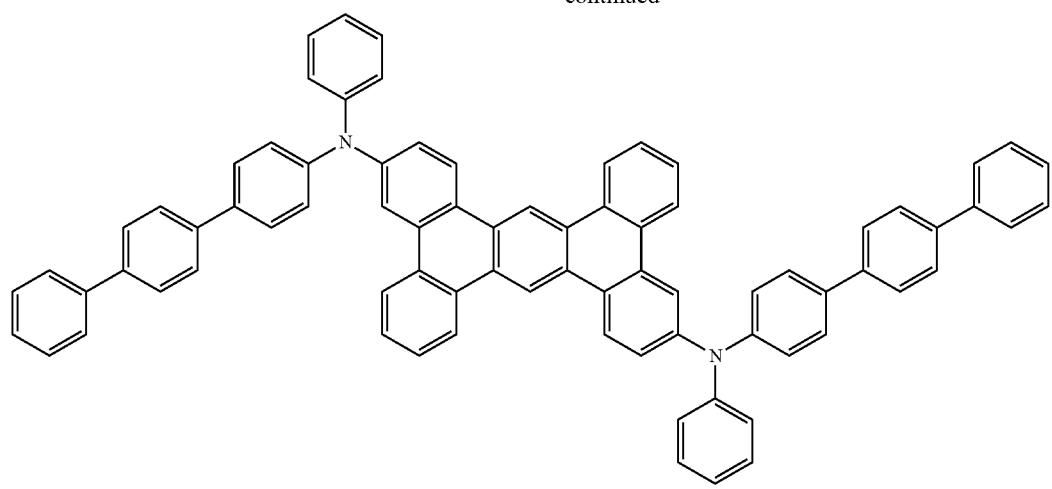
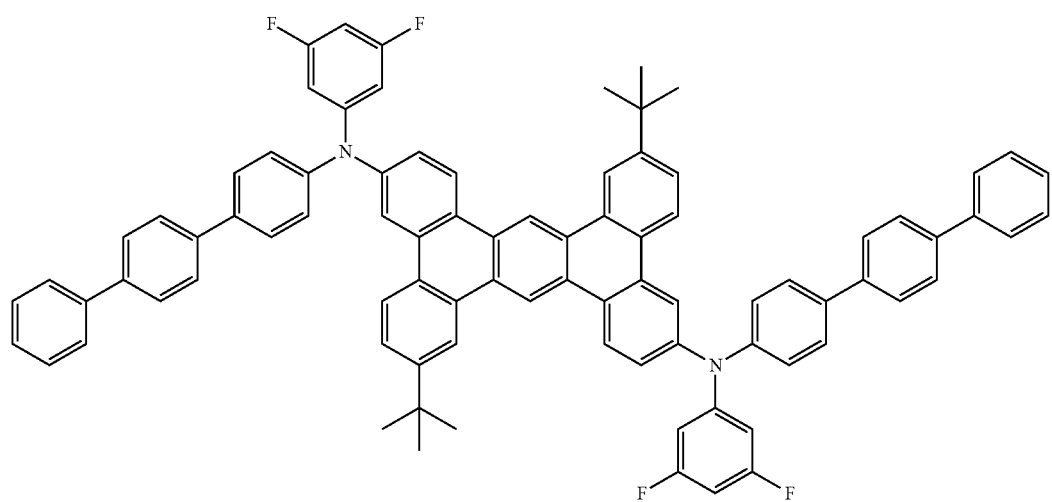
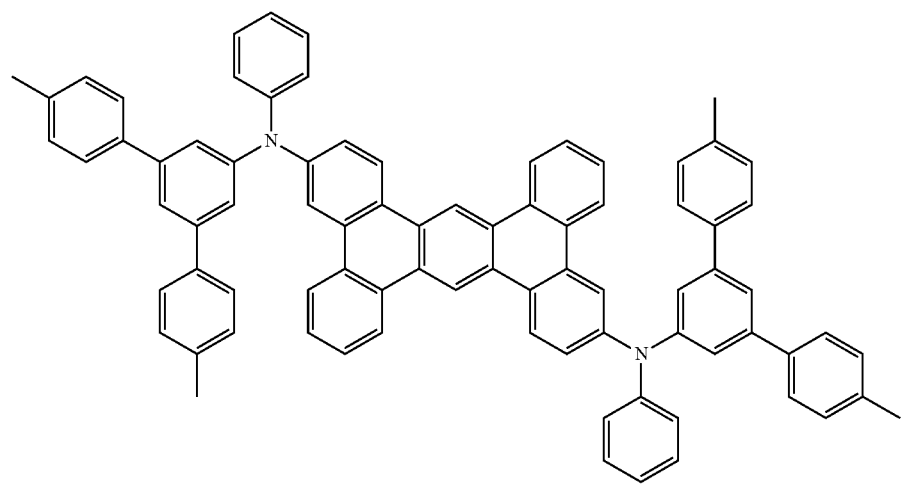

-continued
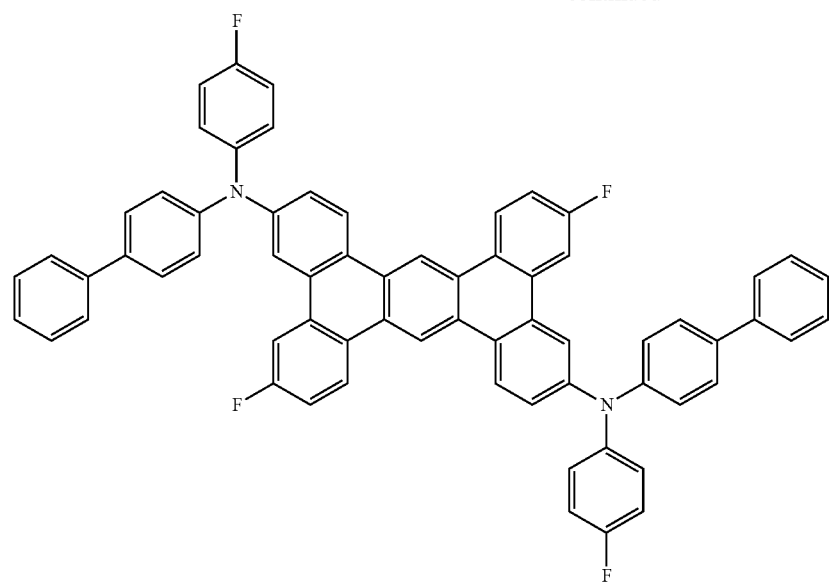
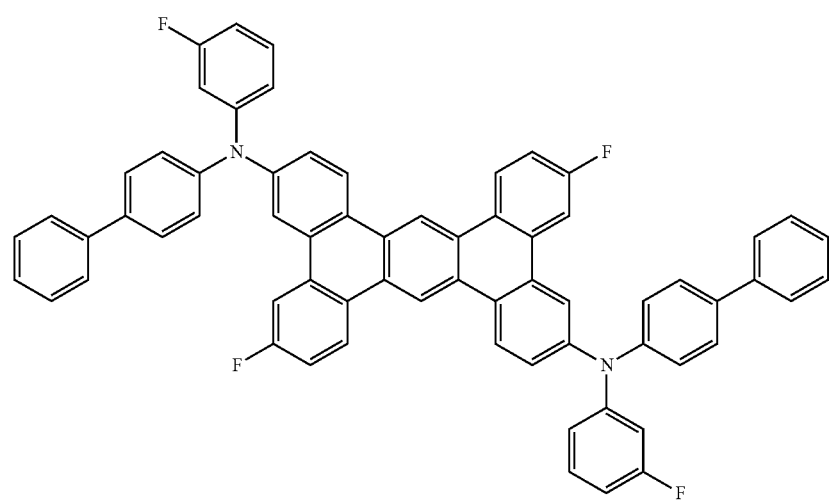
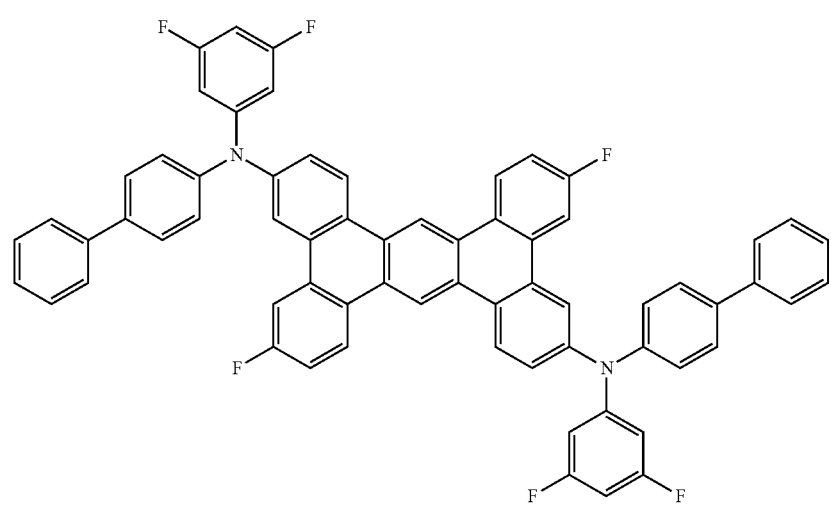

105
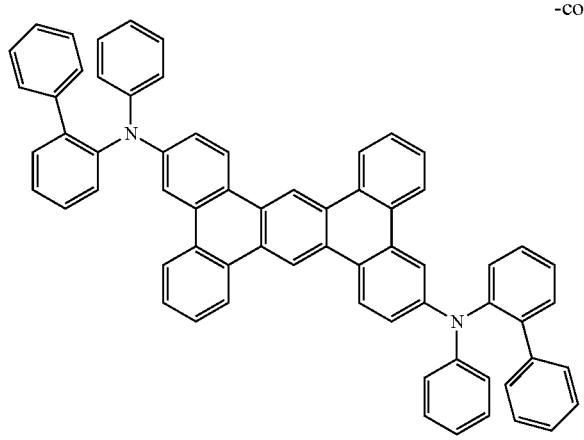
106
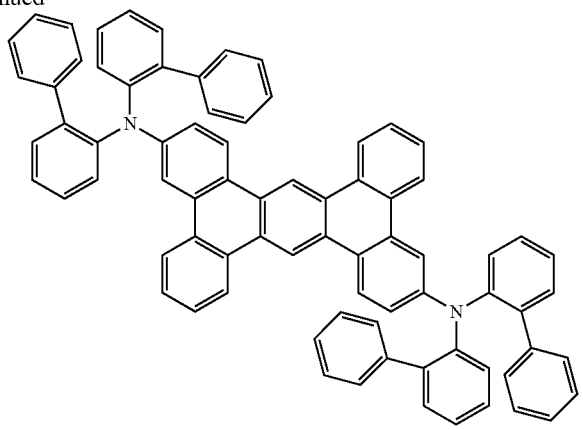
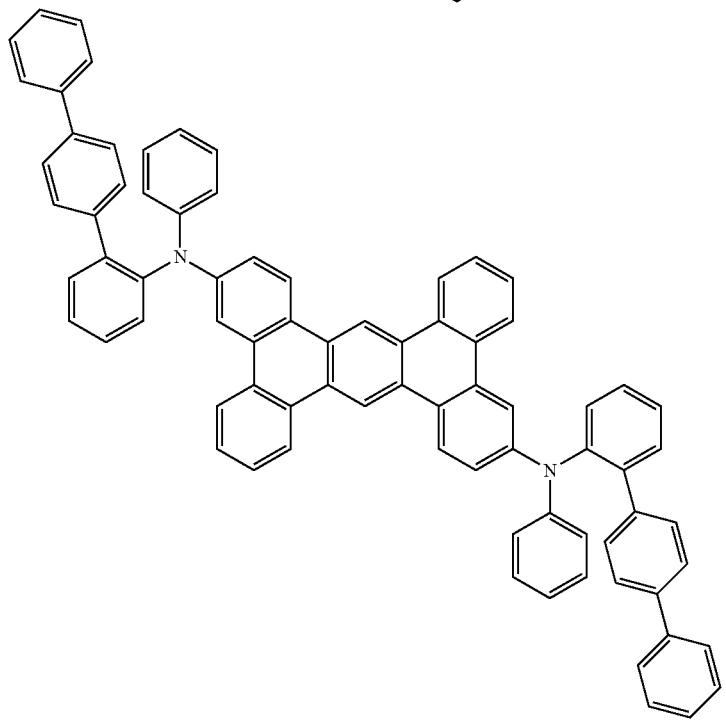
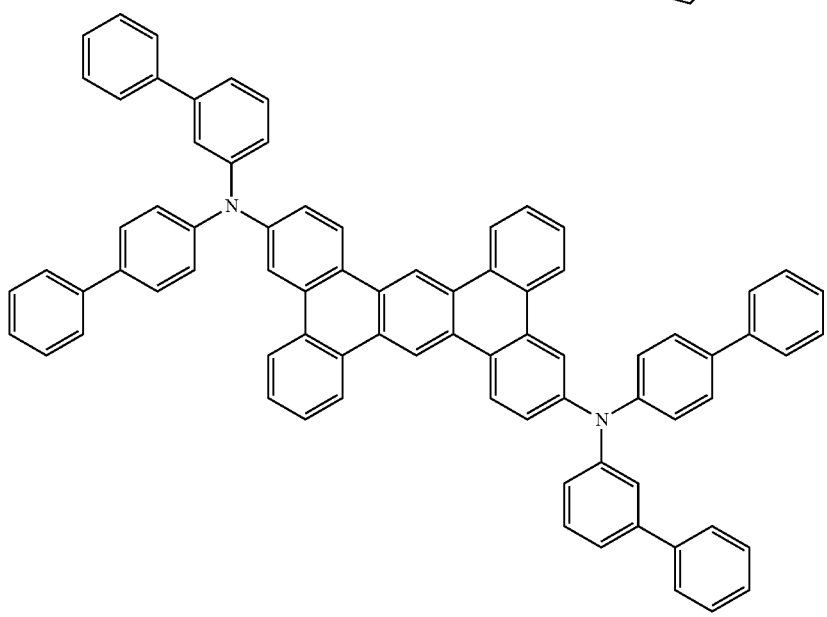

-continued
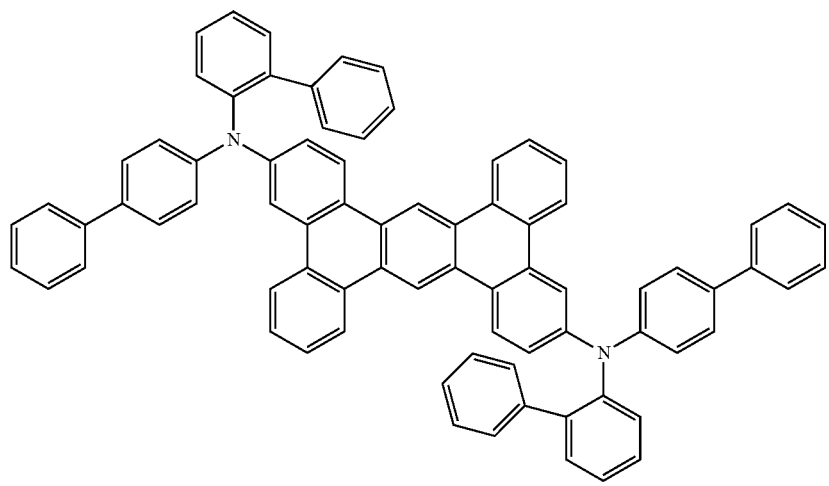
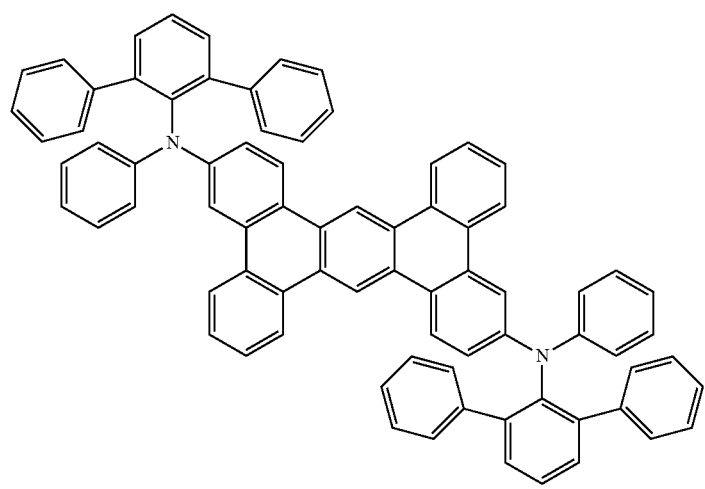
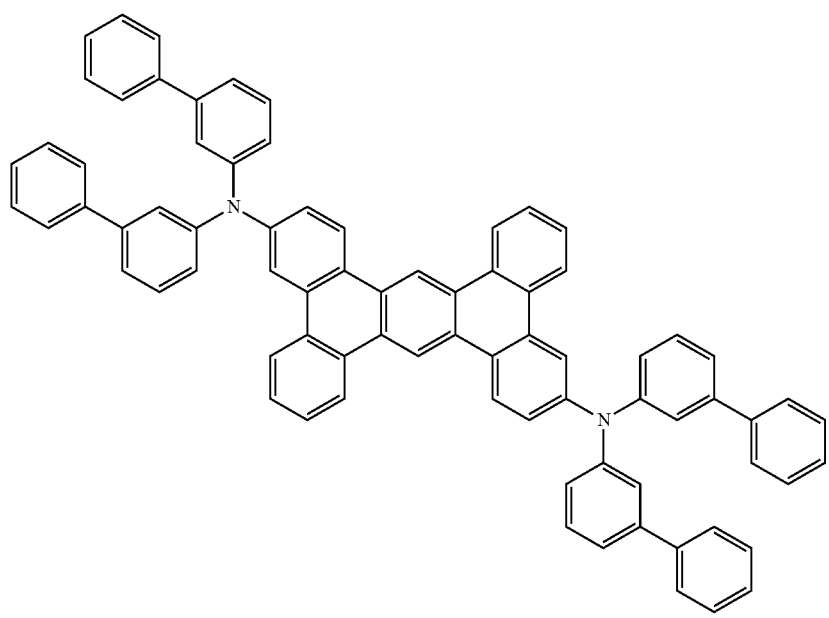

-continued
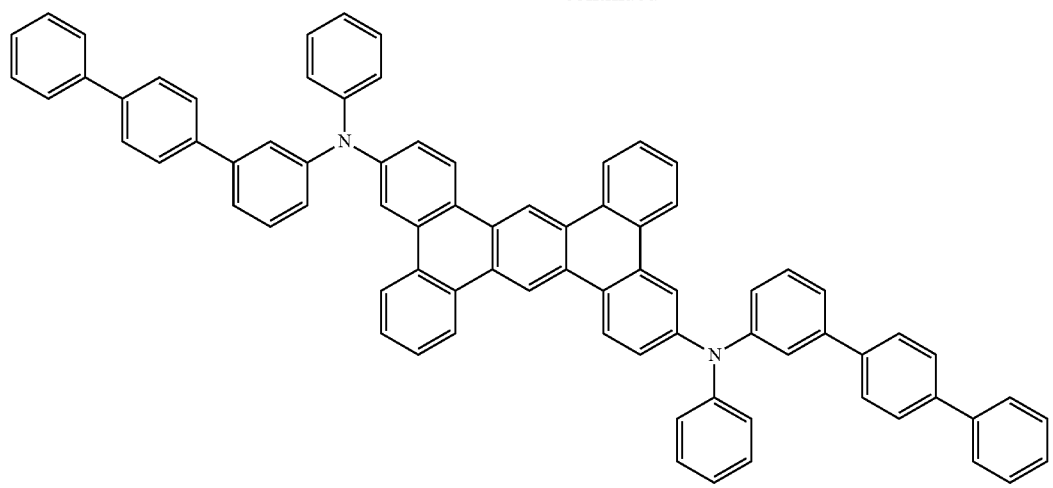
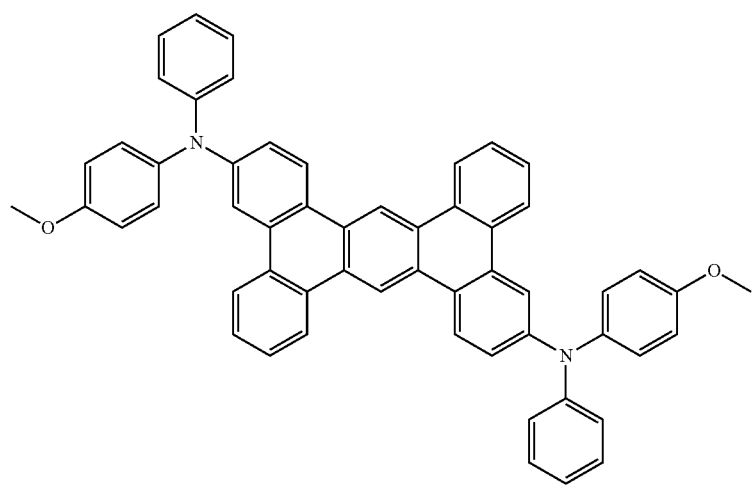
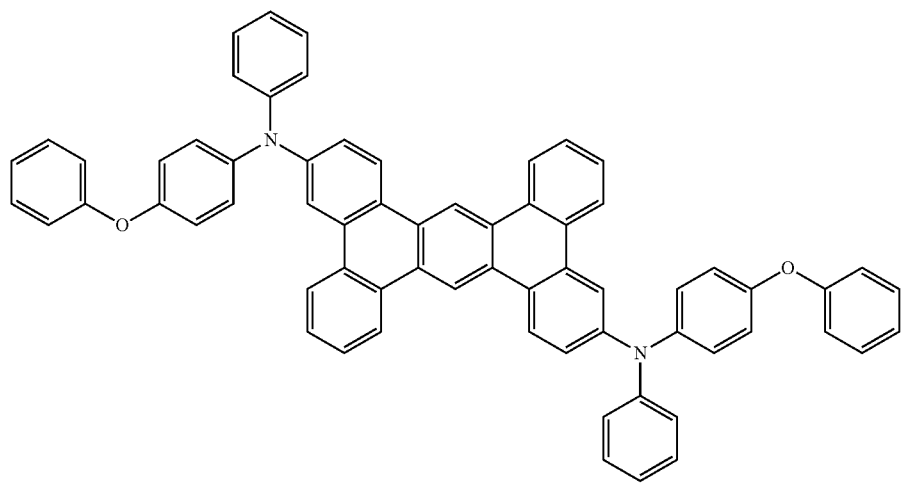

-continued
111 112
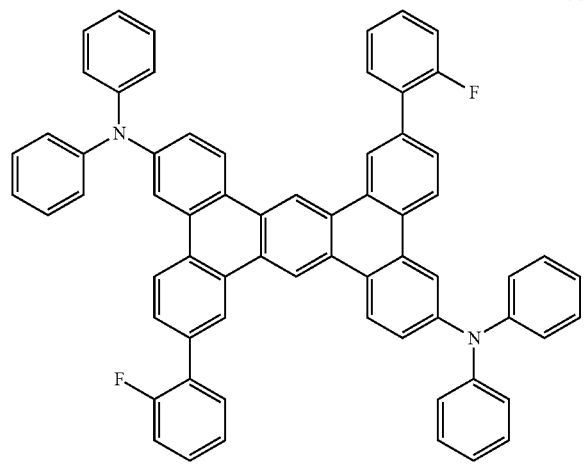 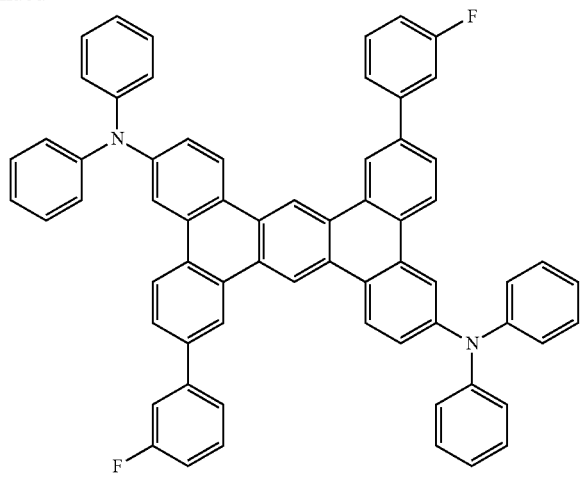
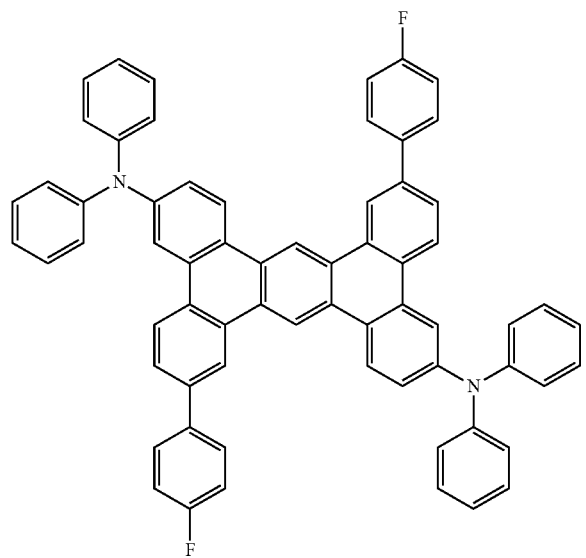 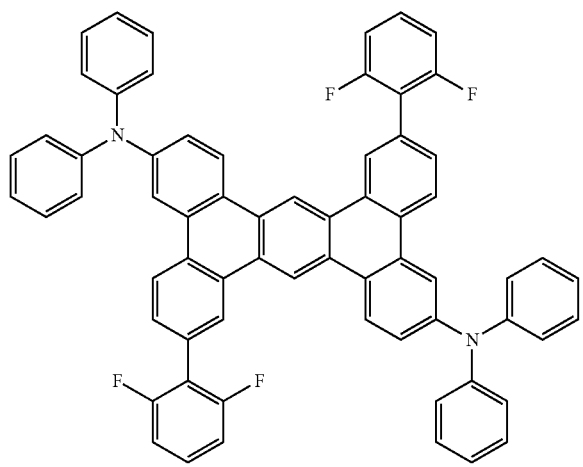
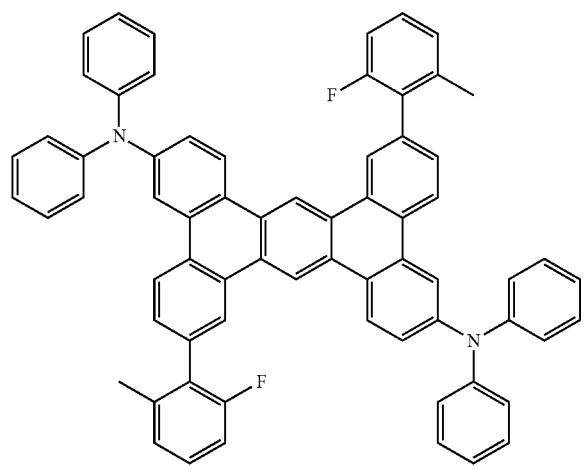 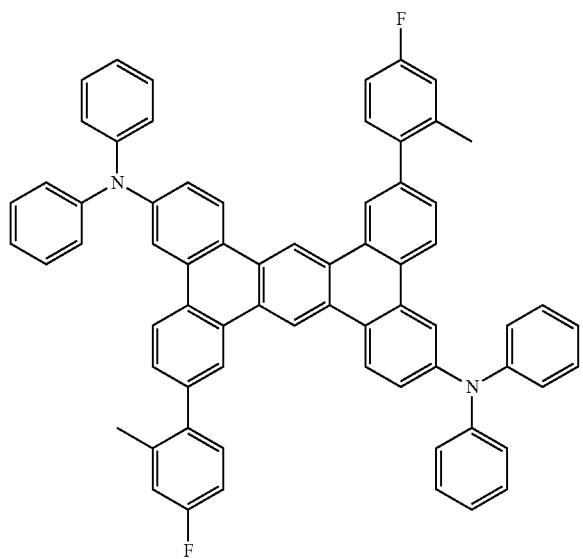

113
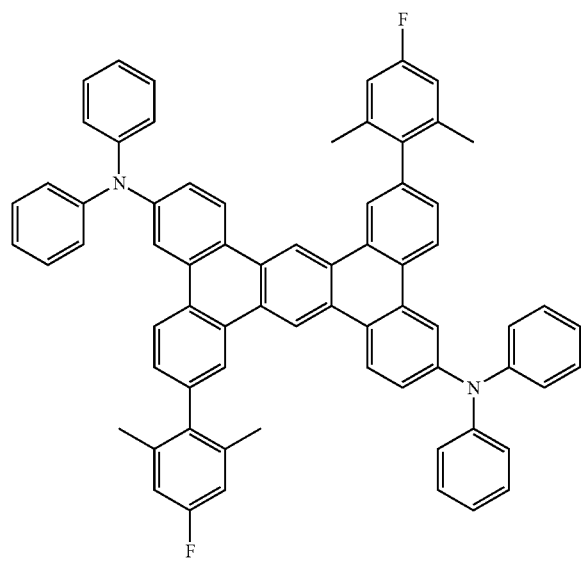
114
-continued
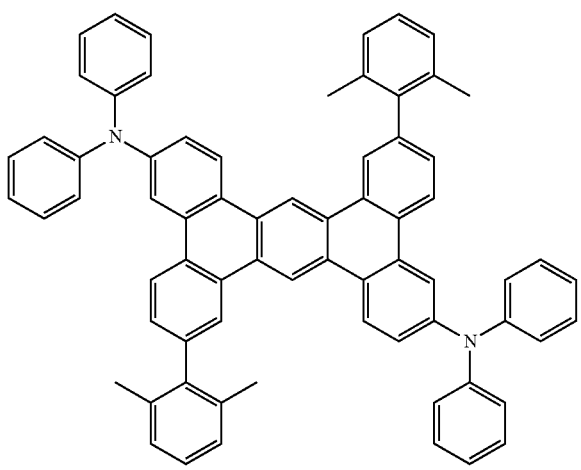
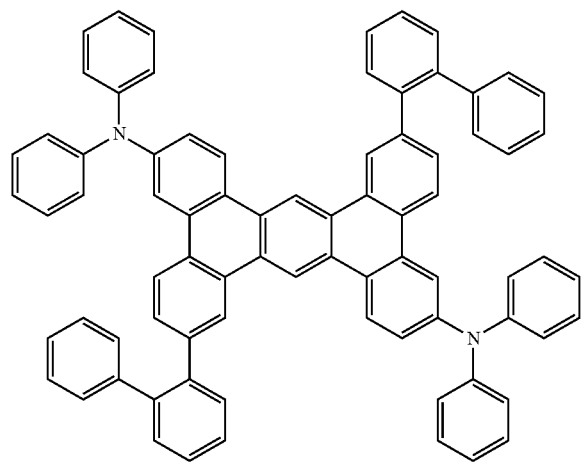
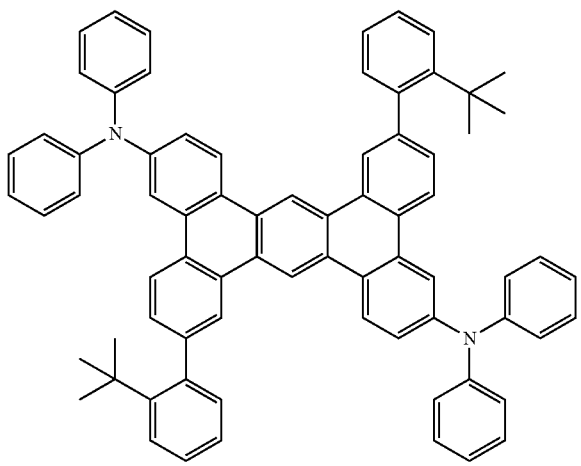
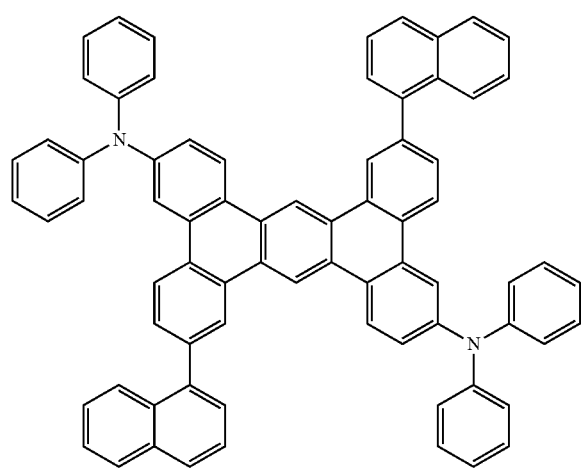
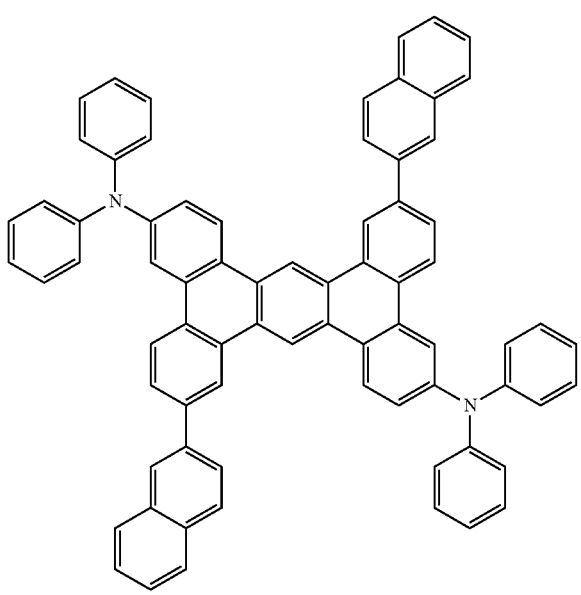

-continued
115
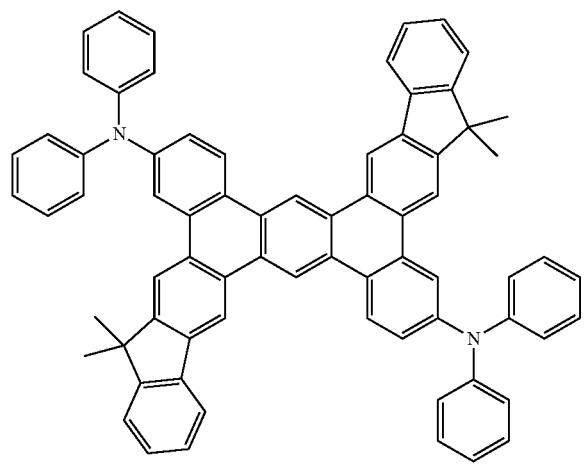
116
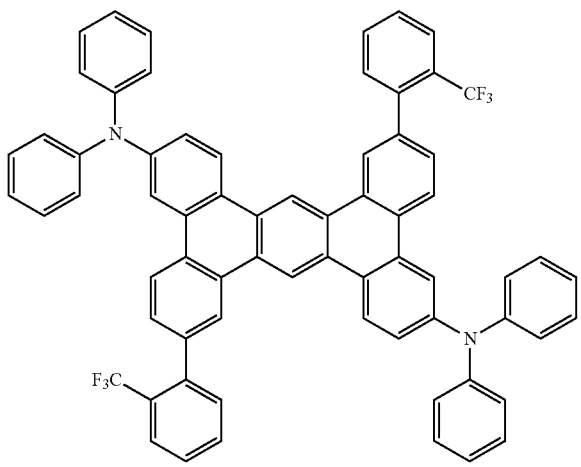
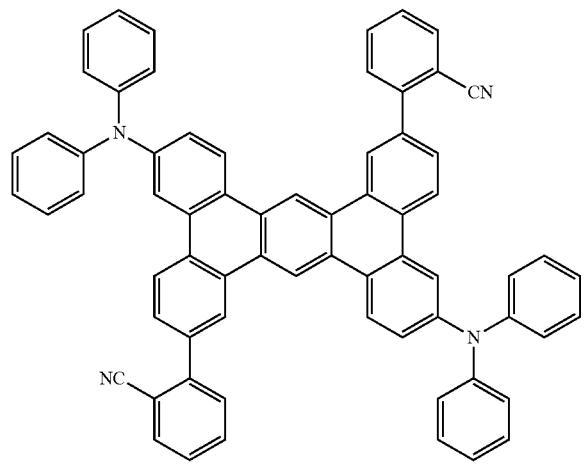
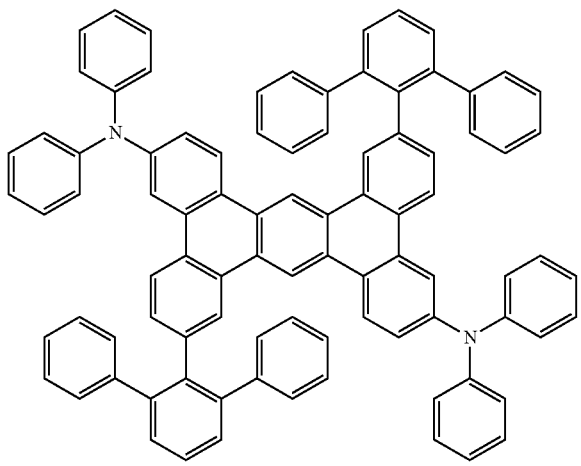
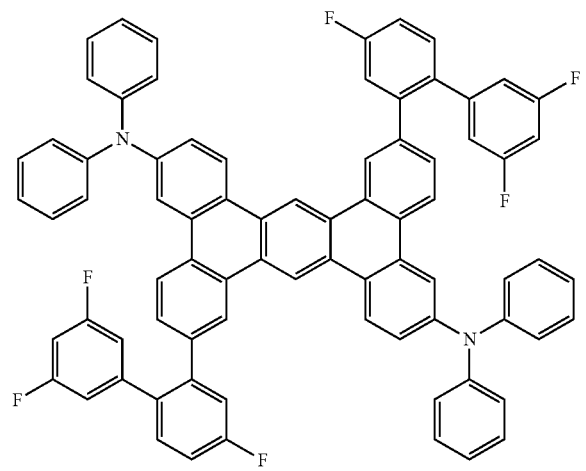
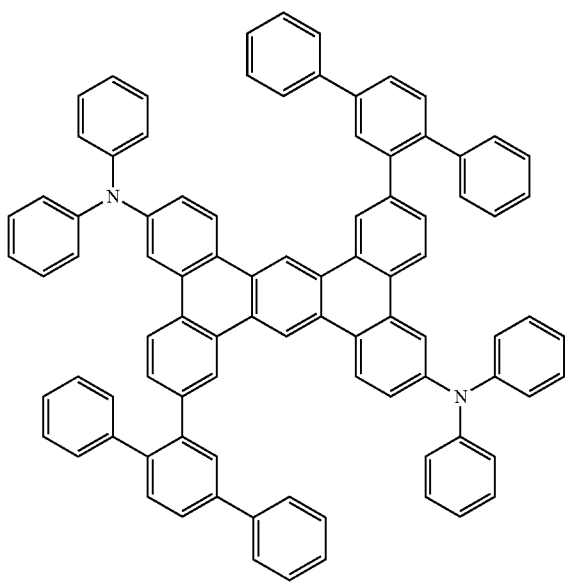

117
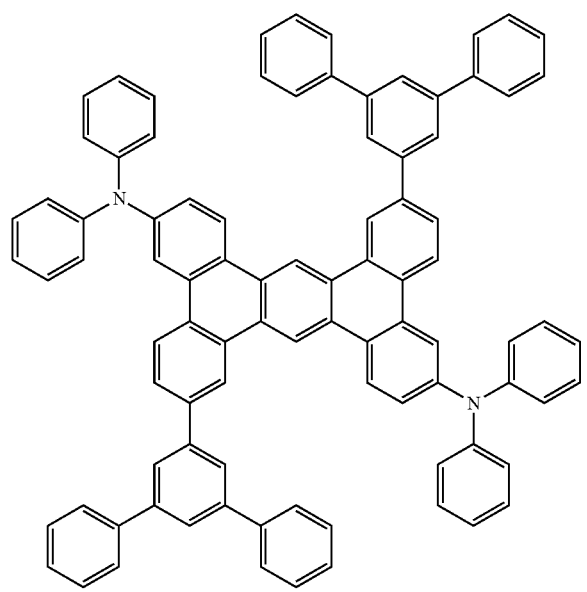
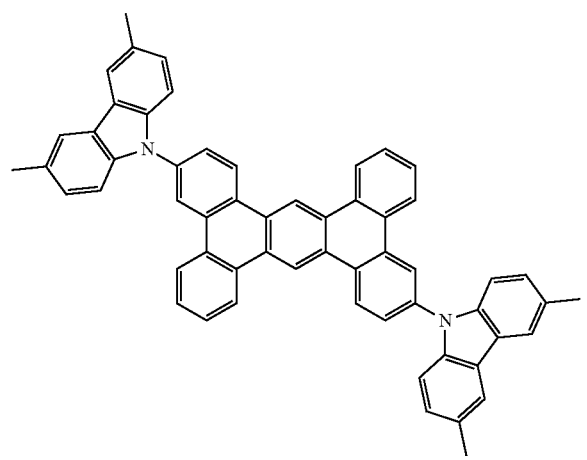
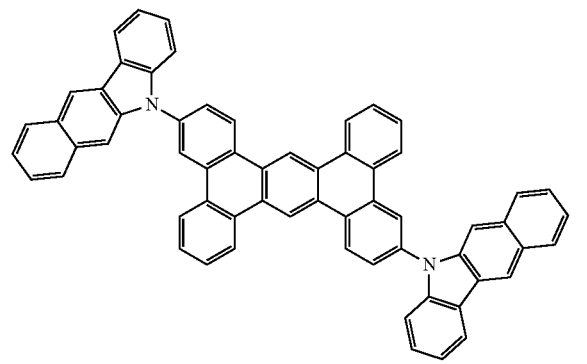
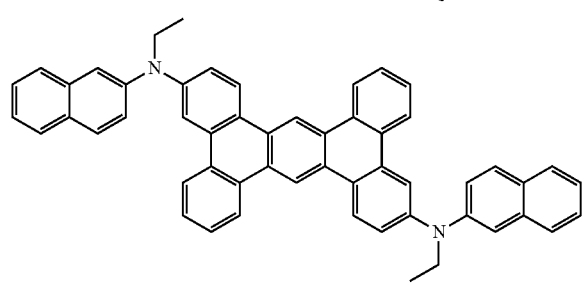
118
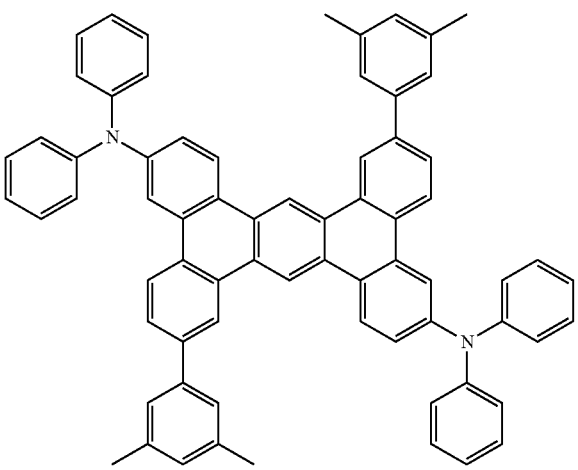
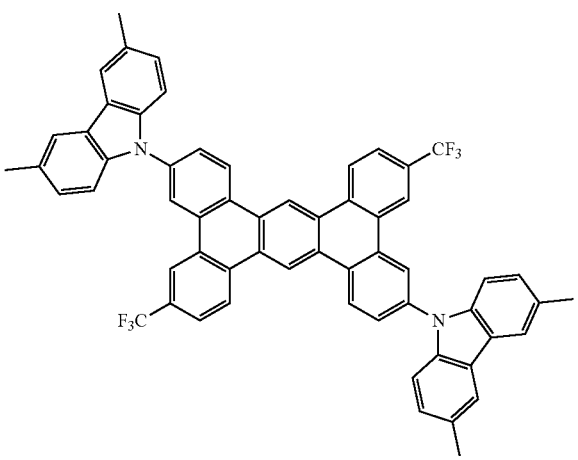
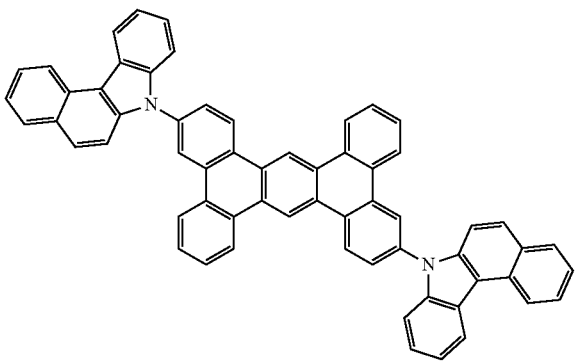
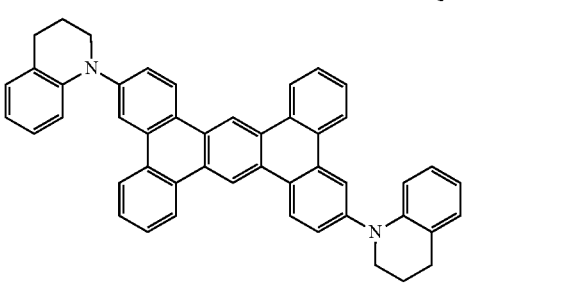

-continued
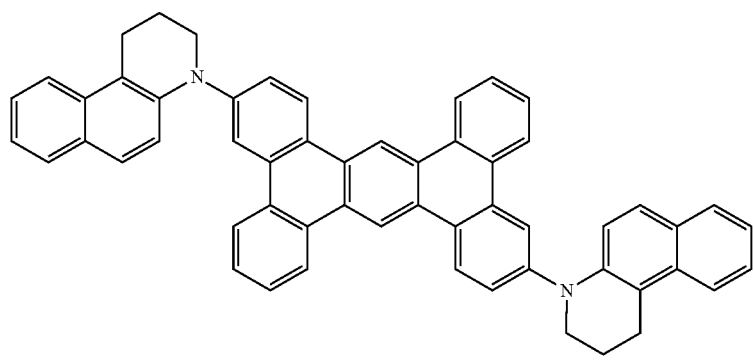
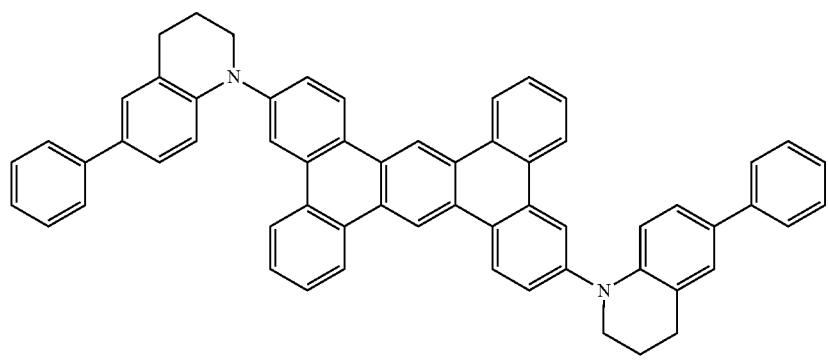
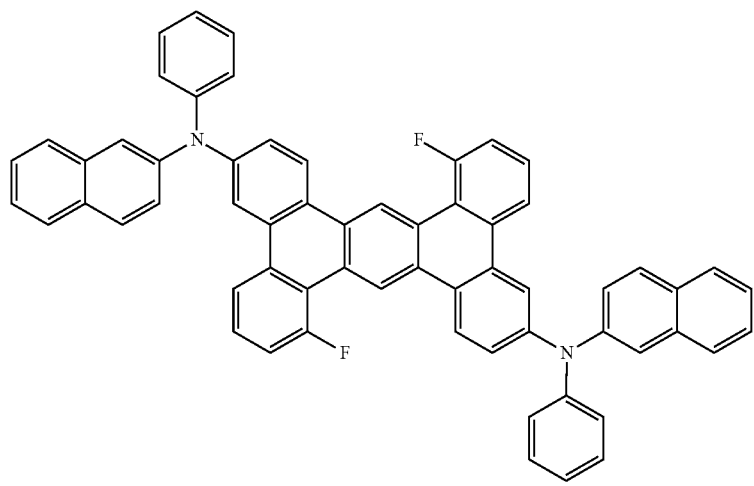
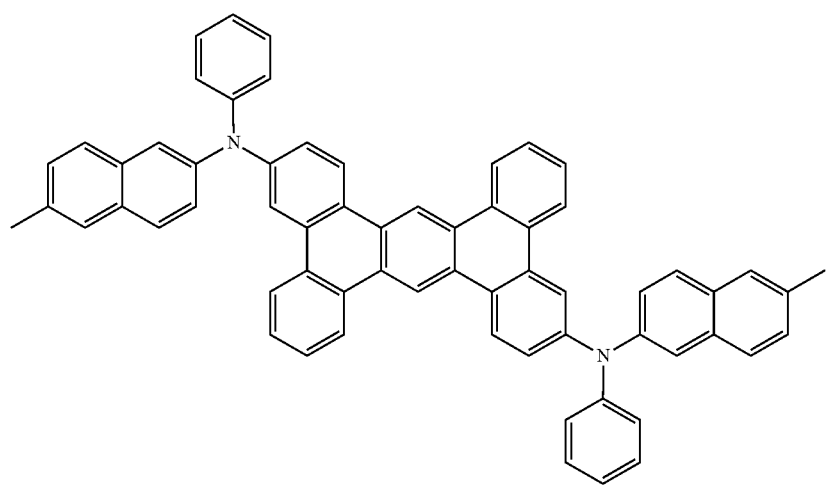

-continued
121
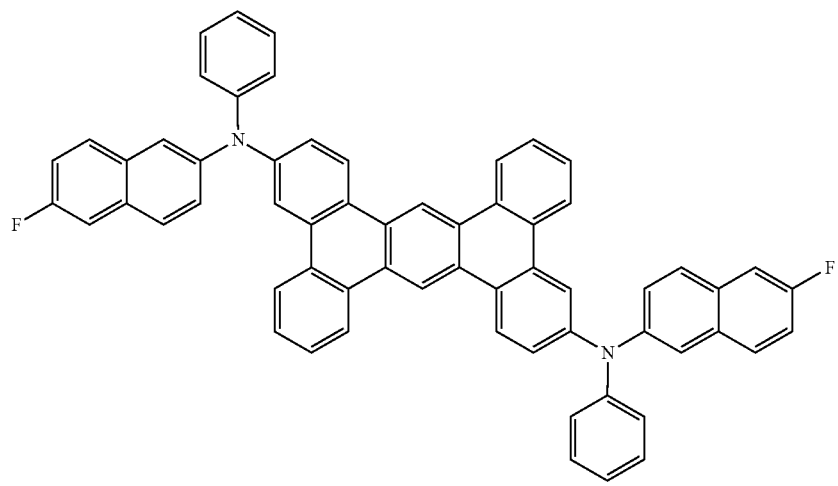
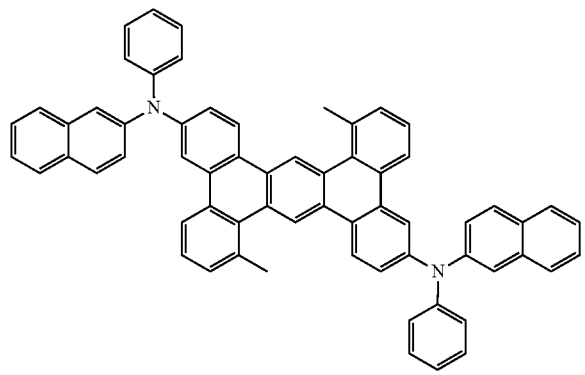
122
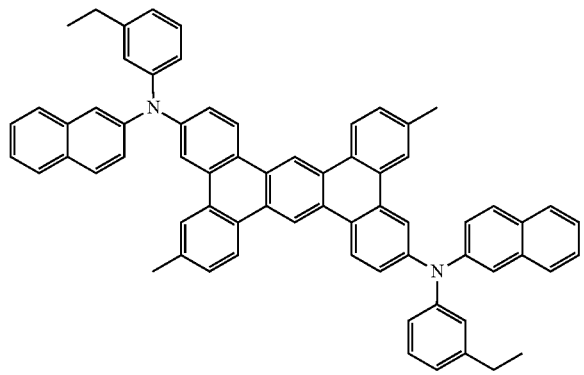
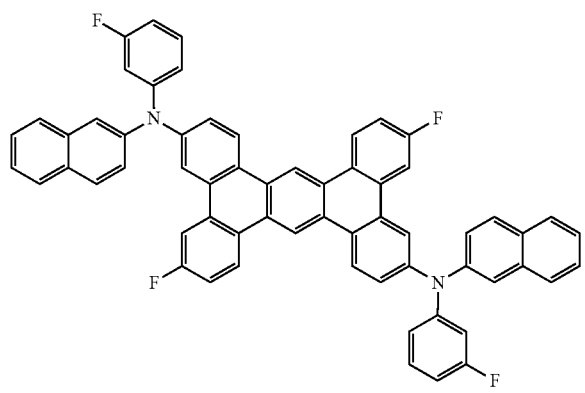
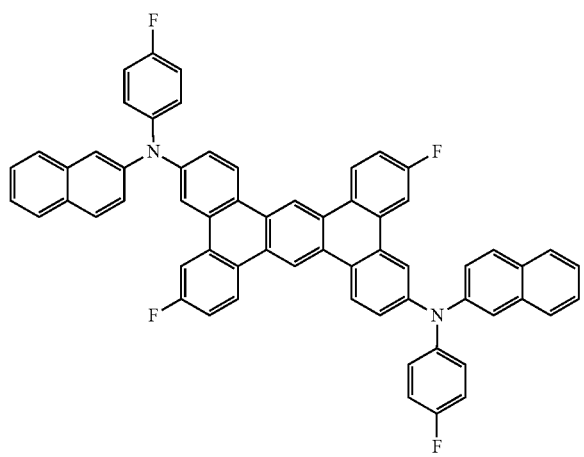

123
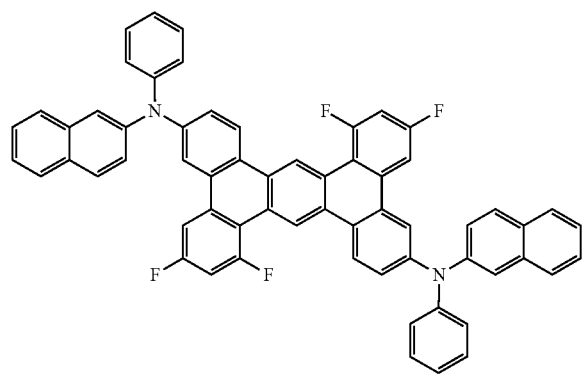
124
-continued
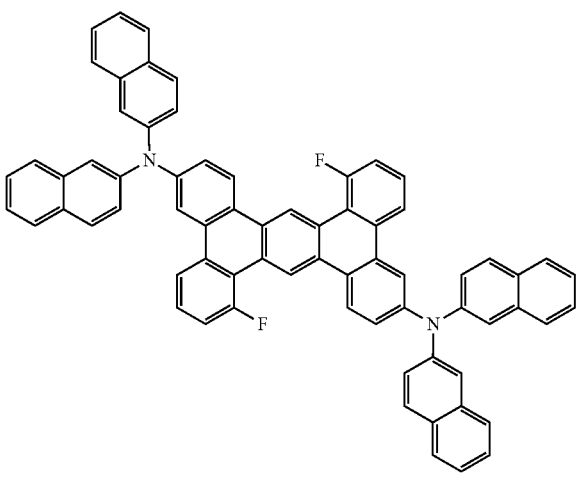
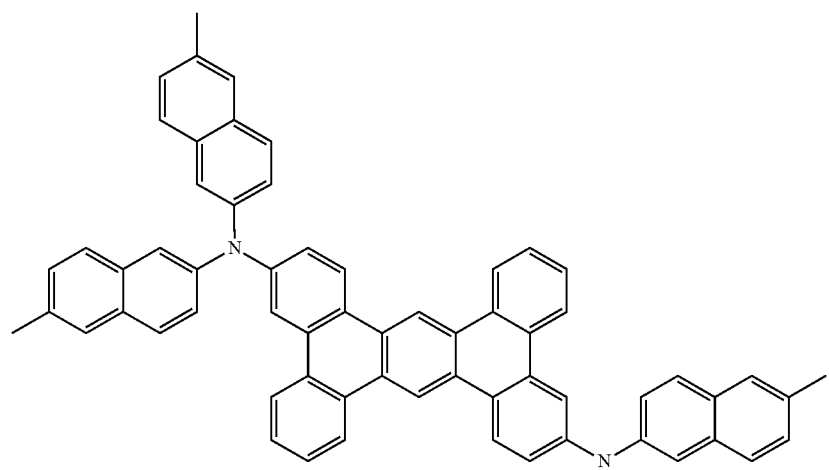
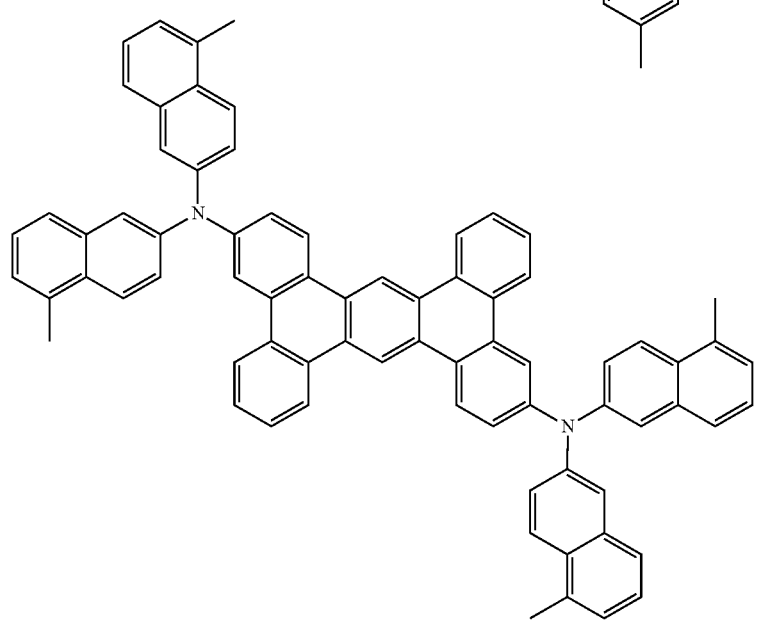

-continued
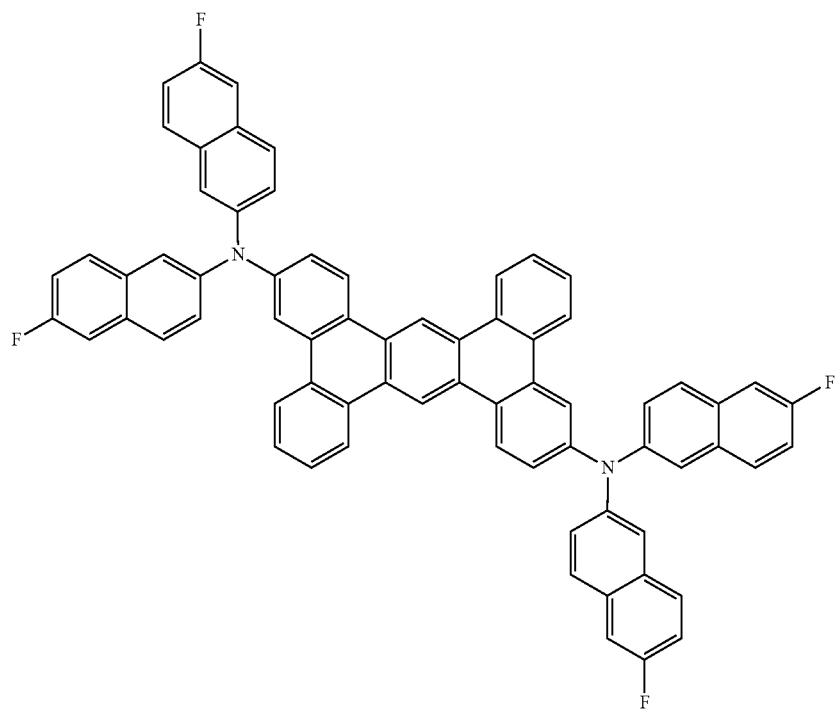
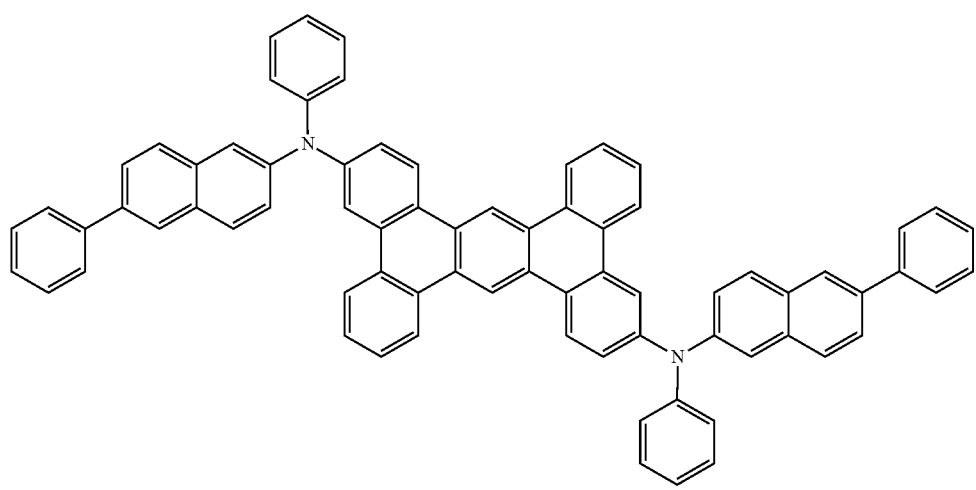
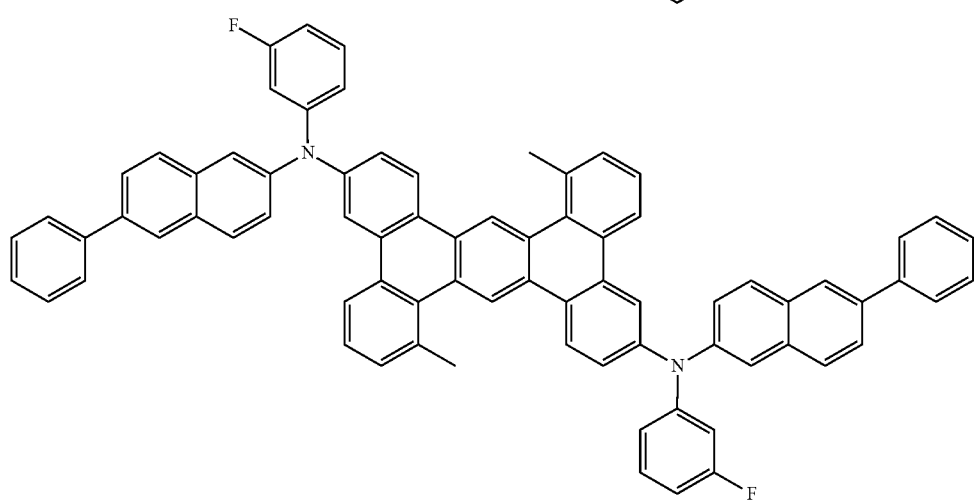

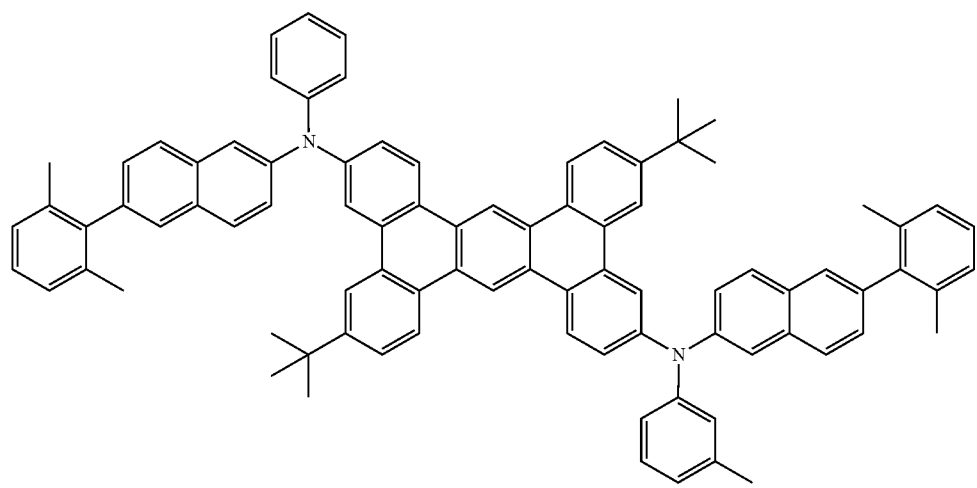
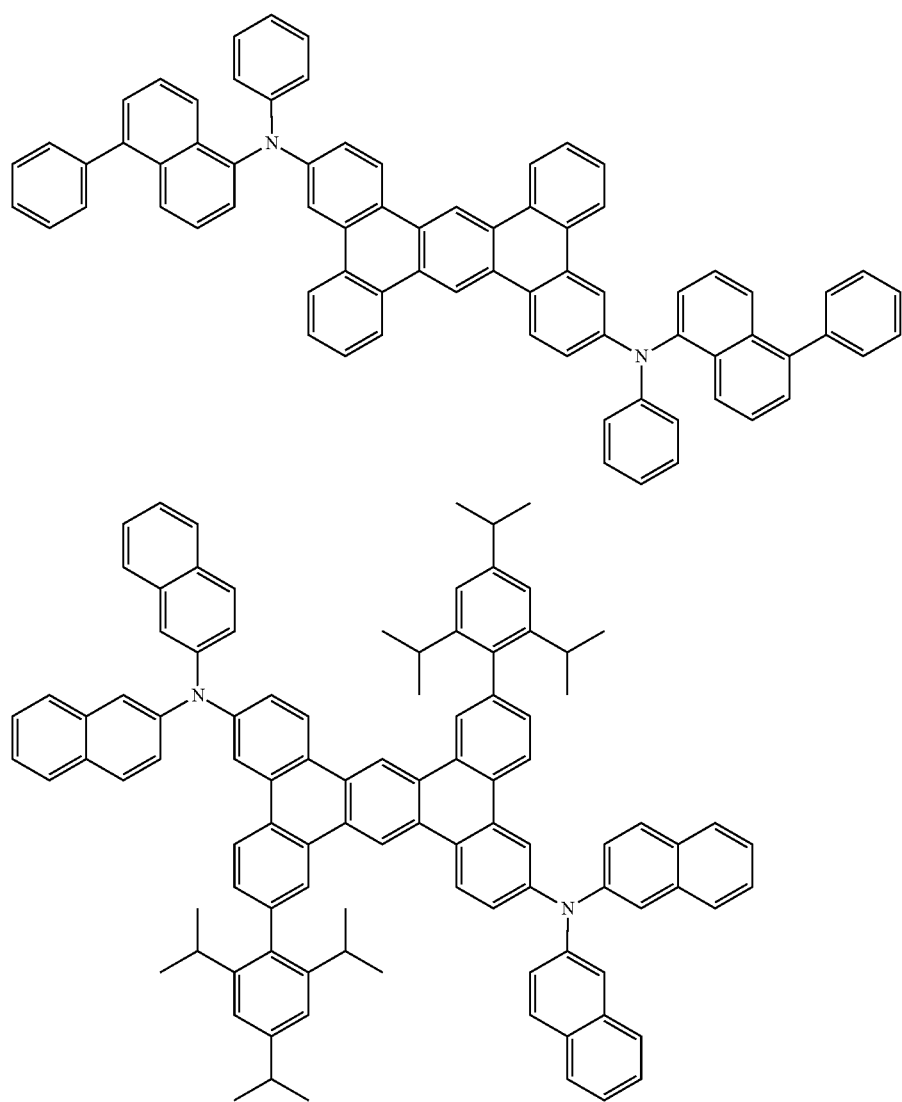

-continued
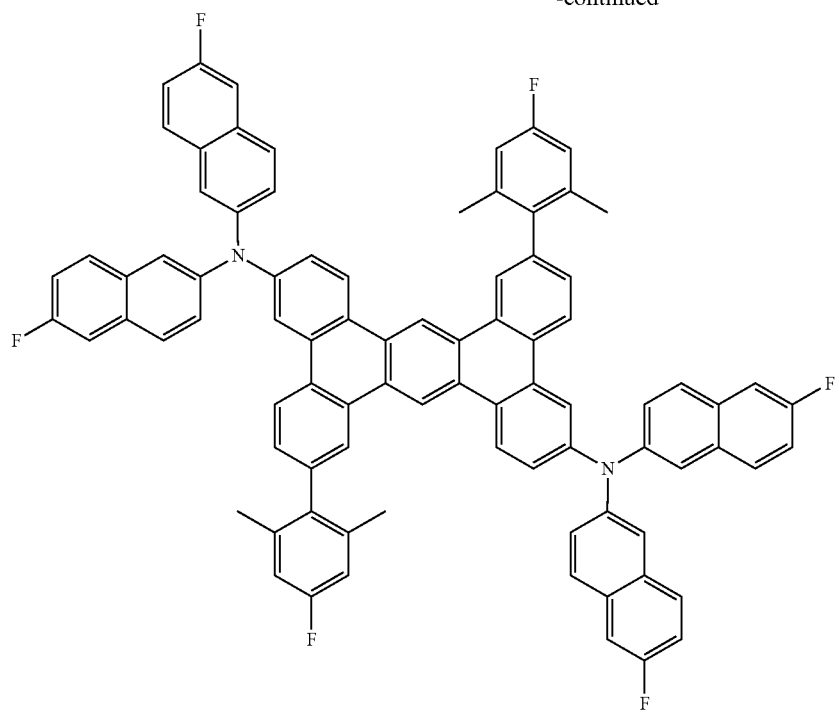
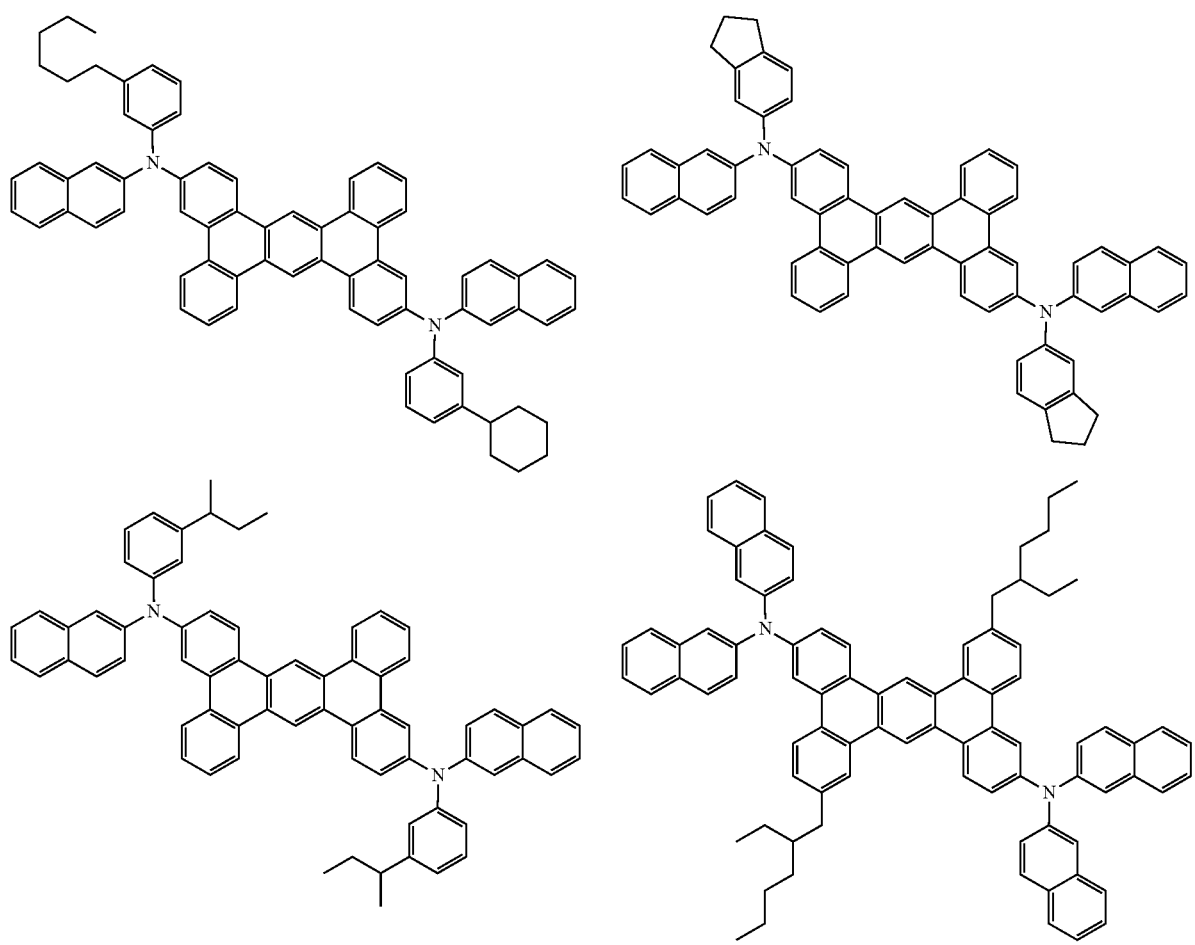

-continued
| 131 | 132 |
|---|---|
| 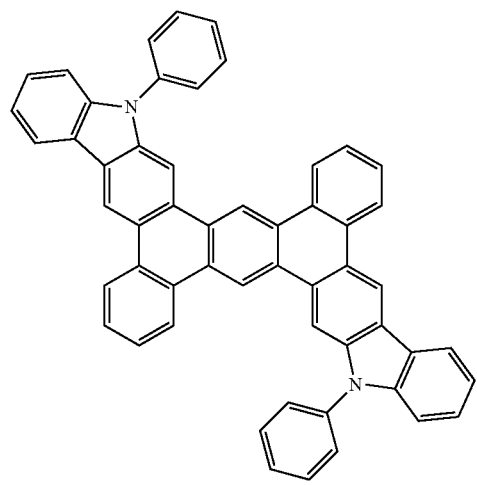 | 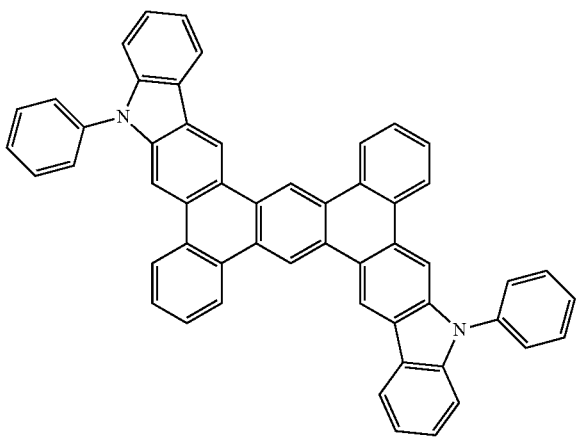 |
| 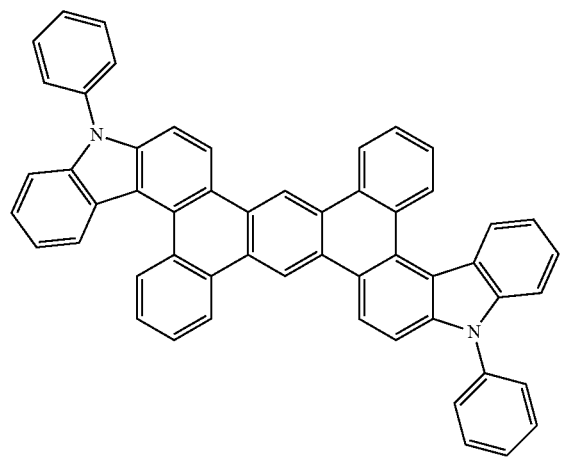 | 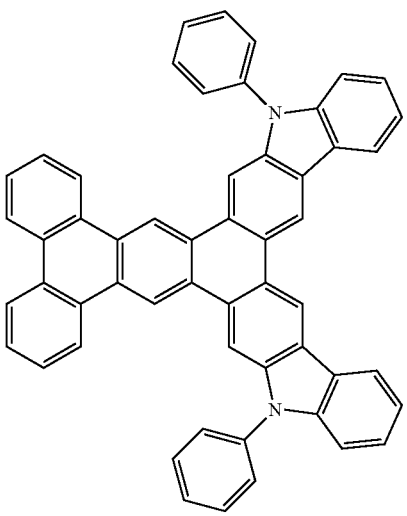 |
| 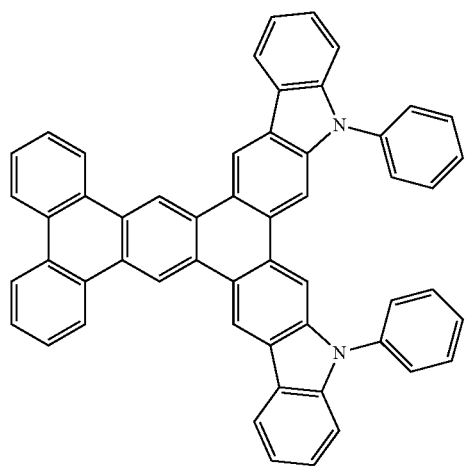 | 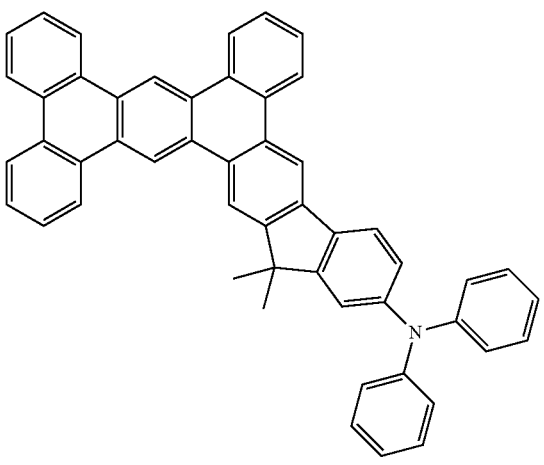 |

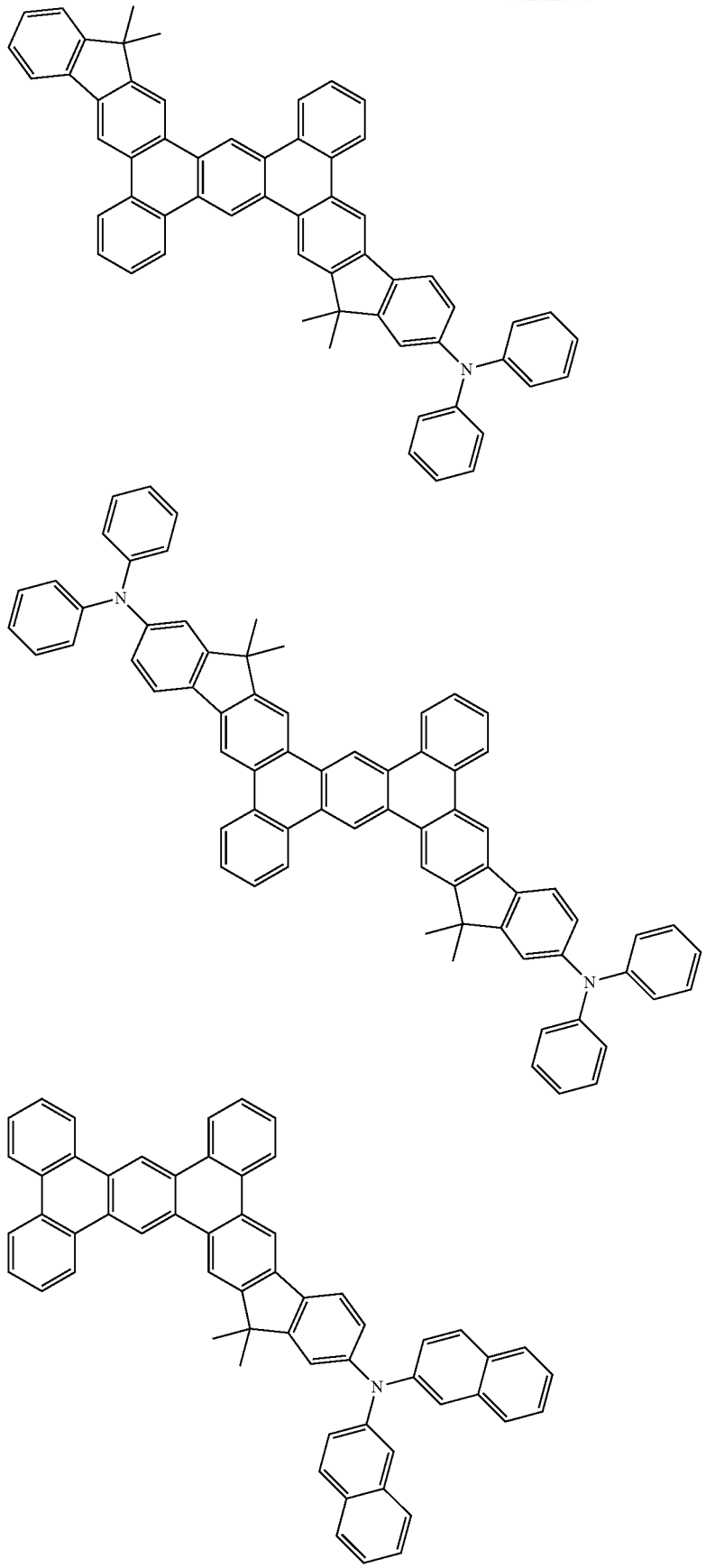

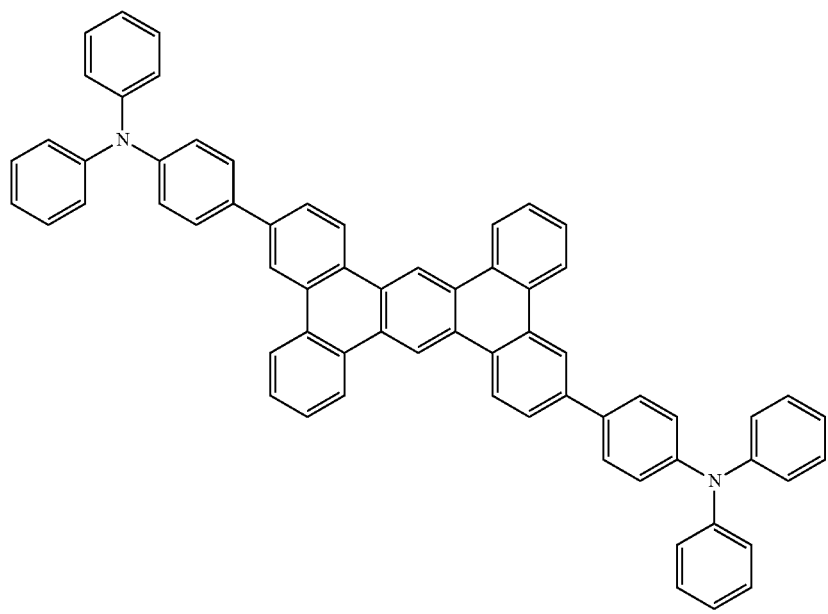
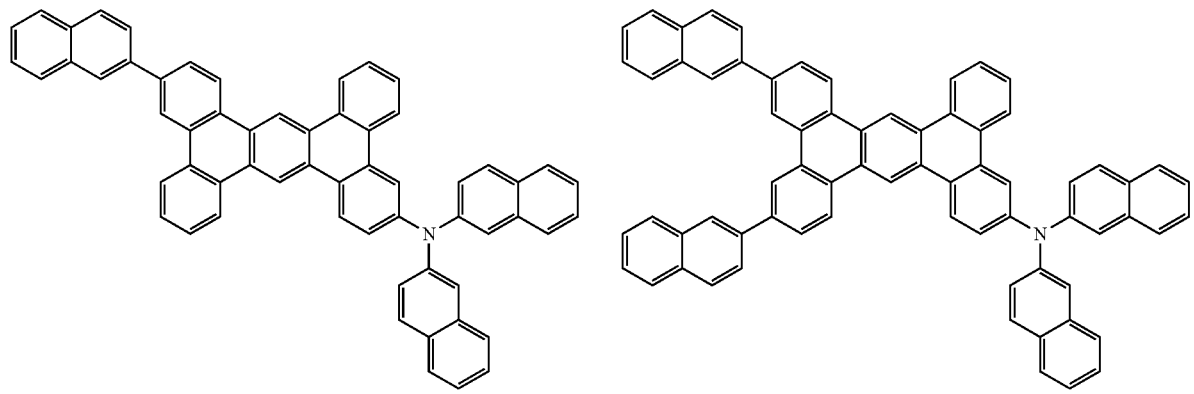
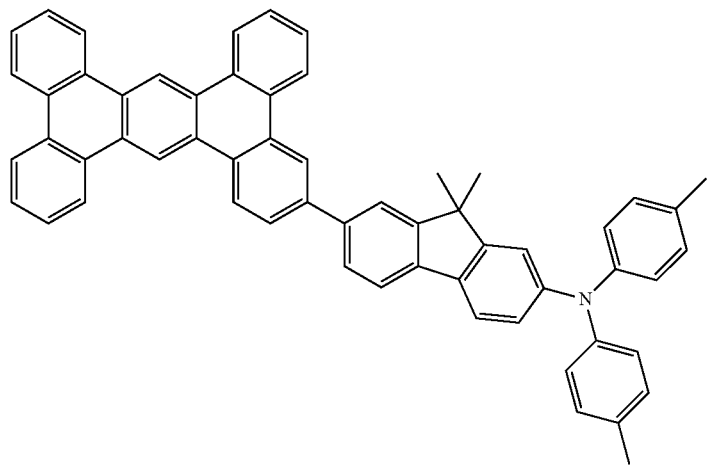

-continued
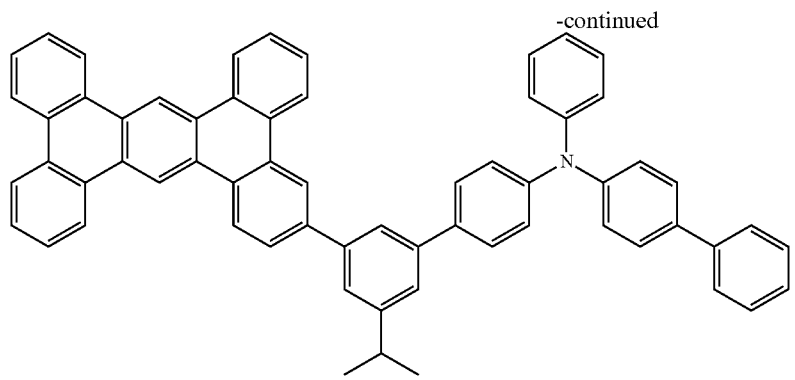
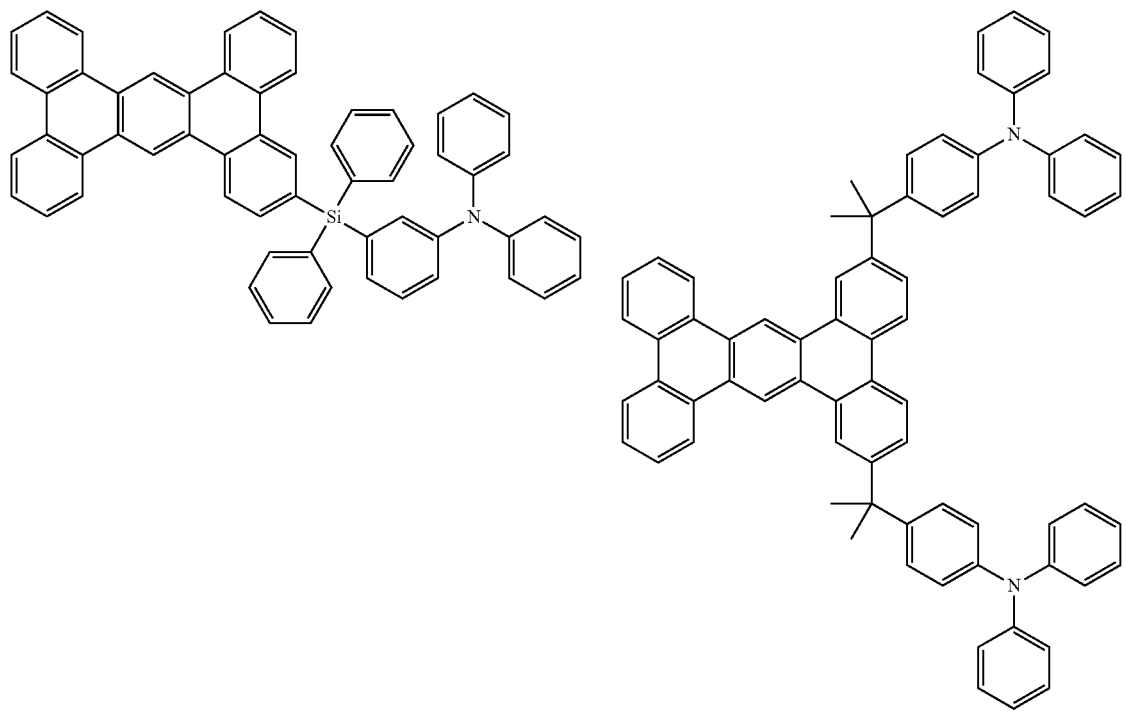
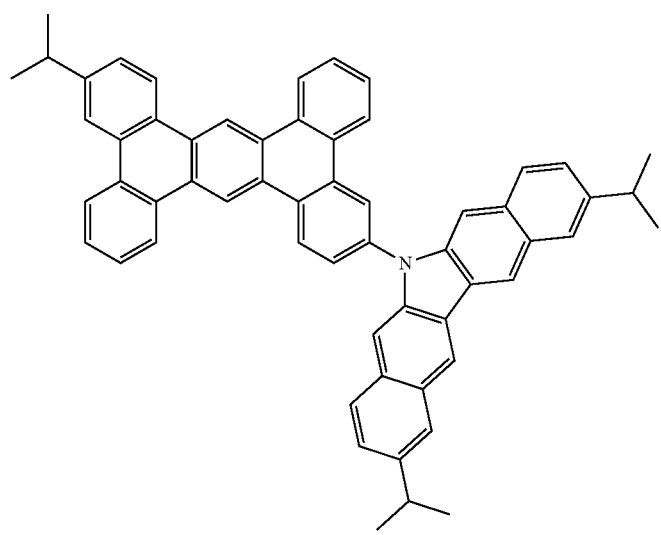

-continued

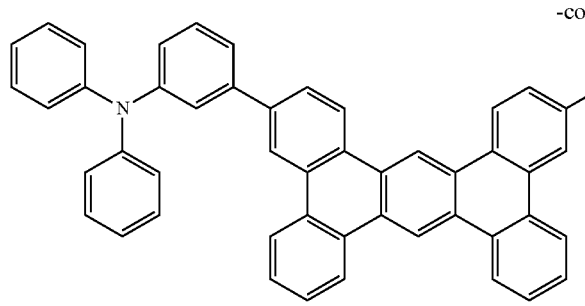

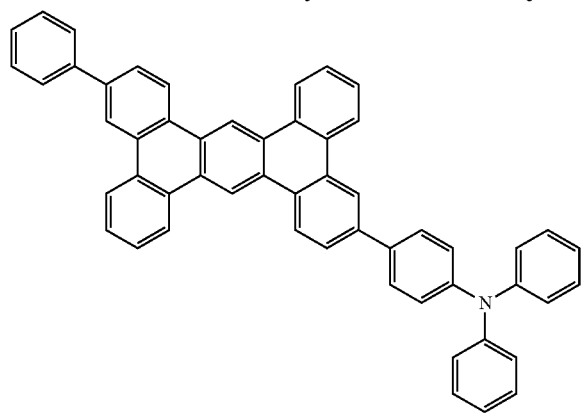

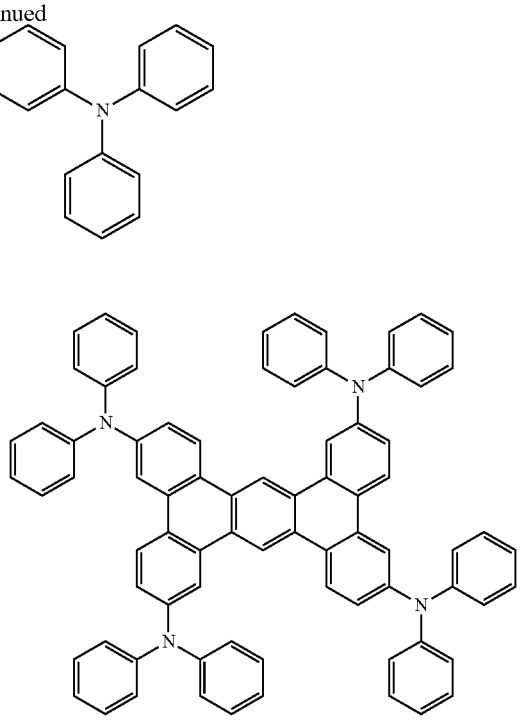

The compound represented by the general formula (1) can be synthesized with a combination of other known reactions. For example, the synthesis can be performed with reference to JP-A-2008-50308.

After the synthesis, purification is preferably carried out by column chromatography, recrystallization, or the like, and then by sublimation purification. Organic impurities can be separated and inorganic salts, residual solvents, or the like can also be removed effectively by the sublimation purification.

In a case where the compound represented by the general formula (1) is used as a light emitting material, from the viewpoint of acquiring blue light emitting with high chromatic purity, the maximum light emitting wavelength in the thin film state is preferably less than 460 nm, more preferably equal to or more than 430 nm and equal to or less than 460 nm, particularly preferably equal to or more than 430 nm and less than 455 nm, still more preferably equal to or more than 435 nm and less than 455 nm, and most preferably equal to or more than 440 nm and less than 455 nm.

<<Configuration of Organic Electroluminescent Element>>

The organic electroluminescent element of the present invention includes a substrate, a pair of electrodes including an anode and a cathode, disposed on the substrate, and at least one layer of organic layers including a light emitting layer, disposed between the electrodes, and at least one of the light emitting layers contains a compound represented by the general formula (1).

The configuration of the organic electroluminescent element of the present invention is not particularly limited. FIG. 1 shows one example of the configuration of the organic electroluminescent element of the present invention. The organic electroluminescent element 10 of FIG. 1 has an organic layer between a pair of electrodes (an anode 3 and a cathode 9) on a substrate 2.

The element configuration of the organic electroluminescent element, the substrate, the cathode, and the anode are described in detail in, for example, JP-A-2008-270736, and the detailed description thereon in the publication may be applied to the present invention.

Hereinbelow, preferred embodiments of the organic electroluminescent element of the present invention will be described in detail in the order of the substrate, the electrodes, the organic layer, the protective layer, a sealing enclosure, a driving method, a light emitting wavelength, and applications.

<Substrate>

The organic electroluminescent element of the present invention has a substrate.

The substrate used in the present invention is preferably a substrate that cannot scatter or diminish light radiated from the organic layer. In a case of the organic material, those having excellent heat resistance, dimensional stability, solvent resistance, electricity insulating properties, and processibility are preferred.

<Electrodes>

The organic electroluminescent element of the present invention has a pair of electrodes including an anode and a cathode, disposed on the substrate.

In terms of the properties of the light emitting element, at least one electrode of a pair of electrodes, the anode and the cathode, is preferably transparent or semi-transparent.

(Anode)

The anode is usually any of those having a function as an electrode of supplying holes into an organic layer, and is not particularly limited in its shape, structure, size, or the like. Further, depending on the use and purpose of the light emitting element, the anode can be suitably selected from the known electrode materials. As described above, the anode is usually provided as a transparent anode.

(Cathode)

The cathode is usually any of those having a function as an electrode of injecting electrons to an organic layer, and is not particularly limited in its shape, structure, size, or the like. Further, depending on the use and purpose of the light emitting element, the cathode can be suitably selected from the known electrode materials.

<Organic Layer>

The organic electroluminescent element of the present invention has at least one layer of the organic layers including the light emitting layer, and disposed between the electrodes, and at least one layer of the light emitting layers may contain a compound represented by the general formula (1).

The organic layer is not particularly limited and can be suitably selected depending on the use and purpose of the organic electroluminescent element. However, the organic layer is preferably formed on a transparent electrode or a semi-transparent electrode. In this case, the organic layer is formed on the whole surface or one surface of the transparent electrode or the semi-transparent electrode.

The shape, the size, the thickness, or the like of the organic layer are not particularly limited, and can be suitably selected depending on the purpose.

Hereinbelow, the configuration of the organic layer, the method for forming an organic layer, preferred embodiments of the respective layers constituting the organic layer, and the materials used in the respective layers in the organic electroluminescent element of the present invention will be described in detail in order.

(Configuration of Organic Layer)

For the organic electroluminescent element of the present invention, the organic layers includes a light emitting layer. The organic layer preferably includes a charge transporting layer. The charge transporting layer refers to a layer in which charges move when voltage is applied to the organic electroluminescent element. Specific examples thereof include a hole injecting layer, a hole transporting layer, an electron blocking layer, a light emitting layer, a hole blocking layer, an electron transporting layer, and an electron injecting layer. If the charge transporting layer is a hole injecting layer, a hole transporting layer, an electron blocking layer, or a light emitting layer, the organic electroluminescent element can be manufactured with low cost and high efficiency.

The compound represented by the general formula (1) is contained in at least one layer of the light emitting layers in the organic layers disposed between the electrodes of the organic electroluminescent element.

However, in a range within not departing the gist of the present invention, the compound represented by the general formula (1) may be contained in the other organic layer of the organic electroluminescent element of the present invention. Examples of the organic layer other than the light emitting layer which may contain the compound represented by the general formula (1) include a hole injecting layer, a hole transporting layer, an electron transporting layer, an electron injecting layer, an exciton blocking layer, and a charge blocking layer (a hole blocking layer, an electron blocking layer, and the like), preferably any of a hole injecting layer, a hole transporting layer, an exciton blocking layer, and a charge blocking layer, and more preferably a hole transporting layer, an exciton blocking layer, and a charge blocking layer.

In a case where the compound represented by the general formula (1) is contained in the light emitting layer, the compound represented by the general formula (1) is preferably contained in the amount of 0.1% to 100% by mass, more preferably contained in the amount of 1% to 50% by mass, and still more preferably 2% to 20% by mass, based on the total mass of the organic layer.

In a case where the compound represented by the general formula (1) is contained in the organic layer other than the light emitting layer, the compound represented by the general formula (1) is preferably contained in the amount of 70% to 100% by mass, more preferably contained in the amount of 80% to 100% by mass, and still more preferably 90% to 100% by mass, based on the total mass of the organic layer.

(Method for Forming Organic Layer)

The respective organic layer in the organic electroluminescent element of the present invention can be suitably formed by any of dry film forming methods such as a deposition method and a sputtering method, wet type film forming methods (solution coating methods) such as a transfer method, a printing method, a spin-coating method, and a bar coating method.

For the organic electroluminescent element of the present invention, the organic layers disposed between a pair of electrodes preferably further include at least a layer formed by the deposition of a composition including the compound represented by the general formula (1).

(Light Emitting Layer)

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light to be emitted. However, the light emitting layer in the present invention is not necessarily limited to the light emission by such a mechanism.

The light emitting layer in the organic electroluminescent element of the present invention may be constituted of only a light emitting material or may be constituted as a mixed layer of a host material and a light emitting material. The light emitting material may be made of a single kind or two or more kinds. The host material is preferably a charge transport material. The host material may be made of a single kind or two or more kinds. Examples thereof include a configuration in which an electron-transporting host material and a hole-transporting host material are mixed. Furthermore, the light emitting layer may contain a material which cannot have charge transporting properties and which cannot emit light.

Moreover, the light emitting layer may be made of a single layer or two or more layers. The respective layers may include the same light emitting materials or host materials, and may also include different materials from each other. In a case where a plurality of light emitting layers are present, the respective light emitting layers may emit light in a different luminous color from each other.

The thickness of the light emitting layer is not particularly limited, but it is usually preferably from 2 nm to 500 nm, and among these, from the viewpoint of external quantum efficiency, it is more preferably from 3 nm to 200 nm, and still more preferably from 5 nm to 100 nm.

For the organic electroluminescent element of the present invention, the light emitting layer contains the compound represented by the general formula (1), and the compound represented by the general formula (1) is used as the light emitting material in the light emitting layer in a more preferred embodiment. The host material used in the present specification is a compound which usually plays a role in injecting or transporting charges in the light emitting layer and is also a compound which cannot substantially emit light itself. As used herein, the term "which cannot substantially emit light" means that the amount of light emitted from the compound which cannot substantially emit light is preferably 5% or less, more preferably 3% or less, and still more preferably 1% or less of the total amount of light emitted in the whole of the element. The compound represented by the general formula (1) may be used as the host material of the light emitting layer.

(Light Emitting Material)

For the organic electroluminescent element of the present invention, the compound represented by the general formula (1) is preferably the light emitting material, however, even in this case, the compound represented by the general formula (1) can be used with a combination with the other light emitting material. In addition, for the organic electroluminescent element of the present invention, in a case where the compound represented by the general formula (1) is used as the host material of the light emitting layer or in a case where the compound is used for the organic layer other than the light emitting layer, the light emitting material other than the compound represented by the general formula (1) is used for the light emitting layer.

The light emitting material which can be used in the present invention may be any of a phosphorescent light emitting material, a fluorescent emitting material, and the like. In addition, the light emitting layer of the present invention can contain two or more types of light emitting materials for improving the chromatic purity or expanding the light emitting wavelength region.

The fluorescent emitting material or the phosphorescent light emitting material which can be used for the organic electroluminescent element of the present invention is disclosed in Paragraph Nos. [0100] to [0164] of JP-A-2008-270736 and Paragraph Nos. [0088] to [0090] of JP-A-2007-266458, and the disclosed description can be applied to the present invention.

Examples of the phosphorescent light emitting material which can be used in the present invention include phosphorescent light emitting compounds disclosed in U.S. Pat. Nos. 6,303,238 and 6,097,147, WO00/57676, WO00/70655, WO01/08230, WO01/39234, WO01/41512, WO02/02714, WO02/15645, WO02/44189, WO05/19373, JP-A-2001-247859, JP-A-2002-302671, JP-A-2002-117978, JP-A-2003-133074, JP-A-2002-235076, JP-A-2003-123982, JP-A-2002-170684, EP Publication No. 1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, JP-A-2007-96259, and among them, examples of the further preferable light emitting material include phosphorescent light emitting metal complex compound such as an Ir complex, a Pt complex, a Cu complex, a Re complex, a W complex, a Rh complex, a Ru complex, a Pd complex, an Os complex, an Eu complex, a Tb complex, a Gd complex, a Dy complex, a Ce complex, and the like. An Ir complex, a Pt complex, or a Re complex is particularly preferable, and among them, an Ir complex, a Pt complex, or a Re complex including coordination of at least one of metal-carbon bond, metal-nitrogen bond, metal-oxygen bond, and metal-sulfur bond is preferable. Further, from the viewpoints of the light emitting efficiency, driving durability, and chromaticity, an Ir complex and a Pt complex are particularly preferable, and an Ir complex is most preferable.

The types of the fluorescent emitting material which can be used in the present invention is not particularly limited, however, other than the compound represented by the general formula (1), examples thereof include benzoxazole, benzimidazole, benzothiazole, styrylbenzene, polyphenyl, diphenyl butadiene, tetraphenylbutadiene, naphthalimide, coumarin, pyran, perinone, oxadiazole, aldazine, pyralidine, cyclopentadiene, bis styrylanthracene, quinacridone, pyrrolopyridine, thiadiazolopyridine, cyclopentadiene, styrylamine, condensed polycyclic aromatic compounds (anthracene, phenanthroline, pyrene, perylene, rubrene, pentacene, or the like), various metal complexes represented by a 8-quinolinol metal complex, a pyrromethene complex, or a rare earth metal complex, a polymer compound such as polythiophene, polyphenylene, or polyphenylene vinylene, organic silane, and derivative thereof.

Additionally, the compound disclosed in Paragraph No. of JP-A-2010-111620 can be used as the light emitting material.

The light emitting layer in the organic electroluminescent element of the present invention may be constituted of only a light emitting material or may be constituted as a mixed layer of a host material and a light emitting material. The light emitting material may be made of a single kind or two or more kinds. The host material is preferably a charge transport material. The host material may be made of a single kind or two or more kinds. Examples thereof include a configuration in which an electron-transporting host material and a hole-transporting host material are mixed. Furthermore, the light emitting layer may contain a material which cannot have charge transporting properties and which cannot emit light.

Moreover, the light emitting layer may be made of a single layer or two or more layers. The respective layers may include the same light emitting materials or host materials, and may also include different materials from each other. In a case where a plurality of light emitting layers are present, the respective light emitting layers may emit light in a different luminous color from each other.

(Host Material)

The host material used in the present specification is a compound which usually plays a role in injecting or transporting charges in the light emitting layer and is also a compound which cannot substantially emit light itself. As used herein, the term "which cannot substantially emit light" means that the amount of light emitted from the compound which cannot substantially emit light is preferably 5% or less, more preferably 3% or less, and still more preferably 1% or less of the total amount of light emitted in the whole of the element.

In addition to the compound represented by the general formula (1), examples of the host material that can be used in the organic electroluminescent element of the present invention include the following compounds:

conductive high-molecular oligomers such as pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, porphyrin-based compounds, aromatic hydrocarbon compounds with fused rings (fluorene, naphthalene, phenanthrene, triphenylene, and the like), polysilane-based compounds, poly(N-vinylcarbazole), aniline-based copolymers, thiophene oligomers, and polythiophene, organic silanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene, phthalocyanine, and a variety of metal complexes typified by metal complexes of 8-quinolinol derivatives and metal complexes having metal phthalocyanine, benzoxazole, or benzothiazole as a ligand thereof, and derivatives thereof (which may have a substituent or a fused ring). In addition, the compounds disclosed in Paragraph No. [0081] or [0083] of JP-A-2010-111620 can be used.

Among these, carbazole, dibenzothiophene, dibenzofuran, arylamine, aromatic hydrocarbon compounds with fused rings, and metal complex are preferred, and aromatic hydrocarbon compounds with fused rings are more particularly preferred for stabilization. As the aromatic hydrocarbon compounds with fused rings, a naphthalene-based compound, an anthracene-based compound, a phenanthrene-based compound, a triphenylene-based compound, and a pyrene-based compound are preferred, an anthracene-based compound and a pyrene-based compound are more preferred, and an anthracene triphenylene-based compound is particularly preferred.

The light emitting element of the present invention preferably contains a compound represented by the following general formula (An-1), as the host material.

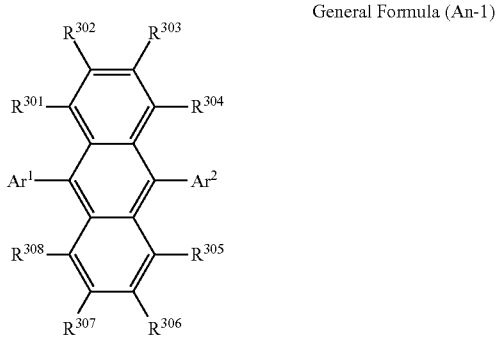

General Formula (An-1)

(In the general formula (An-1), $Ar^1$ and $Ar^2$ each independently represent an aryl group or a heteroaryl group, and $R^{301}$ to $R^{308}$ each independently represent a hydrogen atom or a substituent. $R^{301}$ and $R^{302}$, $R^{302}$ and $R^{303}$, $R^{303}$ and $R^{304}$, $R^{305}$ and $R^{306}$, $R^{306}$ and $R^{307}$, and $R^{307}$ and $R^{308}$ may be combined to each other to form a ring.)

In the general formula (An-1), the aryl group represented by $Ar^1$ and $Ar^2$ is preferably an aryl group having 6 to 36 carbon atoms, more preferably an aryl group having 6 to 18 carbon atoms, particularly preferably an aryl group having 6 to 14 carbon atoms, and more particularly preferably a phenyl group or a naphthyl group.

The heteroaryl group represented by $Ar^1$ and $Ar^2$ is preferably a heteroaryl group having 5 to 20 ring members, and more preferably a heteroaryl group having 5 to 13 ring members. The hetero atom included in the heteroaryl group represented by $Ar^1$ and $Ar^2$ is preferably a nitrogen atom, an oxygen atom and a sulfur atom, and more preferably a nitrogen atom. The number of the hetero atoms included in the heteroaryl group represented by $Ar^1$ and $Ar^2$ is preferably 1 to 3, more preferably 1 or 2, and particularly preferably 1. The heteroaryl group represented by $Ar^1$ and $Ar^2$ is particularly preferably a pyridyl group, a carbazolyl group, a dibenzofuryl group, and a dibenzothiophenyl group.

$Ar^1$ and $Ar^2$ is preferably a phenyl group, a naphthyl group, a pyridyl group, a carbazolyl group, a dibenzofuryl group, a dibenzothiophenyl group, and a group with combination thereof. $Ar^1$ and $Ar^2$ is more preferably a phenyl group or a naphthyl group among them, and at least one of $Ar^1$ and $Ar^2$ is particularly preferably a substituted or unsubstituted phenyl group.

$Ar^1$ and $Ar^2$ may further include substituents. Examples of the substituents include an aryl group, a heteroaryl group, a fluorine atom, an alkyl group (preferably having 1 to 4 carbon atoms), an alkenyl group, a silyl group, and a cyano group.

In the general formula (An-1), examples of the substituents represented by $R^{301}$ and $R^{308}$ include an aryl group, a heteroaryl group, a fluorine atom, an alkyl group, a silyl group, a cyano group, and a group with combination thereof. The substituents thereof are preferably a phenyl group, a naphthyl group, a pyridyl group, a carbazolyl group, a dibenzofuryl group, a dibenzothiophenyl group, a fluorine atom, an alkyl group, a silyl group, a cyano group, and a group with combination thereof, and more preferably a phenyl group, a naphthyl group, and an alkyl group having 1 to 5 carbon atoms (particularly preferably tert-butyl group).

In the general formula (An-1), $R^{301}$ or $R^{308}$ may further include substituents. Examples of the substituents include an aryl group, a heteroaryl group, and an alkyl group, and an aryl group and a heteroaryl group are preferable, and an aryl group having 6 to 18 carbon atoms is more preferable.

In the general formula (An-1), the number of the substituents included in $R^{301}$ or $R^{308}$ is preferably 0 to 4, more preferably 0 or 2, particularly preferably 0 or 1, and more particularly preferably 0.

In the general formula (An-1), the position of the substituents included in $R^{301}$ or $R^{308}$ is preferably $R^{302}$, $R^{303}$, $R^{306}$, or $R^{307}$, and more preferably any one of $R^{302}$ and $R^{303}$ or any one of $R^{306}$ and $R^{307}$.

In the general formula (An-1), $R^{301}$ and $R^{302}$, $R^{302}$ and $R^{303}$, $R^{303}$ and $R^{304}$, $R^{305}$ and $R^{306}$, and $R^{307}$, and $R^{307}$ and $R^{308}$ may be combined to each other to form a ring, however, they are not preferably combined to each other to form a ring.

The compound represented by the general formula (An-1) is preferably a compound represented by the following general formula (An-2).

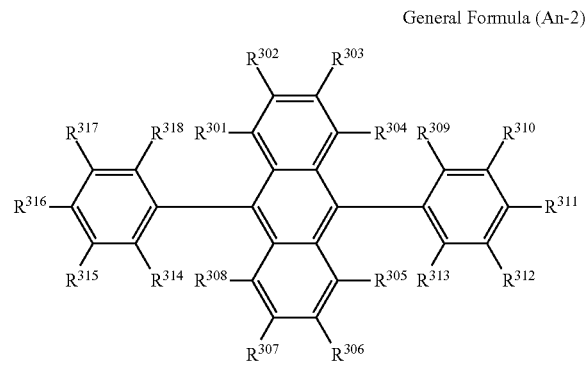

General Formula (An-2)

(In the general formula (An-2), $R^{301}$ and $R^{318}$ each independently represent a hydrogen atom or a substituent. $R^{301}$ and $R^{302}$, $R^{302}$ and $R^{303}$, $R^{303}$ and $R^{304}$, $R^{305}$ and $R^{306}$, $R^{306}$ and $R^{307}$, $R^{307}$ and $R^{308}$, $R^{309}$ and $R^{310}$, $R^{310}$ and $R^{311}$, $R^{311}$ and $R^{312}$, $R^{312}$ and $R^{313}$, $R^{314}$ and $R^{315}$, $R^{315}$ and $R^{316}$, $R^{316}$ and $R^{317}$, and $R^{317}$ and $R^{318}$ may be combined to each other to form a ring.)

The preferred ranges of $R^{301}$ and $R^{308}$ in the general formula (An-2) are the same as the preferred ranges of $R^{301}$ and $R^{308}$ in the general formula (An-1).

In the general formula (An-2), examples of the substituents represented by $R^{309}$ and $R^{318}$ include an aryl group, a heteroaryl group, a fluorine atom, an alkyl group, a silyl group, a cyano group, and a group with combination thereof. The substituents thereof are an aryl group having 6 to 18 carbon atoms, a heteroaryl group having 5 to 20 ring members, a fluorine atom, an alkyl group, an alkenyl group, a silyl group, a cyano group, and a group with combination thereof, more preferably a phenyl group, a naphthyl group, a pyridyl group, a carbazolyl group, a dibenzofuryl group, a dibenzothiophenyl group, a fluoroine atom, an alkyl group, an alkenyl group, a silyl group, a cyano group, and a group with combination thereof, and particularly preferably a phenyl group, a naphthyl group, and a carbazolyl group.

In the general formula (An-1), $R^{309}$ or $R^{318}$ may further include substituents. Examples of the substituents include an aryl group, an alkyl group, and a fluorine atom, and the substituents may be combined to each other to form a ring.

In the general formula (An-1), the number of the substituents included in $R^{309}$ or $R^{318}$ is preferably 0 to 4, more preferably 0 or 2, particularly preferably 0 or 1, and more particularly preferably 0.

In the general formula (An-1), the position of the substituents included in $R^{309}$ or $R^{318}$ is not particularly limited, however, in a case of including the substituents, at least one of $R^{311}$ or $R^{316}$ is preferably included.

In the general formula (An-1), $R^{309}$ and $R^{310}$, $R^{310}$ and $R^{311}$, $R^{311}$ and $R^{312}$, $R^{312}$ and $R^{313}$, $R^{314}$ and $R^{315}$, $R^{315}$ and $R^{316}$, $R^{316}$ and $R^{317}$, and $R^{317}$ and $R^{318}$ may be combined to each other to form a ring, and the formed ring is preferably a 5- or 6-membered ring, and more preferably a 5-membered ring.

Specific examples of the compound represented by the general formula (An-1) are shown below, but the compound represented by the general formula (An-1) which can be used in the present invention is not limitedly interpreted by the specific examples.

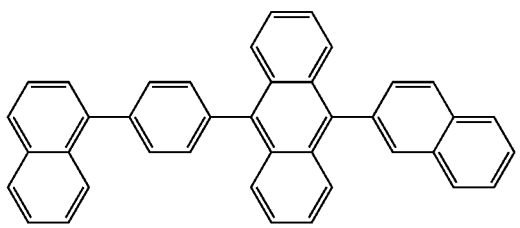

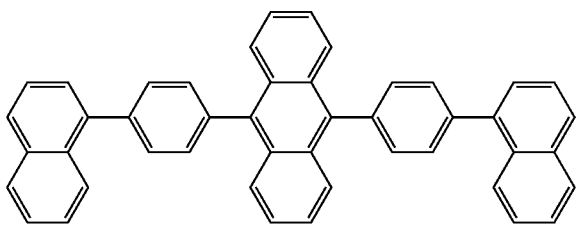

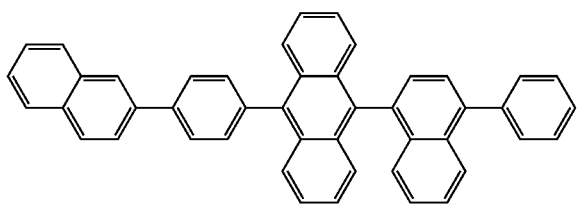

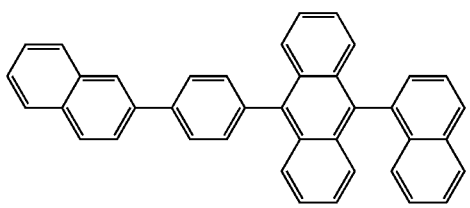

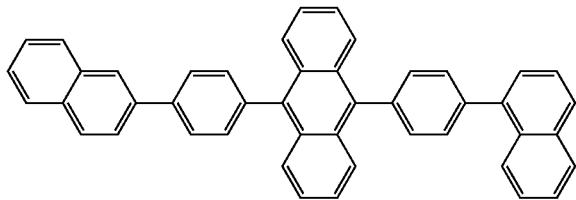

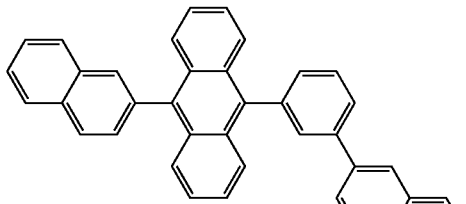

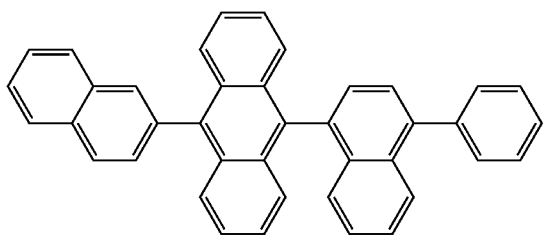

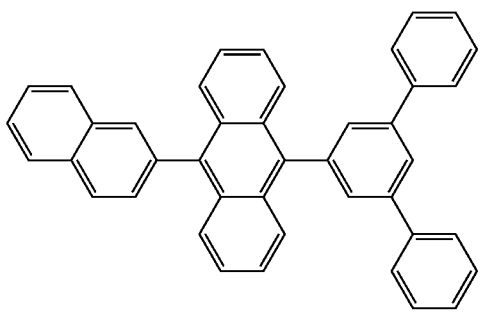

-continued
| 149 | 150 |
|---|---|
| 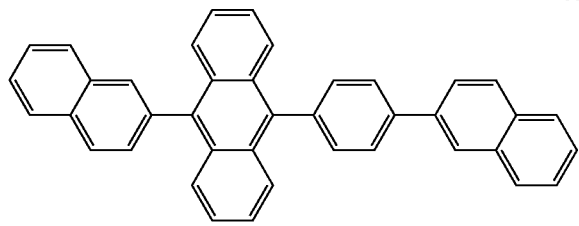 | 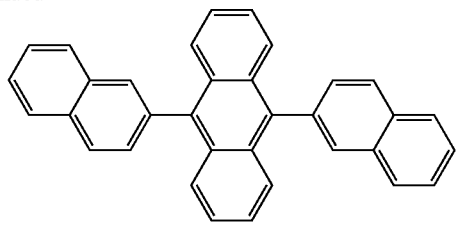 |
| 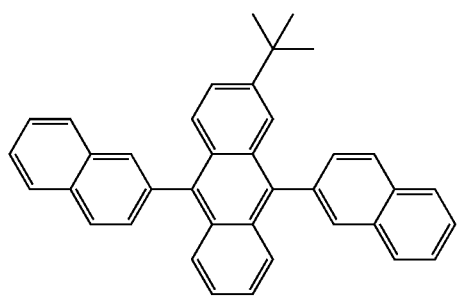 | 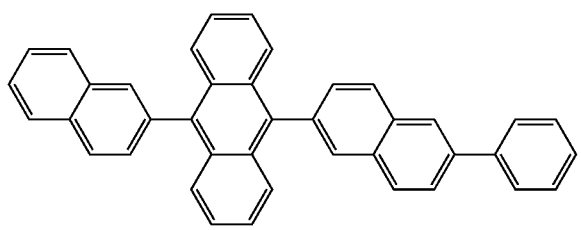 |
| 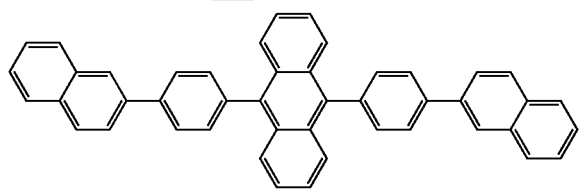 | 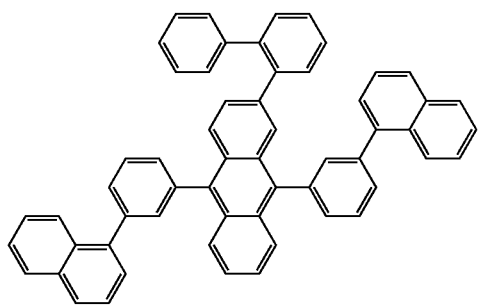 |
| 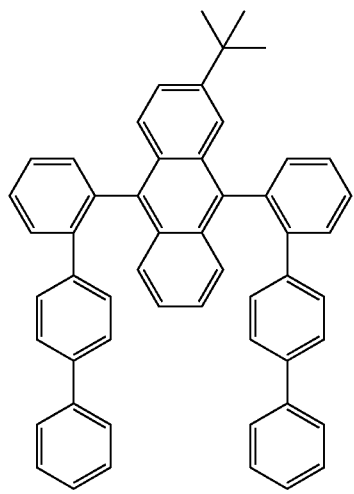 | 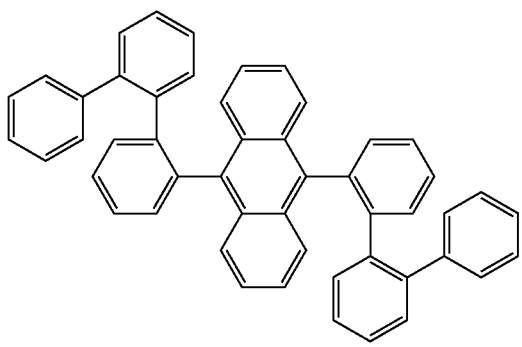 |
| 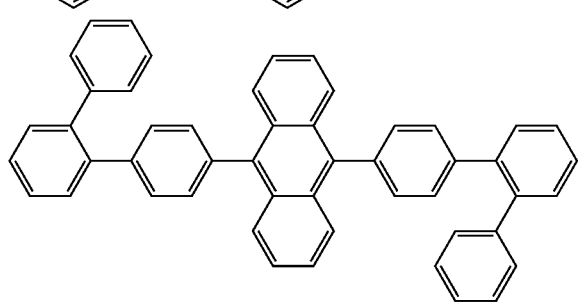 | 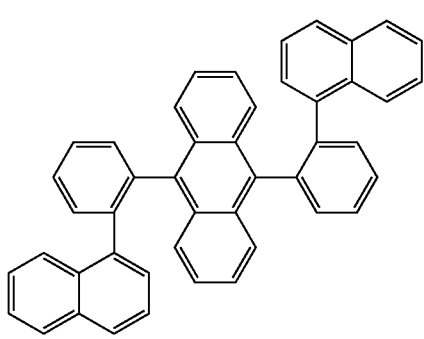 |

151
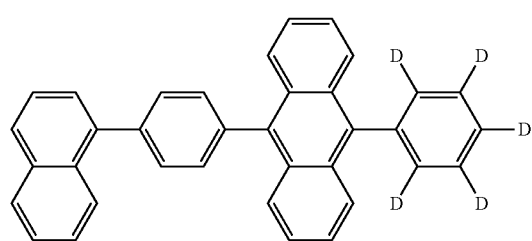
152
-continued
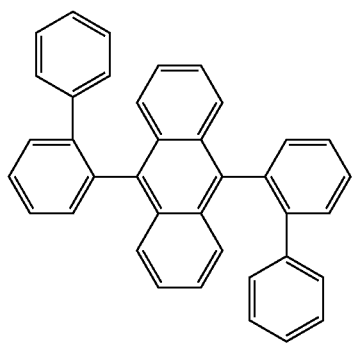
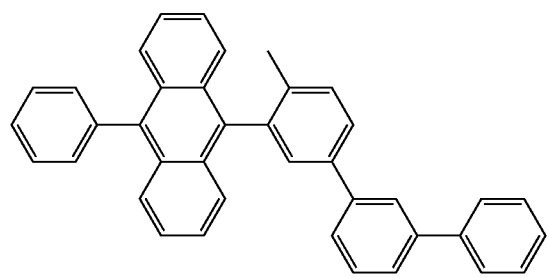
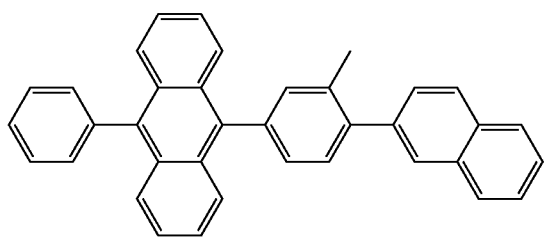
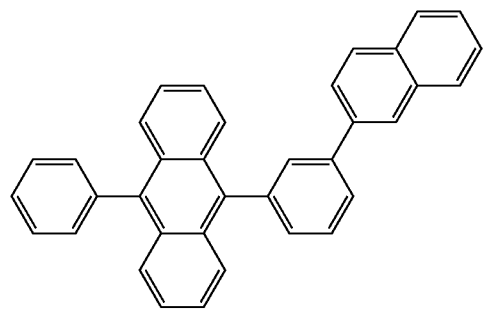
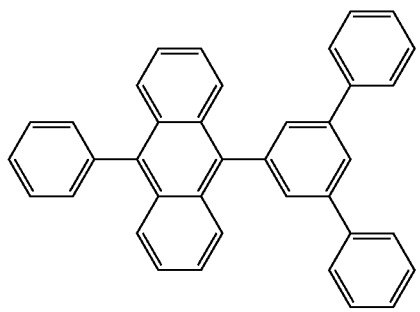
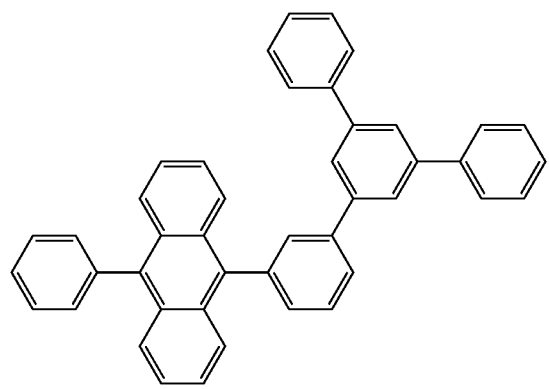
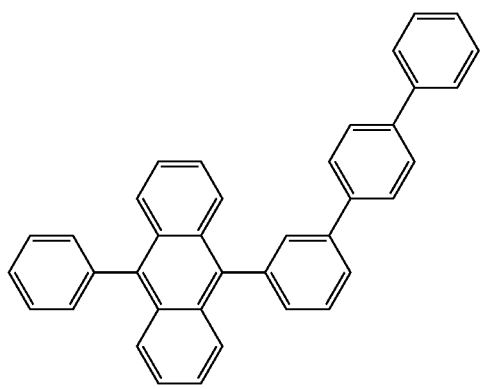
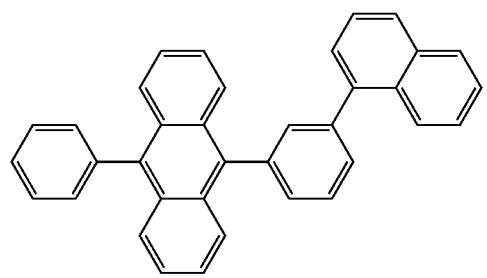
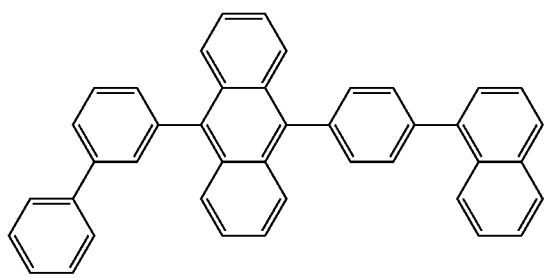

-continued
153
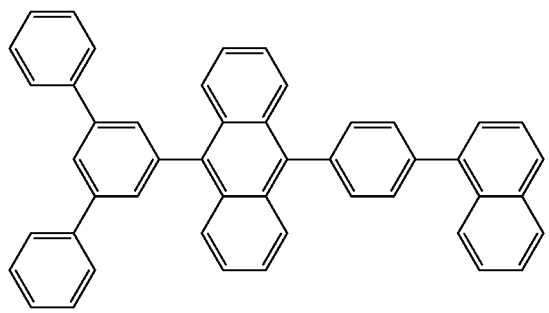
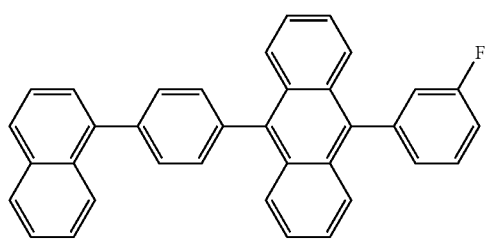
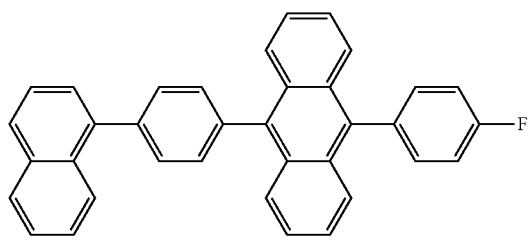
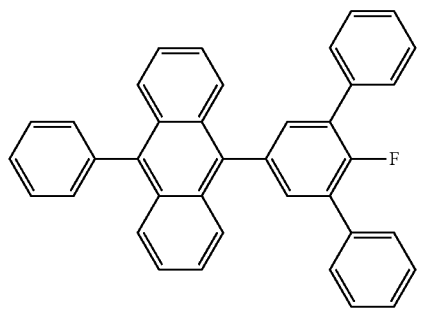
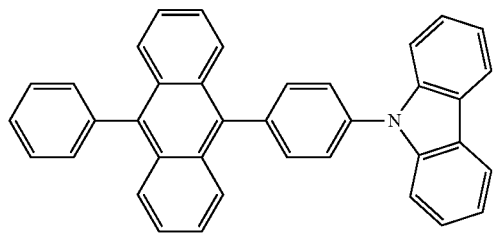
154
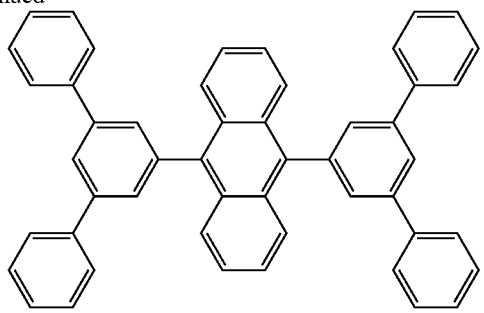
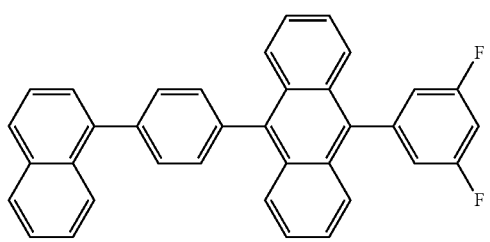
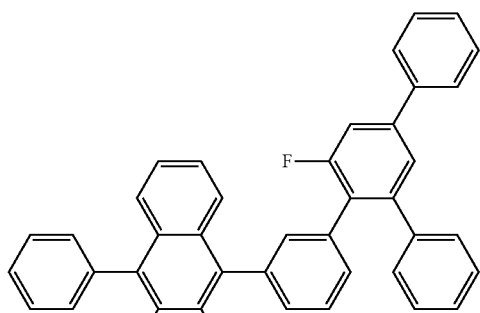
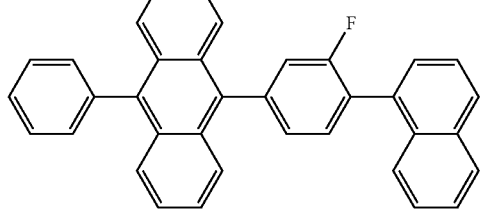
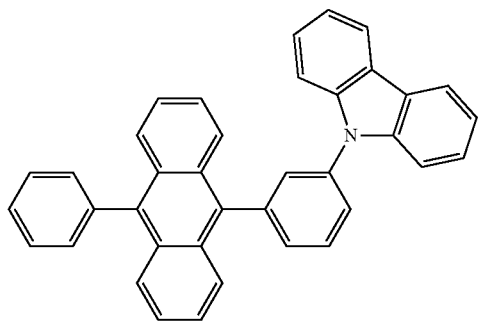

-continued
| 155 | 156 |
|---|---|
| 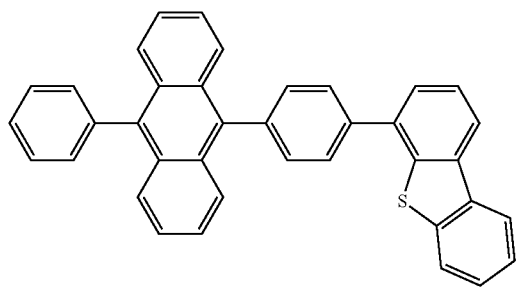 | 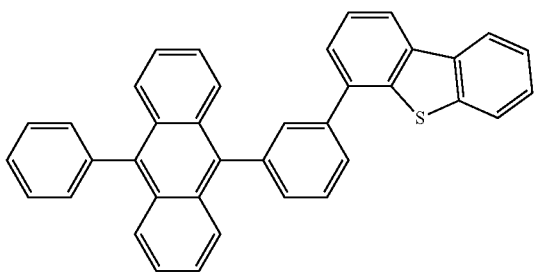 |
| 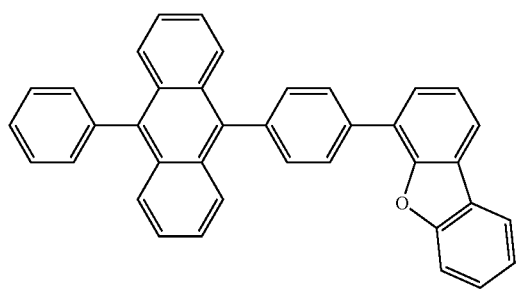 | 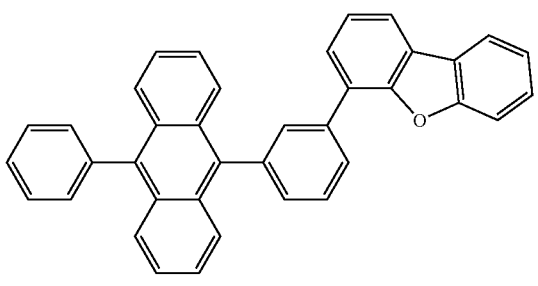 |
| 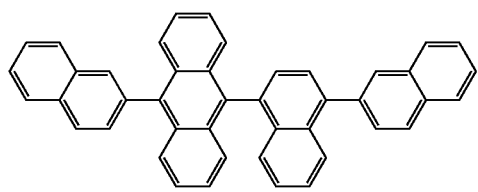 | 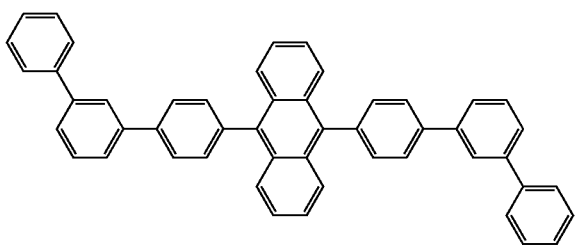 |
| 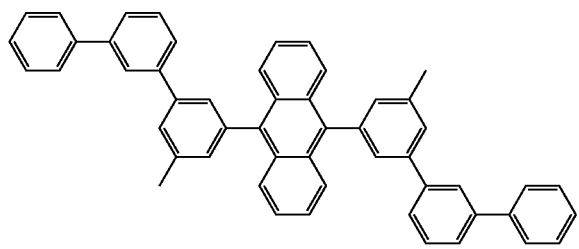 | 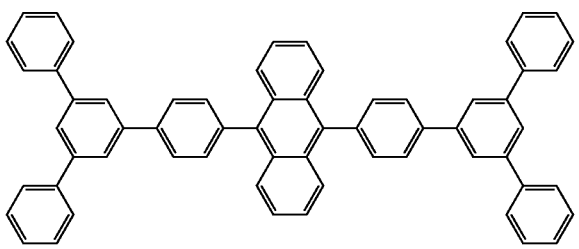 |
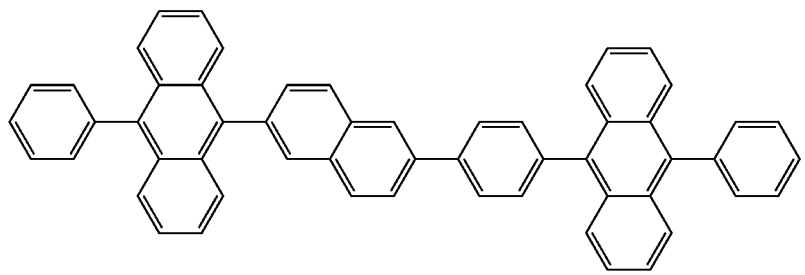

-continued
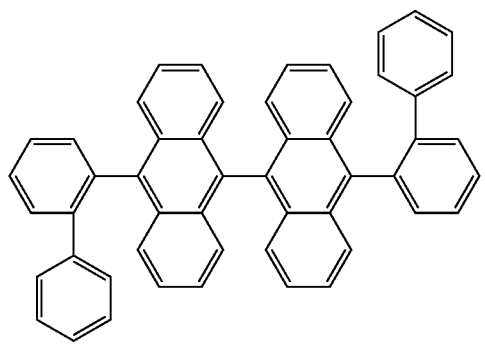
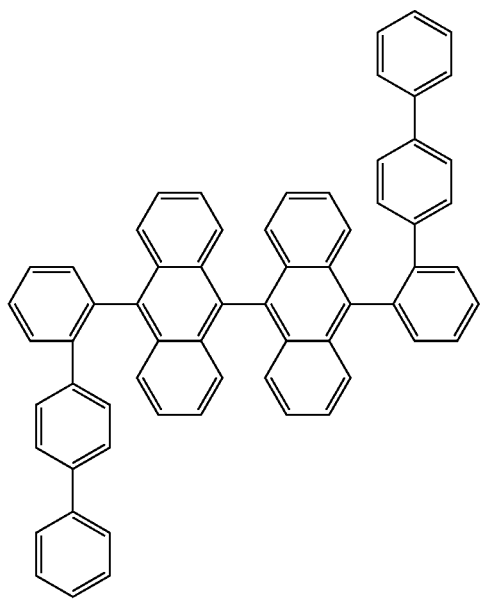
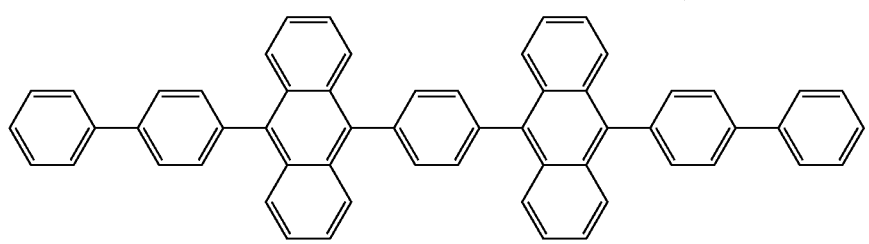
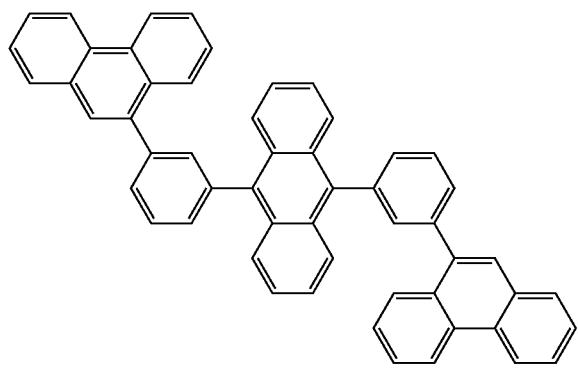
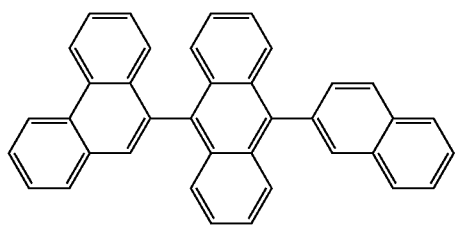
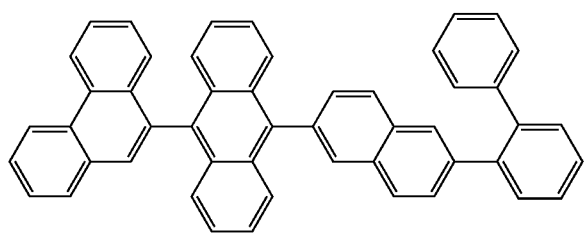
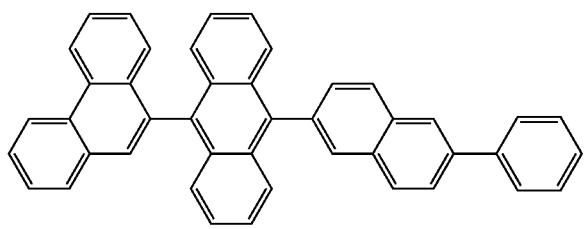
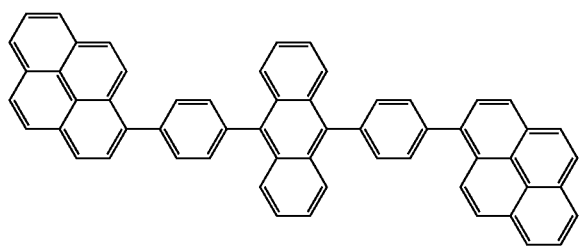
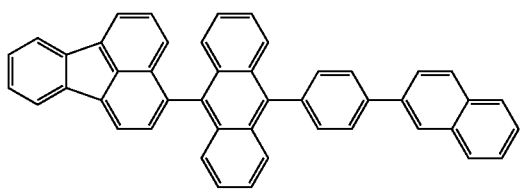

-continued
| 159 | 160 |
|---|---|
| 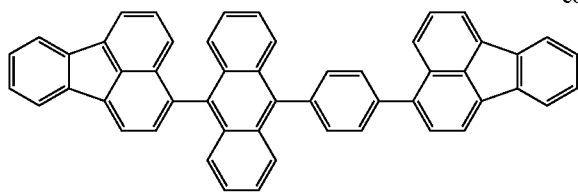 | 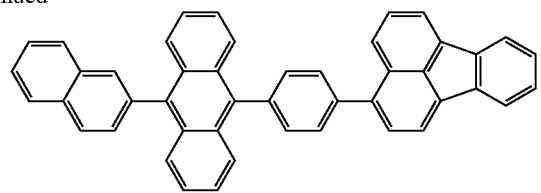 |
| 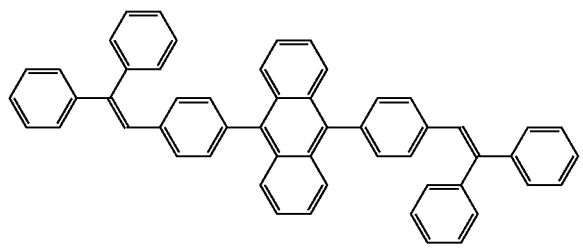 | 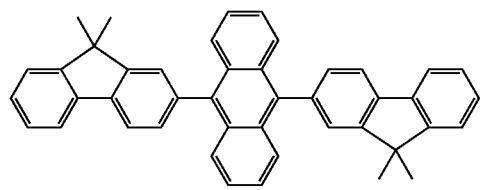 |
| 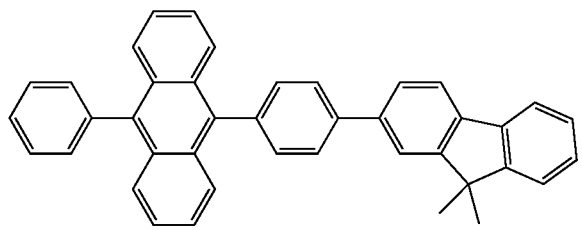 | 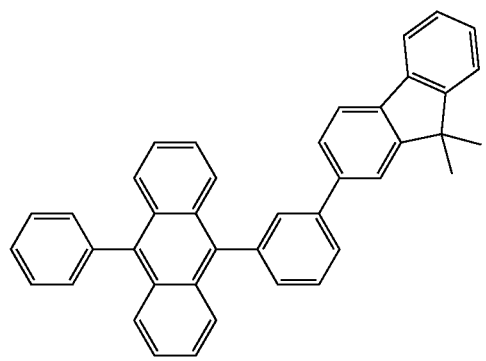 |
| 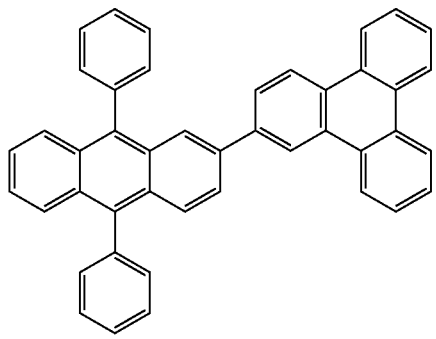 | 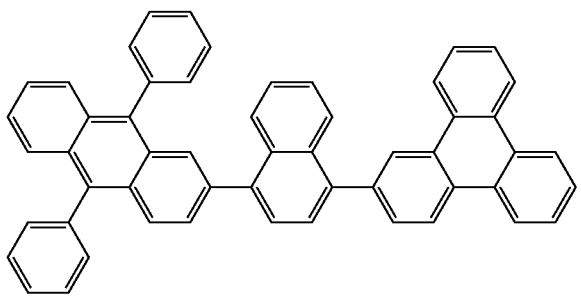 |
| 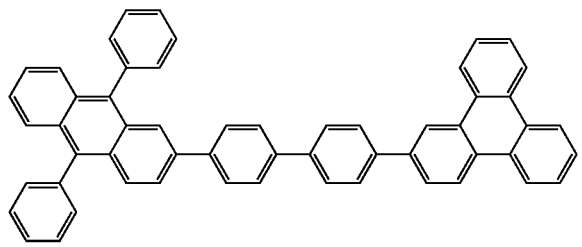 | 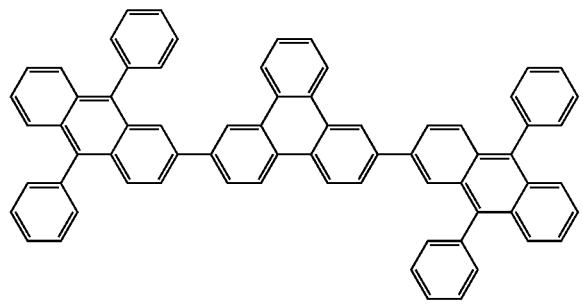 |

-continued
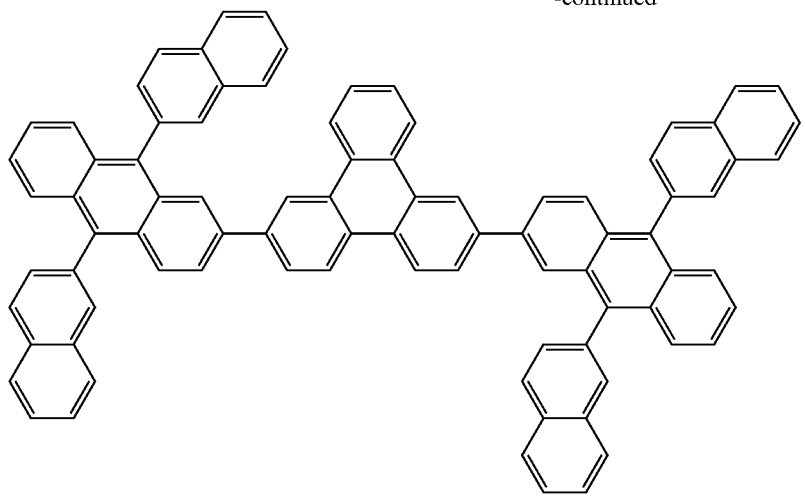
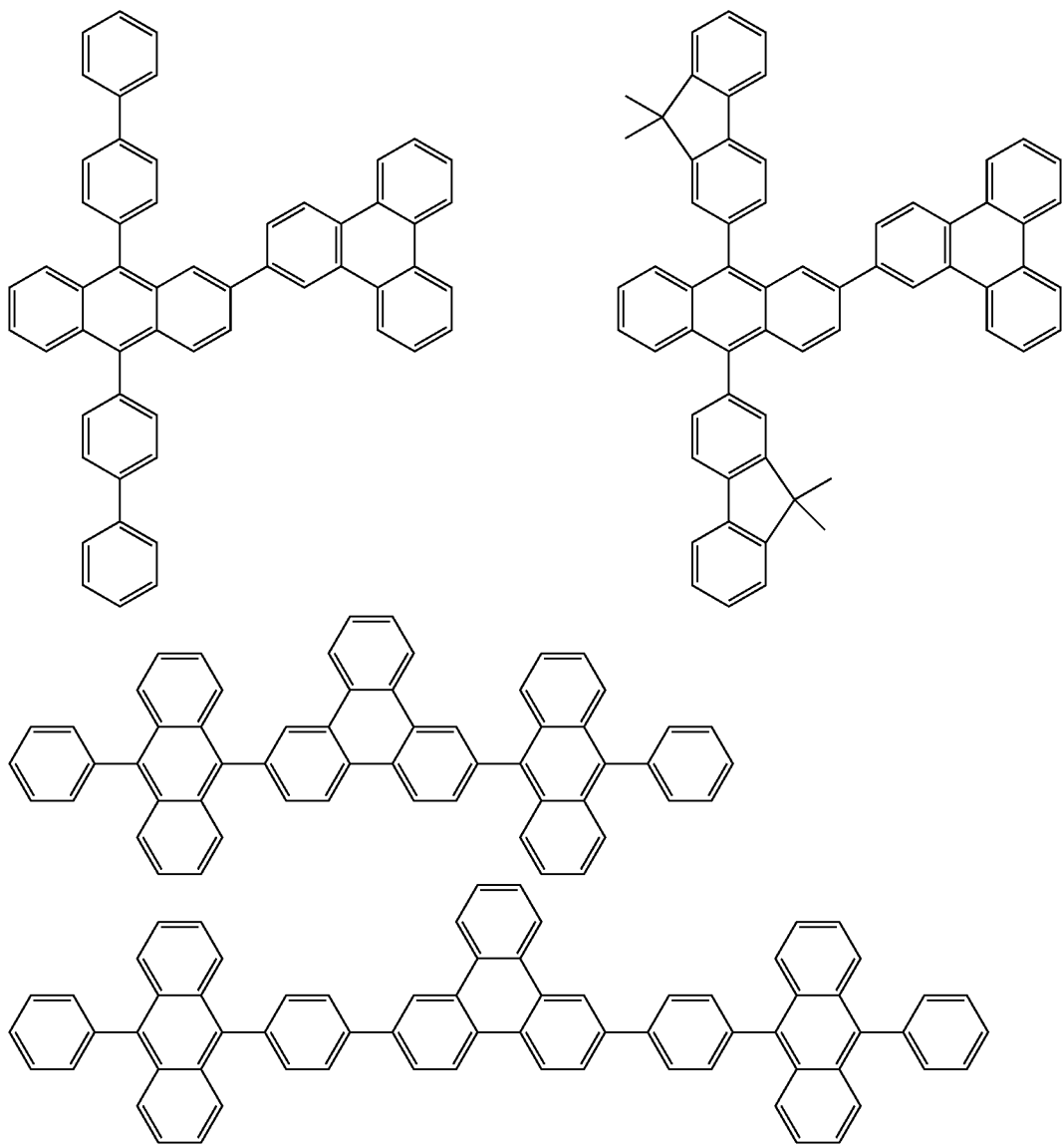

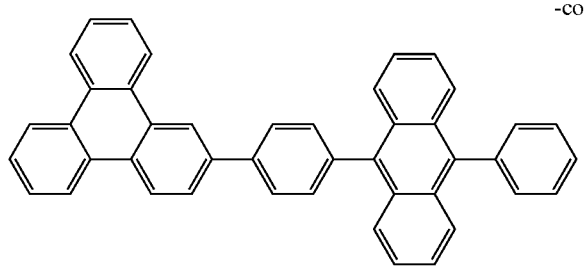

The host material which may be used in the light emitting layer in the organic electroluminescent element of the present invention may be either a hole transporting property host material or an electron transporting property host material.

In the light emitting layer, it is preferable that the lowest excited singlet energy ($S_1$ energy) in the film state of the host material be higher than the $S_1$ energy of the light emitting material, from the viewpoint of chromatic purity, luminous efficiency, and driving durability. $S_1$ of the host material is preferably equal to or more than 0.1 eV, more preferably equal to or more than 0.2 eV, and still more preferably equal to or more than 0.3 eV, with respect to $S_1$ of the light emitting material.

If the $S_1$ in the film state of the host material is lower than the $S_1$ energy of the light emitting material, the light emission is lost, and accordingly, a $S_1$ higher than that of the light emitting material is demanded for the host material. In addition, also in a case where the $S_1$ of the host material is higher than that of the light emitting material, a small difference between the two $S_1$ causes a partial reverse movement of energy from the light emitting material to the host material, which is responsible for a decrease in the efficiency, the chromatic purity, and the durability. Therefore, there is a demand for a host material having sufficiently great $S_1$, and having high chemical stability and carrier injecting/transporting properties.

Moreover, the content of the host compound in the light emitting layer in the organic electroluminescent element of the present invention organic electroluminescent element is not particularly limited, but it is preferably from 15% by mass to 99% by mass, based on the mass of all the compounds forming the light emitting layer, from the viewpoints of light emitting efficiency and driving voltage. In a case where various types of the host compounds including the compound represented by the general formula (An-1) is included in the light emitting layer, the content of the compound represented by the general formula (An-1) is preferably 50% to 99% by mass in the all host compounds.

(Other Layers)

The organic electroluminescent element of the present invention may contain layers other than the light emitting layer.

Examples of the organic layer other than the light emitting layer which may be included in the organic layer include a hole injecting layer, a hole transporting layer, a blocking layer (a hole blocking layer, an exciton blocking layer, and the like), and an electron transporting layer. Examples of the specific layer configuration include those below, but the present invention is not limited to these configurations.

Anode/hole transporting layer/light emitting layer/electron transporting layer/cathode,
Anode/hole transporting layer/light emitting layer/blocking layer/electron transporting layer/cathode,
Anode/hole transporting layer/light emitting layer/blocking layer/electron transporting layer/electron injecting layer/cathode,
Anode/hole injecting layer/hole transporting layer/light emitting layer/blocking layer/electron transporting layer/cathode,
Anode/hole injecting layer/hole transporting layer/light emitting layer/electron transporting layer/electron injecting layer/cathode,
Anode/hole injecting layer/hole transporting layer/light emitting layer/blocking layer/electron transporting layer/electron injecting layer/cathode,
Anode/hole injecting layer/hole transporting layer/blocking layer/light emitting layer/blocking layer/electron transporting layer/electron injecting layer/cathode.

The organic electroluminescent element of the present invention preferably includes at least one layer of (A) organic layers that are preferably disposed between the anode and the light emitting layer. Examples of (A) the organic layer that is preferably disposed between the anode and the light emitting layer include a hole injecting layer, a hole transporting layer, and an electron blocking layer from the anode side.

The organic electroluminescent element of the present invention preferably includes at least one layer of (B) organic layers that are preferably disposed between the cathode and the light emitting layer. Examples of (B) the organic layer that is preferably disposed between cathode and the light emitting layer include an electron injecting layer, an electron transporting layer, and a hole blocking layer from the cathode side.

Specifically, an example of the preferred embodiments of the organic electroluminescent element of the present invention is the embodiment shown in FIG. 1, in which a hole injecting layer 4, a hole transporting layer 5, a light emitting layer 6, a hole blocking layer 7, and an electron transporting layer 8 are laminated in this order as the organic layer from the anode 3 side.

Hereinbelow, these layers other than the light emitting layer which the organic electroluminescent element of the present invention may have will be described.

(A) Organic Layer Preferably Disposed Between Anode and Light Emitting Layer

First, (A) the organic layer preferably disposed between the anode and the light emitting layer will be described.

(A-1) Hole Injecting Layer and Hole Transporting Layer

The hole injecting layer and the hole transporting layer are layers having a function of receiving holes from the anode or the anode side and transporting them to the cathode side.

The light emitting element of the present invention preferably includes at least one layer of the organic layers between the light emitting layer and the anode, and the organic layer preferably includes at least one compound in the compounds represented by the following general formula (Sa-1), general formula (Sb-1), and general formula (Sa-1).

General Formula (Sa-1)

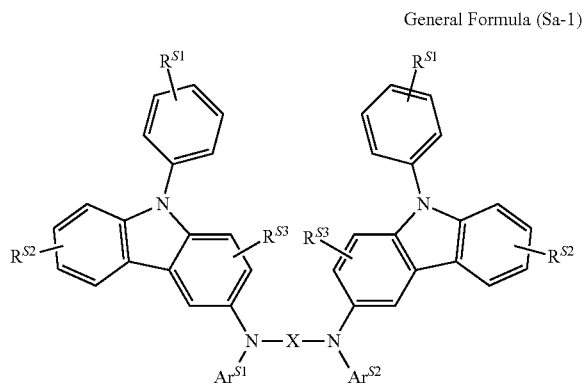

(In the formula, X represents a substituted or unsubstituted alkylene group having 1 to 30 carbon atoms, a substituted or unsubstituted alkenylene group having 2 to 30 carbon atoms, a substituted or unsubstituted allylene group having 6 to 30 carbon atoms, a substituted or unsubstituted heteroallylene group having 2 to 30 carbon atoms, a substituted or unsubstituted heterocyclic group having 2 to 30 carbon atoms, or a group with combination of these groups. $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. $R^{S1}$, $R^{S2}$, and $R^{S3}$ which are adjacent to each other may be bonded to each other to form a saturated carbon ring or an unsaturated carbon ring. $Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms.)

General Formula (Sb-1)

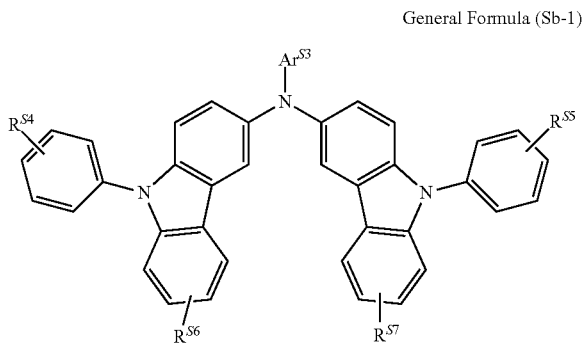

(In the formula, $R^{S4}$, $R^{S5}$, $R^{S6}$, and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. $R^{S4}$, $R^{S5}$, $R^{S6}$, and $R^{S7}$ which are adjacent to each other may be bonded to each other to form a saturated carbon ring or an unsaturated carbon ring. $Ar^{S3}$ represents a substituted or unsubstituted aryl group having 6 to 30 carbon atoms, or a substituted or unsubstituted heteroaryl group having 2 to 30 carbon atoms.)

General Formula (Sc-1)

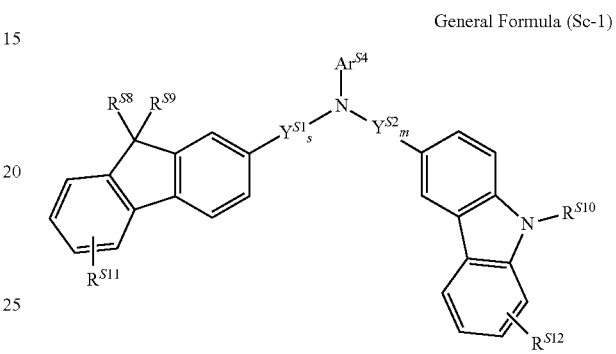

(In the formula, $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. $R^{S11}$ and $R^{S12}$ which are adjacent to each other may be bonded to each other to form a saturated carbon ring or an unsaturated carbon ring. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ each independently represent a substituted or unsubstituted alkylene group having 1 to 30 carbon atoms, or a substituted or unsubstituted allylene group having 6 to 30 carbon atoms. n and m each independently represent an integer of 0 to 5.)

The general formula (Sa-1) will be described. In the general formula (Sa-1), X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, a substituted or unsubstituted heterocyclic group having 2 to 30 carbon atoms, or a group with combination of these groups. X is preferably a substituted or unsubstituted arylene group having 6 to 30 carbon atoms, more preferably substituted or unsubstituted phenylene, substituted or unsubstituted biphenylene, and substituted or unsubstituted naphthylene, and still more preferably substituted or unsubstituted biphenylene.

$R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. $R^{S1}$, $R^{S2}$ and $R^{S3}$ which are adjacent to each other may be bonded to each other to form a saturated carbon ring or an unsaturated carbon ring. Examples of the saturated carbon ring or the unsaturated carbon ring include naphthalene, azulene, anthracene, fluorene, phenalene, and the like. $R^{S1}$, $R^{S2}$, and $R^{S3}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, and a cyano group, and more preferably a hydrogen atom.

$Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms. $Ar^{S1}$ and $Ar^{S2}$ are preferably a substituted or unsubstituted phenyl group.

Next, the general formula (Sb-1) will be described.

In the general formula (Sb-1), $R^{S4}$, $R^{S5}$, $R^{S6}$, and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. $R^{S4}$, $R^{S5}$, $R^{S6}$, and $R^{S7}$ which are adjacent to each other may be bonded to each other to form a saturated carbon ring or an unsaturated carbon ring. Examples of the saturated carbon ring or the unsaturated carbon ring include naphthalene, azulene, anthracene, fluorene, phenalene, and the like. $R^{S4}$, $R^{S5}$, $R^{S6}$, and $R^{S7}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, and a cyano group, and more preferably a hydrogen atom.

$Ar^{S3}$ represents a substituted or unsubstituted aryl group having 6 to 30 carbon atoms, or a substituted or unsubstituted heteroaryl group having 2 to 30 carbon atoms. $Ar^{S3}$ is preferably substituted or unsubstituted phenyl group.

Next, the general formula (Sa-1) will be described.

In the general formula (Sa-1), $R^{S8}$ and R" each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S8}$ and $R^{S9}$ are preferably a substituted or unsubstituted alkyl group having 1 to 30 carbon atoms, and a substituted or unsubstituted aryl group having 6 to 30 carbon atoms, and more preferably a methyl group and a phenyl group. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ is preferably a substituted or unsubstituted aryl group having 6 to 30 carbon atoms, and more preferably a phenyl group. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. $R^{S11}$ and $R^{S12}$ which are adjacent to each other may be bonded to each other to form a saturated carbon ring or an unsaturated carbon ring. Examples of the saturated carbon ring or the unsaturated carbon ring include naphthalene, azulene, anthracene, fluorene, phenalene, and the like. $R^{S11}$ and $R^{S12}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, and a cyano group, and more preferably a hydrogen atom. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ represent a substituted or unsubstituted alkylene group having 1 to 30 carbon atoms, or a substituted or unsubstituted allylene group having 6 to 30 carbon atoms. $Y^{S1}$ and $Y^{S2}$ are preferably a substituted or unsubstituted allylene group having 6 to 30 carbon atoms, and more preferably substituted or unsubstituted phenylene. n is an integer of 0 to 5, preferably an integer of 0 to 3, more preferably an integer of 0 to 2, and sill more preferably an integer of 0. m is an integer of 0 to 5, preferably an integer of 0 to 3, more preferably an integer of 0 to 2, and sill more preferably an integer of 1.

The general formula (Sa-1) is preferably the compound represented by the following general formula (Sa-2).

General Formula (Sa-2)

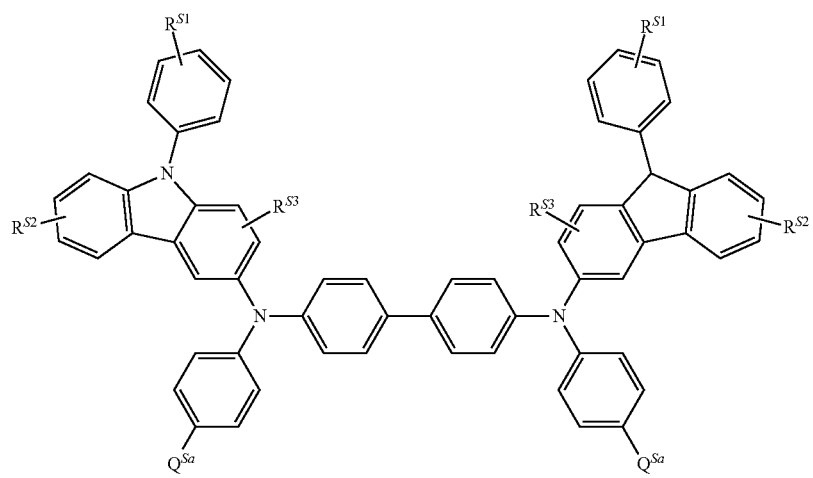

(In the formula, $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. $R^{S1}$, $R^{S2}$, and $R^{S3}$ which are adjacent to each other may be bonded to each other to form a saturated carbon ring or an unsaturated carbon ring. $Q^{Sa}$ independently represent a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, substituted or unsubstituted heterocycle having 2 to 30 carbon atoms, or a substituted or unsubstituted amino group.)

The general formula (Sa-2) will be described. $R^{S1}$, $R^{S2}$, and $R^{S3}$ are the same as that in the general formula (Sa-1), and the preferred ranges are the same. $Q^{Sa}$ independently represent a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, substituted or unsubstituted heterocycle having 2 to 30 carbon atoms, or a substituted or unsubstituted amino group. $Q^{Sa}$ preferably a hydrogen atom, a cyano group, a fluorine atom, a substituted or unsubstituted alkyl group having 1 to 30 carbon atoms, and a substituted or unsubstituted aryl group having 6 to 30 carbon atoms, and more preferably a hydrogen atom, and a substituted or unsubstituted alkyl group having 1 to 30 carbon atoms, and still more preferably a hydrogen atom.

The general formula (Sb-1) is preferably the compound represented by the following general formula (Sb-2).

General Formula (Sb-2)

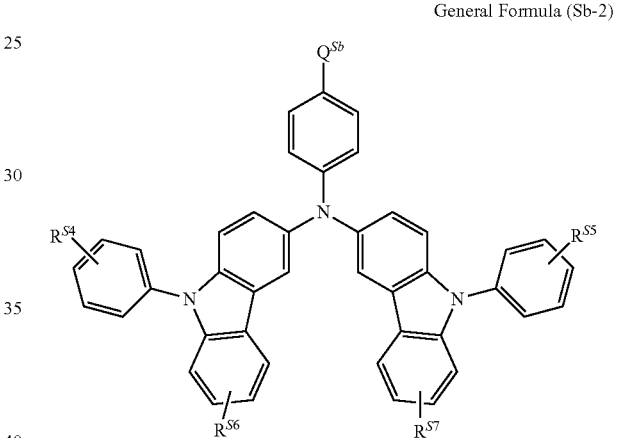

(In the formula, $R^{S4}$, $R^{S5}$, $R^{S6}$, and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. $R^{S4}$, $R^{S5}$, $R^{S6}$, and $R^{S7}$ which are adjacent to each other may be bonded to each other to form a saturated carbon ring or an unsaturated carbon ring. $Q^{Sb}$ independently represent a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, substituted or unsubstituted heterocycle having 2 to 30 carbon atoms, or a substituted or unsubstituted amino group.)

The general formula (Sb-2) will be described. $R^{S4}$, $R^{S5}$, $R^{S6}$, and $R^{S7}$ are the same as that in the general formula (Sb-1), and the preferred ranges are the same. $Q^{Sa}$ independently represent a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, substituted or unsubstituted heterocycle having 2 to 30 carbon atoms, or a substituted or unsubstituted amino group. $Q^{Sa}$ is preferably a hydrogen atom, a cyano group, a fluorine atom, a substituted or unsubstituted alkyl group having 1 to 30 carbon atoms, and a substituted or unsubstituted aryl group having 6 to 30 carbon atoms, and more preferably a hydrogen atom, and a substituted or unsubstituted alkyl group having 1 to 30 carbon atoms, and still more preferably a hydrogen atom.

The general formula (Sc-1) is preferably the compound represented by the following formula (Sc-2).

General Formula (Sc-2)

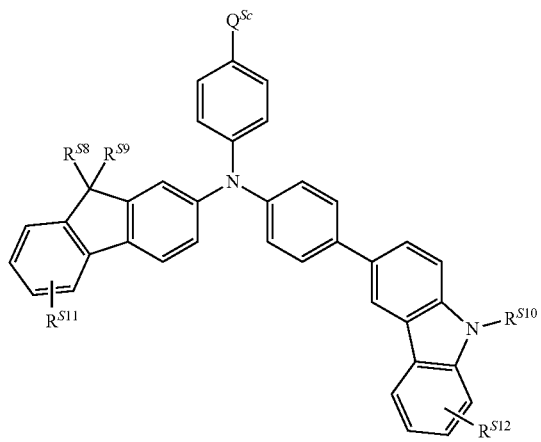

(In the formula, $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, or a substituted or unsubstituted fused polycyclic group having 5 to 30 carbon atoms, a hydroxy group, a cyano group, or a substituted or unsubstituted amino group. $R^{S11}$ and $R^{S12}$ which are adjacent to each other may be bonded to each other to form a saturated carbon ring or an unsaturated carbon ring. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, substituted or unsubstituted heterocycle having 2 to 30 carbon atoms, or a substituted or unsubstituted amino group.)

The general formula (Sc-2) will be described. $R^{S8}$, $R^{S9}$, $R^{S10}$, $R^{S11}$, and $R^{S12}$ are the same as that in the general formula (Sc-1), and the preferred ranges are the same. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, substituted or unsubstituted heterocycle having 2 to 30 carbon atoms, or a substituted or unsubstituted amino group. $Q^{Sc}$ is preferably a hydrogen atom, a cyano group, a fluorine atom, a substituted or unsubstituted alkyl group having 1 to 30 carbon atoms, and a substituted or unsubstituted aryl group having 6 to 30 carbon atoms, and more preferably a hydrogen atom, and a substituted or unsubstituted aryl group having 6 to 30 carbon atoms, and still more preferably a phenyl group.

Specific examples of the compounds represented by the general formula (Sa-1), (Sb-1), and (Sc-1) include the followings. However, the present invention is not limited to the following specific examples.

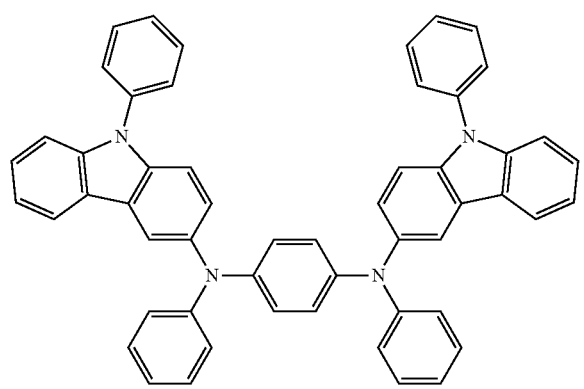

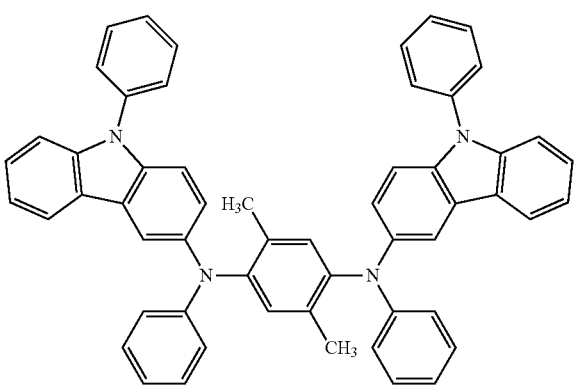

-continued
3 4
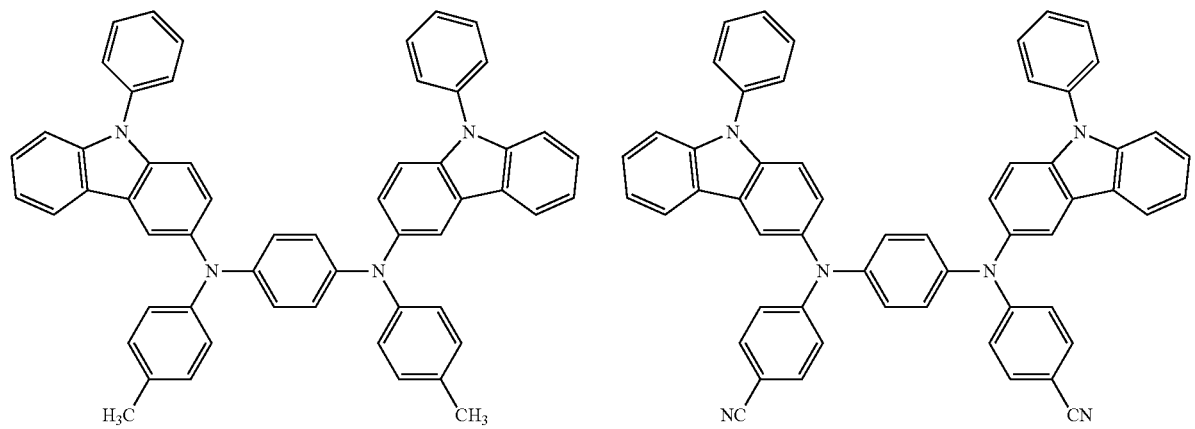
5 6
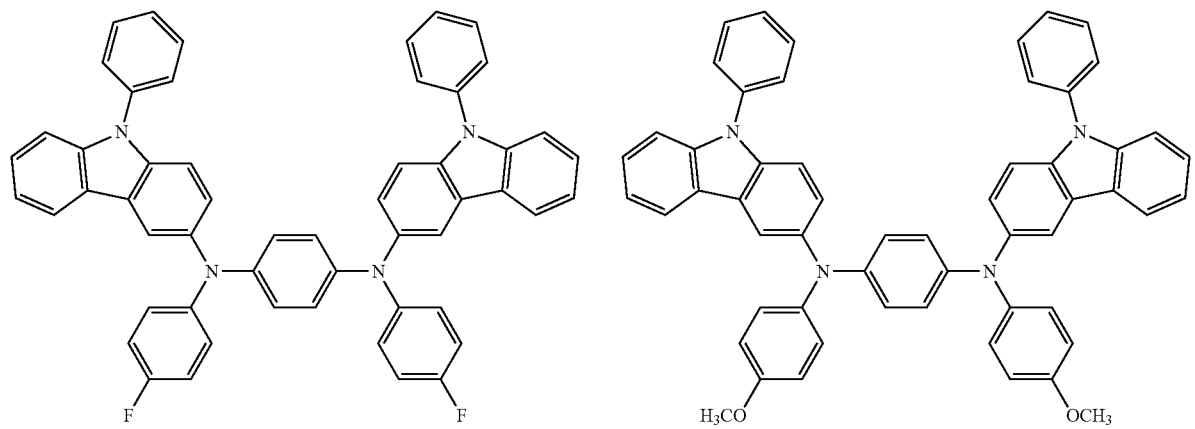
7 8
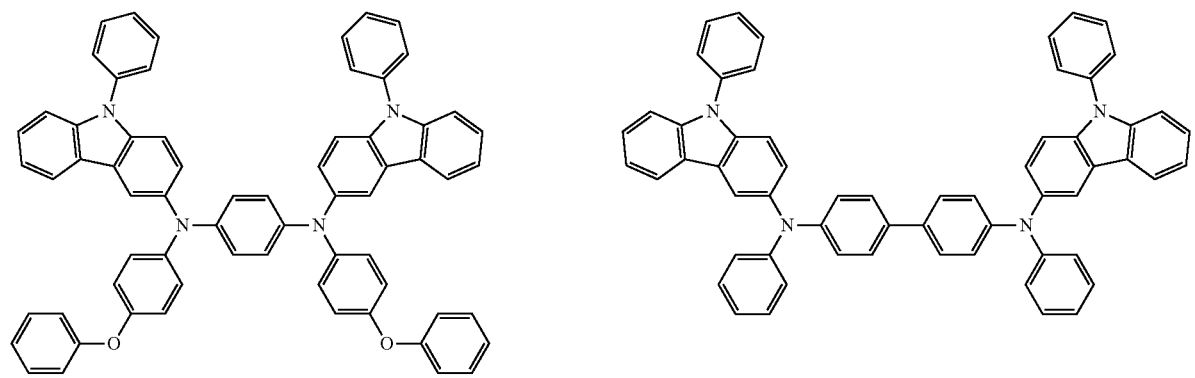

-continued
9
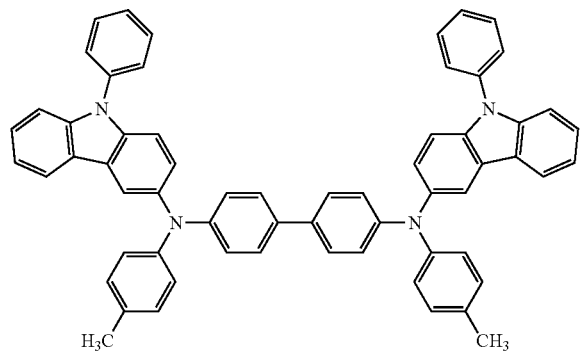
10
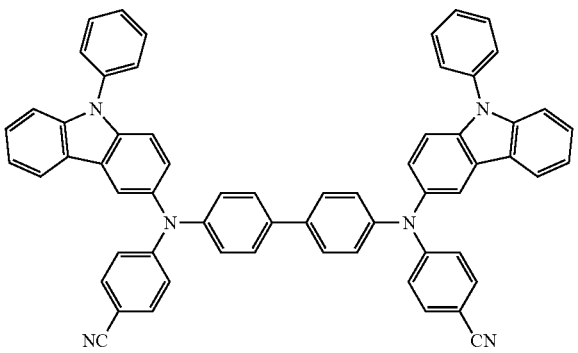
11
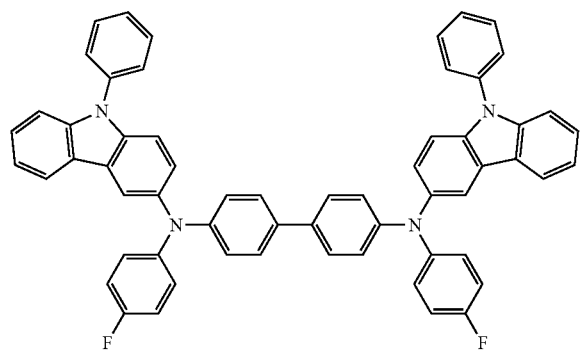
12
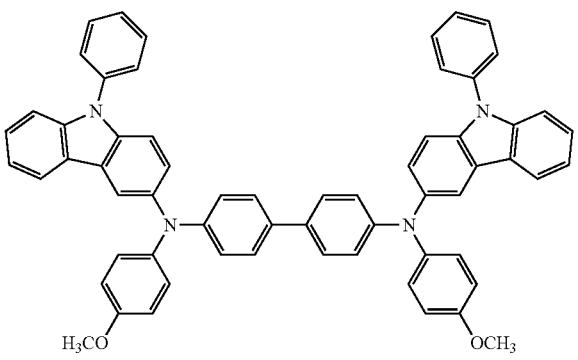
13
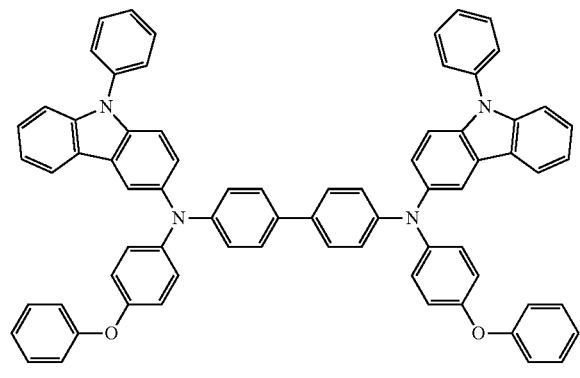
14
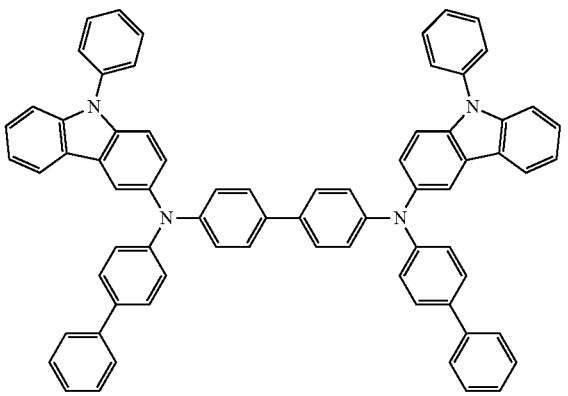
15
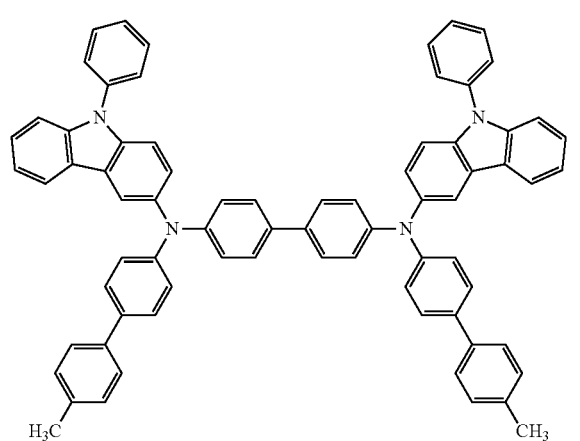
16
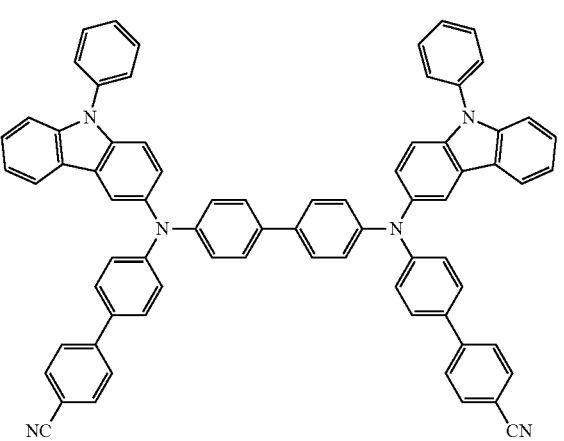

-continued
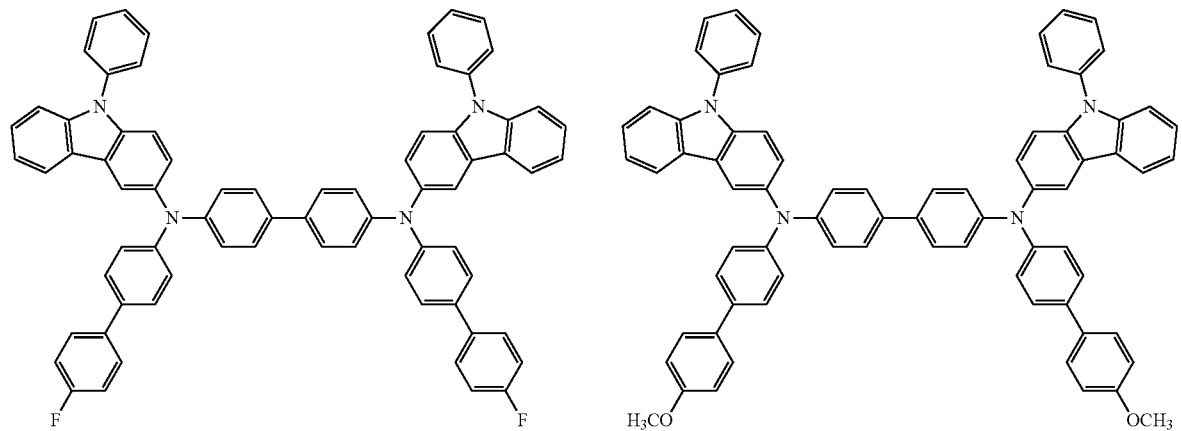
17
18
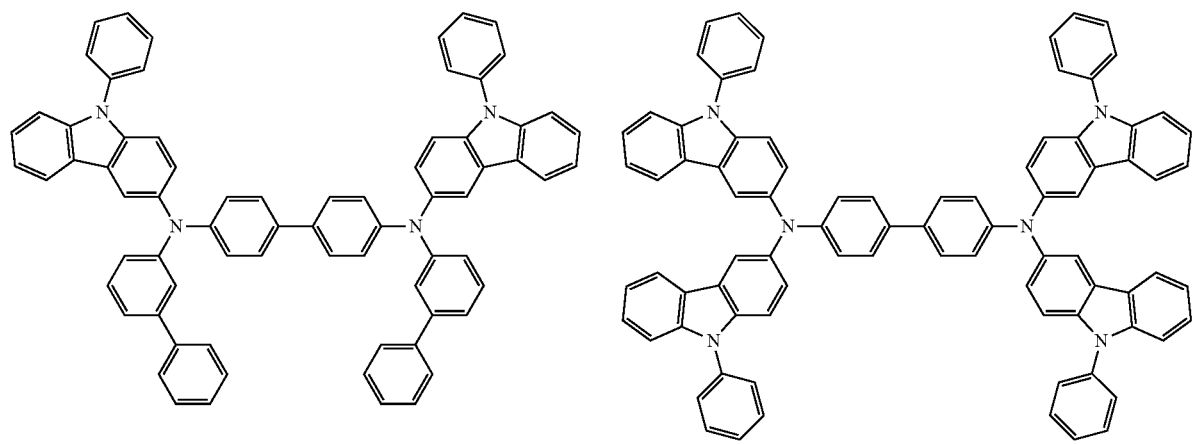
19
20
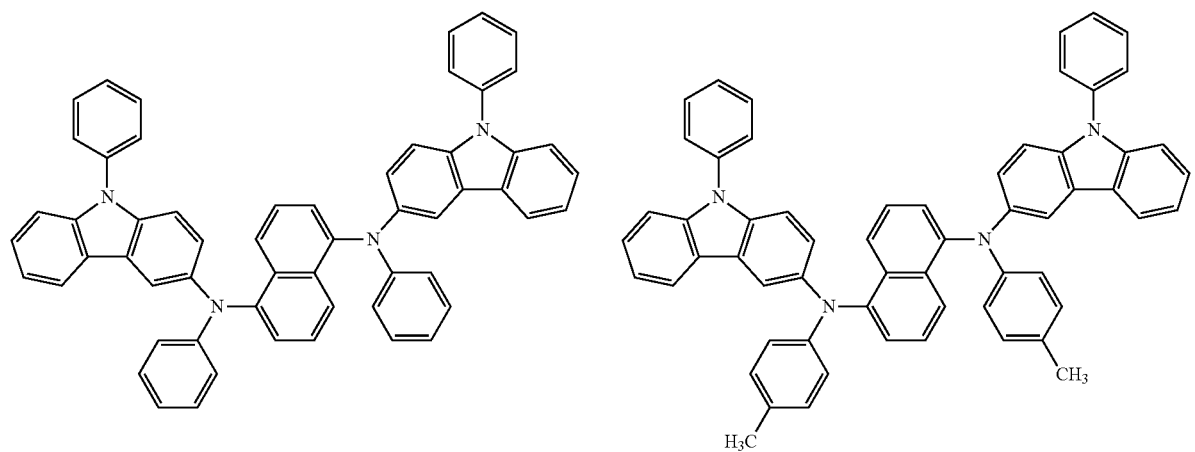
21
22

-continued
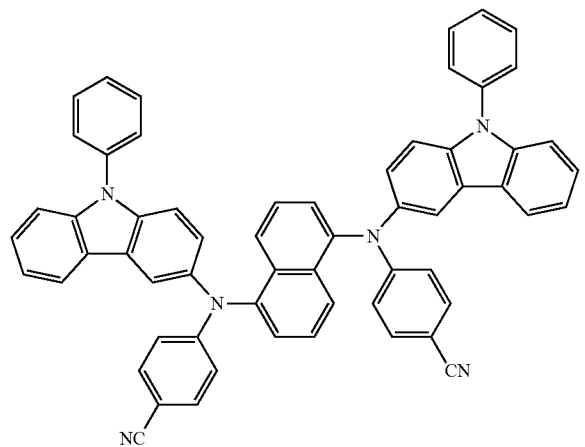
23
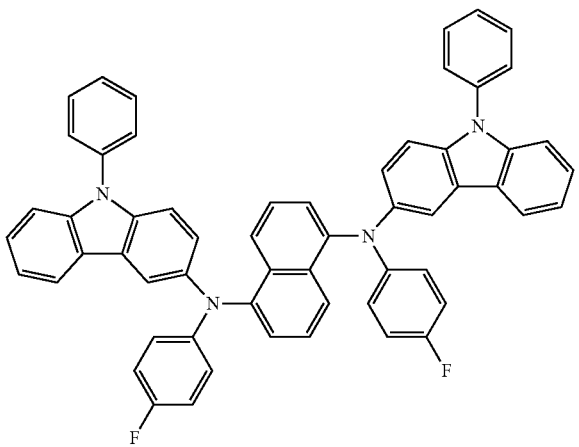
24
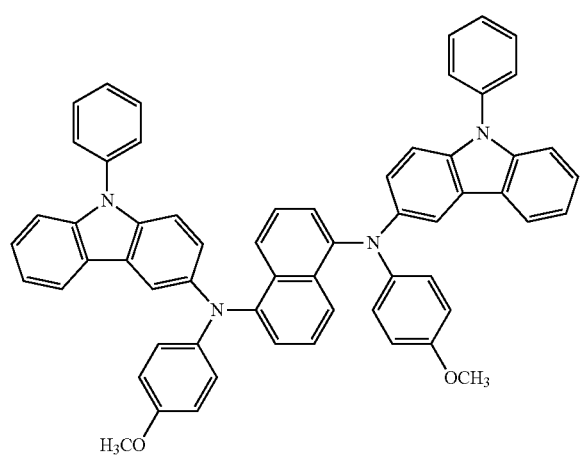
25
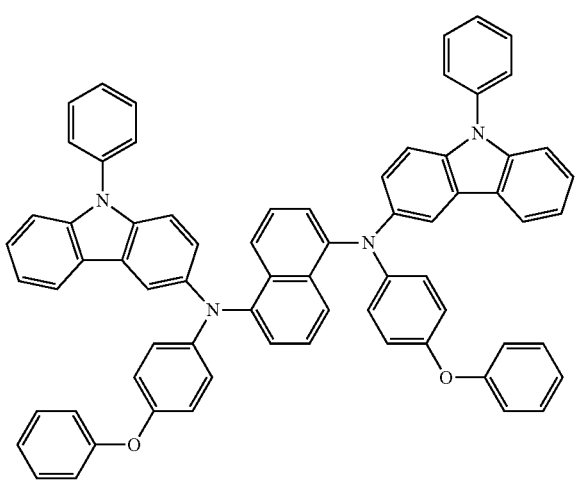
26
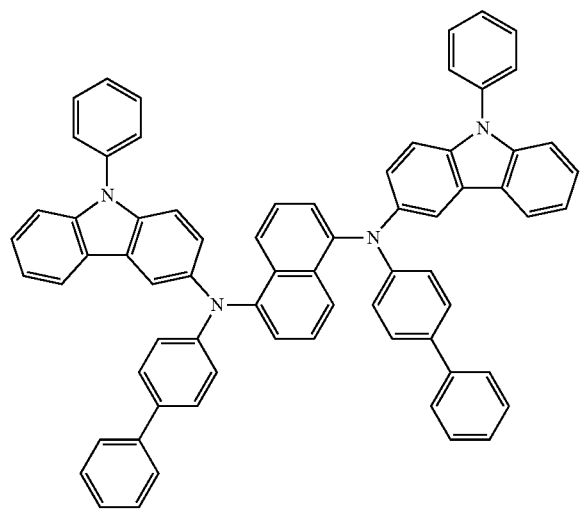
27

-continued
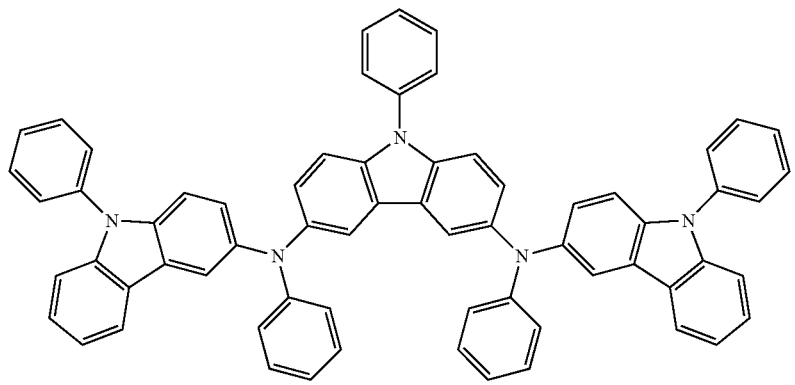
28
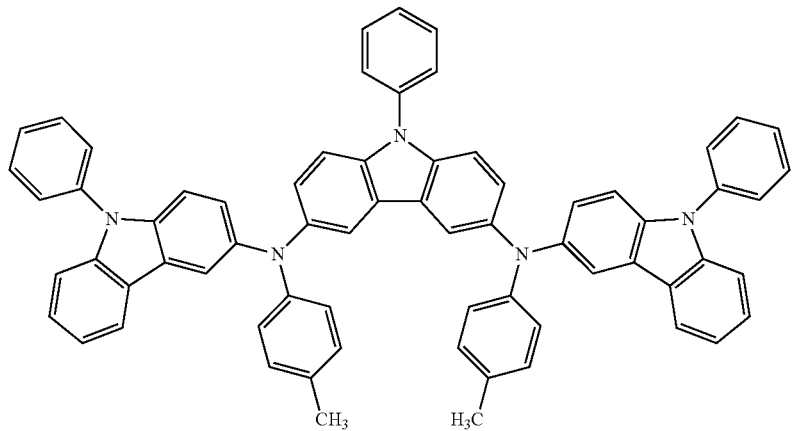
29
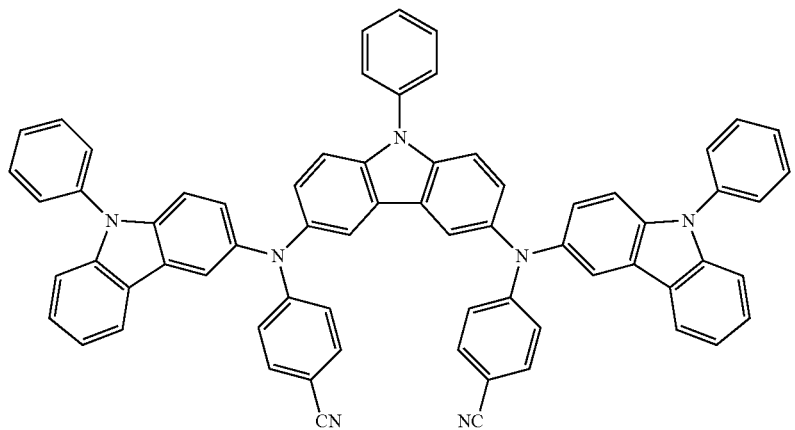
30

31
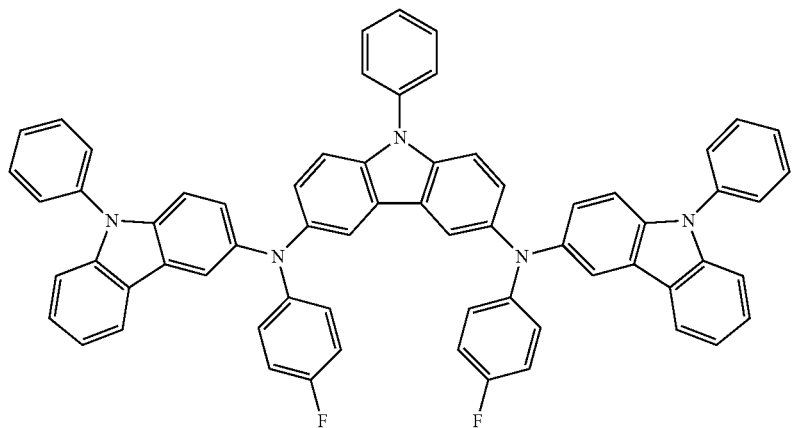
32
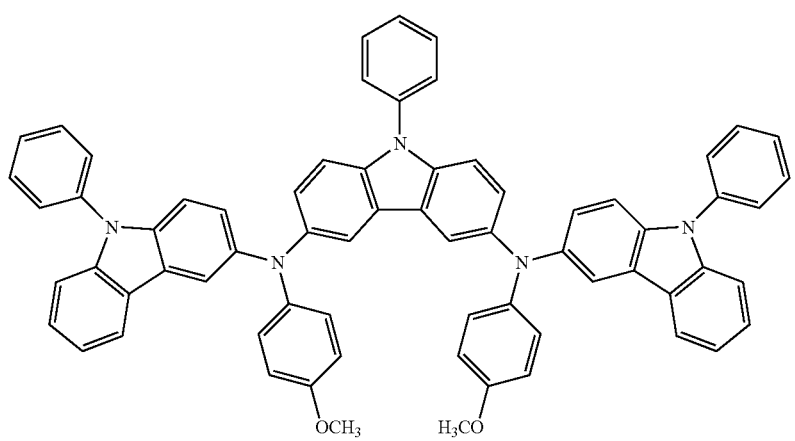
33
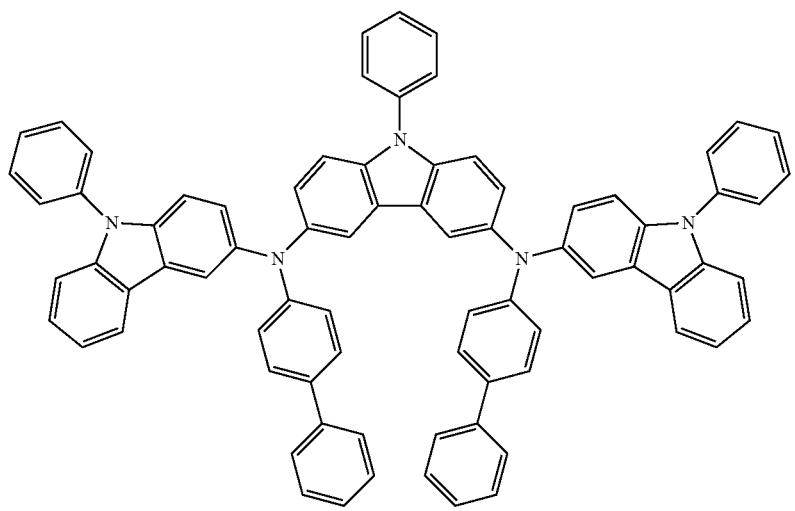

34
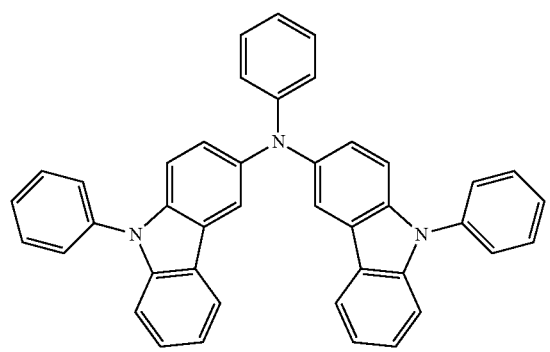
35
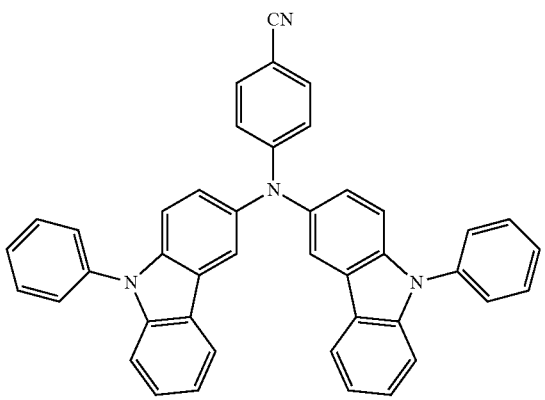
36
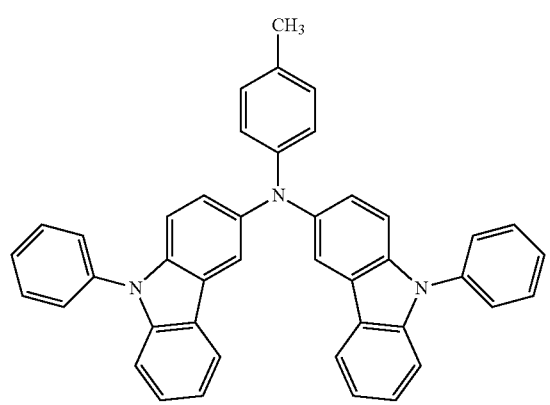
37
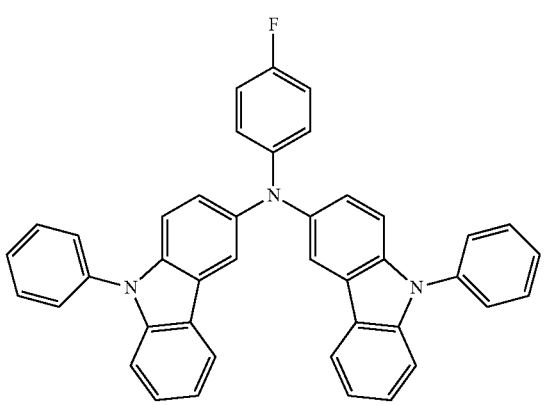
38
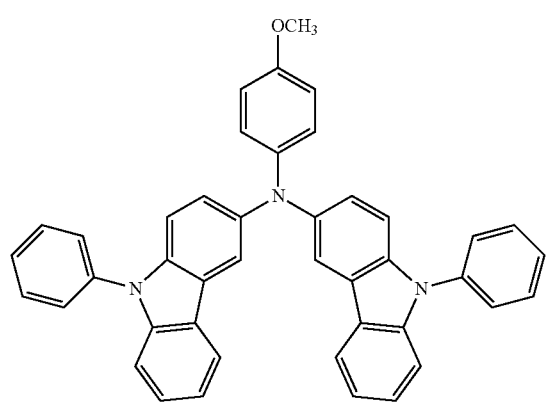
39
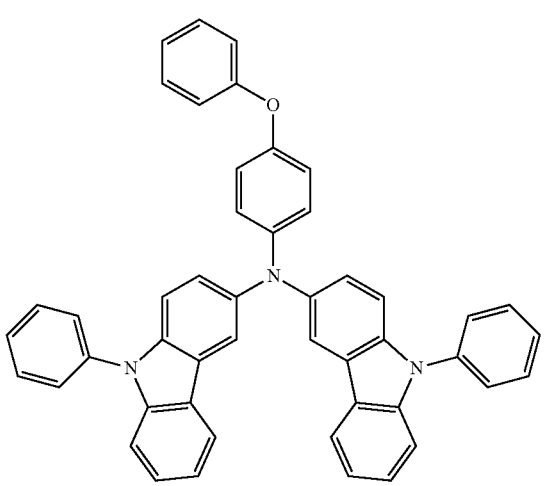

40
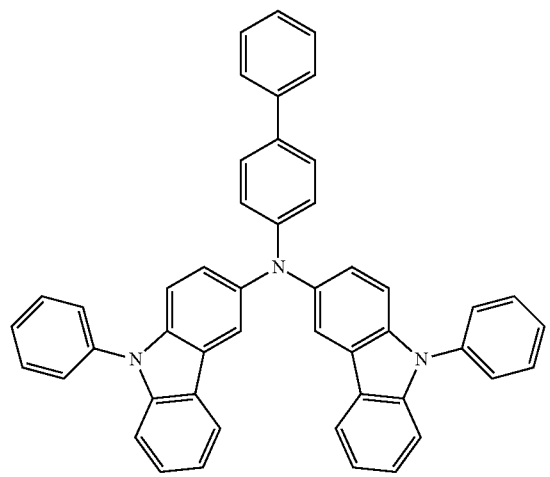
41
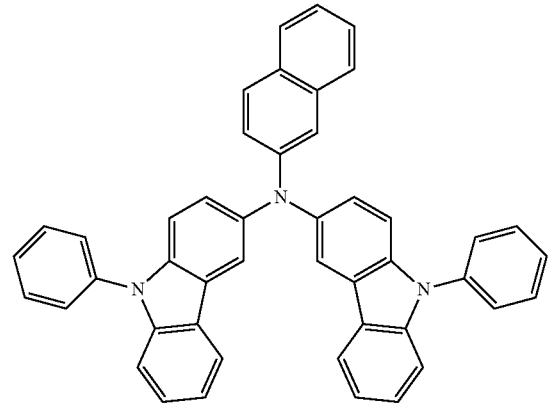
42
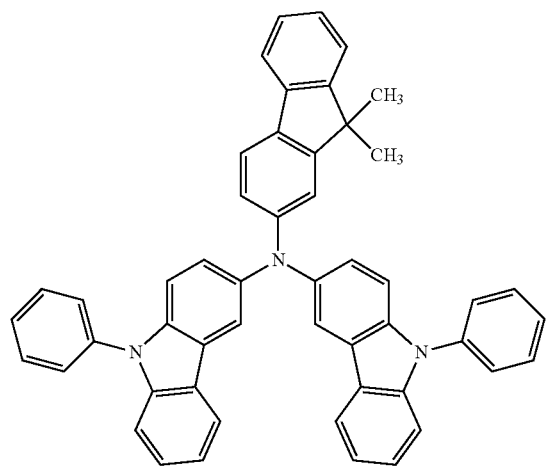
43
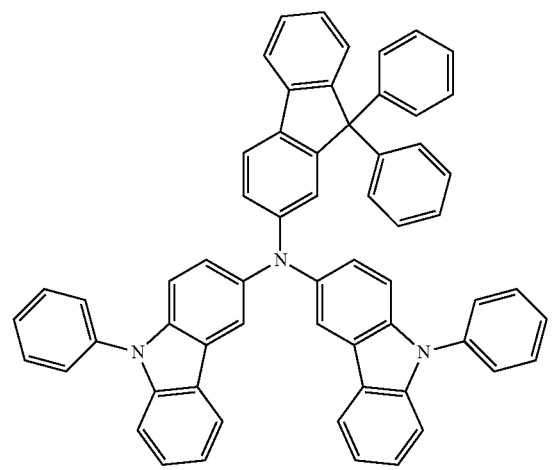
44
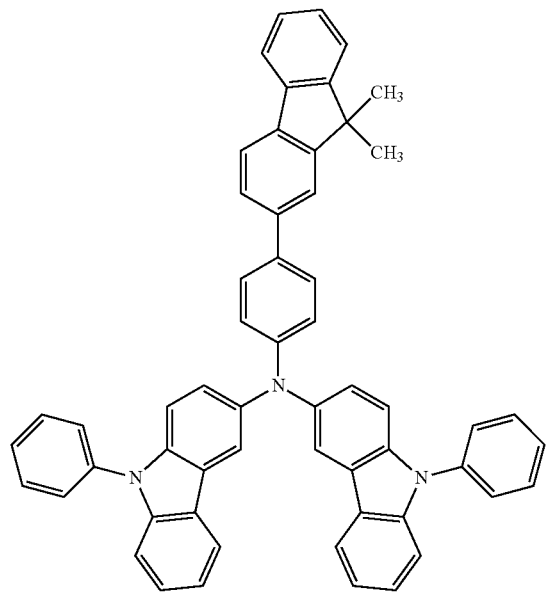
45
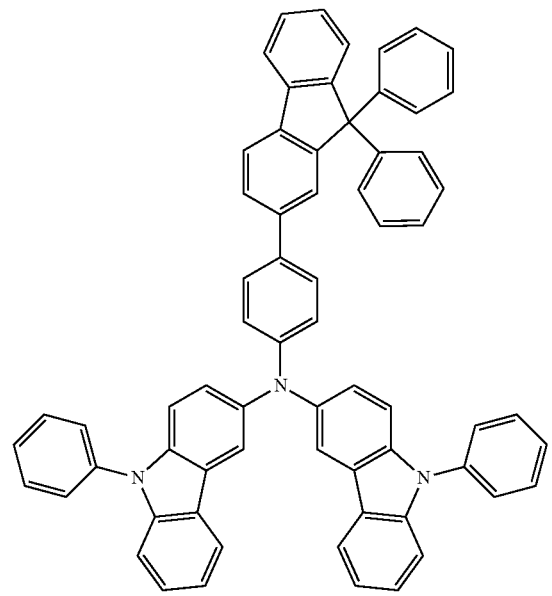

-continued
46
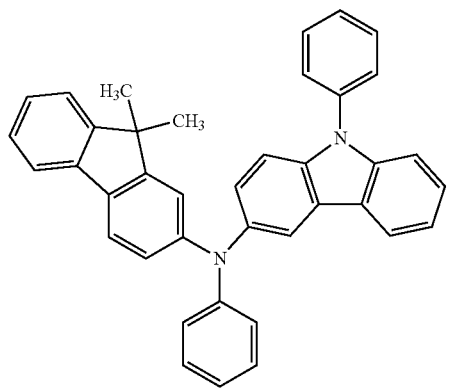
47
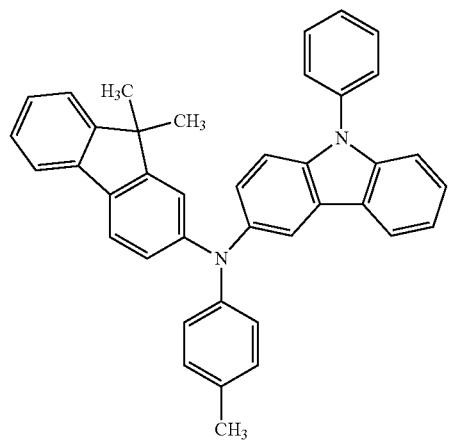
48
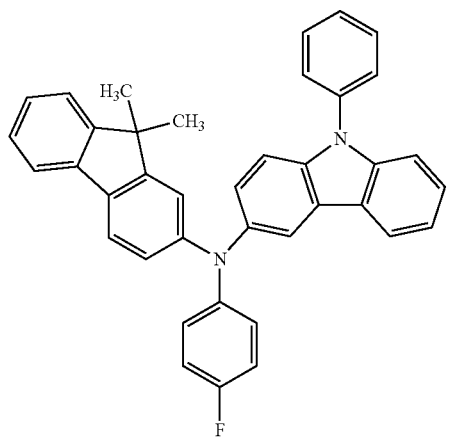
49
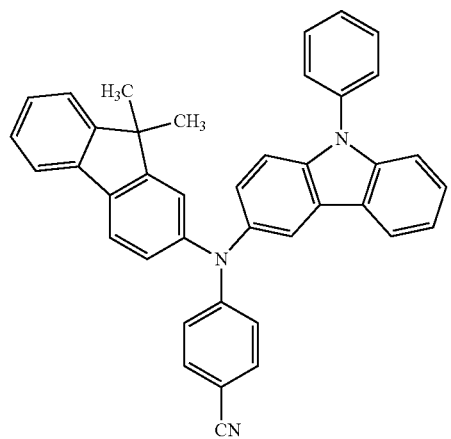
50
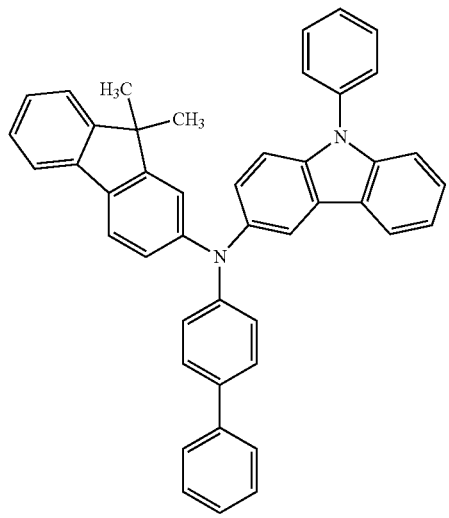
51
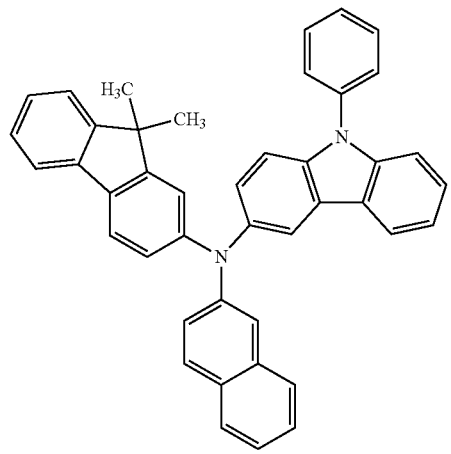

-continued
52
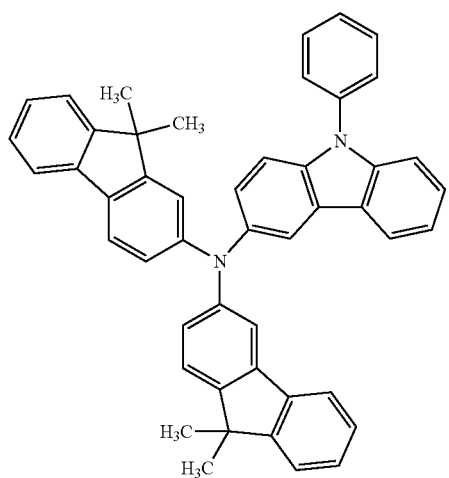
53
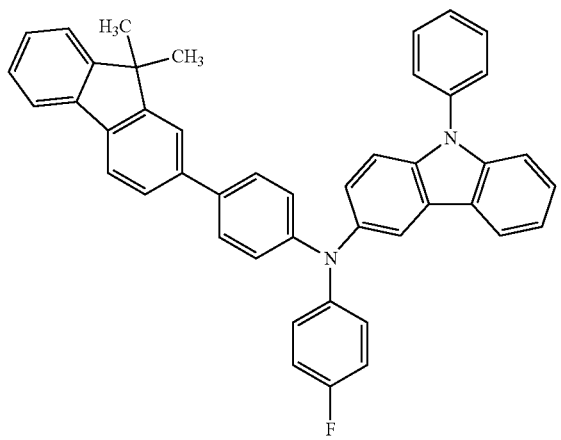
54
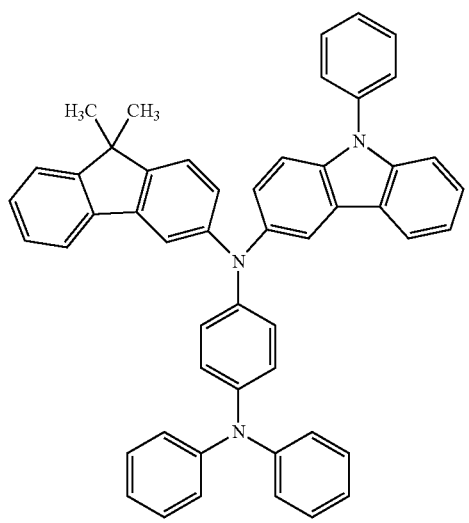
55
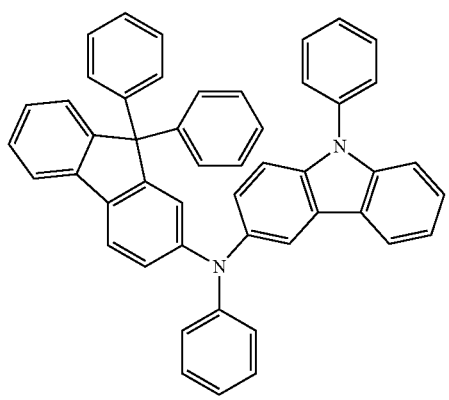
56
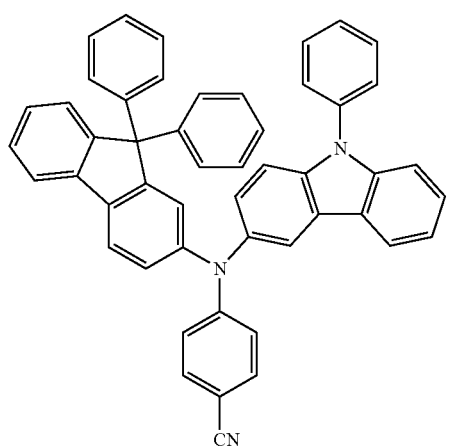
57
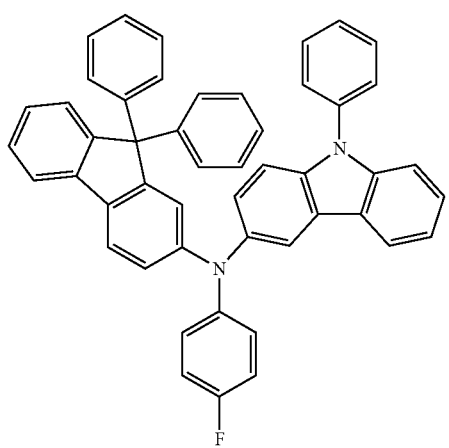

-continued
58
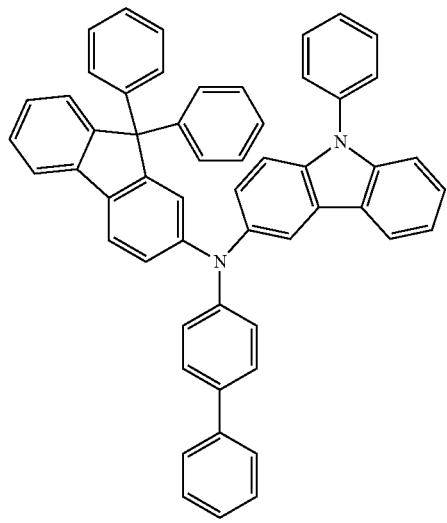
59
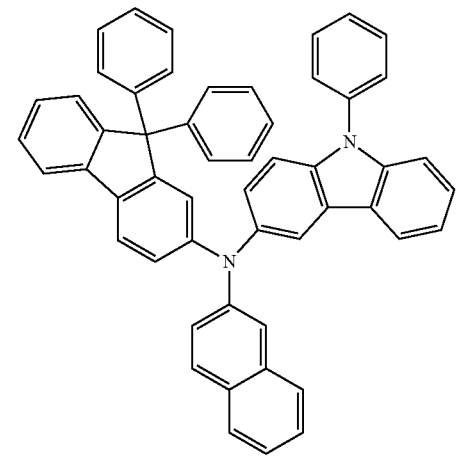
60
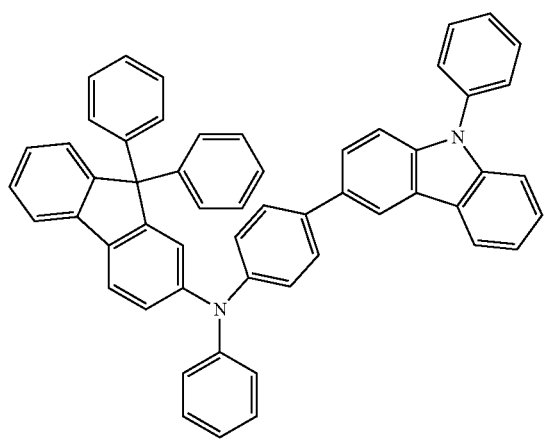
61
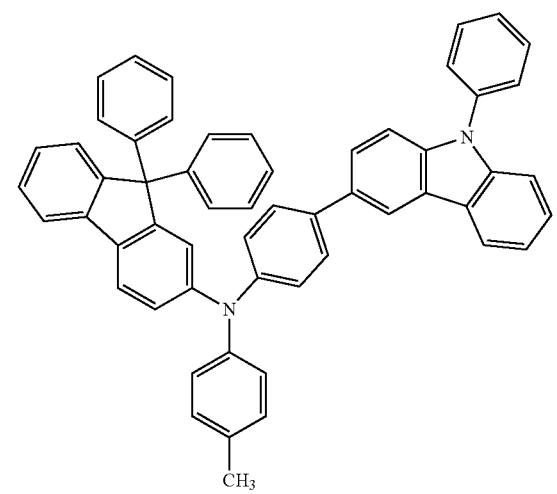
62
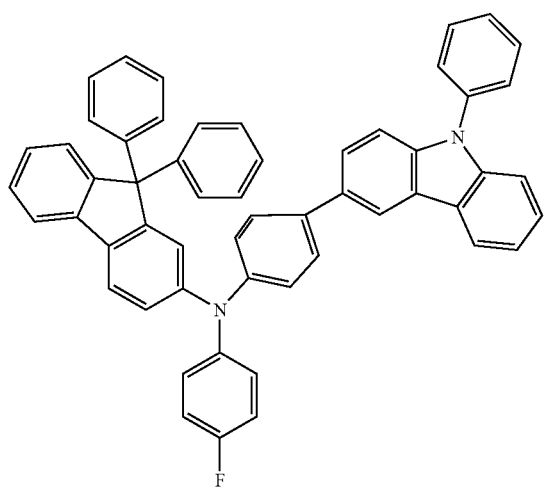
63
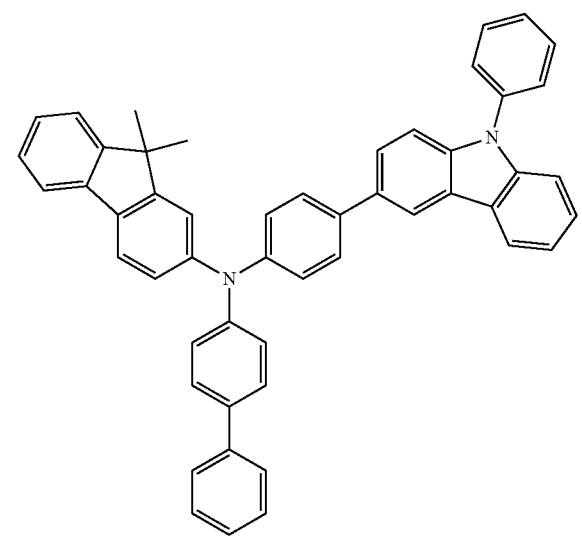
The compound represented by the general formula (Sa-1), (Sb-1), or (Sc-1) can be synthesized by the method described in JP-A-2007-318101. After the synthesis, purification is preferably carried out by column chromatography, recrystallization, reprecipitation, or the like, and then by sublimation purification. Organic impurities can be separated and inorganic salts, residual solvents, moisture, or the like can be removed effectively by the sublimation purification.

In the light emitting element of the present invention, the compound represented by the general formula (Sa-1), (Sb-1), or (Sc-1) is preferably contained in the organic layer between the light emitting layer and the anode, and among them, is more preferably contained in the layer on the anode side adjacent to the light emitting layer, and is particularly preferably a hole transporting material contained in a hole transporting layer.

The compound represented by the general formula (Sa-1), (Sb-1), or (Sc-1) is preferably contained in the amount of 70 to 100% by mass, and more preferably 85 to 100% by mass, based on the total mass of the organic layer added.

[Compound Represented By General Formula (M-3)]

The organic electroluminescent element of the present invention is a material which is particularly preferably used in an organic layer (A), preferably disposed between the anode and the light emitting layer, and examples thereof include at least one kind of the compound represented by the following general formula (M-3).

The compound represented by the general formula (M-3) is more preferably contained in the organic layer adjacent to the light emitting layer between the light emitting layer and the anode, but it is not limited in its uses and may be further contained in any of other layers in the organic layer. The layer to which the compound represented by the general formula (M-3) is introduced may be any one or plural layers of a light emitting layer, a hole injecting layer, a hole transporting layer, an electron transporting layer, an electron injecting layer, and a charge blocking layer.

The organic layer adjacent to the light emitting layer between the light emitting layer and the anode, which contains the compound represented by the general formula (M-3), is more preferably an electron blocking layer or a hole transporting layer.

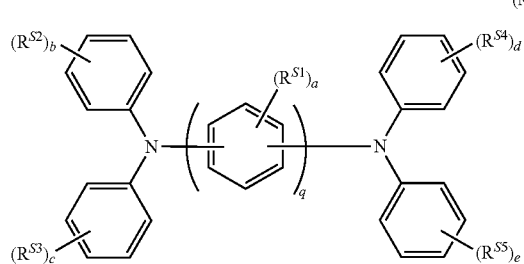

(M-3)

In the general formula (M-3), $R^{31}$ to $R^{35}$ each independently represent an alkyl group, a cycloalkyl group, an alkenyl group, an alkynyl group, —CN, a perfluoroalkyl group, a trifluorovinyl group, —$CO_2R$, —C(O)R, —$NR_2$, —$NO_2$, —OR, a halogen atom, an aryl group, or a heteroaryl group, and may also have a substituent Z. R's each independently represent a hydrogen atom, an alkyl group, a perhaloalkyl group, an alkenyl group, an alkynyl group, a heteroalkyl group, an aryl group, or a heteroaryl group. When a plurality of $R^{31}$'s to $R^{35}$'s are present, they may be bonded to each other to form a ring and further have a substituent Z.

a represents an integer of 0 to 4, and when a plurality of $R^{S1}$'s are present, they may be the same as or different from each other and may be bonded to each other to form a ring. b to e each independently represent an integer of 0 to 5, and when each of a plurality of $R^{S2}$'s to $R^{S5}$'s are present, they may be the same as or different from each other, and any two out of them may be bonded to each other to form a ring.

q is an integer of 1 to 5, and when q is 2 or more, the plurality of $R^{S1}$'s may be the same as or different from each other, and may be bonded to each other to form a ring.

The alkyl group may have a substituent and may be saturated or unsaturated. Examples of the group which may be used for substitution include the above-described substituents Z. Examples of the alkyl group represented by $R^{S1}$ to $R^{S5}$ preferably include alkyl groups having 1 to 8 carbon atoms in total, and more preferably alkyl groups having 1 to 6 carbon atoms in total, for example, a methyl group, an ethyl group, an i-propyl group, a cyclohexyl group, and a tert-butyl group.

The cycloalkyl group may have a substituent, and may be saturated or unsaturated. Examples of the group which may be used for substitution include the above-described substituents Z. Examples of the cycloalkyl group represented by $R^{S1}$ to $R^{S5}$ preferably include cycloalkyl groups having 4 to 7 ring members, and more preferably cycloalkyl groups having 5 to 6 carbon atoms in total, for example, a cyclopentyl group and a cyclohexyl group.

Examples of the alkenyl group represented by $R^{S1}$ to $R^{S5}$ include ones preferably having 2 to 30 carbon atoms, more preferably 2 to 20 carbon atoms, and particularly preferably 2 to 10 carbon atoms, for example, vinyl, allyl, 1-propenyl, 1-isopropenyl, 1-butenyl, 2-butenyl, and 3-pentenyl.

Examples of the alkynyl group represented by $R^{S1}$ to $R^{S5}$ include ones preferably having 2 to 30 carbon atoms, more preferably 2 to 20 carbon atoms, and particularly preferably to 10 carbon atoms, for example, ethynyl, propargyl, 1-propynyl, and 3-pentynyl.

Examples of the perfluoroalkyl group represented by $R^{S1}$ to $R^{S5}$ include those in which all the hydrogen atoms of the above-described alkyl group are substituted with fluorine atoms.

Preferred examples of the aryl group represented by $R^{S1}$ to $R^{S5}$ include a substituted or unsubstituted aryl group having 6 to 30 carbon atoms, for example, a phenyl group, a tolyl group, a biphenyl group, and a terphenyl group.

The heteroaryl group represented by $R^{S1}$ to $R^{S5}$ is preferably a heteroaryl group having 5 to 8 carbon atoms, and more preferably a 5- or 6-membered substituted or unsubstituted heteroaryl group, and examples thereof include a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a triazolyl group, a benzothiazolyl group, an isothiazolyl group, a benzisothiazolyl group, a thiadiazolyl group, an isoxazolyl group, a benzisoxazolyl group, a pyrrolidinyl, piperidinyl group, a piperadinyl group, an imidazolidinyl group, a thiazolinyl group, a sulfolanyl group, a carbazolyl group, a dibenzofuryl group, a dibenzothienyl group, and a pyridindolyl group. Preferred examples thereof include a pyridyl group, a pyrimidinyl group, an imidazolyl group, and a thienyl group, and more preferably a pyridyl group and a pyrimidinyl group.

$R^{S1}$ to $R^{S5}$ are preferably a hydrogen atom, an alkyl group, a cyano group, a trifluoromethyl group, a perfluoroalkyl group, a dialkylamino group, a fluoro group, an aryl group, or a heteroaryl group, more preferably a hydrogen atom, an alkyl group, a cyano group, a trifluoromethyl group, a fluoro group, or an aryl group, and still more preferably a hydrogen atom, an alkyl group, or an aryl group. The substituent Z is preferably an alkyl group, an alkoxy group, a fluoro group, a cyano group, or a dialkylamino group, and more preferably a hydrogen atom or an alkyl group.

Any two of $R^{S1}$ to $R^{S5}$ may be bonded to each other to form a fused 4- to 7-membered ring, and the fused 4- to 7-membered ring is cycloalkyl, aryl, or heteroaryl, and the fused 4- to 7-membered ring may further have a substituent Z. The definitions and preferred ranges thereof of the cycloalkyl, aryl, and heteroaryl thus formed are the same as for the cycloalkyl group, the aryl group, and the heteroaryl group defined by $R^{S1}$ to $R^{S5}$.

In a case where the compound represented by the general formula (M-3) is used in a hole transporting layer, the compound represented by the general formula (M-3) is preferably contained in the amount of 50 to 100% by mass, more preferably 80 to 100% by mass, and particularly preferably 95 to 100% by mass.

In addition, in a case where the compound represented by the general formula (M-3) is used in a plurality of organic layers, the compound is preferably contained in an amount of the above-described range in each layer.

The thickness of the hole transporting layer including the compound represented by the general formula (M-3) is preferably from 1 nm to 500 nm, more preferably from 3 nm to 200 nm, and still more preferably from 5 nm to 100 nm. Further, the hole transporting layer is preferably provided to be adjacent to the light emitting layer.

Specific examples of the compound represented by the general formula (M-3) are shown below, but the present invention is not limited thereto.

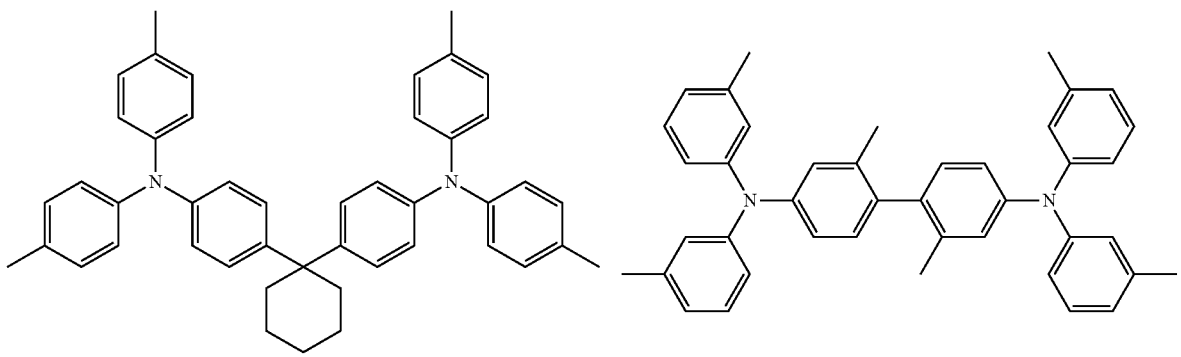

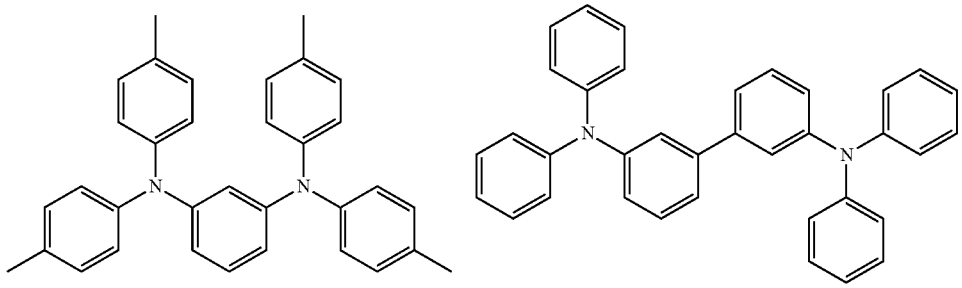

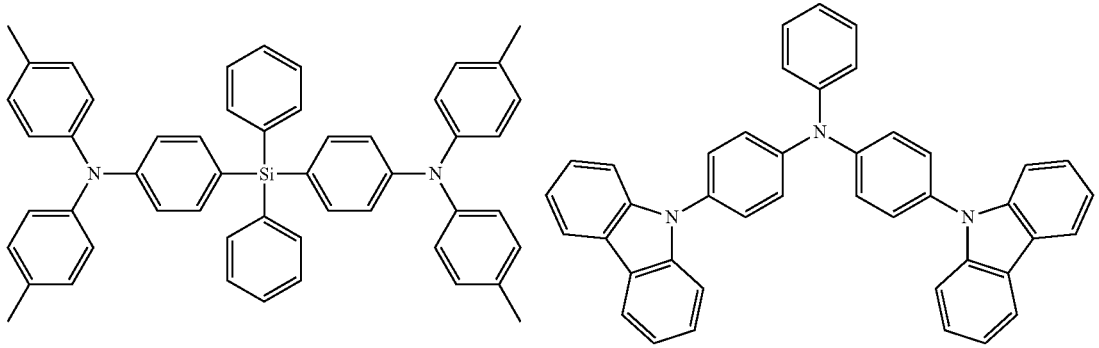

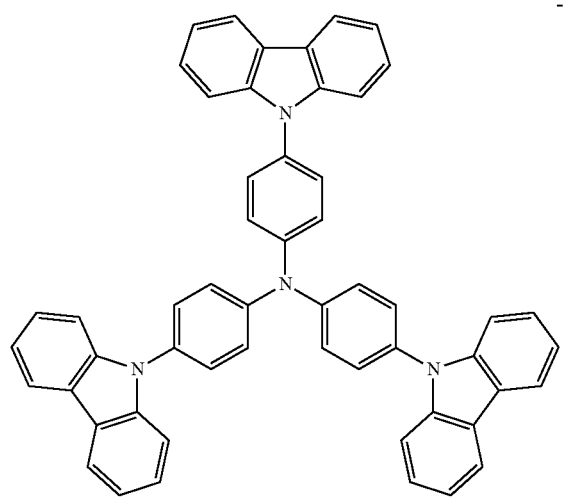
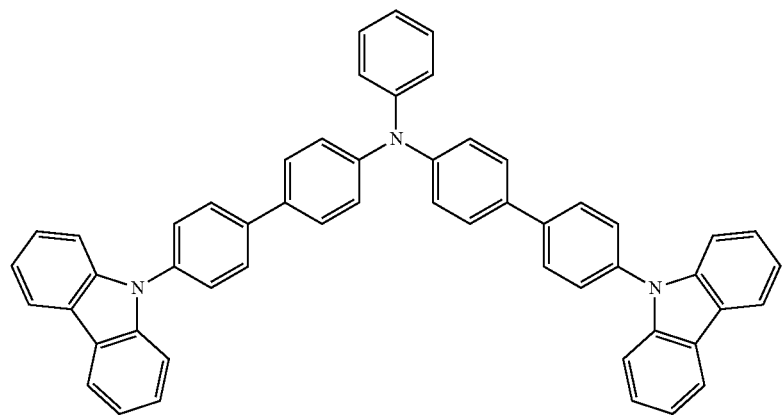
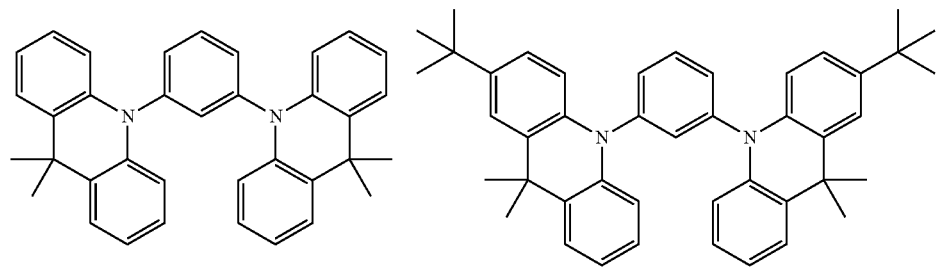
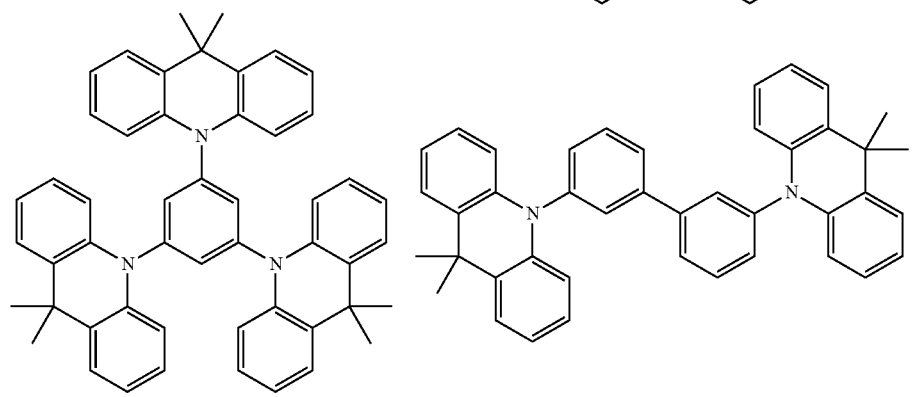

201 202
-continued
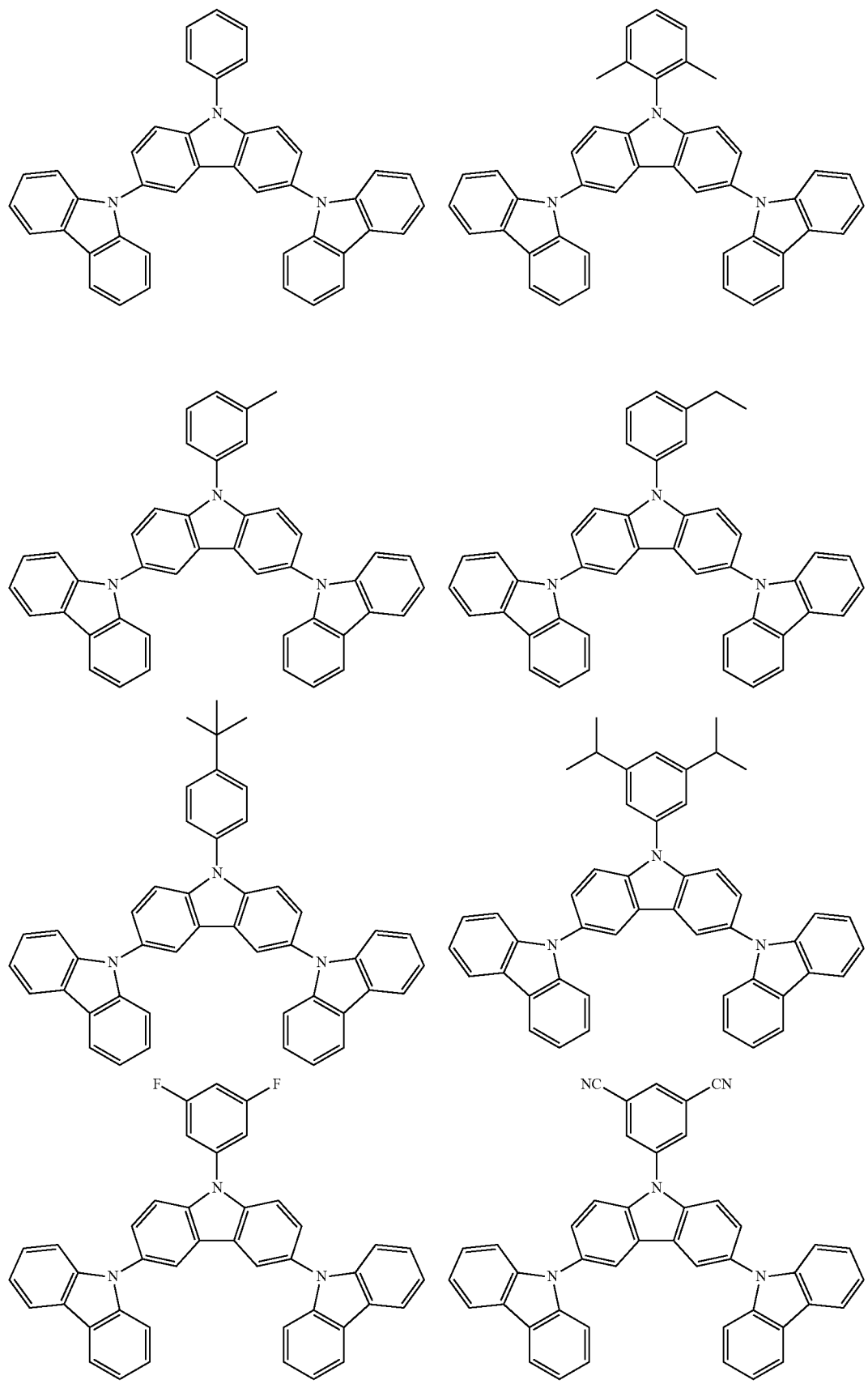

203 204
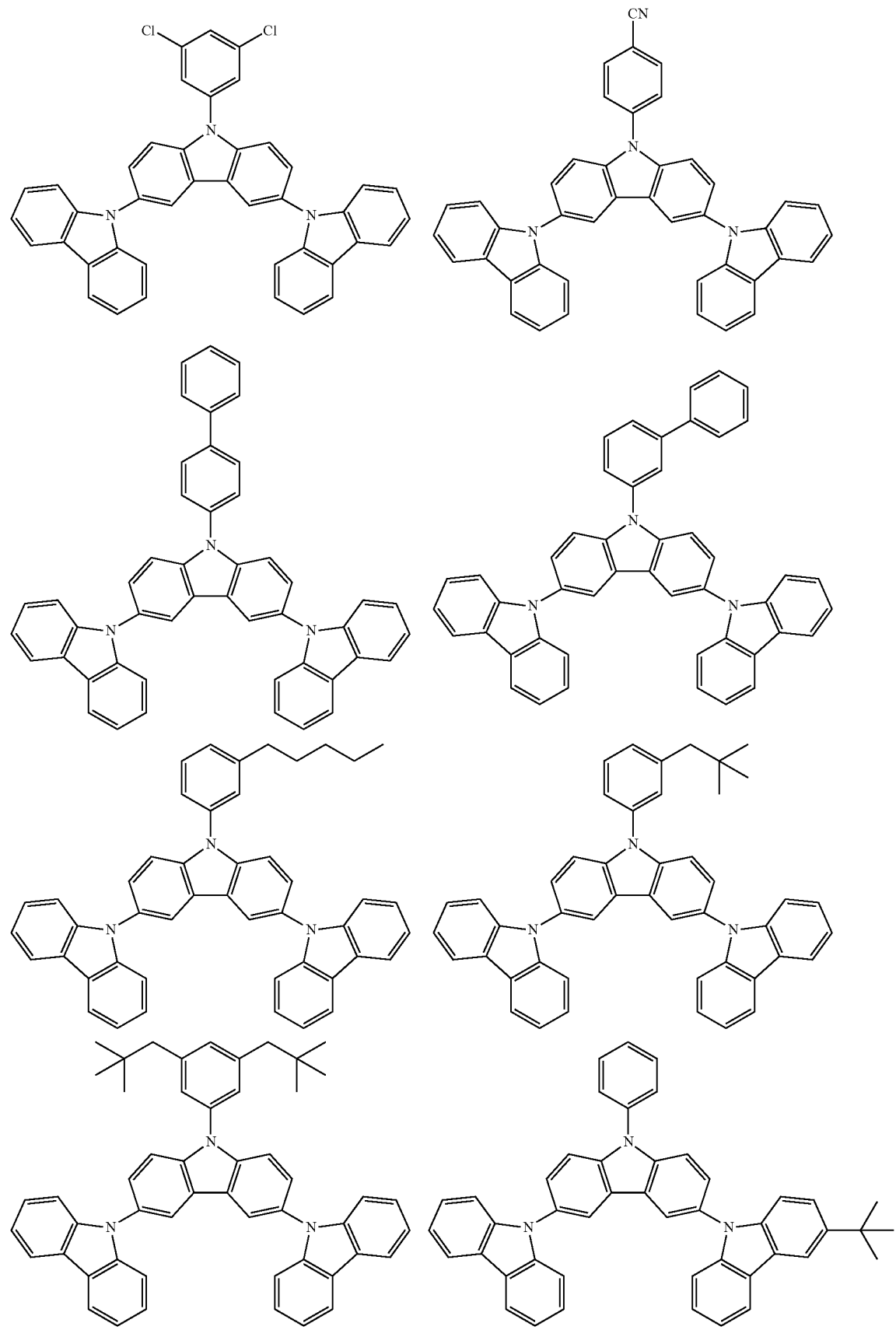
-continued

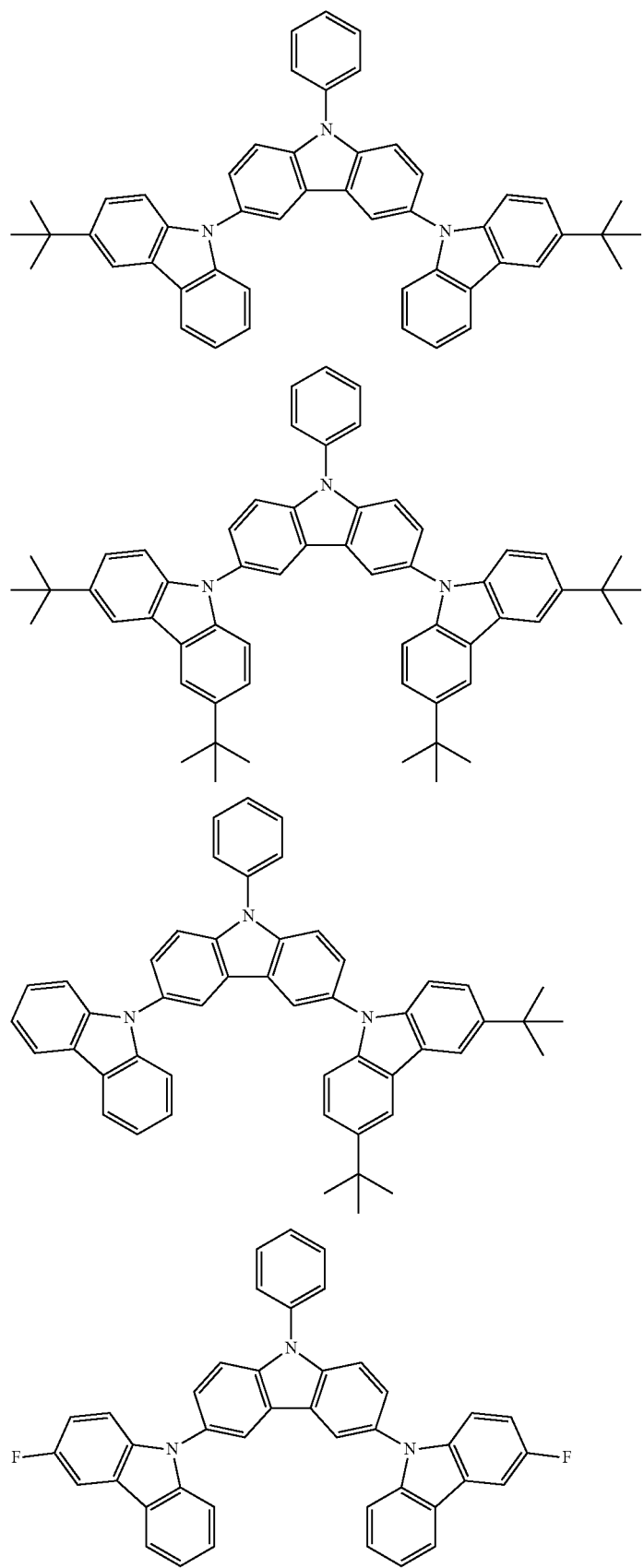

207 208
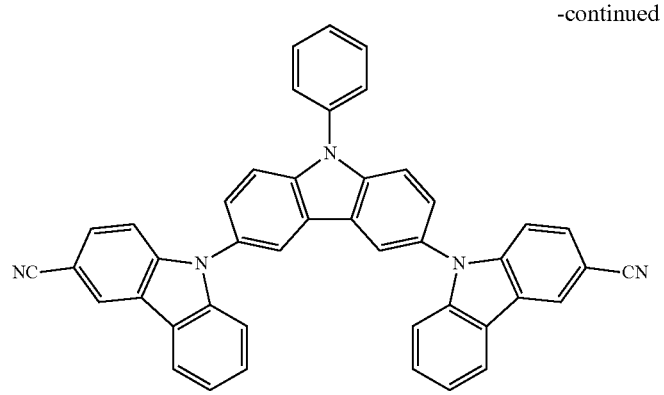
-continued
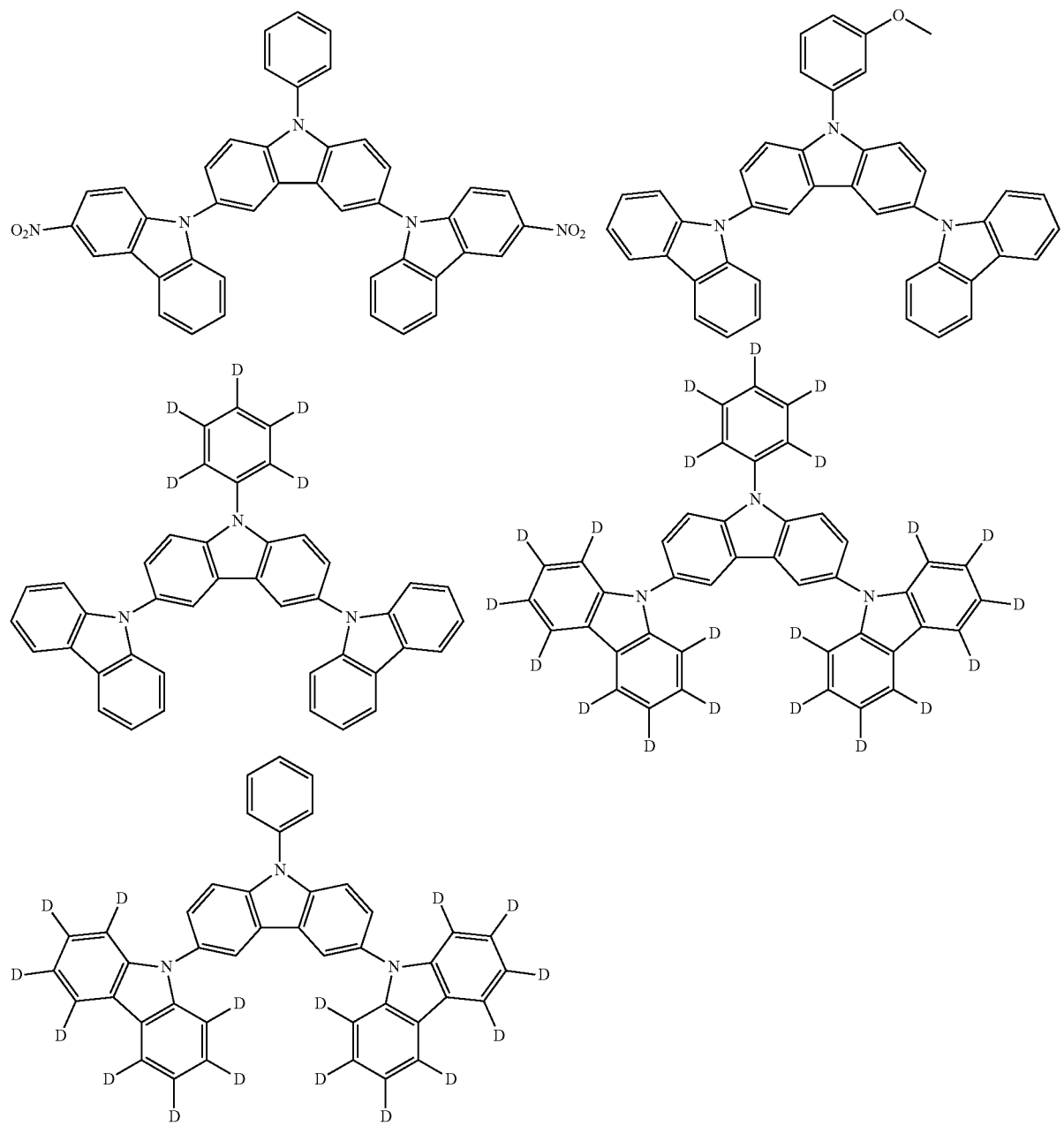

209 210
-continued
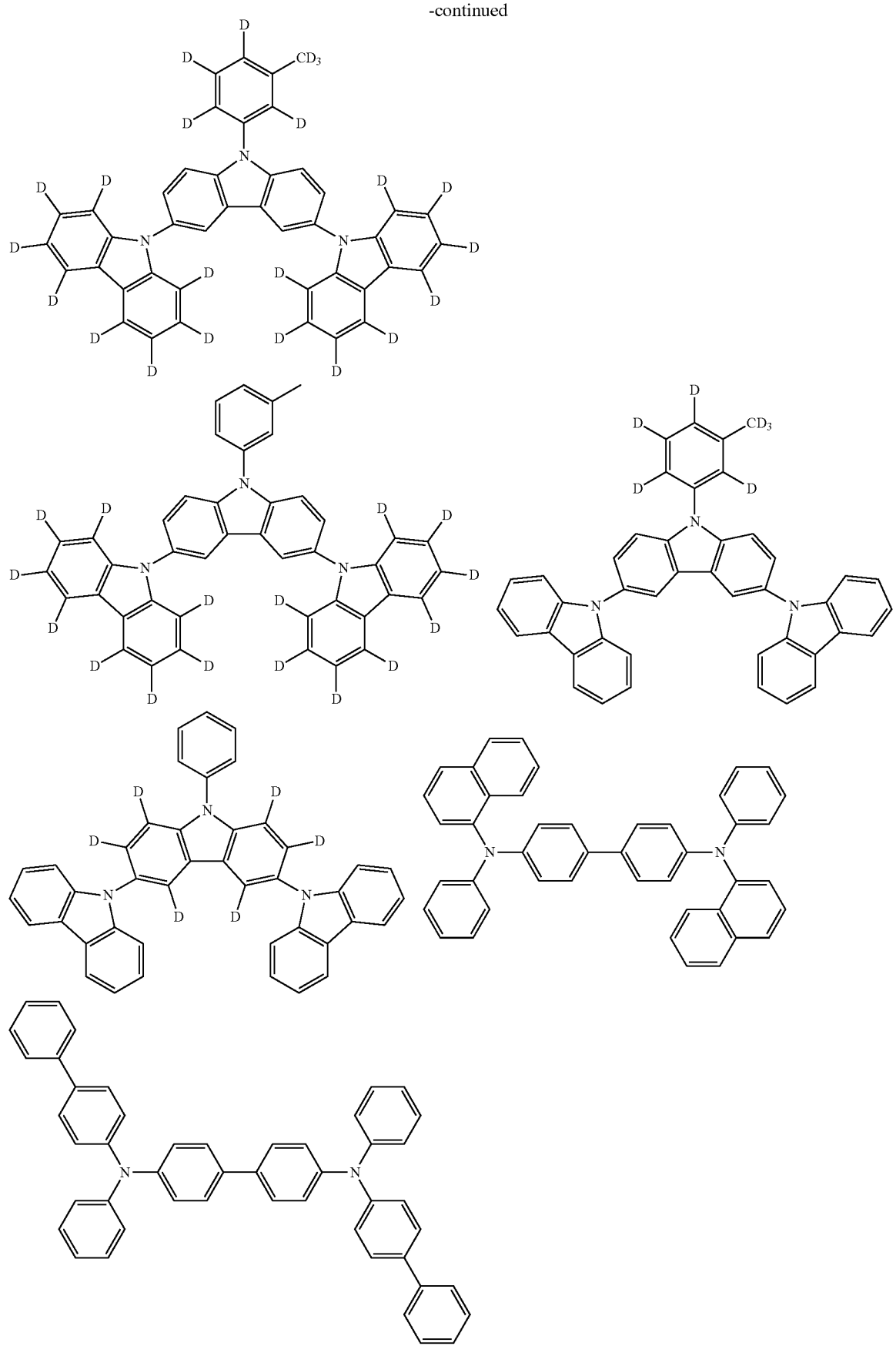

-continued
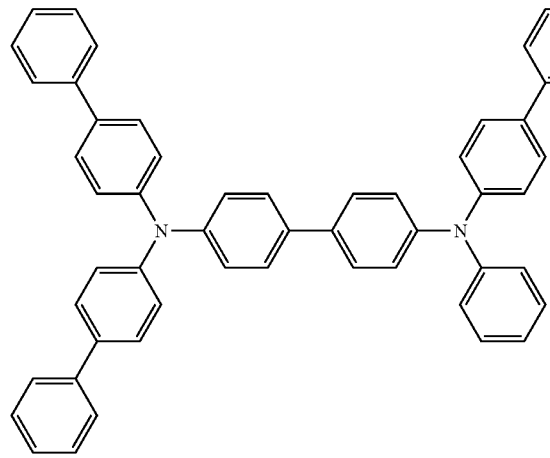
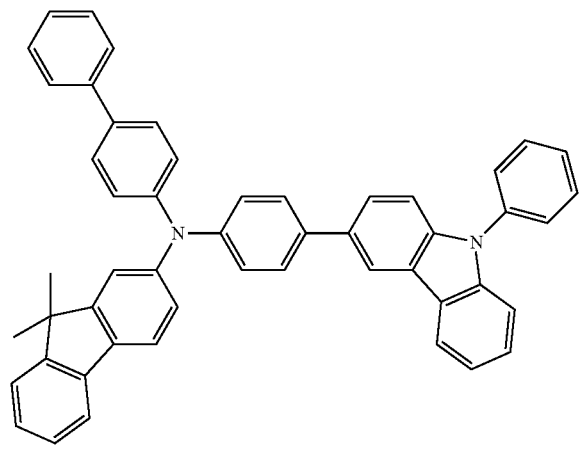
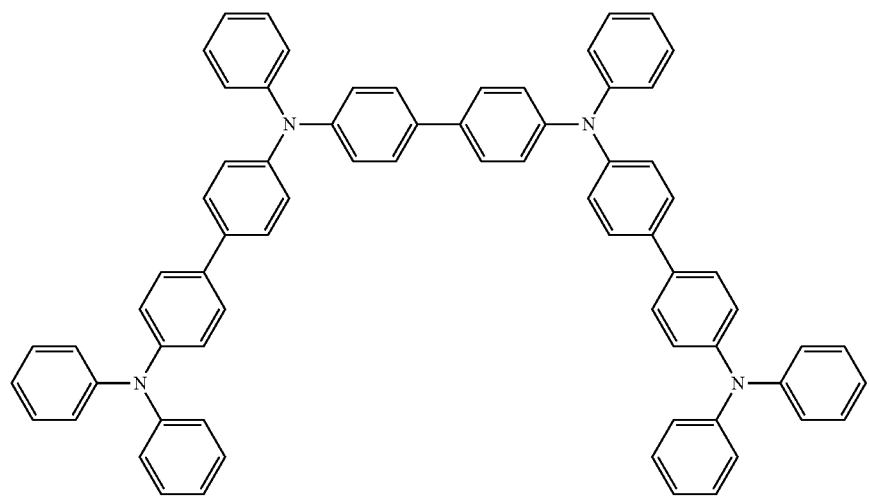

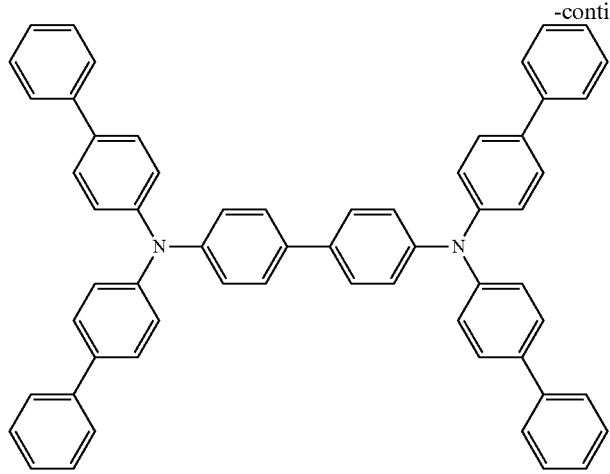
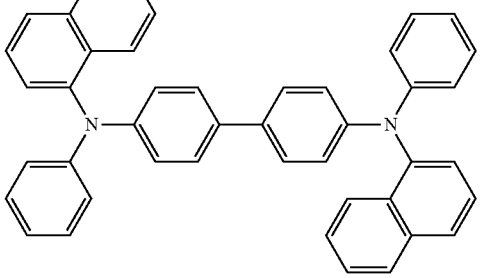

-continued

In addition, the detailed description on the hole injecting layer and the hole transporting layer in Paragraph Nos. [0165] to [0167] of JP-A-2008-270736 can also be applied to the present invention. In addition, the detailed description in Paragraph Nos. [0250] to [0339] of JP-A-2011-71452 can also be applied to the hole injecting layer and the hole transporting layer of the present invention. The compound represented by the general formula (1) is preferably applied to the hole injecting layer and the hole transporting layer.

The hole injecting layer preferably contains an electron receptive dopant. By incorporating the electron receptive dopant in the hole injecting layer, there are effects in which, for example, the hole injecting properties are improved, the driving voltage is lowered, and the efficiency is improved. The electron receptive dopant may be any one of organic materials and inorganic materials as long as it is capable of withdrawing electrons from doped material and generating radical cations. Examples thereof include TCNQ compounds such as tetracyanoquinodimethane (TCNQ) and tetrafluorotetracyanoquinodimethane ($F_4$-TCNQ), hexaazatriphenylene compounds such as hexacyanohexaazatriphenylene (HAT-CN), and molybdenum oxide.

The electron receptive dopant in the hole injecting layer is preferably contained in the amount of 0.01% by mass to 50% by mass, more preferably 0.1% by mass to 40% by mass, and still more preferably 0.2% by mass to 30% by mass, based on the mass of all the compounds forming the hole injecting layer.

(A-2) Electron Blocking Layer

The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer on the anode side.

As an example of the organic compound constituting the electron blocking layer, those exemplified above as the hole transporting materials may be applied.

The thickness of the electron blocking layer is preferably from 1 nm to 500 nm, more preferably from 3 nm to 100 nm, and still more preferably from 5 nm to 50 nm.

The electron blocking layer may have either a single layer structure composed of one or more materials selected from the above-exemplified materials or a multilayer structure composed of a plurality of layers having the same composition or different compositions.

The material used in the electron blocking layer preferably has higher $S_1$ energy than that of the light emitting material in views of chromatic purity, luminous efficiency, and driving durability. $S_1$ in a film state of the material used for the electron blocking layer is preferably equal to or more than 0.1 eV, more preferably equal to or more than 0.2 eV, and still more preferably equal to or more than 0.3 eV, with respect to $S_1$ of the light emitting material.

(B) Organic Layer Preferably Disposed Between Cathode and Light Emitting Layer

First, (B) the organic layer preferably disposed between the cathode and the light emitting layer will be described.

(B-1) Electron Injecting Layer and Electron Transporting Layer

The electron injecting layer and the electron transporting layer are layers having a function of receiving electrons from the cathode or the cathode side and transporting them to the anode side. The electron injecting material and the electron transporting material used in these layers may be either a low-molecular compound or a high-molecular compound.

As the electron transporting material, for example, the compound represented by the general formula (1) can be used. As the other electron transporting materials, any one selected from aromatic ring tetracarboxylic acid anhydrides, such as pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyrandioxide derivatives, carbodiimide derivatives, fluorenylidenemethane derivatives, distyrylpyrazine derivatives, naphthalene, and perylene; various metal complexes typified by metal complexes of phthalocyanine derivatives or 8-quinolinol derivatives and metal complexes having metal phthalocyanine, benzoxazole, or benzothiazole as a ligand thereof, organic silane derivatives typified by silol, hydrocarbon compounds with fused rings, such as naphthalene, anthracene, phenanthrene, triphenylene, and pyrene is preferred, and any one selected from pyridine derivatives, benzimidazole derivatives, imidazopyridine derivatives, metal complexes, and hydrocarbon compounds with fused rings are more preferred.

The thickness of each of the electron injecting layer and the electron transporting layer is preferably 500 nm or less from the viewpoint that the driving voltage is decreased.

The thickness of the electron transporting layer is preferably from 1 nm to 500 nm, more preferably from 5 nm to 200 nm, and still more preferably from 10 nm to 100 nm. The thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one or more materials selected from the above-exemplified materials or a multilayer structure composed of a plurality of layers having the same composition or different compositions.

The electron injecting layer preferably contains an electron donating dopant. By incorporating the electron donating dopant in the electron injecting layer, there are effects that, for example, the electron injecting properties are improved, the driving voltage is lowered, and the efficiency is improved. The electron donating dopant may be any one of organic materials and inorganic materials as long as it is capable of giving electrons to the material to be doped and generating radical anions, and examples thereof include dihydroimidazole compounds such as tetrathiafulvalene (TTF), tetrathianaphthacene (TTT), and bis-[1,3-diethyl-2-methyl-1,2-dihydrobenzimidazolyl], lithium, and cesium.

The electron donating dopant in the electron injecting layer is preferably contained in the amount of 0.01 to 50% by mass, more preferably 0.1 to 40% by mass, and still more preferably 0.5 to 30% by mass, based on the mass of all the compounds forming the electron injecting layer.

(B-2) Hole Blocking Layer

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

Since the $S_1$ energy of the organic compound in the film state constituting the hole blocking layer prevents the energy movement of excitons produced in the light emitting layer, and thus, cannot lower the luminous efficiency, a higher $S_1$ energy of the light emitting material is preferred.

As one example of the organic compound constituting the hole blocking layer, for example, the compound represented by the general formula (1) can be used.

Examples of the organic compounds constituting the hole blocking layer, other than the compound represented by the general formula (1), include aluminum complexes such as aluminum (iii) bis(2-methyl-8-quinolinato) 4-phenylphenolate (abbreviated as "BAlq"), triazole derivatives, and phenanthroline derivatives such as 2,9-dimethyl-4,7-diphenyl-1,10-phenanthroline (abbreviated as "BCP").

The thickness of the hole blocking layer is preferably from 1 nm to 500 nm, more preferably from 3 nm to 100 nm, and still more preferably from 5 nm to 50 nm.

The hole blocking layer may have either a single layer structure composed of one or more materials selected from the above-exemplified materials or a multilayer structure composed of a plurality of layers having the same composition or different compositions.

The material used in the hole blocking layer preferably has higher $S_1$ energy than that of the light emitting material in views of chromatic purity, luminous efficiency, and driving durability. $S_1$ in a film state of the material used for the hole blocking layer is preferably equal to or more than 0.1 eV, more preferably equal to or more than 0.2 eV, and still more preferably equal to or more than 0.3 eV, with respect to $S_1$ of the light emitting material.

(B-3) Material which is Particularly Preferably Used in Organic Layer, Preferably Disposed between Cathode and Light Emitting Layer For the organic electroluminescent element of the present invention, examples of the material which is particularly preferably used in the materials for an organic layer (B), preferably disposed between the cathode and the light emitting layer include the compound represented by the general formula (1), a compound represented by the following general formula (P-1), and a compound represented by the following general formula (O-1).

A compound represented by the general formula (O-1) and a compound represented by the general formula (P-1) will be described below.

The organic electroluminescent element of the present invention preferably includes at least one layer of organic layers between the light emitting layer and the cathode, and the organic layer preferably contains at least one of compounds represented by the following general formula (O-1), from the viewpoint of efficiency or driving voltage of an element. Hereinafter, the general formula (O-1) will be described.

General Formula (O-1)

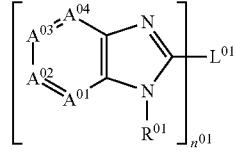

(In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and the plurality of $R^A$'s may be the same as or different from each other. $L^{O1}$ represents any of divalent or hexavalent linking groups with an aryl ring or a heteroaryl ring. $n^{O1}$ represents an integer of 2 to 6).

$R^{O1}$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $R^{O1}$ is preferably an aryl group or a heteroaryl group, and more preferably an aryl group. Preferred examples of the substituent in a case where the aryl group of $R^{O1}$ has a substituent include an alkyl group, an aryl group, or a cyano group, more preferably an alkyl group or an aryl group, and still more preferably an aryl group. In a case where the aryl group of $R^{O1}$ has a plurality of substituents, the plurality of substituents may be bonded to each other to form a 5- or 6-membered ring. The aryl group of $R^{O1}$ is preferably a phenyl group which may have a substituent selected from Substituent Group A, more preferably a phenyl group which may be substituted with an alkyl group or an aryl group, and still more preferably an unsubstituted phenyl group or a 2-phenylphenyl group.

$A^{O1}$ to $A^{O4}$ each independently represent C—$R^A$ or a nitrogen atom. It is preferable that 0 to 2 out of $A^{O1}$ to $A^{O4}$ be nitrogen atoms; and it is more preferable that 0 or 1 out of $A^{O1}$ to $A^{O4}$ be nitrogen atoms. It is preferable that all of $A^{O1}$ to $A^{O4}$ be C—$R^A$, or $A^{O1}$ be a nitrogen atom, and $A^{O2}$ to $A^{O4}$ be C—$R^A$; it is more preferable that $A^{O1}$ be a nitrogen atom, and $A^{O2}$ to $A^{O4}$ be C—$R^A$; it is still more preferable that $A^{O1}$ be a nitrogen atom, $A^{O2}$ to $A^{O4}$ be C—$R^A$, and $R^A$ be all hydrogen atoms.

$R^A$ represents a hydrogen atom, an alkyl group (preferably having 1 to 8 carbon atoms), an aryl group (preferably having 6 to 30 carbon atoms), or a heteroaryl group (preferably having 4 to 12 carbon atoms), and may have a substituent selected from the above-described Substituent Group A. Further, a plurality of $R^A$'s may be the same as or different from each other. $R^A$ is preferably a hydrogen atom or an alkyl group, and more preferably a hydrogen atom.

$L^{O1}$ represents a divalent to hexavalent linking group including an aryl ring (preferably having 6 to 30 carbon atoms) or a heteroaryl ring (preferably having 4 to 12 carbon atoms). $L^{O1}$ is preferably an allylene group, a heteroallylene group, an aryltriyl group, or a heteroaryltriyl group, more preferably a phenylene group, a biphenylene group, or a benzenetriyl group, and still more preferably a biphenylene group or a benzenetriyl group. $L^{O1}$ may have a substituent selected from the above-described Substituent Group A, and in a case of having the substituent, the substituent is preferably an alkyl group, an aryl group, or a cyano group. Specific examples of $L^{O1}$ include the following.

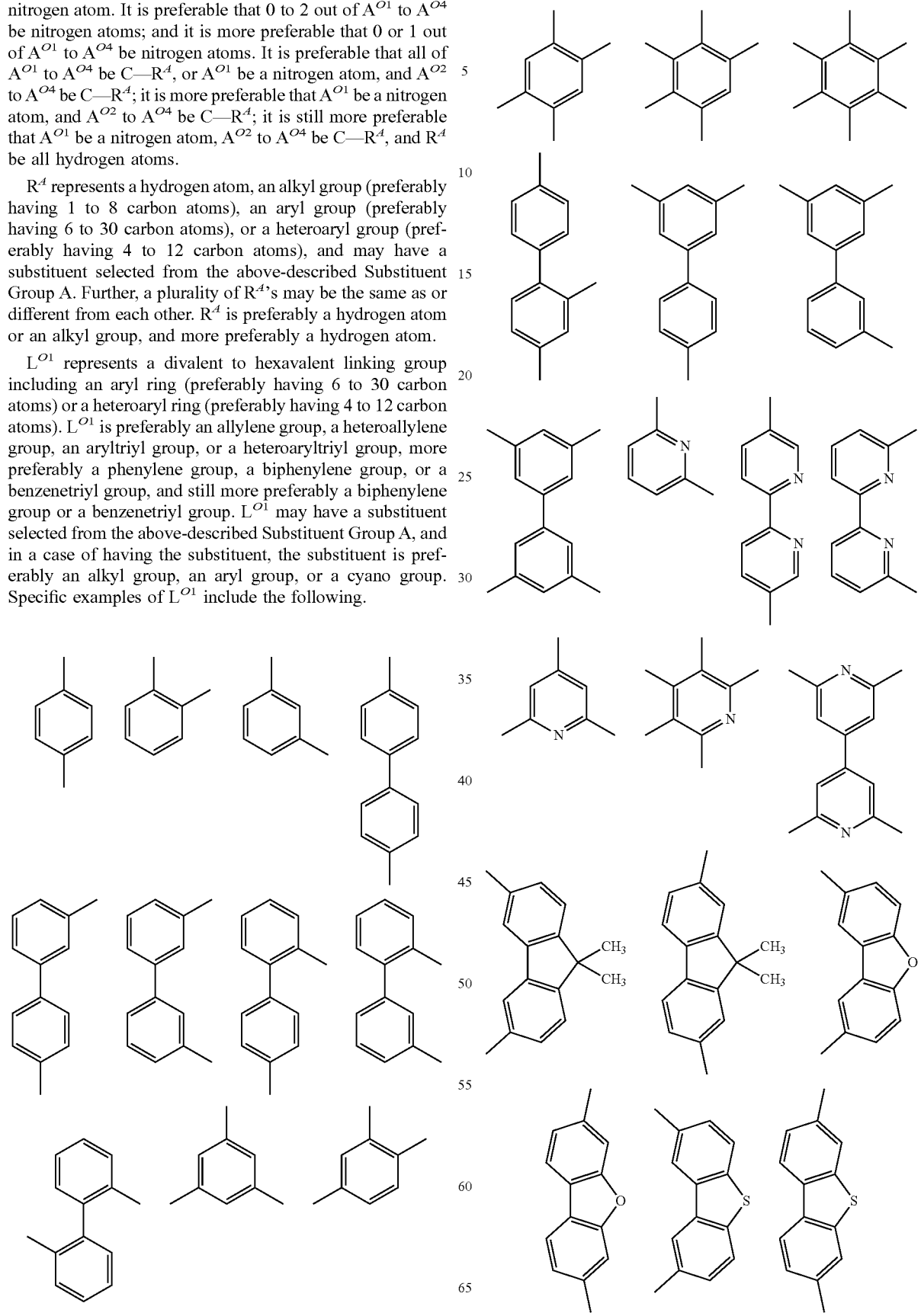

-continued

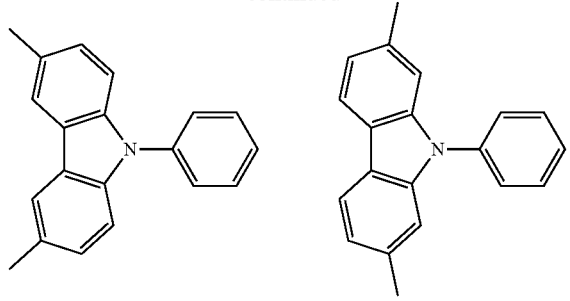

$n^{O1}$ represents an integer of 2 to 6, preferably an integer of 2 to 4, and more preferably 2 or 3. $n^{O1}$ is most preferably 3 from the viewpoint of the efficiency of an element, or most preferably 2 from the viewpoint of the durability of an element.

The glass transition temperature (Tg) of the compound represented by the general formula (O-1) is preferably from 100° C. to 300° C., more preferably from 120° C. to 300° C., and still more preferably from 140° C. to 300° C., from the viewpoint of stability during storage at a high temperature, or stable operation during driving at a high temperature or against heat generation during driving.

Specific examples of the compound represented by the general formula (O-1) are shown below, but the compound represented by the general formula (O-1) which can be used in the present invention is not limitedly interpreted by the specific examples.

OM-1

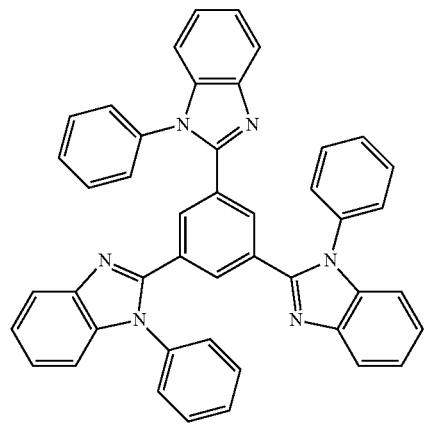

OM-2

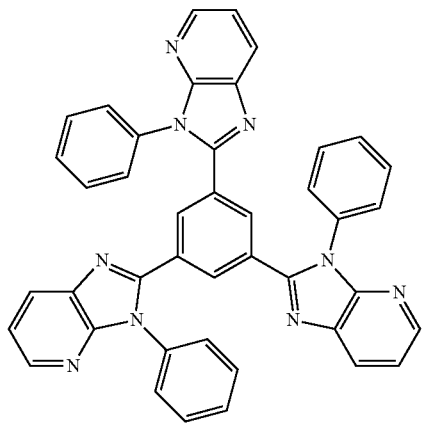

OM-3

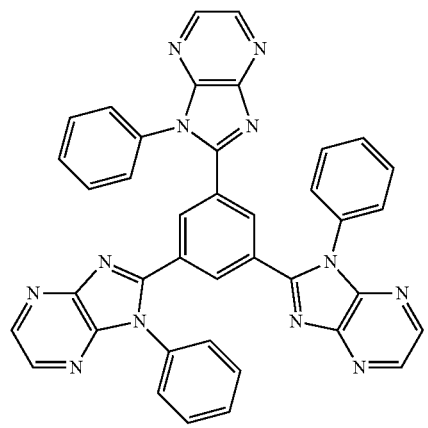

OM-4

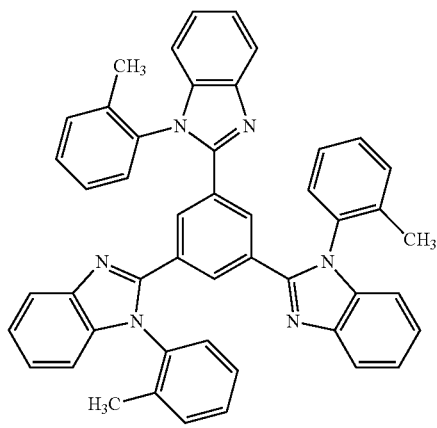

-continued
OM-5
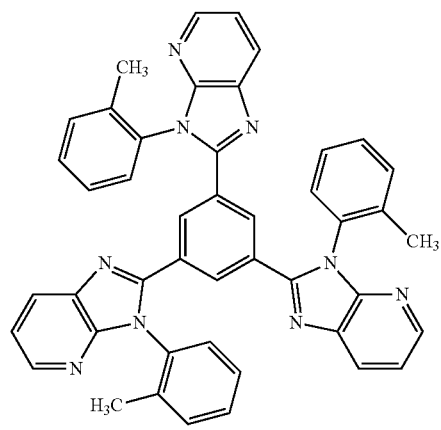
OM-6
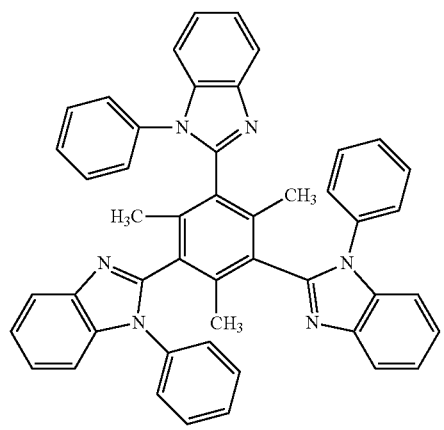
OM-7
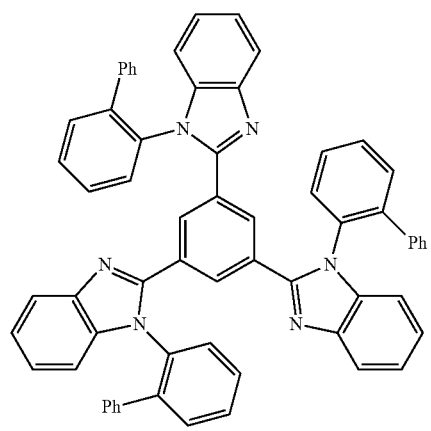
OM-8
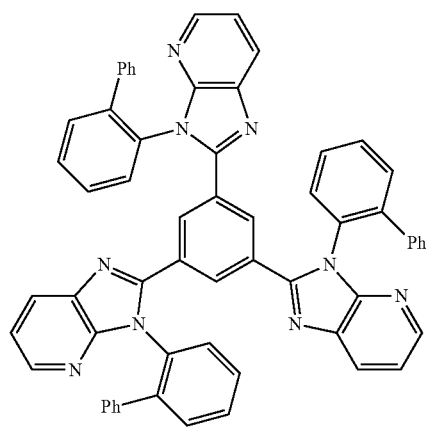
OM-9
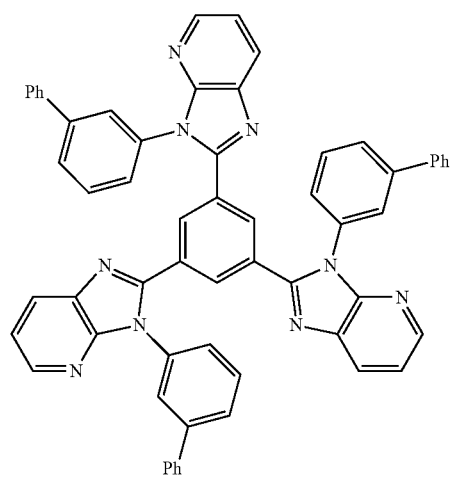
OM-10
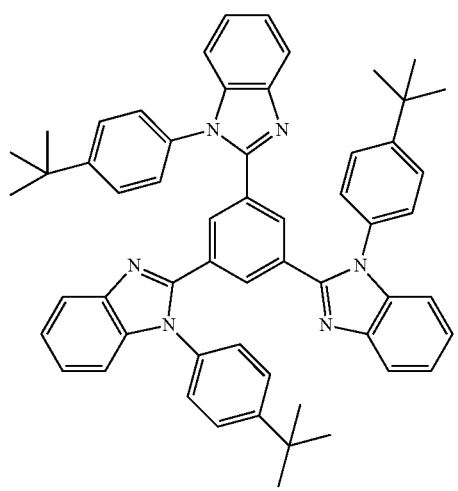

-continued
OM-11
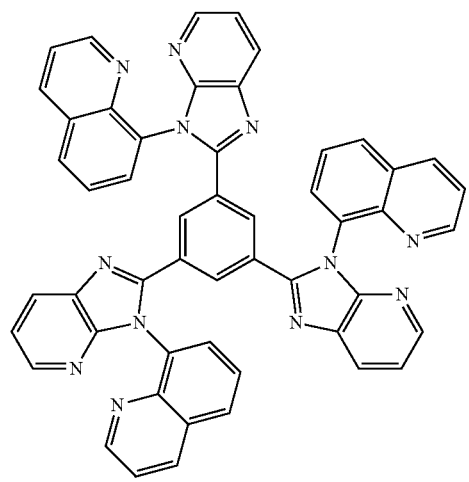
OM-12
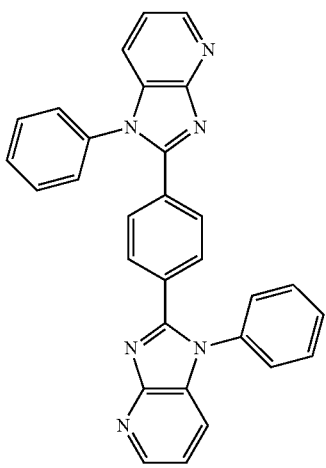
OM-13
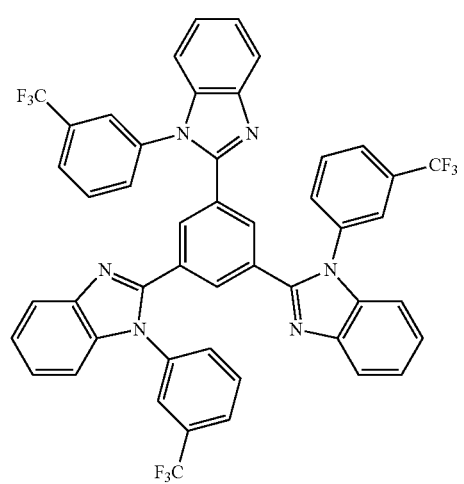
OM-14
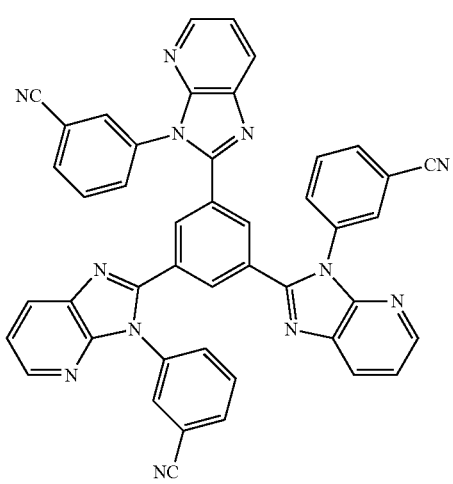
OM-15
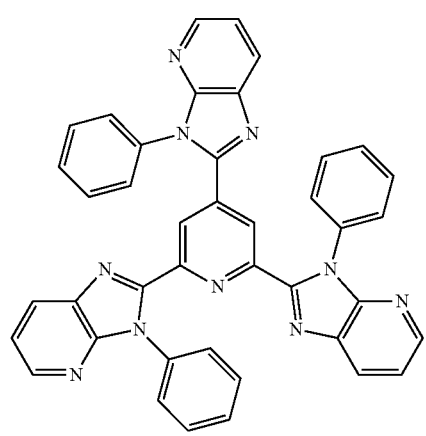
OM-16
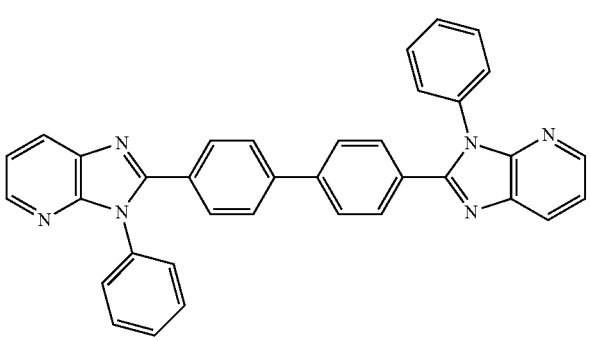

-continued
OM-17
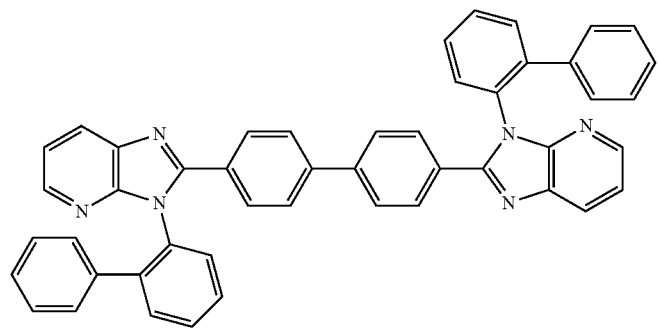
OM-18
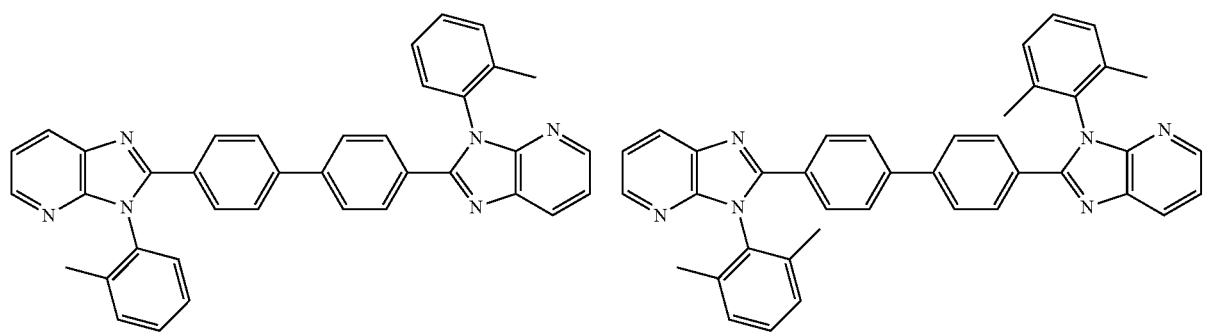
OM-19
OM-20
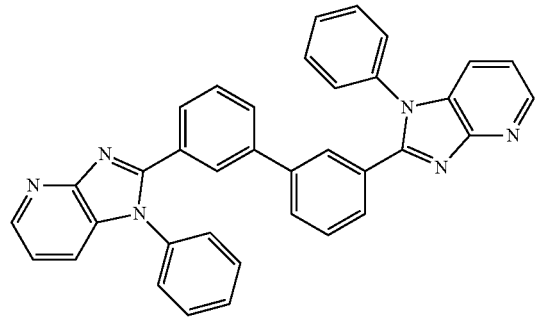
OM-21
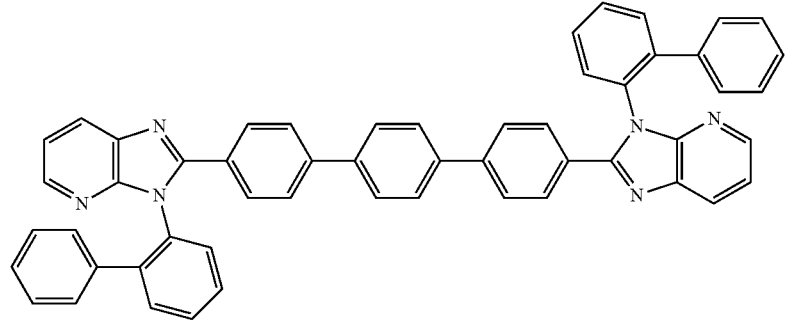
OM-22
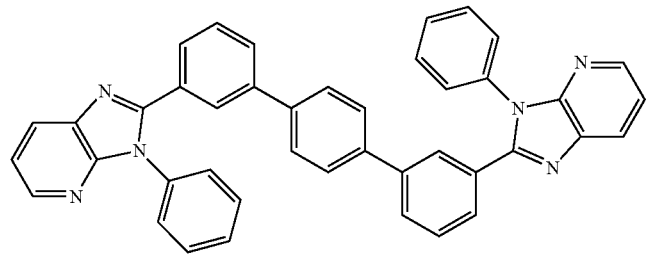

-continued

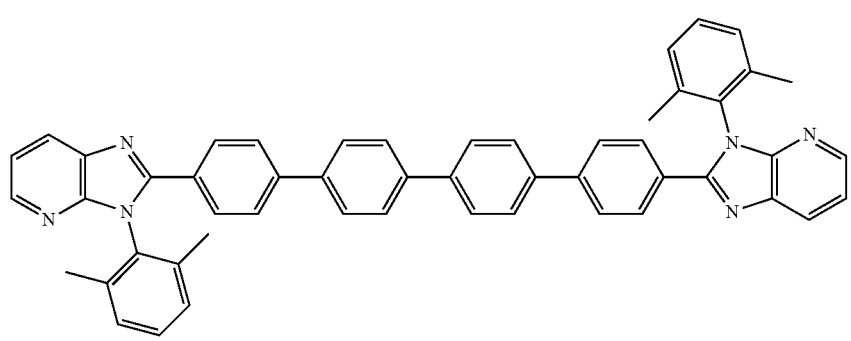

OM-23

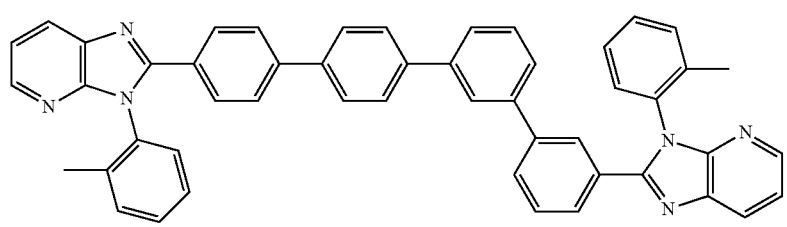

OM-24

The compound represented by the general formula (O-1) can be synthesized by the method described in JP-A-2001-335776. After the synthesis, purification is preferably carried out by column chromatography, recrystallization, reprecipitation, or the like, and then by sublimation purification. Organic impurities can be separated and inorganic salts, residual solvents, moisture, or the like can be removed effectively by the sublimation purification.

In the organic electroluminescent element of the present invention, the compound represented by the general formula (0-1) is preferably included in the organic layer between the light emitting layer and the cathode, however, it is more preferably included in the layer on the cathode side adjacent to the light emitting layer.

The compound represented by the general formula (O-1) is preferably contained in the amount of 70 to 100% by mass, and more preferably 85 to 100% by mass, based on the total mass of the organic layer added.

The organic electroluminescent element of the present invention preferably includes at least one layer of organic layers between the light emitting layer and the cathode, and it is preferable that the organic layer contain at least one of compounds represented by the following general formula (P), from the viewpoint of efficiency or the driving voltage of an element. Hereinafter, the general formula (P) will be described.

General Formula (P)

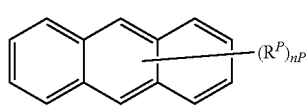

In the general formula (P), $R^P$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. nP represents an integer of 1 to 10, and in a case where there are a plurality $R^P$'s, these may be the same as or different from each other. At least one of $R^P$ is a substituent represented by the following general formulae (P-1) to (P-3).

General Formula (P-1)

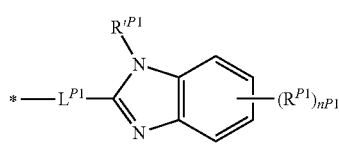

General Formula (P-2)

General Formula (P-3)

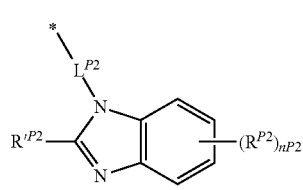

General Formula (P-4)

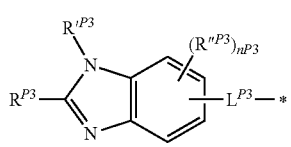

General Formula (P-5)

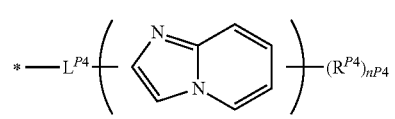

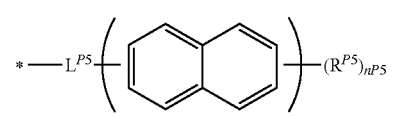

The general formula (P-4) is more preferably the following general formula (P-4').

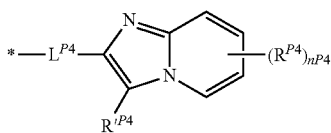

General Formula (P-4')

The general formula (P-5) is more preferably the following general formula (P-5').

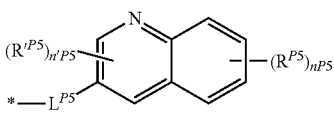

General Formula (P-5')

(In the general formulae (P-1) to (P-5), $R^{P1}$ to $R^{P5}$, $R^{\prime P1}$ to $R^{\prime P3}$, $R^{\prime P5}$, and $R^{\prime\prime P3}$ each represent an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $n^{P1}$ to $n^{P2}$, $n^{P4}$, and $n^{P5}$ represent an integer of 0 to 4, and $n^{P3}$ and $n^{P5}$ represent an integer of 0 to 2, and in a case where any of $R^{P1}$ to $R^{P5}$, $R^{\prime P1}$ to $R^{\prime P3}$, $R^{\prime P5}$, and $R^{\prime\prime P3}$ exist more than one, they may be the same as or different from each other. $L^{P1}$ to $L^{P5}$ represent any one of a single bond and a divalent linking groups consisting of an aryl ring, or a heteroaryl ring. * represents a bonding position with the anthracene ring of the general formula (P)).

A preferred substituent other than the substituents represented by (P-1) to (P-5) as $R^{P}$ is an aryl group, more preferably any one of a phenyl group, a biphenyl group, a terphenyl group, and a naphthyl group, and still more preferably a naphthyl group.

$R^{P1}$ to $R^{P5}$, $R^{\prime P1}$ to $R^{\prime P3}$, $R^{\prime P5}$, and $R^{\prime\prime P3}$ are preferably any one of an aryl group and a heteroaryl group, more preferably an aryl group, still more preferably any one of a phenyl group, a biphenyl group, a terphenyl group, and a naphthyl group, and most preferably a phenyl group.

$L^{P1}$ to $L^{P5}$ are preferably any one of a single bond and a divalent linking groups consisting of an aryl ring, more preferably any one of a single bond, phenylene, biphenylene, terphenylene, and naphthylene, and still more preferably any one of a single bond, phenylene, and naphthylene.

Specific examples of the compound represented by the general formula (P) are shown below, but the compound represented by the general formula (P) which can be used in the present invention is not limitedly interpreted by the specific examples.

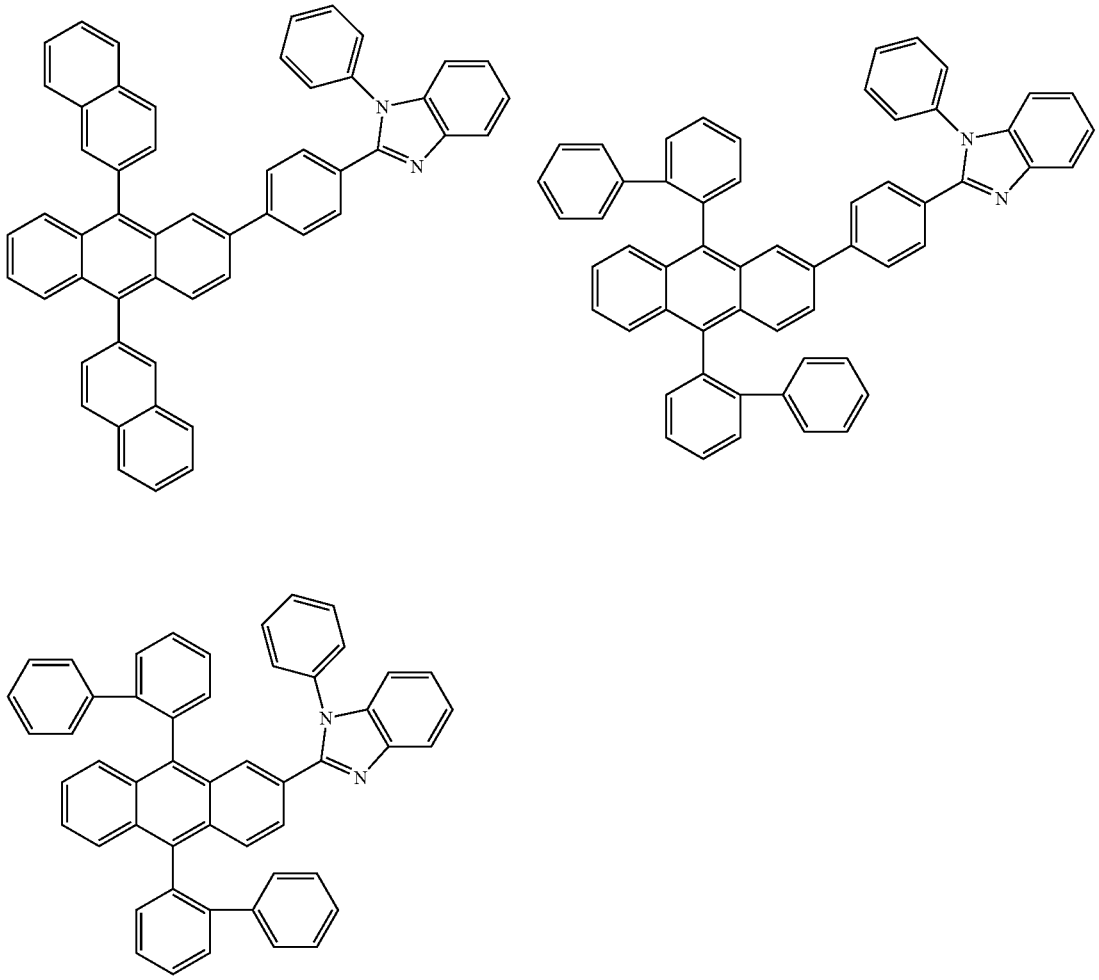

-continued
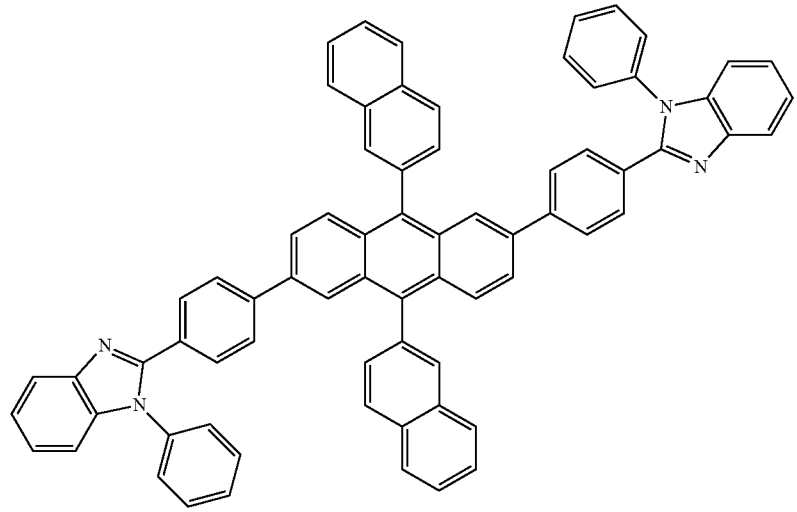
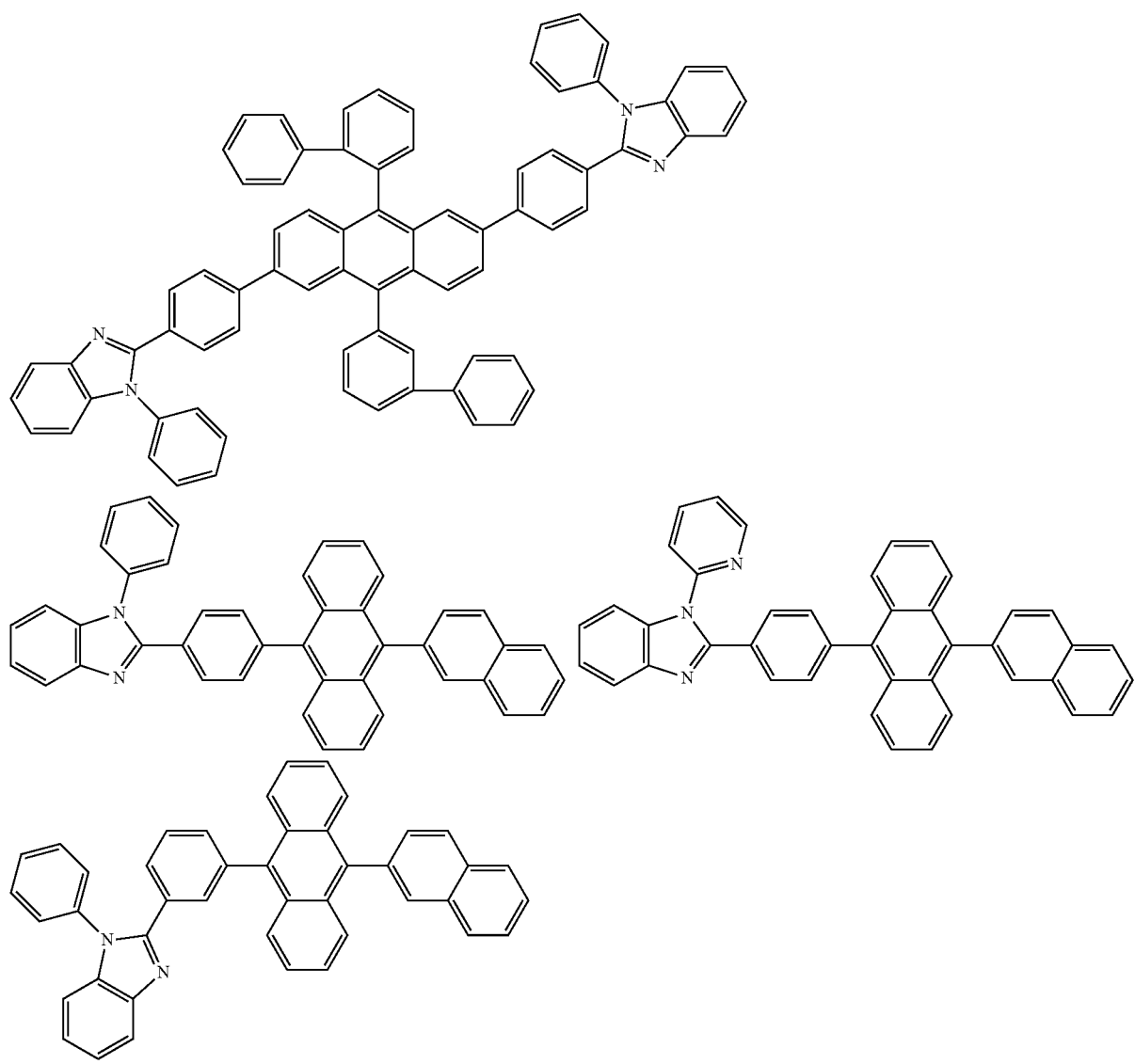

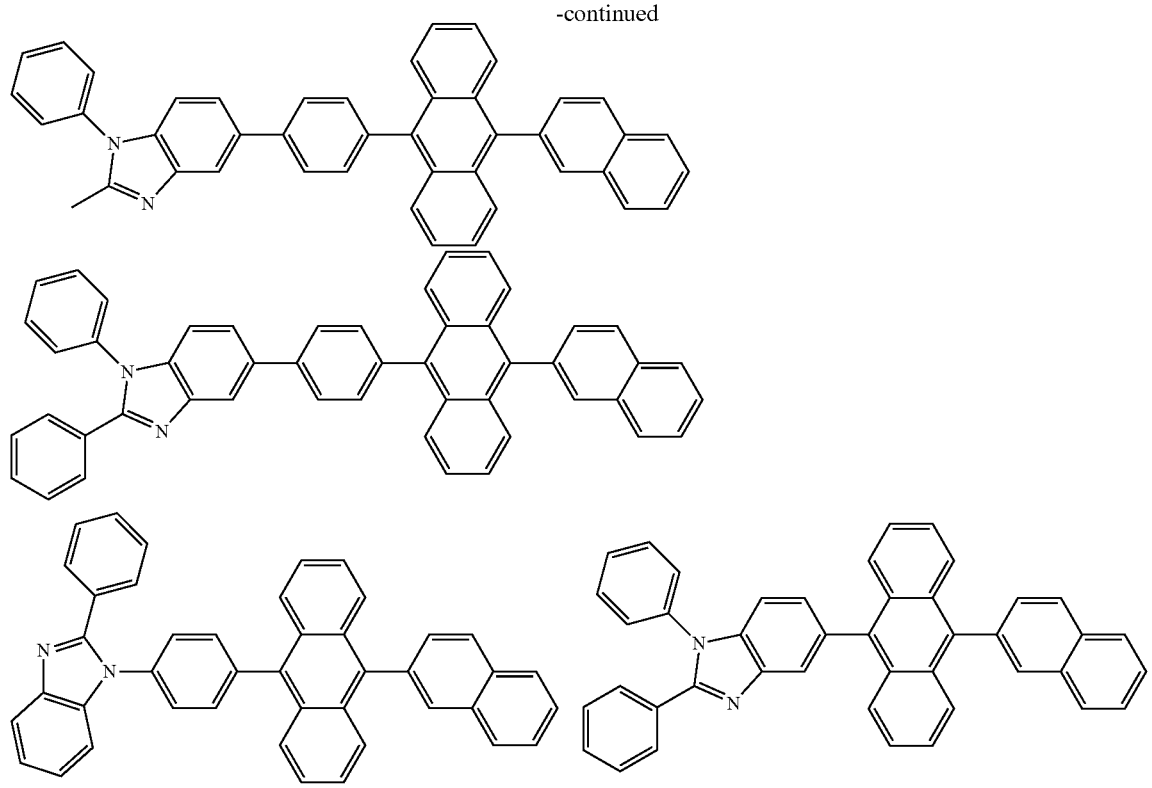

The compound represented by the general formula (P) can be synthesized by the method described in WO2003/060956 and WO2004/080975. After the synthesis, purification is preferably carried out by column chromatography, recrystallization, reprecipitation, or the like, and then by sublimation purification. Organic impurities can be separated and inorganic salts, residual solvents, moisture, or the like can be removed effectively by the sublimation purification.

In the organic electroluminescent element of the present invention, the compound represented by the general formula (P) is preferably included in the organic layer between the light emitting layer and the cathode, and more preferably in the layer adjacent to the cathode.

The compound represented by the general formula (P) is preferably contained in the amount of 70 to 100% by mass, and more preferably 85 to 100% by mass, based on the total mass of the organic layer added.

Preferred examples of the material other than the material used in the electron injecting layer or the electron transporting layer in the organic electroluminescent element of the present invention include silole compounds described in JP-A-09-194487 or the like, phosphine oxide compounds described in JP-A-2006-73581 or the like, nitrogen-containing aromatic 6-membered ring hetero compounds described in JP-A-2005-276801, JP-A-2006-225320, WO2005/085387, or the like, compounds having nitrogen-containing aromatic 6-membered hetero structures and carbazole structures, described in WO2003/080760, WO2005/085387, or the like, and aromatic hydrocarbon compounds described in US2009/0009065, WO2010/134350, Japanese PCT National Publication No. 2010-535806 (naphthalene compounds, anthracene compounds, triphenylene compounds, phenanthrene compounds, pyrene compounds, fluoranthene compounds, and the like).

<Protective Layer>
In the present invention, the entirety of the organic electric element may be protected by a protective layer.
For the protective layer, the detailed description in, for example, Paragraph Nos. [0169] to [0170] of JP-A-2008-270736 can also be applied to the present invention. Further, the materials for the protective layer may be either inorganic materials or organic materials.

<Sealing Enclosure>
For the organic electroluminescent element of the present invention, the entirety of the element may be sealed with a sealing enclosure.
For the sealing enclosure, the detailed description in Paragraph No. [0171] of JP-A-2008-270736 may be applied to the present invention.

<Driving Method>
The organic electroluminescent element of the present invention can emit light by applying a direct current (it may contain an alternate current component, if necessary), voltage (typically, from 2 volts to 15 volts) or a direct current between the anode and the cathode.

As a driving method of the organic electroluminescent element of the present invention, driving methods described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 may be applied.

The external quantum efficiency of the organic electroluminescent element of the present invention is preferably 5% or more, more preferably 6% or more, and still more preferably 7% or more. For the numerical value of the external quantum efficiency, the maximum value of the external quantum efficiency when the element is driven at 20° C., or a value of the external quantum efficiency around 300 cd/m² to 400 cd/m² when the element is driven at 20° C. can be used.

The internal quantum efficiency of the organic electroluminescent element of the present invention is preferably 30% or more, more preferably 50% or more, and still more preferably 70% or more. The internal quantum efficiency of the element is calculated by dividing the external quantum efficiency by the light extraction efficiency. The light extraction efficiency in usual organic EL elements is about 20%, but by taking into consideration the shape of a substrate, the shape of an electrode, the thickness of an organic layer, the thickness of an inorganic layer, the refractive index of an organic layer, the refractive index of an inorganic layer, or the like, it is possible to increase the light extraction efficiency to 20% or more.

<Light Emitting Wavelength>

The organic electroluminescent element of the present invention is not limited in its light emitting wavelength, but is preferably used for blue or white light emission. Among these, in the organic electroluminescent element of the present invention, the compound represented by the general formula (1) is preferably used to emit light as a light emitting material, and particularly preferably used to emit blue light.

<Use of Organic Electroluminescent Element of the Present Invention>

The organic electroluminescent element of the present invention can be suitably used for display elements, displays, backlights, electrophotography, illumination light sources, recording light sources, exposure light sources, readout light sources, signs, billboards, interior decorations, optical communications, and the like, and particularly preferably for devices driven in a region of high-intensity luminescence, such as a light emitting device, an illumination device, and a display device.

[Light Emitting Device]

The light emitting device of the present invention may include the organic electroluminescent element of the present invention.

Next, the light emitting device of the present invention will be described with reference to FIG. 2.

The light emitting device of the present invention is formed by using the organic electroluminescent element.

Figure 2:
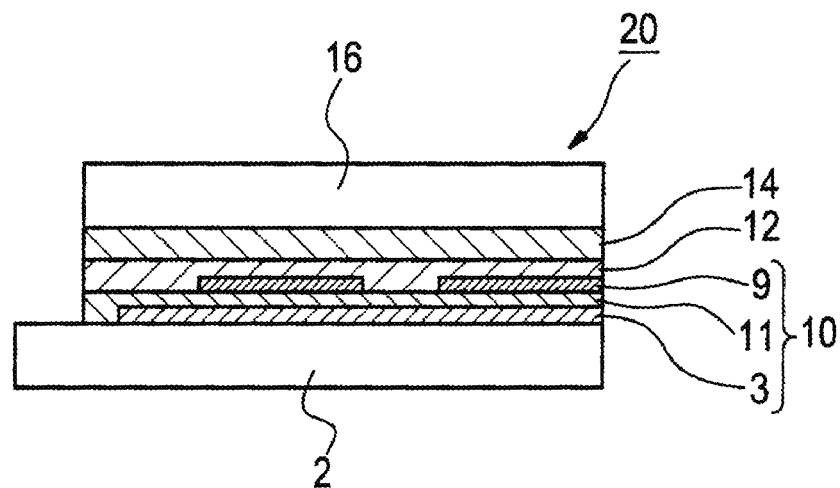
FIG. 2 is a schematic view showing one example of the light emitting device according to the present invention.

FIG. 2 is a cross-sectional view schematically showing one example of the light emitting device of the present invention. The light emitting device 20 in FIG. 2 includes a transparent substrate 2 (supporting substrate), an organic electroluminescent element 10, a sealing enclosure 16, and the like.

The organic electroluminescent element 10 is formed by laminating an anode (first electrode) 3, an organic layer 11, and a cathode (second electrode) 9 onto the substrate 2 in this order. In addition, a protective layer 12 is laminated onto the cathode 9, and a sealing enclosure 16 is further provided on the protective layer 12 via an adhesive layer 14. Incidentally, a part of each of the electrodes 3 and 9, a diaphragm, an insulating layer, and the like are omitted.

Here, a photocurable adhesive such as an epoxy resin, or a thermosetting adhesive can be used for the adhesive layer 14, and for example, a thermosetting adhesive sheet may also be used as the adhesive layer 14.

The light emitting device of the present invention is not particularly limited in its use, and it can be used as not only an illumination device but also a display device of a television, a personal computer, a mobile phone, electronic paper, or the like.

[Illumination Device]

The illumination device of the present invention includes the organic electroluminescent element of the present invention.

Next, the illumination device of the present invention will be described with reference to FIG. 3.

Figure 3:
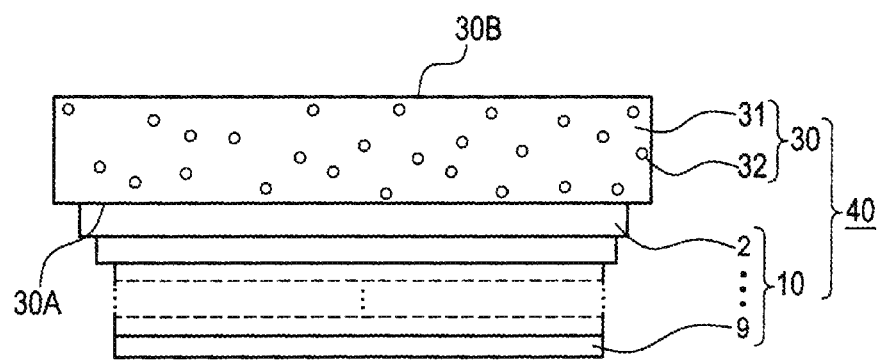
FIG. 3 is a schematic view showing one example of the illumination device of the present invention.

FIG. 3 is a cross-sectional view schematically showing one example of the illumination device of the present invention. The illumination device 40 of the present invention includes, as shown in FIG. 3, the above-described organic EL element 10 and a light scattering member 30. More specifically, the illumination device 40 is configured such that the substrate 2 of the organic EL element 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particles 32 include transparent fine resin particles. A known product can be used for both the glass substrate and the transparent resin fine particles. In such an illumination device 40, when light emitted from the organic electroluminescent element 10 is incident on the light incident surface 30A of the scattering member 30, the incident light is scattered by the light scattering member 30 and the scattered light is output as illuminating light from the light output surface 30B.

[Display Device]

The display device of the present invention includes the organic electroluminescent element of the present invention.

The display device of the present invention can be used for, for example, a display device of a television, a personal computer, a mobile phone, electronic paper, or the like.

EXAMPLES

Hereinbelow, the features of the present invention will be described in more detail with reference to Examples and Comparative Examples. The materials, use amounts, ratios, process details, process sequences, and the like shown in Examples below may be appropriately modified without departing from the spirit of the present invention. Accordingly, the scope of the present invention should not be construed to be limited to the specific examples shown below.

The structural formulae of the compounds used in Examples and Comparative Examples are collectively shown below.

Compound 1
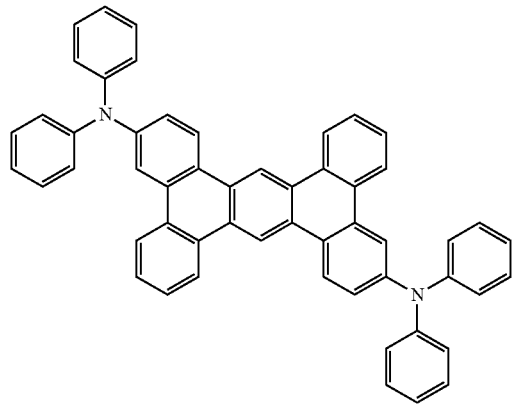
Compound 2
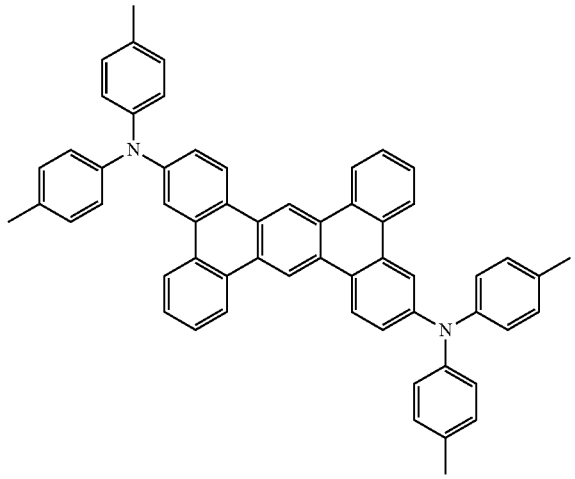
Compound 3
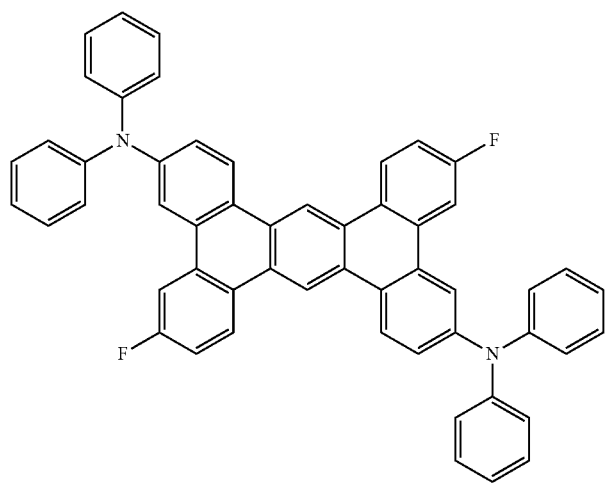
Compound 4
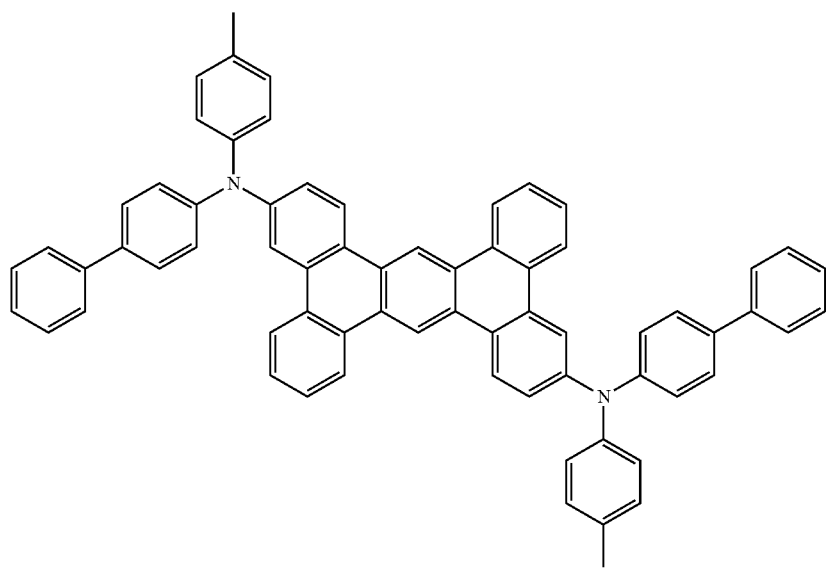

-continued
Compound 5
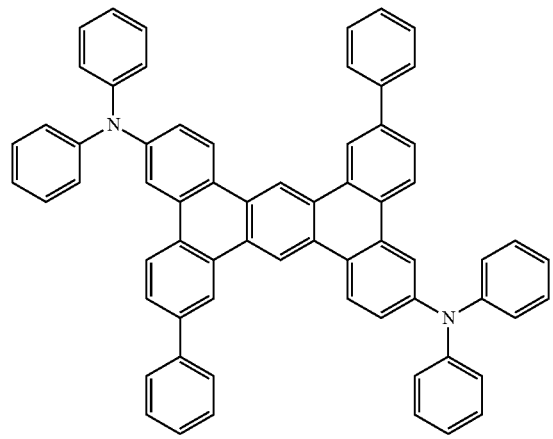
Compound 6
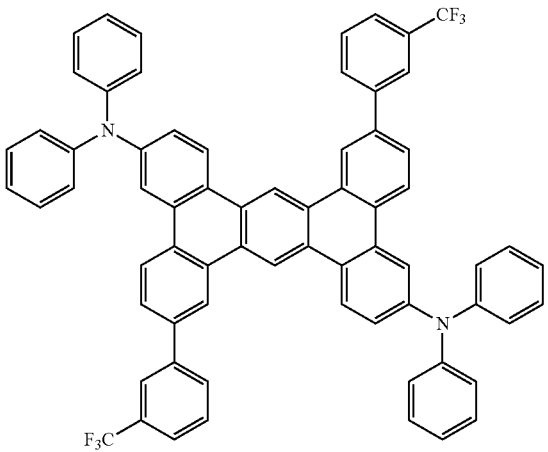
Compound 7
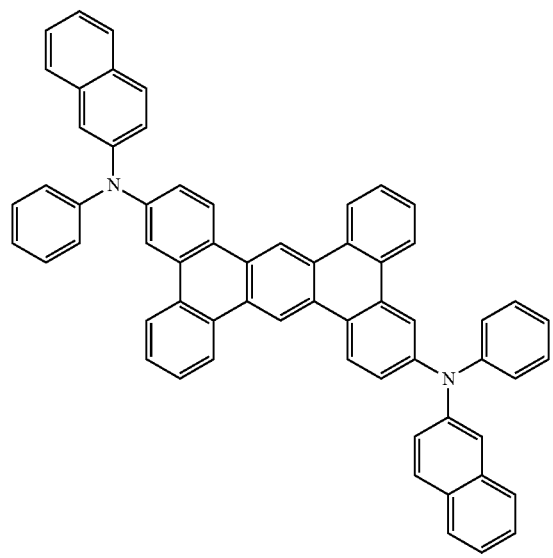
Compound 8
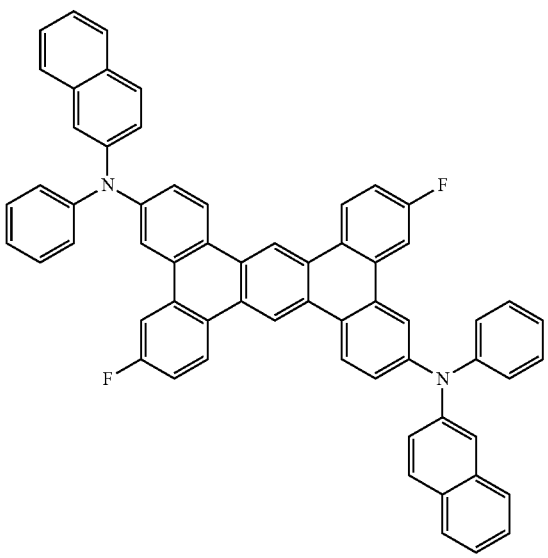
Compound 9
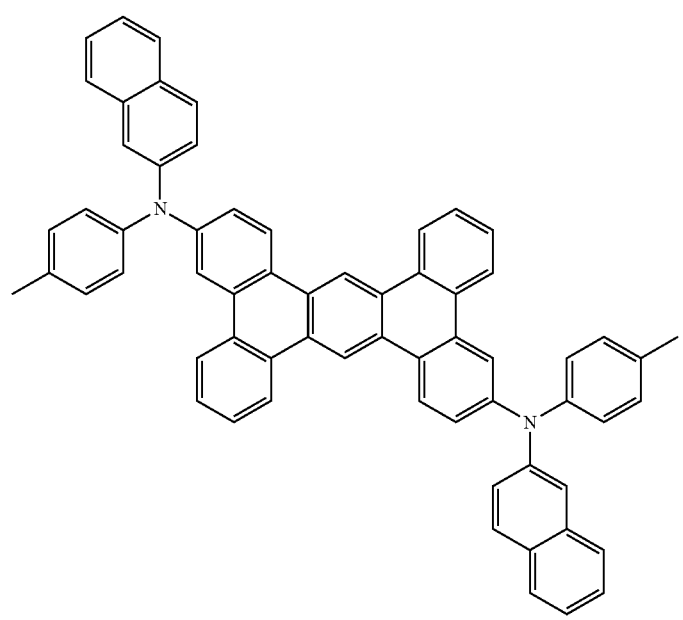

Compound 10
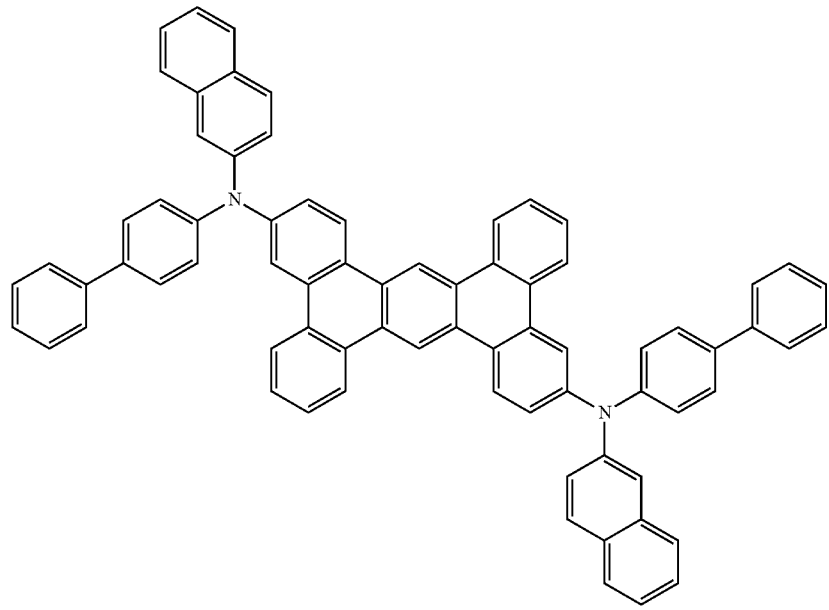
Compound 11
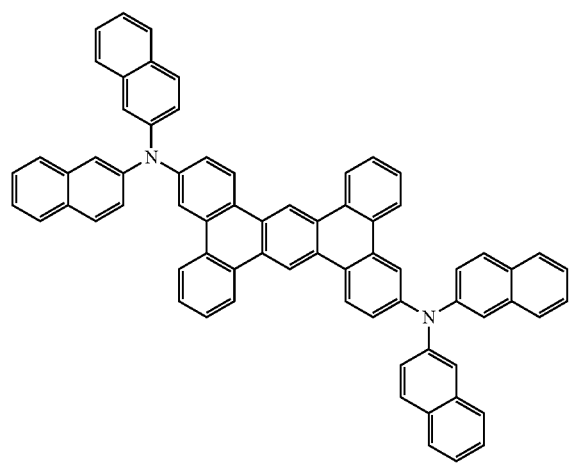
Compound 12
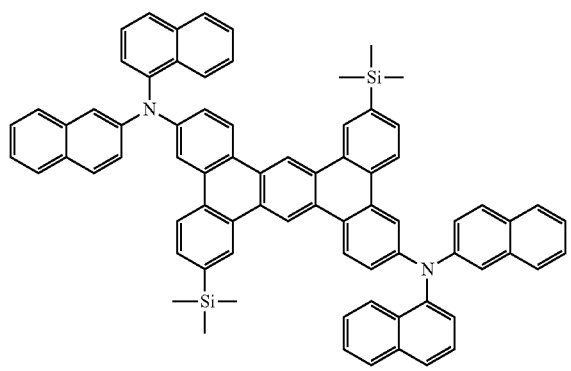
Compound 13
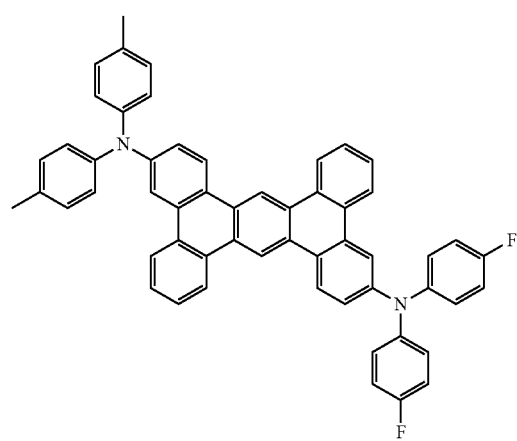
Compound 14
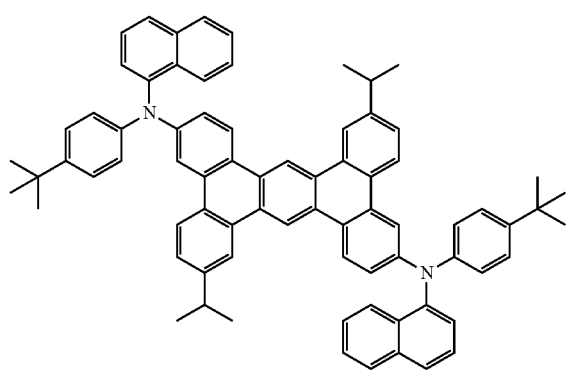

Compound 15
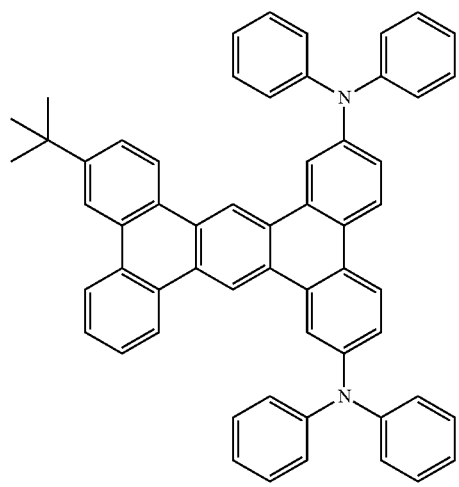
Compound 16
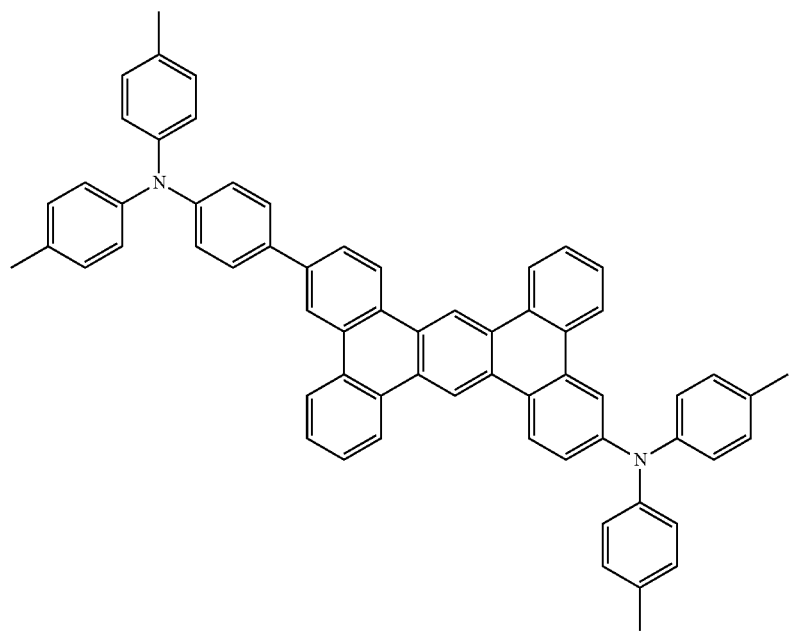

Compound 17
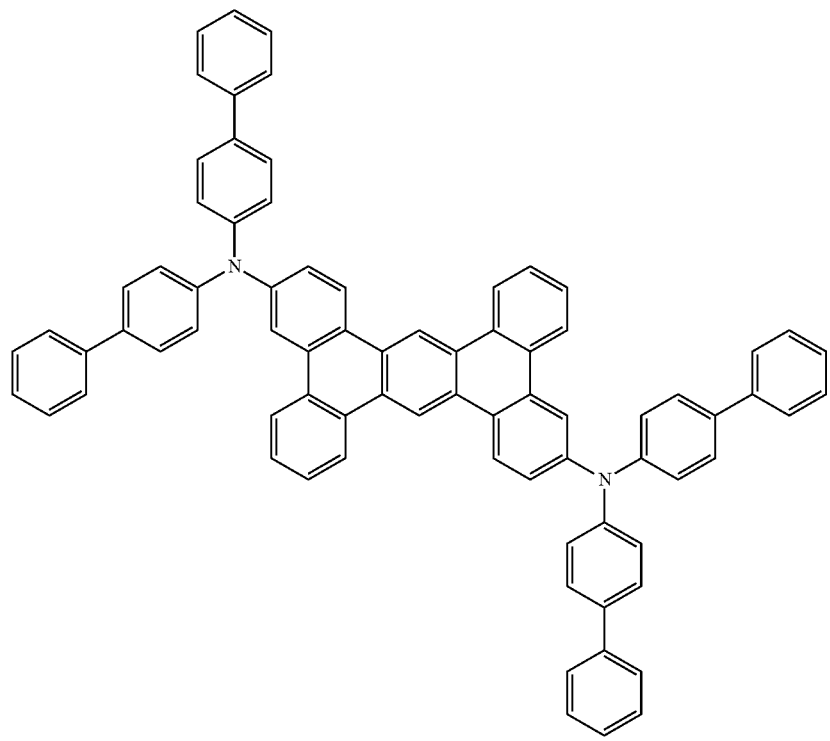
Compound 18
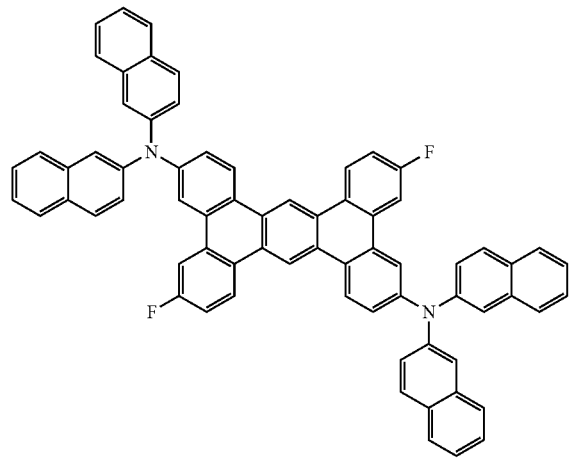
Compound 19
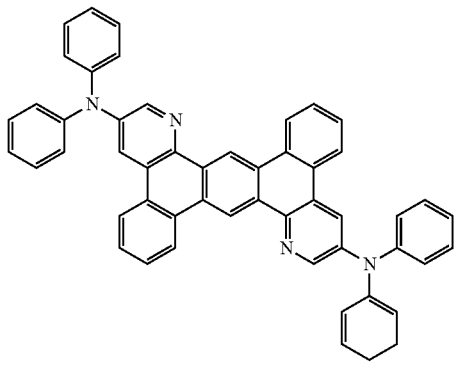

-continued
Compound 20
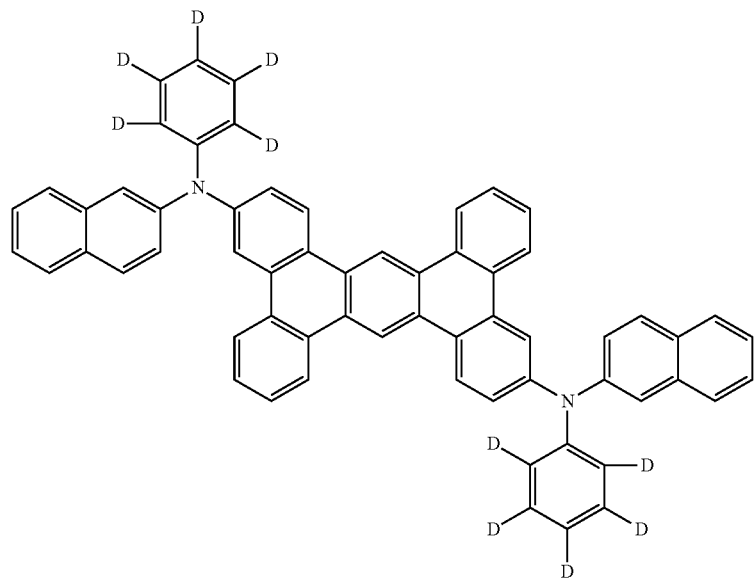
Compound 21
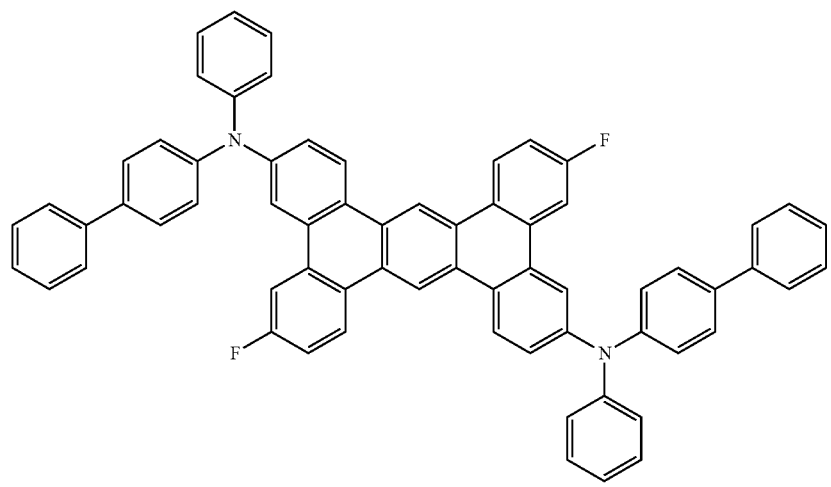
Compound 22
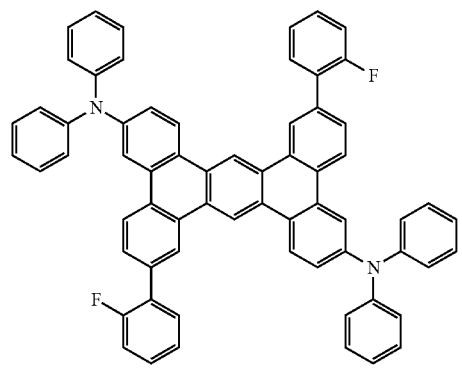
Compound 23
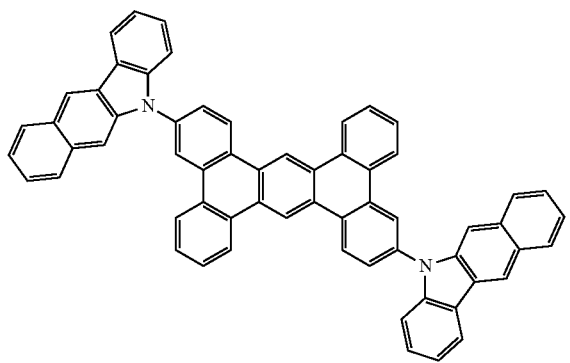

Compound 24
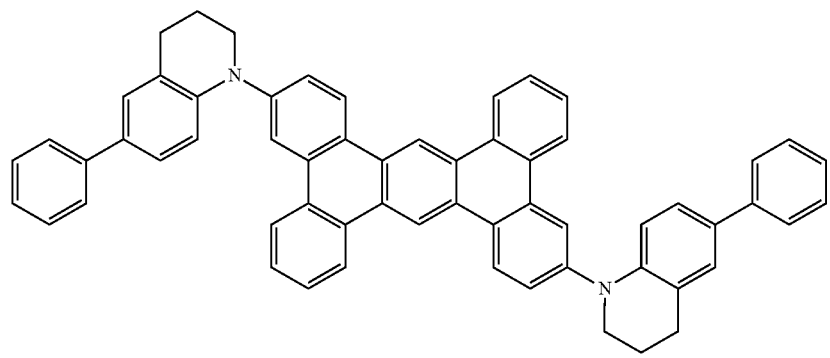
Compound 25
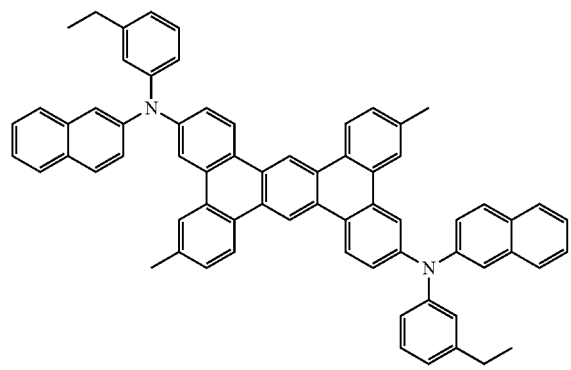
Compound 26
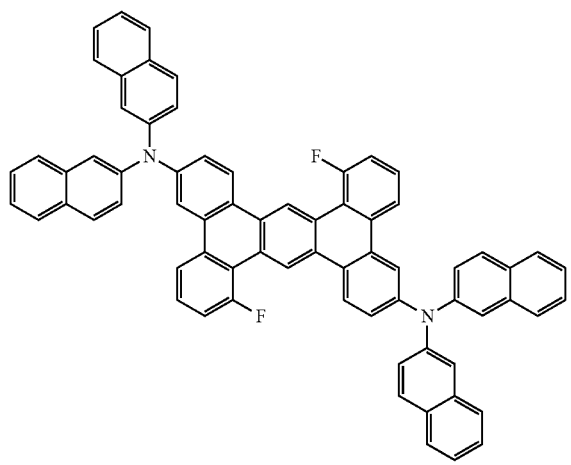
Compound 27
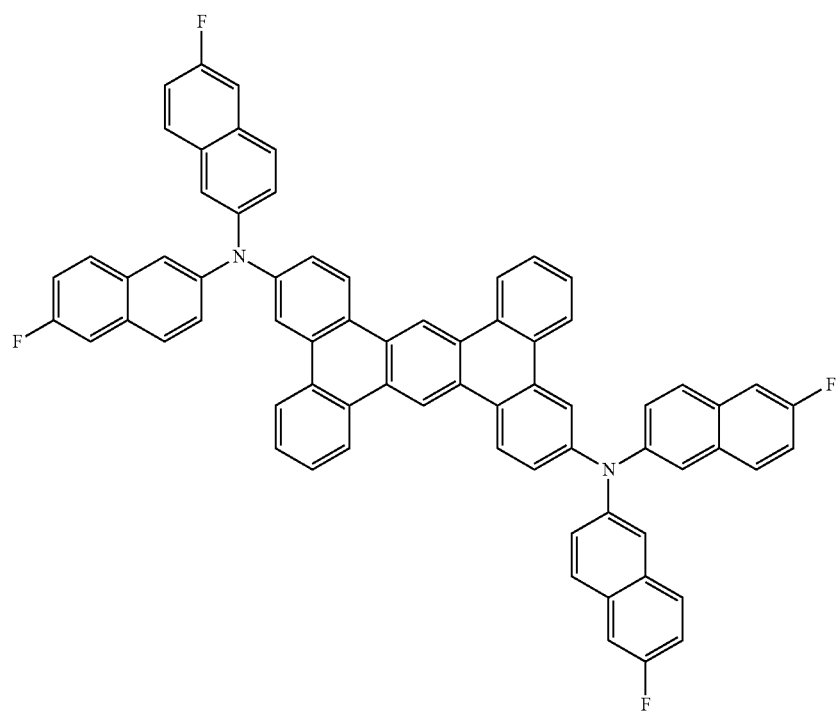

Compound 28
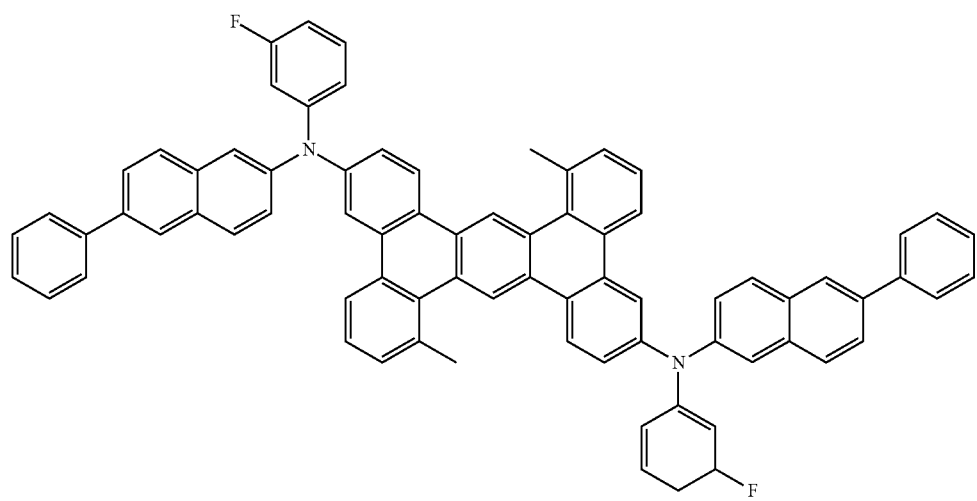
Compound 29
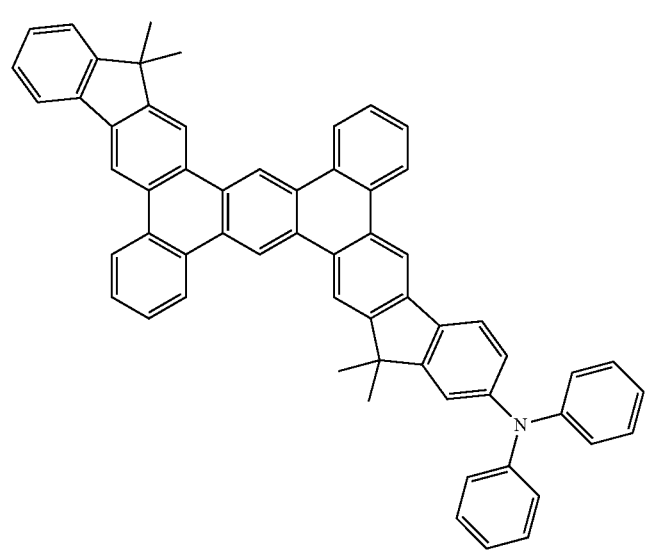
Compound 30
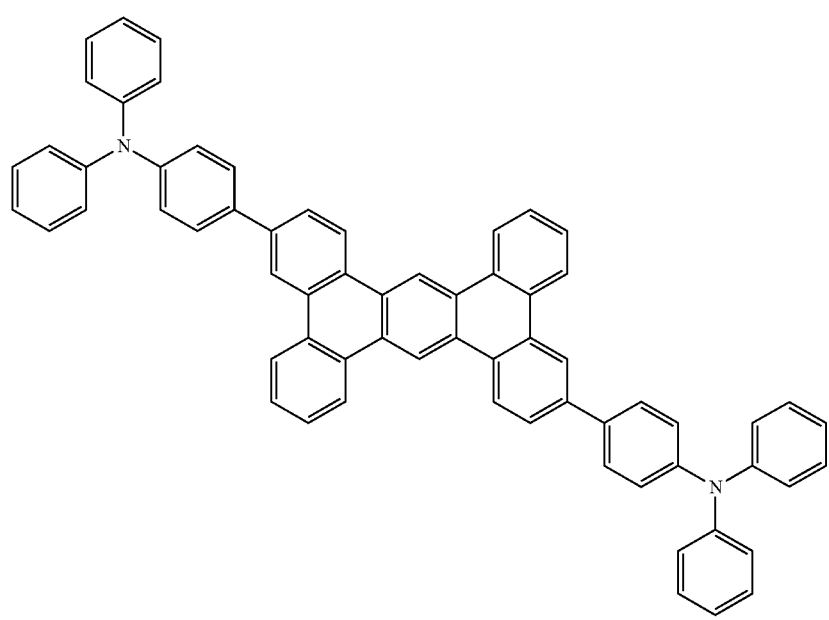

-continued
Compound 31
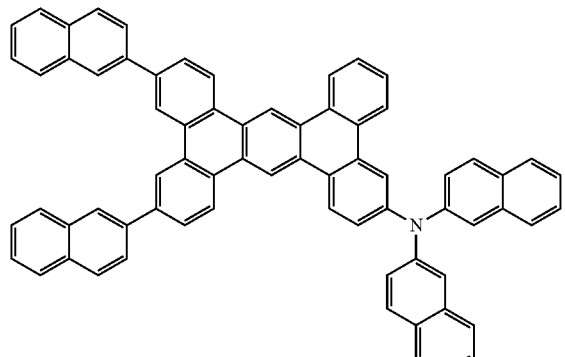
Comparative Compound 1
Compound 32
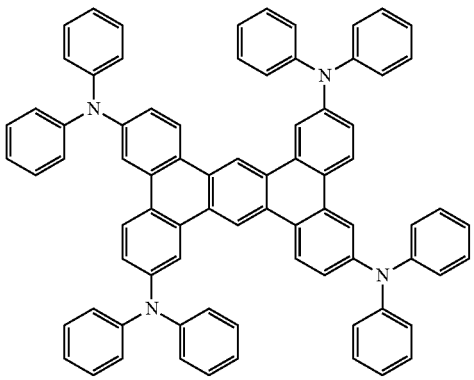
Comparative Compound 2
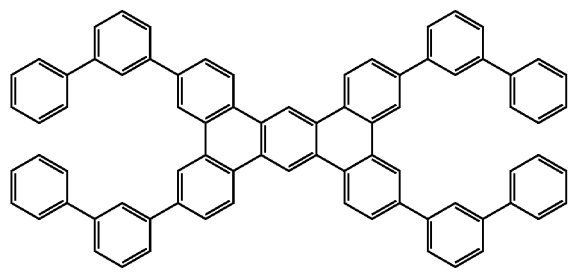
Comparative Compound 3
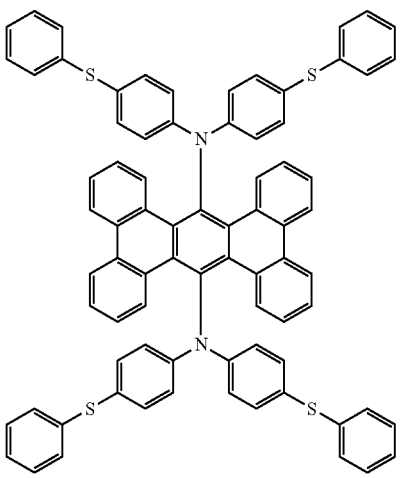
Comparative Compound 4
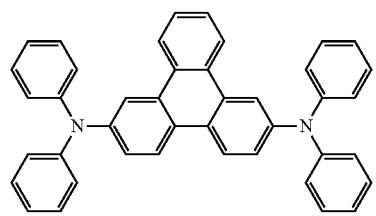
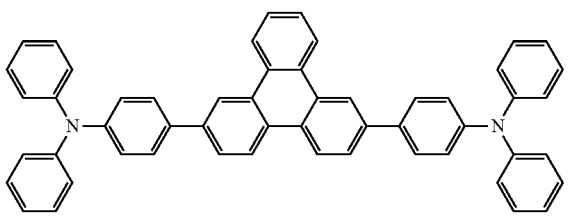
Comparative Compound 1 is the compound described in JP-A-2008-50308, Comparative Compound 2 is the compound described in JP-A-2007-157899 and JP-A-2007-227717, Comparative Compound 3 is the compound described in JP-A-11-251063, and Comparative Compound 4 is the compound described in JP-A-2009-292760.
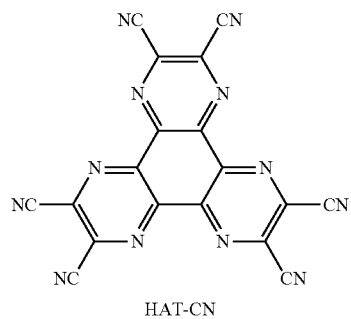
HAT-CN -continued
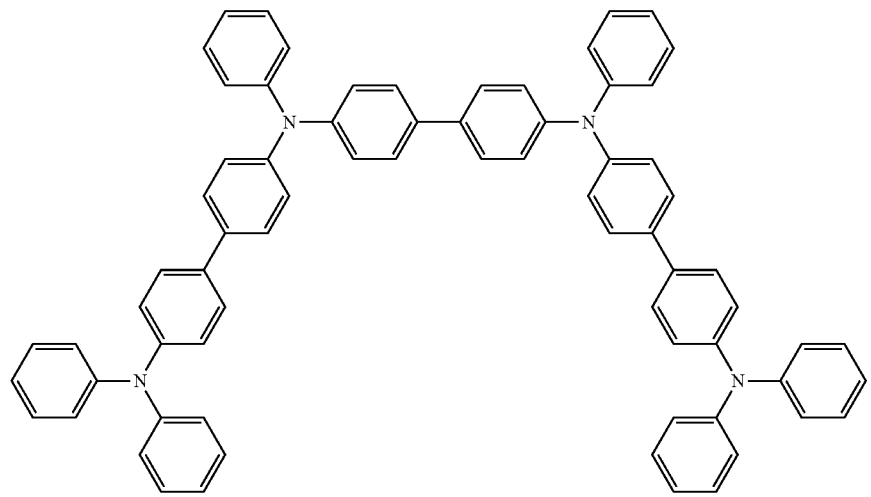
HI-1
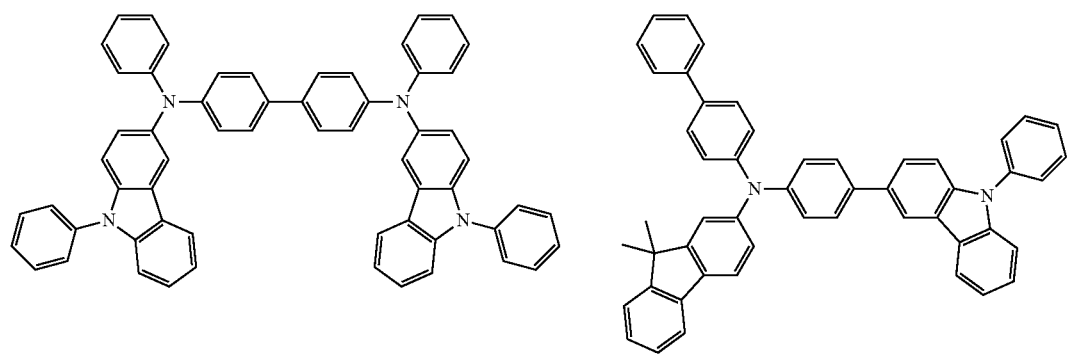
HI-2
HT-1
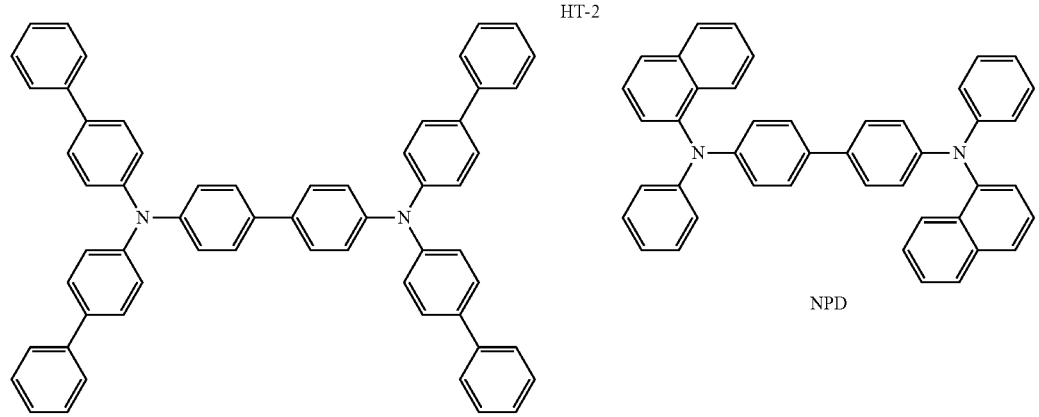
HT-2
NPD
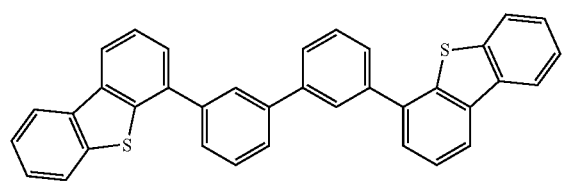
H-1
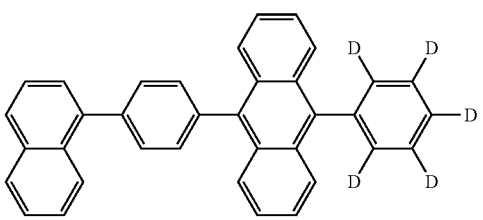
H-2

-continued
H-3
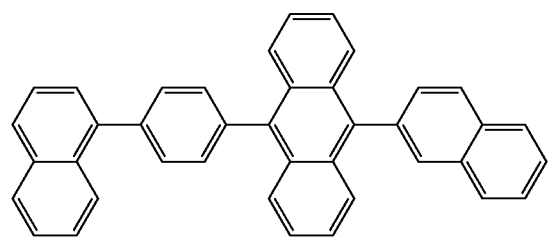
H-4
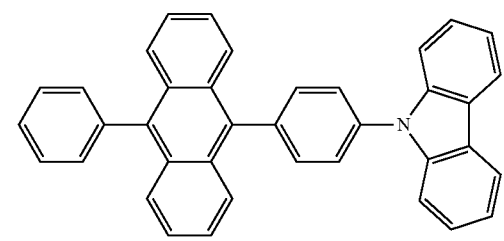
ET-1
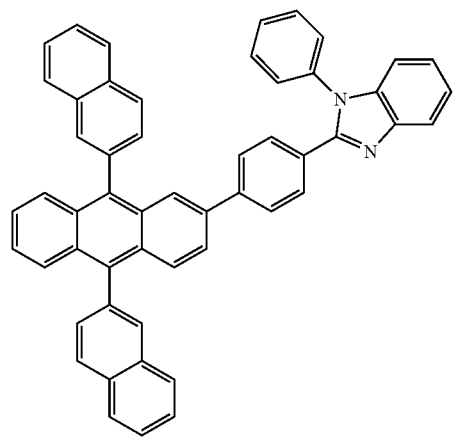
ET-2
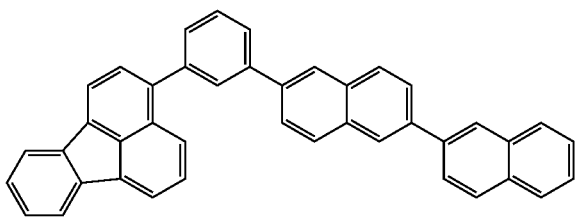
ET-3
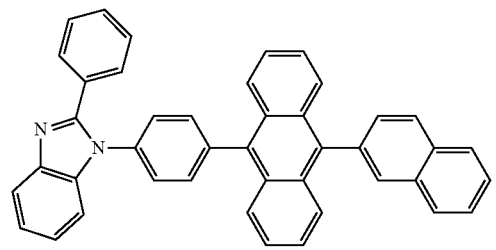
ET-4
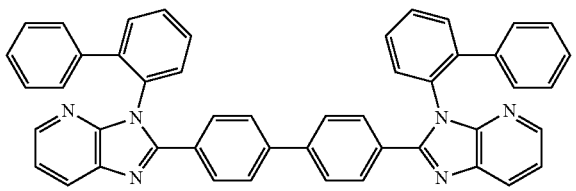
ET-5
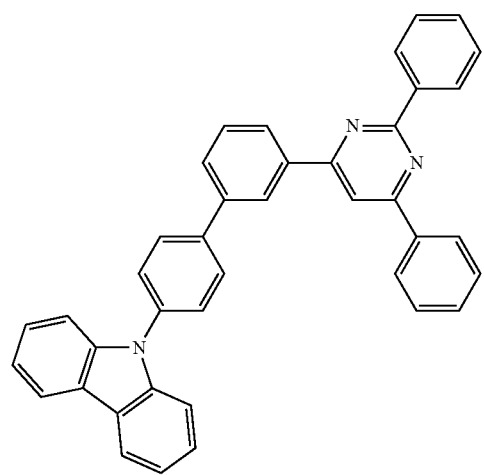
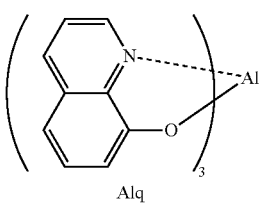
Alq

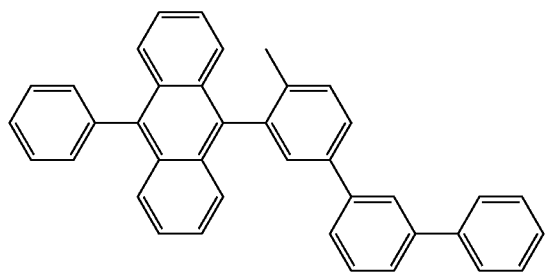
H-5

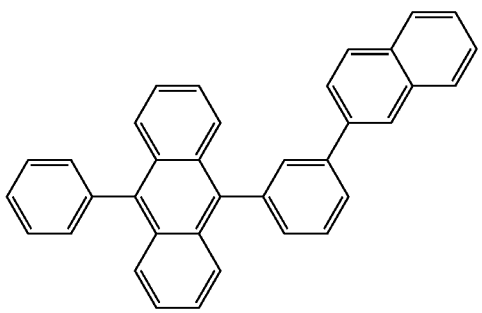
H-6

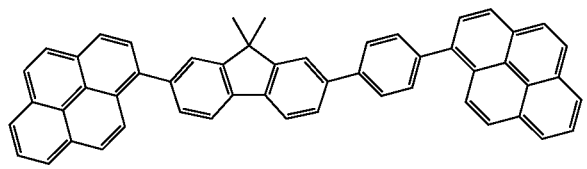
H-7

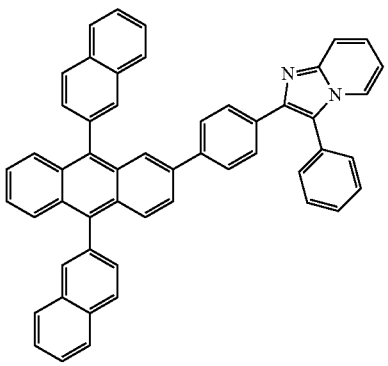
ET-6

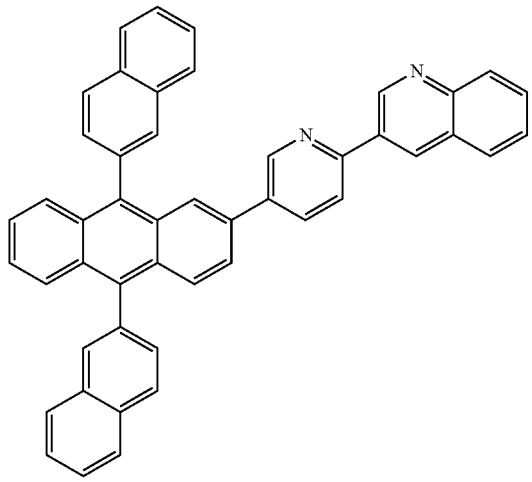
ET-7

Example 1

1. Synthesis of Compound Represented by General Formula (1)

The compound represented by the general formula (1) can be synthesized by the method described in the present specification, or a combination of other known reactions. The compounds 1 to 32 were synthesized by similar methods with the synthesis method described in JP-A-2008-50308.

The $^1$H-NMR data of the compounds 1, 2, 3, 4, 5, 7, 8, 9, 10, 11, and 18 are shown, as representatives.

(Compound 1)

$^1$H NMR (400 MHz, in CDCl$_3$); δ (ppm)=9.73 (s, 2H), 8.88 (d, 2H), 8.79 (d, 2H), 8.33 (d, 2H), 8.30 (d, 2H), 7.69 (t, 2H), 7.58 (t, 2H), 7.48 (dd, 2H), 7.35-7.25 (m, 16H), 7.10 (t, 4H) ppm.

(Compound 2)

$^1$H NMR (400 MHz, in DMSO-d$_6$); δ (ppm)=9.86 (s, 2H), 9.22 (d, 2H), 9.14 (d, 2H), 8.24 (d, 2H), 8.18 (d, 2H), 7.75 (t, 2H), 7.66 (t, 2H), 7.32 (dd, 2H), 7.21 (d, 8H), 7.10 (d, 8H), 2.33 (s, 12H) ppm.

(Compound 3)

$^1$H NMR (400 MHz, in CDCl$_3$); δ (ppm)=9.61 (s, 2H), 8.84-8.80 (m, 2H), 8.74 (d, 2H), 8.17 (d, 2H), 7.90 (dd, 2H), 7.50 (dd, 2H), 7.43-7.24 (m, 18H), 7.12 (t, 4H) ppm.

(Compound 4)

$^1$H NMR (400 MHz, in DMSO-d$_6$); δ (ppm)=9.92 (s, 2H), 9.24 (t, 4H), 8.35-8.32 (m, 4H), 7.76 (t, 2H), 7.75-7.65 (m, 10H), 7.49-7.43 (m, 6H), 7.34 (t, 2H), 7.27-7.18 (m, 12H), 2.36 (s, 6H) ppm.

(Compound 5)

$^1$H NMR (400 MHz, in CDCl$_3$); δ (ppm)=9.82 (s, 2H), 9.03 (s, 2H), 8.80 (d, 2H), 8.39-8.37 (m, 4H), 7.85 (t, 6H), 7.57 (t, 4H), 7.50-7.42 (m, 4H), 7.36-7.26 (m, 16H), 7.10 (t, 4H) ppm.

(Compound 7)

$^1$H NMR (400 MHz, in DMSO-d$_6$); δ (ppm)=9.95 (s, 2H), 9.28 (d, 4H), 8.36 (d, 2H), 8.30 (d, 2H), 7.95-7.90 (m, 4H), 7.78-7.73 (m, 4H), 7.66-7.61 (m, 4H), 7.49-7.41 (m, 12H), 7.29 (d, 4H), 7.20 (t, 2H) ppm.

(Compound 8)

$^1$H NMR (400 MHz, in CDCl$_3$); δ (ppm)=9.64 (s, 2H), 8.85-8.77 (m, 4H), 8.23 (s, 2H), 7.91-7.81 (m, 6H), 7.66-7.52 (m, 6H), 7.44-7.35 (m, 12H), 7.31-7.14 (m, 6H) ppm.

(Compound 9)

$^1$H NMR (400 MHz, in CDCl$_3$); δ (ppm)=9.75 (s, 2H), 8.87 (d, 2H), 8.79 (d, 2H), 8.37 (d, 2H), 8.29 (d, 2H), 7.80 (t, 4H), 7.68 (t, 2H), 7.63 (d, 2H), 7.57-7.49 (m, 6H), 7.45-7.37 (m, 6H), 7.18 (q, 8H), 2.40 (s, 6H) ppm.

(Compound 10)

$^1$H NMR (400 MHz, in CDCl$_3$); δ (ppm)=9.80 (s, 2H), 8.90 (d, 2H), 8.86 (d, 2H), 8.46 (d, 2H), 8.32 (d, 2H), 7.83 (d, 4H), 7.72-7.36 (m, 34H) ppm.

(Compound 11)

$^1$H NMR (400 MHz, in DMSO-d$_6$); δ (ppm)=9.97 (s, 2H), 9.31-9.26 (m, 4H), 8.43 (d, 2H), 8.32 (d, 2H), 7.98-7.91 (m, 8H), 7.79-7.72 (m, 6H), 7.68 (dd, 4H), 7.61 (t, 2H), 7.54 (dd, 2H), 7.49-7.47 (m, 12H) ppm.

(Compound 18)

$^1$H NMR (400 MHz, in CDCl$_3$); δ (ppm)=9.68 (s, 2H), 8.87-8.80 (m, 4H), 8.29 (s, 2H), 7.90-7.83 (m, 10H), 7.66-7.59 (m, 10H), 7.50-7.38 (m, 14H) ppm.

Comparative Compounds 1 to 4 were synthesized with reference to the publications in which each compound is described.

Example 2

2. Evaluation of Material Physical Property

<Evaluation of Material Physical Property>

Figure 4:
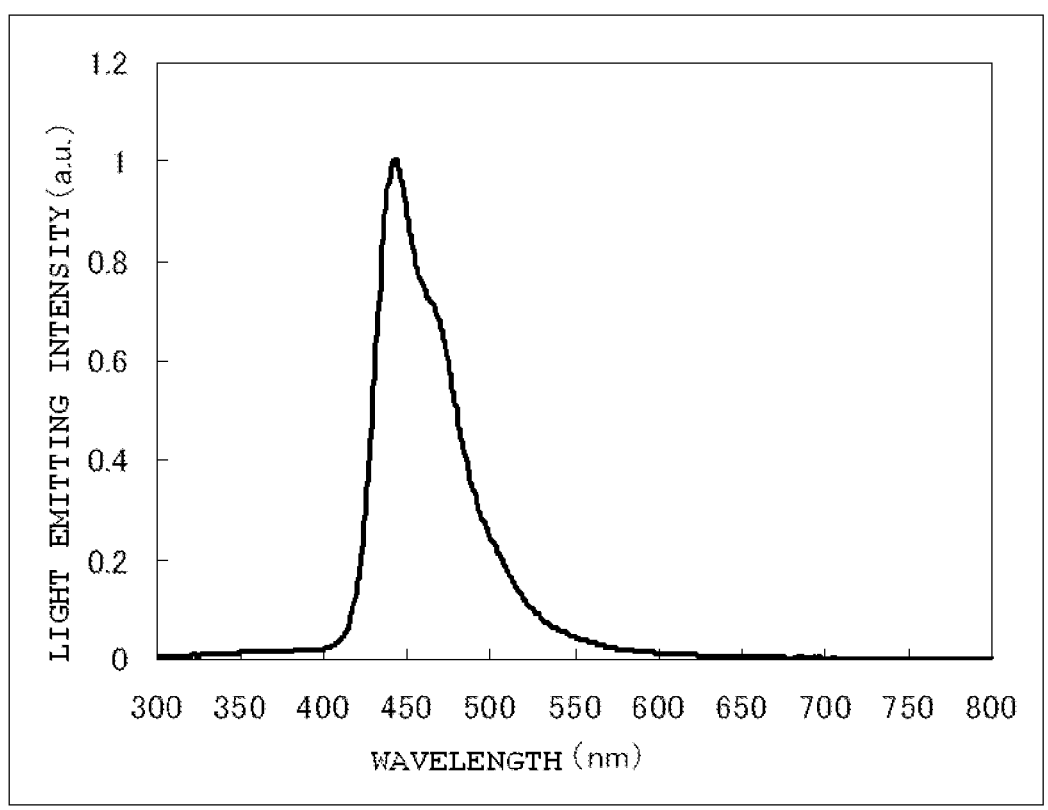
FIG. 4 is a light emitting spectrum of a compound 1 of the present invention.

H-1 and each light emitting material were deposited on a 0.7 mm-thick and 2.5 cm-square quartz glass substrate by vacuum deposition so as to have a mass ratio of (95:5), to form a film having a thickness of 50 nm. The obtained film was illustrated with UV light of 350 nm, the light emitting spectrum at the time of light emitting was measured using a fluorescence spectrophotometer (FP-6300 manufactured by JASCO Corporation), the light emitting wavelength (nm) and the spectral line half width (energy difference (eV) of the long wavelength and the short wavelength when the light emitting maximum value is set to 1) were acquired, and then, each of them were described in three stages of O, X, and Δ as shown below. In addition, the light emitting spectrum of the Compound 1 is shown in FIG. 4 as an example.

(Light Emitting Wavelength)
- O: equal to or more than 435 nm and less than 455 nm
- Δ: less than 435 nm
- x: equal to or more than 455 nm (Spectral Line Half Width)
- O: less than 0.30 eV
- Δ: equal to or more than 0.30 and less than 0.35 eV
- x: equal to or more than 0.35 eV

TABLE 1

| Light emitting material | Light emitting wavelength | Spectral line half width | Note |
|---|---|---|---|
| Compound 1 | O | O | Present Invention |
| Compound 2 | O | O | Present Invention |
| Compound 3 | O | O | Present Invention |
| Compound 4 | O | O | Present Invention |
| Compound 5 | O | O | Present Invention |
| Compound 6 | O | O | Present Invention |
| Compound 7 | O | O | Present Invention |
| Compound 8 | O | O | Present Invention |
| Compound 9 | O | O | Present Invention |
| Compound 10 | O | O | Present Invention |
| Compound 11 | O | O | Present Invention |
| Compound 12 | O | O | Present Invention |
| Compound 13 | O | O | Present Invention |
| Compound 14 | O | O | Present Invention |
| Compound 15 | O | O | Present Invention |
| Compound 16 | O | Δ | Present Invention |
| Compound 17 | O | O | Present Invention |
| Compound 18 | O | O | Present Invention |
| Compound 19 | O | O | Present Invention |
| Compound 20 | O | O | Present Invention |
| Compound 21 | O | O | Present Invention |
| Compound 22 | O | O | Present Invention |
| Compound 23 | O | O | Present Invention |
| Compound 24 | O | O | Present Invention |
| Compound 25 | O | O | Present Invention |
| Compound 26 | O | O | Present Invention |
| Compound 27 | O | O | Present Invention |
| Compound 28 | O | O | Present Invention |
| Compound 29 | O | Δ | Present Invention |
| Compound 30 | O | Δ | Present Invention |
| Compound 31 | O | Δ | Present Invention |
| Compound 32 | O | O | Present Invention |
| Comparative Compound 1 | Δ | X | Comparative Example |
| Comparative Compound 2 | X | Δ | Comparative Example |
| Comparative Compound 3 | Δ | X | Comparative Example |
| Comparative Compound 4 | O | X | Comparative Example |

Example 3

<Preparation/Evaluation of Element>

All of the materials used in the preparation of the elements were subjected to sublimation purification, and as a result, it was confirmed that chromatic purity (254 nm of absorption intensity area ratio) was equal to or more than 99.9% by a high performance liquid chromatography (TSKgel ODS-100Z manufactured by Tosho Corporation).

A 0.5 mm-thick and 2.5 cm-square glass substrate (manufactured by Geomatec Co., Ltd., surface resistance: 10 Ω/square) having an ITO film was put into a cleaning container. After the ultrasonic cleaning in 2-propanol, the glass substrate was subjected to a UV-ozone treatment for 30 minutes. The organic compound layers were deposited sequentially on the transparent anode (ITO film) by a vacuum deposition method.

First layer: HAT-CN: film thickness 10 nm
Second layer: HT-1: film thickness 30 nm
Third layer: H-2 and the light emitting material disclosed in the following Table 2 (mass ratio 95:5): film thickness 30 nm
Fourth layer: ET-1: film thickness 30 nm Lithium fluoride 1 nm and metal aluminum 100 nm were deposited sequentially thereon to obtain a cathode.

The obtained laminate was put in a glove box purged with a nitrogen gas without bringing it into contact with the atmosphere, and then sealed with a sealing can made of glass and an ultraviolet curing adhesive (XNR5516HV, manufactured by Nagase Chemical Co., Ltd.) to obtain Organic Electroluminescent elements 1-1 to 1-7 in which the light emitting portion is 2 mm×2 mm square, and Comparative Elements 1-1 to 1-4 for comparison. The following tests were performed for each obtained organic electroluminescent element. The results obtained by evaluating from viewpoints of the light emitting efficiency, the chromatic purity, and the driving chromaticity change are shown in the following Table 2.

(a) Light Emitting Efficiency

Using Source Measure Unit 2400 manufactured by TOYO Corporation, direct voltage was applied to each element to make them emit light and the brightness thereof was measured using a luminance meter (BM-8 manufactured by TOPCON CORPORATION). The light emitting spectrum and the light emitting wavelength were measured using Spectrum Analyzer PMA-11 manufactured by Hamamatsu Photonics K.K. Based on these, external quantum efficiency (η) with the brightness around 1000 cd/m$^2$ was calculated by a brightness conversion method. In the following Table 2, values of the external quantum efficiency of Comparative Elements 1 to 4 were set to 1.0 and shown with relative values. The numerical values are preferably large, since it shows excellent efficiency.

(b) Chromatic Purity

Chromaticity (x, y) from the light emitting spectrum when each organic electroluminescent element emits light to a brightness of 1000 cd/m$^2$ was acquired (CIE 1931 color system). The y value at this time was evaluated by four stages with the following criteria.

⊙: equal to or more than 0.03 and equal to or less than 0.08
○: equal to or more than 0.025 and less than 0.03, equal to or more than 0.08 and less than 0.10
Δ: equal to or more than 0.02 and less than 0.025, equal to or more than 0.10 and less than 0.15
x: less than 0.02, equal to or more than 0.15

(c) Driving Chromaticity Change

Direct voltage was applied to each organic electroluminescent element to make them emit light to a brightness of 1000 cd/m$^2$, and then chromaticity (x', y') at the time when the brightness is decreased to 500 cd/m$^2$ was acquired from the light emitting spectrum (CiE 1931 color system). Change of the y value before and after the driving degradation Δy (=|y'−Δy|) was evaluated by four stages with the following criteria.

⊙: less than 0.01
○: equal to or more than 0.01 and less than 0.02
Δ: equal to or more than 0.02 and less than 0.03
x: equal to or more than 0.03

TABLE 2

| Element No. | Light emitting material | Light emitting color | Light emitting efficiency (relative value) | Chromatic purity | Driving chromaticity change |
|---|---|---|---|---|---|
| Element 1-1 | Compound 1 | Blue | 1.3 | ⊙ | ⊙ |
| Element 1-2 | Compound 2 | Blue | 1.4 | ⊙ | ⊙ |
| Element 1-3 | Compound 4 | Blue | 1.3 | ⊙ | ⊙ |
| Element 1-4 | Compound 7 | Blue | 1.4 | ⊙ | ⊙ |
| Element 1-5 | Compound 8 | Blue | 1.4 | ⊙ | ⊙ |
| Element 1-6 | Compound 10 | Blue | 1.5 | ⊙ | ⊙ |
| Element 1-7 | Compound 11 | Blue | 1.5 | ⊙ | ⊙ |
| Element 1-8 | Compound 13 | Blue | 1.3 | ⊙ | ⊙ |
| Element 1-9 | Compound 16 | Blue | 1.3 | Δ | ⊙ |
| Element 1-10 | Compound 17 | Blue | 1.5 | ⊙ | ⊙ |
| Element 1-11 | Compound 20 | Blue | 1.4 | ⊙ | ⊙ |
| Element 1-12 | Compound 23 | Blue | 1.3 | ⊙ | ⊙ |
| Element 1-13 | Compound 28 | Blue | 1.6 | ⊙ | ⊙ |
| Element 1-14 | Compound 30 | Blue | 1.6 | ○ | ⊙ |
| Element 1-15 | Compound 32 | Blue | 1.3 | ⊙ | ⊙ |
| Comparative Element 1-1 | Comparative Compound 1 | Blue | 0.6 | X | X |
| Comparative Element 1-2 | Comparative Compound 2 | Blue- green | 0.7 | X | X |
| Comparative Element 1-3 | Comparative Compound 3 | Blue | 1.1 | X | X |
| Comparative Element 1-4 | Comparative Compound 4 | Blue | 1.0 | X | Δ |

Example 4

The organic electroluminescent element was prepared in the same manner as Example 3, except for changing the layer configuration as shown below, and the same evaluation as Example 3 was performed. The results are shown in the following Table 3. In addition, the light emitting efficiency of the following Table 3 is shown with a relative value when the external quantum efficiency of Comparative Element 2-3 is set to 1.0.

First layer: Hi-1: film thickness 50 nm
Second layer: HT-2: film thickness 45 nm
Third layer: H-3 and light emitting material disclosed in the following Table 3 (mass ratio 95:5): film thickness 25 nm
Fourth layer: ET-2: film thickness 5 nm
Fifth layer: ET-3: film thickness 20 nm

TABLE 3

| Element No. | Light emitting material | Light emitting color | Light emitting efficiency (relative value) | Chromatic purity | Driving chromaticity change |
|---|---|---|---|---|---|
| Element 2-1 | Compound 3 | Blue | 1.4 | ⊙ | ⊙ |
| Element 2-2 | Compound 4 | Blue | 1.4 | ⊙ | ⊙ |
| Element 2-3 | Compound 5 | Blue | 1.3 | ⊙ | ⊙ |
| Element 2-4 | Compound 6 | Blue | 1.3 | ○ | ⊙ |
| Element 2-5 | Compound 9 | Blue | 1.4 | ⊙ | ⊙ |
| Element 2-6 | Compound 12 | Blue | 1.4 | ⊙ | ⊙ |
| Element 2-7 | Compound 14 | Blue | 1.4 | ⊙ | ⊙ |
| Element 2-8 | Compound 15 | Blue | 1.2 | ○ | ⊙ |
| Element 2-9 | Compound 18 | Blue | 1.5 | ⊙ | ⊙ |
| Element 2-10 | Compound 19 | Blue | 1.2 | ⊙ | ○ |
| Element 2-11 | Compound 22 | Blue | 1.2 | ⊙ | ⊙ |
| Element 2-12 | Compound 24 | Blue | 1.2 | ⊙ | ○ |
| Element 2-13 | Compound 27 | Blue | 1.5 | ⊙ | ⊙ |
| Element 2-14 | Compound 29 | Blue | 1.5 | ○ | ⊙ |
| Element 2-15 | Compound 31 | Blue | 1.3 | ○ | ⊙ |
| Comparative Element 2-1 | Comparative Compound 1 | Blue | 0.5 | X | X |
| Comparative Element 2-2 | Comparative Compound 3 | Blue | 1.1 | X | X |
| Comparative Element 2-3 | Comparative Compound 4 | Blue | 1.0 | X | X |

Example 5

The organic electroluminescent element was prepared in the same manner as Example 3, except for changing the layer configuration as shown below, and the same evaluation as Example 3 was performed. The results are shown in the following Table 4. In addition, the light emitting efficiency of the following Table 4 is shown with a relative value when the external quantum efficiency of Organic Electroluminescent Element 3-4 for comparison is set to 1.0.

First layer: Hi-2: film thickness 10 nm
Second layer: NPD: film thickness 30 nm
Third layer: host material and light emitting material disclosed in the following Table 4 (95:5): film thickness 30 nm
Fourth layer: electron transporting material disclosed in the following Table 4: film thickness 10 nm
Fifth layer: Alq: film thickness 20 nm

TABLE 4

| Element No. | Host material | Light emitting material | Electron transporting material | Light emitting color | Light emitting efficiency (relative value) | Chromatic purity | Driving chromaticity change |
|---|---|---|---|---|---|---|---|
| Element 3-1 | H-1 | Compound 1 | ET-4 | Blue | 1.5 | ⊙ | ⊙ |
| Element 3-2 | H-4 | Compound 5 | ET-4 | Blue | 1.6 | ⊙ | ⊙ |
| Element 3-3 | H-1 | Compound 8 | ET-4 | Blue | 1.7 | ⊙ | ⊙ |
| Element 3-4 | H-4 | Compound 9 | ET-5 | Blue | 1.7 | ⊙ | ⊙ |
| Element 3-5 | H-1 | Compound 10 | ET-5 | Blue | 1.6 | ⊙ | ⊙ |
| Element 3-6 | H-5 | Compound 7 | ET-6 | Blue | 1.6 | ⊙ | ⊙ |
| Element 3-7 | H-6 | Compound 11 | ET-6 | Blue | 1.7 | ⊙ | ⊙ |
| Element 3-8 | H-5 | Compound 16 | ET-6 | Blue | 1.6 | ○ | ⊙ |
| Element 3-9 | H-7 | Compound 17 | ET-7 | Blue | 1.7 | ⊙ | ⊙ |
| Element 3-10 | H-1 | Compound 20 | ET-6 | Blue | 1.6 | ⊙ | ⊙ |
| Element 3-11 | H-6 | Compound 21 | ET-6 | Blue | 1.7 | ⊙ | ⊙ |
| Element 3-12 | H-6 | Compound 25 | ET-7 | Blue | 1.6 | ⊙ | ⊙ |
| Element 3-13 | H-7 | Compound 26 | ET-7 | Blue | 1.5 | ⊙ | ⊙ |
| Element 3-14 | H-7 | Compound 27 | ET-4 | Blue | 1.7 | ⊙ | ⊙ |
| Element 3-15 | H-5 | Compound 29 | ET-7 | Blue | 1.7 | ○ | ⊙ |
| Element 3-16 | H-2 | Compound 30 | ET-6 | Blue | 1.7 | ○ | ⊙ |
| Element 3-17 | H-3 | Compound 31 | ET-6 | Blue | 1.5 | ○ | ⊙ |
| Element 3-18 | H-6 | Compound 32 | ET-4 | Blue | 1.5 | ⊙ | ⊙ |
| Comparative Element 3-1 | H-1 | Comparative Compound 1 | ET-4 | Blue | 0.9 | X | X |
| Comparative Element 3-2 | H-4 | Comparative Compound 2 | ET-4 | Blue-green | 0.8 | X | X |
| Comparative Element 3-3 | H-1 | Comparative Compound 3 | ET-5 | Blue | 1.3 | X | X |
| Comparative Element 3-4 | H-4 | Comparative Compound 4 | ET-5 | Blue | 1.0 | X | Δ |

(Evaluation of Organic EL Element (coating))

—Preparation of Coating Liquid for Forming Light Emitting Layer—

MEK (methyl ethyl ketone) (98.99% by mass) was mixed to the Compound 1 (0.1% by mass) and the host material H-1 (0.9% by mass) to obtain a coating liquid 1 for forming a light emitting layer.

ITO was deposited on a glass substrate having a size of 25 mm×25 mm×0.7 mm so as to have a thickness of 150 nm, to prepare a transparent supporting substrate. The transparent supporting substrate was etched and cleaned.

On this ITO glass substrate, 2 parts by mass of PTPDES-2 (manufactured by CHEMIPRO KASEI KAISHA, LTD., Tg=205° C.) represented by the following structural formula was dissolved in 98 parts by mass of electronic industrial cyclohexanone (manufactured by KANTO CHEMICAL CO., INC.), was subjected to spin coating (at 2,000 rpm, for 20 seconds) so as to have a thickness of about 40 nm, and then, drying at 120° C. for 30 minutes and an annealing process at 160° C. for 10 minutes were performed, and accordingly, a hole injecting layer was formed.

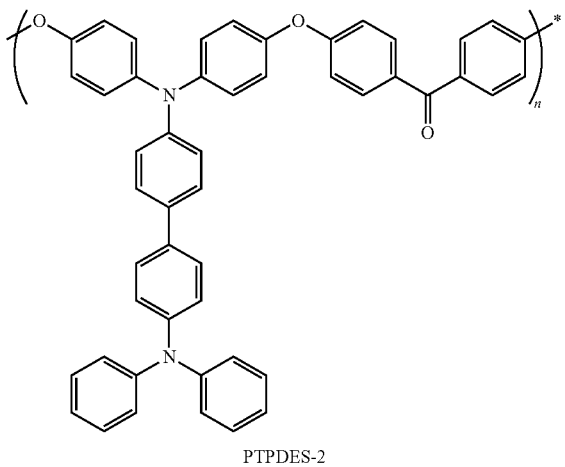

PTPDES-2

The coating liquid 1 for forming a light emitting layer was spin coated (at 1,300 rpm for 30 seconds) onto this hole injecting layer so as to have a thickness of about 40 nm to obtain a light emitting layer.

Then, as an electron transporting layer, BAlq (bis(2-methyl-8-quinolinato)-4-(phenyl-phenolate)-aluminium (III)) represented by the following structural formula was formed on the light emitting layer so as to have a thickness of 40 nm by a vacuum deposition method.

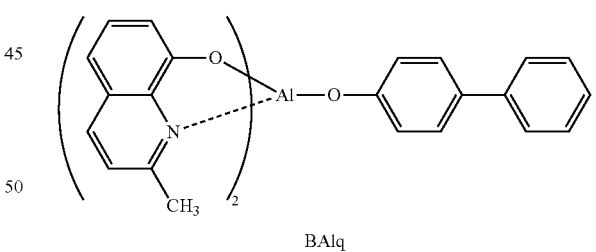

BAlq

As an electron injecting layer, lithium fluoride (LiF) was formed on the electron transporting layer so as to have a thickness of 1 nm by a vacuum deposition method. Further, metal aluminum was deposited to have a thickness of 70 nm to obtain a cathode.

The laminate prepared as described above was put in a glove box purged with an argon gas, and then sealed with a sealing can made of stainless and an ultraviolet curing adhesive (XNR5516HV, manufactured by Nagase Chemical Co., Ltd.) to obtain an Organic Electroluminescent Element 4-1.

Organic Electroluminescent Elements 4-2 and 4-3, and Comparative Elements 4-1 and 4-2 were obtained using a coating liquid prepared in the same manner as the coating liquid 1 for forming a light emitting layer, except for changing the compound 1 into a compound disclosed in Table 5.

The same evaluation as Example 1 was performed for the Organic Electroluminescent Elements 4-1 to 4-3 and Comparative Elements 4-1 and 4-2. The results are shown in the following Table 5. In addition the light emitting efficiency of the following Table 5 is shown with a relative value when the external quantum efficiency of the Organic Electroluminescent Element 4-1 for comparison is set to 1.0.

TABLE 5

| Element No. | Light emitting material | Light emitting color | Chromatic purity | Light emitting efficiency (relative value) | Driving chromaticity change |
|---|---|---|---|---|---|
| Element 4-1 | Compound 12 | Blue | ◯ | 1.7 | ◯ |
| Element 4-2 | Compound 14 | Blue | ◯ | 1.5 | ◯ |
| Element 4-3 | Compound 20 | Blue | ◯ | 1.8 | ⊙ |
| Element 4-4 | Compound 25 | Blue | ◯ | 1.8 | ⊙ |
| Comparative Element 4-1 | Comparative Compound 1 | Blue | X | 0.8 | X |
| Comparative Element 4-2 | Comparative Compound 4 | Blue | X | 1.0 | X |

From Tables above, it can be seen that the compound of the present invention has high light emitting efficiency, excellent blue chromatic purity, and small chromaticity change which occurs with the driving degradation.

On the other hand, it could be seen that the respective comparative elements using Comparative Compound 1 described in JP-A-2008-50308 has poor light emitting efficiency, chromatic purity, and chromaticity change which occurs with the driving degradation.

It could be seen that the respective comparative elements using Comparative Compound 2 described in JP-A-2007-157899 and JP-A-2007-227717 has poor light emitting efficiency, chromatic purity, and chromaticity change which occurs with the driving degradation.

It could be seen that the comparative elements using Comparative Compound 3 described in JP-A-11-251063 has poor chromatic purity and chromaticity change which occurs with the driving degradation.

It could be seen that the respective comparative elements using Comparative Compound 4 described in JP-A-2009-292760 has poor light emitting efficiency and chromatic purity, and poor chromaticity change which occurs with the driving degradation due to the element configuration.

DESCRIPTION OF REFERENCE NUMERALS AND SIGNS

2 SUBSTRATE
3 ANODE
4 HOLE INJECTING LAYER
5 HOLE TRANSPORTING LAYER
6 LIGHT EMITTING LAYER
7 HOLE BLOCKING LAYER
8 ELECTRON TRANSPORTING LAYER
9 CATHODE
10 ORGANIC ELECTROLUMINESCENT ELEMENT
11 ORGANIC LAYER
12 PROTECTIVE LAYER
14 ADHESIVE LAYER
16 SEALING ENCLOSURE
20 LIGHT EMITTING DEVICE
30 LIGHT SCATTERING MEMBER
31 TRANSPARENT SUBSTRATE
30A LIGHT INCIDENT SURFACE
30B LIGHT OUTPUT SURFACE
32 FINE PARTICLES
40 ILLUMINATION DEVICE

What is claimed:

1. A compound represented by the following general formula (1):

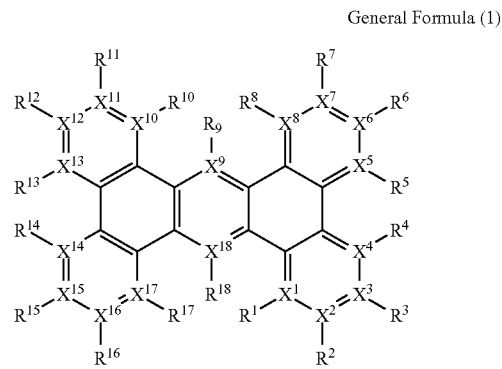

General Formula (1)

wherein: $R^1$ to $R^{18}$ each independently represents a hydrogen atom or a substituent, and at least one of $R^1$ to $R^8$ and $R^{10}$ to $R^{17}$ represents -L-$NR^{19}R^{20}$; $R^{19}$ and $R^{20}$ each independently represent any of an alkyl group, an aryl group, and a heteroaryl group; $R^{19}$ and $R^{20}$ may be combined to each other to form a ring, L represents a single bond or a divalent linking group, $X^1$ to $X^{18}$ each independently represent a carbon atom or a nitrogen atom, and when $X^1$ to $X^{18}$ represent nitrogen atoms, $R^1$ to $R^{18}$ are not present, and wherein at least one of $X^1$ to $X^{18}$ represents a nitrogen atom.

2. The compound according to claim 1, in which at least one of $R^3$, $R^6$, $R^{12}$, and $R^{15}$, of the compound is -L-$NR^{19}R^{20}$.

3. The compound according to claim 1, in which both $R^{19}$ and $R^{20}$ of the compound are aryl groups.

4. The compound according to claim 1, in which two of $X^1$ to $X^{18}$ of the compound are nitrogen atoms.

5. The compound according to claim 1, in which two of $R^1$ to $R^{18}$ of the compound represent -L-$NR^{19}R^{20}$.

6. The compound according to claim 1, in which L of the compound represents a single bond.

7. An organic electroluminescent element comprising a substrate, a pair of electrodes comprising an anode and a cathode disposed on the substrate, and at least one organic layer comprising a light emitting layer disposed between the electrodes, wherein the light emitting layer comprises a light emitting material represented by the following General Formula (1):

General Formula (1)

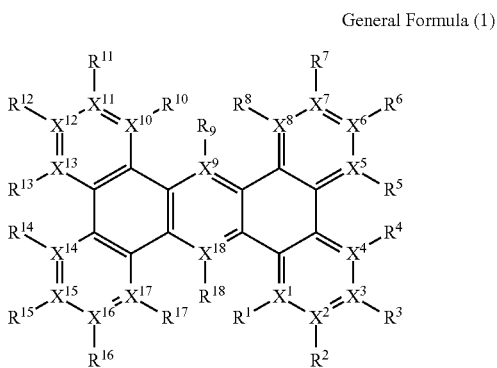

wherein $R^1$ to $R^{18}$ each independently represents a hydrogen atom or a substituent, and at least one of $R^1$ to $R^8$ and $R^{10}$ to $R^{17}$ represents -L-$NR^{19}R^{20}$; $R^{19}$ and $R^{20}$ each independently represent any of an alkyl group, an aryl group, and a heteroaryl group; $R^{19}$ and $R^{20}$ may be combined to each other to form a ring, L represents a single bond or a divalent linking group, $X^1$ to $X^{18}$ each independently represent a carbon atom or a nitrogen atom, and when $X^1$ to $X^{18}$ represent nitrogen atoms, $R^1$ to $R^{18}$ are not present, and wherein at least one of $X^1$ to $X^{18}$ represents a nitrogen atom.

8. The organic electroluminescent element according to claim 7, in which at least one of $R^3$, $R^6$, $R^{12}$, and $R^{15}$ of the compound is -L-$NR^{19}R^{20}$.

9. The organic electroluminescent element according to claim 7, in which both $R^{19}$ and $R^{20}$ of the compound are aryl groups.

10. The organic electroluminescent element according to claim 7, in which two of $X^1$ to $X^{18}$ of the compound are nitrogen atoms.

11. The organic electroluminescent element according to claim 7, in which two of $R^1$ to $R^{18}$ of the compound represent -L-$NR^{19}R^{20}$.

12. The organic electroluminescent element according to claim 7, in which L of the compound represents a single bond.

* * * * *